US012523932B2

(12) United States Patent
Hatakeyama et al.

(10) Patent No.: US 12,523,932 B2
(45) Date of Patent: Jan. 13, 2026

(54) RESIST COMPOSITION AND PATTERN FORMING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 879 days.

(21) Appl. No.: 17/716,256

(22) Filed: Apr. 8, 2022

(65) Prior Publication Data

US 2022/0350243 A1 Nov. 3, 2022

(30) Foreign Application Priority Data

Apr. 14, 2021 (JP) ................................ 2021-068375

(51) Int. Cl.

| | |
|---|---|
| ***G03F 7/004*** | (2006.01) |
| ***C07C 205/57*** | (2006.01) |
| ***C07C 233/54*** | (2006.01) |
| ***C07C 311/09*** | (2006.01) |
| ***C07C 317/44*** | (2006.01) |
| ***C07C 381/12*** | (2006.01) |
| ***C07D 327/08*** | (2006.01) |
| ***C07D 333/54*** | (2006.01) |
| ***C07D 333/76*** | (2006.01) |
| ***G03F 7/038*** | (2006.01) |
| ***G03F 7/039*** | (2006.01) |

(52) U.S. Cl.

CPC .......... *G03F 7/0045* (2013.01); *C07C 205/57* (2013.01); *C07C 233/54* (2013.01); *C07C 311/09* (2013.01); *C07C 317/44* (2013.01); *C07C 381/12* (2013.01); *C07D 327/08* (2013.01); *C07D 333/54* (2013.01); *C07D 333/76* (2013.01); *G03F 7/0382* (2013.01); *G03F 7/0392* (2013.01)

(58) Field of Classification Search

CPC .... G03F 7/0045; G03F 7/0382; G03F 7/0392; G03F 7/0397; G03F 7/004; G03F 7/2004; C07C 205/57; C07C 233/54; C07C 381/12

See application file for complete search history.

(56) References Cited

U.S. PATENT DOCUMENTS

| | | | | |
|---|---|---|---|---|
| 7,482,108 | B2 | 1/2009 | Matsumaru et al. | |
| 9,063,414 | B2 | 6/2015 | Ichikawa et al. | |
| 10,180,625 | B2 | 1/2019 | Nagamine et al. | |
| 10,248,022 | B2 | 4/2019 | Ohashi et al. | |
| 10,520,811 | B2 | 12/2019 | Tatakeyama et al. | |
| 2002/0012866 | A1 | 1/2002 | Nishiyama et al. | |
| 2003/0224285 | A1 | 12/2003 | Nakao et al. | |
| 2005/0042543 | A1 | 2/2005 | Kanna et al. | |
| 2009/0035692 | A1 | 2/2009 | Tarutani et al. | |
| 2014/0065546 | A1 | 3/2014 | Hatakeyama | |
| 2017/0075217 | A1* | 3/2017 | Hatakeyama | C07C 219/02 |
| 2018/0239249 | A1* | 8/2018 | Hatakeyama | G03F 7/0382 |
| 2019/0155155 | A1 | 5/2019 | Hatakeyama et al. | |
| 2021/0048748 | A1 | 2/2021 | Hatakeyama et al. | |

FOREIGN PATENT DOCUMENTS

| | | | |
|---|---|---|---|
| JP | 2002-207294 | A | 7/2002 |
| JP | 2003-207886 | A | 7/2003 |
| JP | 2005-070316 | A | 3/2005 |
| JP | 2006-45311 | A | 2/2006 |
| JP | 2006-178317 | A | 7/2006 |
| JP | 2006-258979 | A | 9/2006 |
| JP | 2007-114431 | A | 5/2007 |
| JP | 2012-189977 | A | 10/2012 |
| JP | 2017-72691 | A | 4/2017 |
| JP | 2017-202993 | A | 11/2017 |
| JP | 2018-136527 | A | 8/2018 |
| KR | 10-2009-0013127 | A | 2/2009 |
| KR | 10-2014-0031807 | A | 3/2014 |
| KR | 10-2021-0020833 | A | 2/2021 |
| TW | 201812447 | A | 4/2018 |

OTHER PUBLICATIONS

Office Action dated Mar. 12, 2024, issued in counterpart KR application No. 10-2022-0044600, with English translation. (19 pages).

Kishikawa et al., "Assessment of trade-off between resist resolution and sensitivity for optimization of hyper-NA immersion lithography", SPIE, 2007, vol. 6520, 65203L-1, (9 pages).

Office Action dated Dec. 15, 2023, issued in counterpart TW Application No. 111113579. (6 pages).

Office Action dated Nov. 19, 2024, issued in counterpart JP application No. 2022-049188, with English translation. (8 pages).

* cited by examiner

*Primary Examiner* — Stewart A Fraser

(74) *Attorney, Agent, or Firm* — WHDA, LLP

(57) ABSTRACT

A resist composition comprising a sulfonium salt of a carboxylic acid having a nitro-substituted benzene ring is provided. The carboxylic acid is free of iodine and bromine, and when the benzene ring is fluorinated, the number of fluorine atoms is up to 3. The resist composition offers a high sensitivity, reduced LWR and improved CDU independent of whether it is of positive or negative tone.

15 Claims, No Drawings

RESIST COMPOSITION AND PATTERN FORMING PROCESS

CROSS-REFERENCE TO RELATED APPLICATION

This non-provisional application claims priority under 35 U.S.C. § 119(a) on Patent Application No. 2021-068375 filed in Japan on Apr. 14, 2021, the entire contents of which are hereby incorporated by reference.

TECHNICAL FIELD

This invention relates to a resist composition and a patterning process using the composition.

BACKGROUND ART

To meet the demand for higher integration density and operating speed of LSIs, the effort to reduce the pattern rule is in rapid progress. As the use of 5G high-speed communications and artificial intelligence (AI) is widely spreading, high-performance 20 devices are needed for their processing. As the advanced miniaturization technology, manufacturing of microelectronic devices at the 5-nm node by the lithography using EUV of wavelength 13.5 nm has been implemented in a mass scale. Studies are made on the application of EUV lithography to 3-nm node devices of the next generation and 2-nm node devices of the next-but-one generation.

As the feature size reduces, image blurs due to acid diffusion become a problem. To insure resolution for fine patterns with a size of 45 nm et seq., not only an improvement in dissolution contrast is important as previously reported, but the control of acid diffusion is also important as reported in Non-Patent Document 1. Since chemically amplified resist compositions are designed such that sensitivity and contrast are enhanced by acid diffusion, 30 an attempt to minimize acid diffusion by reducing the temperature and/or time of post-exposure bake (PEB) fails, resulting in drastic reductions of sensitivity and contrast.

A triangular tradeoff relationship among sensitivity, resolution, and edge roughness (LWR) has been pointed out. Specifically, a resolution improvement requires to suppress acid diffusion whereas a short acid diffusion distance leads to a decline of sensitivity.

The addition of an acid generator capable of generating a bulky acid is an effective means for suppressing acid diffusion. It was then proposed to incorporate repeat units derived from an onium salt having a polymerizable unsaturated bond in a polymer. Since this polymer functions as an acid generator, it is referred to as polymer-bound acid generator.

Patent Document 1 discloses a sulfonium or iodonium salt having a polymerizable unsaturated bond, capable of generating a specific sulfonic acid. Patent Document 2 discloses a sulfonium salt having a sulfonic acid directly attached to the backbone.

Resist compositions adapted for the ArF lithography are typically based on (meth)acrylate polymers having acid labile groups. On these acid labile groups, deprotection reaction takes place with strong acids generated from photoacid generators such as sulfonic acids having fluorine substituted at α-position (referred to as "α-fluorinated sulfonic acids", hereinafter), but not with weak acids such as α-non-fluorinated sulfonic acids and carboxylic acids. When a sulfonium or iodonium salt capable of generating strong acid is mixed with a sulfonium or iodonium salt capable of generating weak acid, the sulfonium or iodonium salt capable of generating weak acid undergoes ion exchange with the strong acid. Through the ion exchange, the strong acid once generated upon light exposure is converted back to the sulfonium or iodonium salt. Then the sulfonium or iodonium salt of weak acid functions as a quencher.

Resist compositions comprising sulfonium or iodonium salts capable of generating carboxylic acids as the quencher are known. For example. Patent Documents 3 to 7 disclose resist compositions to which sulfonium salts of salicylic acid, sulfonium salts of fluorinated salicylic acid, sulfonium inner salts of carboxylic acid, iodonium inner salts of carboxylic acid, and iodonium salts of fluorinated nitrobenzoic acid are added as the quencher.

Like photoacid generators, the quenchers of sulfonium or iodonium salt type are photo-decomposable. This means that the amount of quencher in the exposed region is reduced. Since acid is generated in the exposed region, the concentration of acid becomes relatively high as the amount of quencher is reduced. This leads to a contrast enhancement. However, the acid diffusion in the exposed region cannot be suppressed, indicating a difficulty of acid diffusion control. The iodonium salts are readily decomposable by nucleophilic attacks of heat or bases, indicating that the resist solution suffers the problem of poor storage stability.

CITATION LIST

Patent Document 1: JP-A 2006-045311 (U.S. Pat. No. 7,482,108)
Patent Document 2: JP-A 2006-178317
Patent Document 3: JP-A 2007-114431
Patent Document 4: JP-A 2017-072691 (U.S. Pat. No. 10,180,625)
Patent Document 5: JP-A 2017-202993 (U.S. Pat. No. 10,248,022)
Patent Document 6: JP-A 2012-189977 (U.S. Pat. No. 9,063,414)
Patent Document 7: JP-A 2018-136527 (U.S. Pat. No. 10,520,811)
Non-Patent Document 1: SPIE Vol. 6520 65203L-1 (2007)

DISCLOSURE OF INVENTION

It is desired to have a quencher capable of reducing the roughness (LWR) of line patterns or the dimensional uniformity (CDU) of hole patterns and improving the sensitivity of a resist composition. Image blurs due to acid diffusion must be significantly reduced before the demand can be met.

An object of the invention is to provide a resist composition which exhibits a high sensitivity, reduced LWR, and improved CDU independent of whether it is of positive or negative tone, and a pattern forming process using the same.

The inventors have found that a sulfonium salt of a carboxylic acid having a specific nitrobenzene ring is advantageous in that both the nitro group and the sulfonium salt are effective for suppressing acid diffusion, and the carboxylic acid having a specific nitrobenzene ring generated upon light exposure is effective for suppressing swell in alkaline developer, and that a resist composition using the sulfonium salt as a quencher exhibits reduced LWR, improved CDU, high resolution, and wide process margin.

In one aspect, the invention provides a resist composition comprising a sulfonium salt of a carboxylic acid having a benzene ring substituted with at least one nitro group, wherein the carboxylic acid is free of iodine and bromine, and when the benzene ring is substituted with fluorine, the number of fluorine atoms is up to 3.

Preferably, the sulfonium salt has the formula (A).

(A)

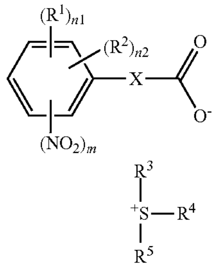

Herein $R^1$ is each independently chlorine, hydroxy group, amino group, or a $C_1$-$C_{20}$ hydrocarbyl group. $C_1$-$C_{20}$ hydrocarbyloxy group, $C_2$-$C_{20}$ hydrocarbylcarbonyloxy group, $C_2$-$C_{20}$ hydrocarbyloxycarbonyl group, $C_2$-$C_{20}$ hydrocarbyloxycarbonyloxy group, or $C_1$-$C_{20}$ hydrocarbylsulfonyl group, which may contain fluorine, chlorine, hydroxy, amino, ether bond or ester bond, or —$N(R^{1A})(R^{1B})$, —$N(R^{1C})$—C(═O)$R^{1D}$, —$N(R^{1C})$—C(═O)—O—$R^{1D}$, or —$N(R^{1E})$—S(═O)$_2$—$R^{1F}$, $R^{1A}$ and $R^{1B}$ are each independently hydrogen or a $C_1$-$C_6$ saturated hydrocarbyl group, $R^{1C}$ and $R^{1E}$ are each independently hydrogen or a $C_1$-$C_6$ saturated hydrocarbyl group which may contain halogen, hydroxy moiety. $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety. $R^{1D}$ and $R^{1F}$ are each independently a $C_1$-$C_{16}$ aliphatic hydrocarbyl group. $C_6$-$C_{14}$ aryl group or $C_7$-$C_{15}$ aralkyl group, which may contain halogen, hydroxy moiety, $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety. $R^2$ is fluorine. $R^3$ to $R^5$ are each independently halogen or a $C_1$-$C_{20}$ hydrocarbyl group which may contain a heteroatom, $R^3$ and $R^4$ may bond together to form a ring with the sulfur atom to which they are attached. X is a single bond or a $C_1$-$C_{20}$ divalent linking group which may contain an ether bond, carbonyl moiety, ester bond, amide bond, sultone ring, lactam ring, carbonate bond, halogen, hydroxy moiety or carboxy moiety, m is an integer of 1 to 3, n1 is an integer of 0 to 3, n2 is an integer of 0 to 3, and $1 \le m+n1+n2 \le 5$.

More preferably, the sulfonium salt has the formula (A)-1:

(A)-1

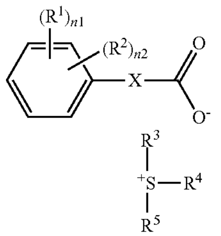

wherein $R^1$ to $R^5$, X, n1, and n2 are as defined above.

The resist composition may further comprise an acid generator capable of generating a strong acid. More preferably, the acid generator generates a sulfonic acid, imide acid or methide acid.

The resist composition may further comprise an organic solvent and/or a surfactant.

In a preferred embodiment, the resist composition further comprises a base polymer.

Most often, the base polymer comprises repeat units having the formula (a1) or repeat units having the formula (a2).

(a1)

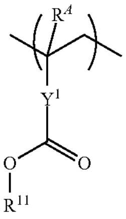

(a2)

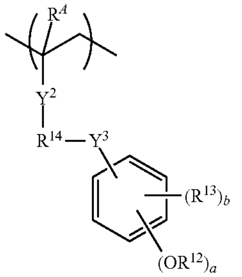

Herein $R^A$ is each independently hydrogen or methyl. $Y^1$ is a single bond, phenylene group, naphthylene group, or a $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ are each independently an acid labile group. $R^{13}$ is fluorine, trifluoromethyl, cyano or a $C_1$-$C_6$ saturated hydrocarbyl group. $R^{14}$ is a single bond or a $C_1$-$C_6$ alkanediyl group in which some carbon may be replaced by an ether bond or ester bond, "a" is 1 or 2, b is an integer of 0 to 4, and the sum of a+b is from 1 to 5.

In a preferred embodiment, the resist composition is a chemically amplified positive resist composition.

In another preferred embodiment, the base polymer is free of an acid labile group. The resist composition is a chemically amplified negative resist composition.

In a preferred embodiment, the base polymer further comprises repeat units of at least one type selected from repeat units having the formulae (f1) to (f3).

(f1)

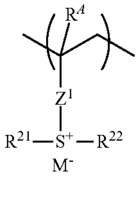

-continued (f2)

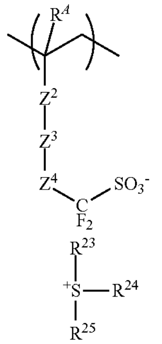

(f3)

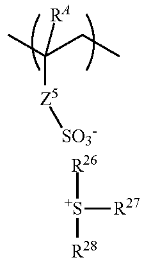

Herein $R^A$ is each independently hydrogen or methyl. $Z^1$ is a single bond, a $C_1$-$C_6$ aliphatic hydrocarbylene group, phenylene, naphthylene, or a $C_7$-$C_{18}$ group obtained by combining the foregoing, or —O—$Z^{11}$—, —C(=O)—O—$Z^{11}$— or —C(=O)—NH—$Z^{11}$—, $Z^{11}$ is a $C_1$-$C_6$ aliphatic hydrocarbylene group, phenylene, naphthylene, or a $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{11}$—C(=O)—O—, —$Z^{31}$—O— or —$Z^{31}$—O—C(=O)—, $Z^{31}$ is a $C_1$-$C_{12}$ hydrocarbylene group, phenylene group, or a $C_7$-$C_{18}$ group obtained by combining the foregoing, which may contain a carbonyl moiety, ester bond, ether bond, iodine or bromine. $Z^4$ is a methylene, 2,2,2-trifluoro-1,1-ethanediyl or carbonyl group. $Z^5$ is a single bond, methylene, ethylene, phenylene, fluorinated phenylene, trifluoromethyl-substituted phenylene, —O—$Z^{11}$—. —C(=O)—O—$Z^{51}$— or —C(=O)—NH—$Z^{51}$—, $Z^{51}$ is a $C_1$-$C_6$ aliphatic hydrocarbylene group, phenylene, fluorinated phenylene, or trifluoromethyl-substituted phenylene group, which may contain a carbonyl moiety, ester bond, ether bond or hydroxy moiety. R″ to $R^{23}$ are each independently halogen or a $C_1$-$C_{20}$ hydrocarbyl group which may contain a heteroatom, $R^{23}$ and $R^{24}$, or $R^{26}$ and $R^{27}$ may bond together to form a ring with the sulfur atom to which they are attached. $M^-$ is a non-nucleophilic counter ion.

In another aspect, the invention provides a pattern forming process comprising the steps of applying the resist composition defined above onto a substrate to form a resist film thereon, exposing the resist film to high-energy radiation, and developing the exposed resist film in a developer.

Typically, the high-energy radiation is i-line of wavelength 365 nm, ArF excimer laser of wavelength 193 nm, KrF excimer laser of wavelength 248 nm, EB, or EUV of wavelength 3 to 15 inn.

Advantageous Effects of Invention

The sulfonium salt of a carboxylic acid having a specific nitrobenzene ring serves as a quencher capable of suppressing acid diffusion. It is successful in restraining acid diffusion performance and improving LWR and CDU. A resist composition having improved LWR and CDU can be designed.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line designates a valence bond. As used herein, the term "fluorinated" refers to a fluorine-substituted or fluorine-containing compound or group. The terms "group" and "moiety" are interchangeable.

The abbreviations and acronyms have the following meaning.

EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity

Resist Composition

One embodiment of the invention is a resist composition comprising a sulfonium salt of a carboxylic acid having a specific nitrobenzene ring as a quencher.

Sulfonium Salt

The sulfonium salt of a carboxylic acid having a specific nitrobenzene ring is specifically a sulfonium salt of a carboxylic acid having a benzene ring substituted with at least one nitro group. The carboxylic acid is free of iodine and bromine, and when the benzene ring is substituted with fluorine, the number of fluorine atoms is up to 3.

The sulfonium salt of a carboxylic acid having a nitrobenzene ring is typically represented by the formula (A).

(A)

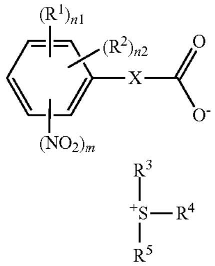

In formula (A), $R^1$ is each independently chlorine, hydroxy group, amino group, or a $C_1$-$C_{20}$ hydrocarbyl group, $C_1$-$C_{20}$ hydrocarbyloxy group, $C_2$-$C_{20}$ hydrocarbylcarbonyloxy group, $C_2$-$C_{20}$ hydrocarbyloxycarbonyl group, $C_2$-$C_{20}$ hydrocarbyloxycarbonyloxy group, or $C_1$-$C_{20}$ hydrocarbylsulfonyl group, which may contain fluorine, chlorine, hydroxy moiety, amino moiety, ether bond or ester bond, or —N($R^{1A}$)($R^{1B}$), —N($R^{1C}$)—C(=O)—$R^{1D}$, —N($R^{1C}$)—C (=O)—O—$R^{1D}$, or —N($R^{1E}$)—S(=O)$_2$—$R^{1F}$. $R^{1A}$ and $R^{1B}$ are each independently hydrogen or a $C_1$-$C_6$ saturated hydrocarbyl group. $R^{1C}$ and $R^{1E}$ are each independently hydrogen or a $C_1$-$C_6$ saturated hydrocarbyl group which may contain halogen, hydroxy moiety, $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety. $R^{1D}$ and $R^{1F}$ are each independently a $C_1$-$C_{16}$ aliphatic hydrocarbyl group. $C_6$-$C_{14}$ aryl group or $C_7$-$C_{15}$ aralkyl group, which may contain halogen, hydroxy moiety. $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety.

The $C_1$-$C_{20}$ hydrocarbyloxy group and hydrocarbyl moiety in the $C_2$-$C_{20}$ hydrocarbylcarbonyloxy group, $C_2$-$C_{20}$ hydrocarbyloxycarbonyl group, $C_2$-$C_{20}$ hydrocarbyloxycarbonyloxy group, and $C_1$-$C_{20}$ hydrocarbylsulfonyl group may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexyhnethyl, norbornyl, and adamantyl; $C_2$-$C_{20}$ alkenyl groups such as vinyl, propenyl, butenyl and hexenyl: $C_3$-$C_{20}$ cyclic unsaturated aliphatic hydrocarbyl groups such as cyclohexenyl and norbornenyl; $C_2$-$C_{20}$ alkynyl groups such as ethynyl, propynyl and butynyl: $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propyhnaphthyl, isopropylnaphthyl, n-butylnaphthyl, isobutylnaphthyl, sec-butylnaphthyl, and tert-butylnaphthyl; $C_7$-$C_{20}$ aralkyl groups such as benzyl and phenethyl; and combinations thereof. In the foregoing groups, some or all of the hydrogen atoms may be substituted by fluorine, chlorine, hydroxy or amino moiety, and some constituent —$CH_2$— may be replaced by an ether bond or ester bond.

Examples of the $C_1$-$C_6$ saturated hydrocarbyl group represented by $R^{1A}$. $R^{1B}$, $R^{1C}$ and $R^{1E}$ include those exemplified above for the alkyl and cyclic saturated hydrocarbyl group, but of 1 to 6 carbon atoms. The $C_1$-$C_{16}$ aliphatic hydrocarbyl group represented by $R^{1D}$ and $R^{1F}$ may be saturated or unsaturated and straight, branched or cyclic. Examples thereof include alkyl groups such as methyl, ethyl, n-propyl, isopropyl, n-butyl, isobutyl, sec-butyl, tert-butyl, n-pentyl, neopentyl, n-hexyl, n-heptyl, n-octyl, 2-ethylhexyl, n-nonyl, n-decyl, n-undecyl, n-dodecyl, n-tridecyl, n-pentadecyl, and n-hexadecyl; cyclic saturated hydrocarbyl groups such as cyclopentyl and cyclohexyl: alkenyl groups such as vinyl, 1-propenyl, 2-propenyl, butenyl and hexenyl; and cyclic unsaturated hydrocarbyl groups such as cyclohexenyl. Examples of the $C_6$-$C_{14}$ aryl group represented by $R^{1D}$ and $R^{1F}$ include phenyl, tolyl, xylyl, 1-naphthyl, and 2-naphthyl. Examples of the $C_7$-$C_{15}$ aralkyl group represented by $R^{1D}$ and $R^{1F}$ include benzyl, phenethyl, naphthylmethyl, naphthylethyl, fluorenylmethyl and fluorenylethyl.

In formula (A), $R^2$ is fluorine.

In formula (A), X is a single bond or a $C_1$-$C_2$ divalent linking group which may contain an ether bond, carbonyl moiety, ester bond, amide bond, sultone ring, lactam ring, carbonate bond, halogen, hydroxy moiety or carboxy moiety.

In formula (A), m is an integer of 1 to 3, n1 is an integer of 0 to 3, n2 is an integer of 0 to 3, and 1≤m+n1+n2≤5.

The nitro group is in the state of resonance to which the nitrogen atom having a positive charge and one of the two oxygen atoms having a negative charge contribute. The nitro group interacts with the strong acid generated from the acid generator to prevent the acid from diffusion. Further, through the above-mentioned mechanism, that is, ion exchange with a sulfonium salt, the strong acid generated from the acid generator undergoes ion exchange with the sulfonium salt of a carboxylic acid having a nitrobenzene ring, losing its acid strength. The acid diffusion is controlled by these two effects, with the advantage that acid diffusion is suppressed as compared with the sulfonium salts of benzoic acid or salicylic acid.

The nitro group is preferably attached to the benzene ring at 2-position as shown by the following formula (A)-1. Then the carboxy group generated upon light exposure forms a hydrogen bond with the nitro group to form a ring, thereby preventing any swell in alkaline developer.

(A)-1

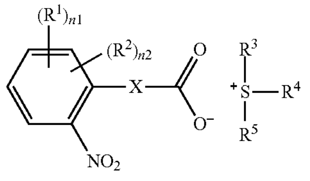

Herein $R^1$ to R, X, n1 and n2 are as defined above.

Examples of the carboxylate anion in the sulfonium salt having formula (A) are shown below, but not limited thereto.

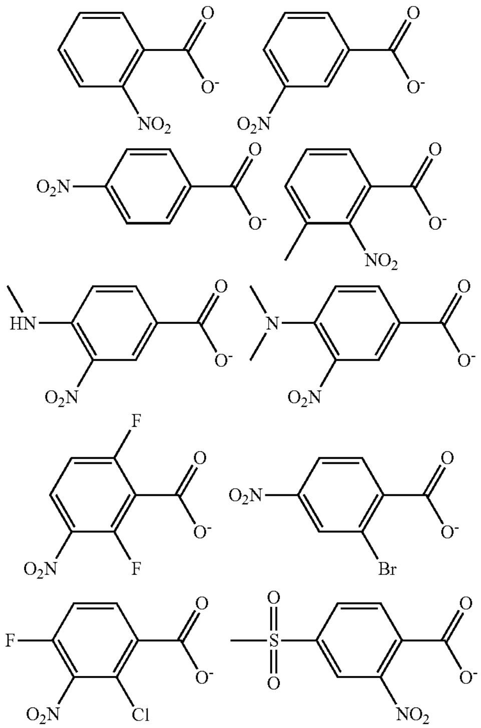

-continued
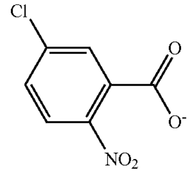
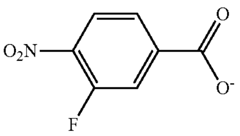
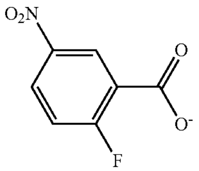
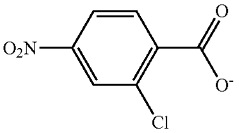
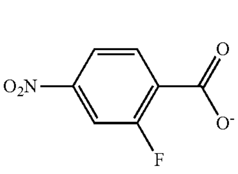
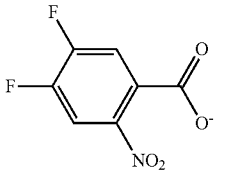
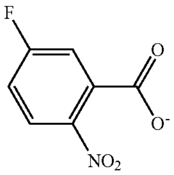
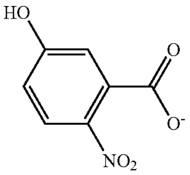
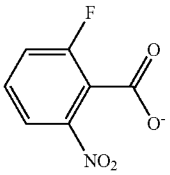
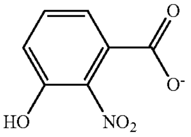
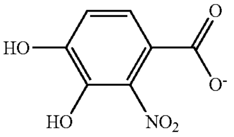
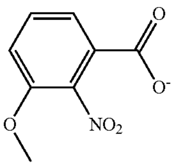
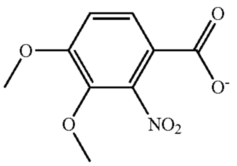
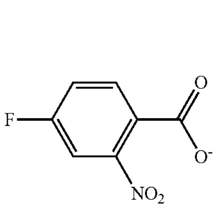
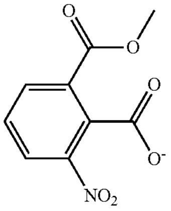
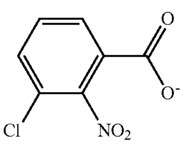
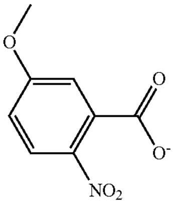
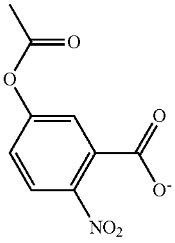
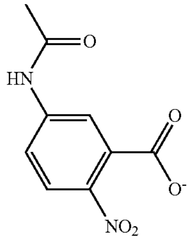
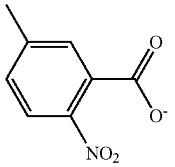
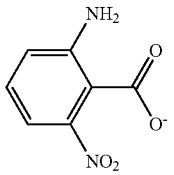
-continued
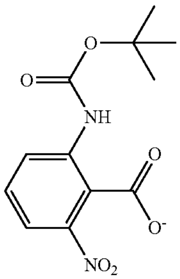
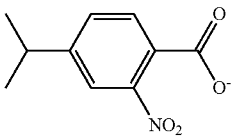
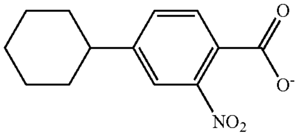
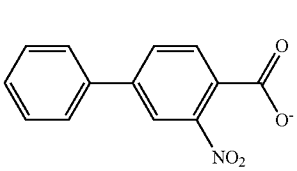
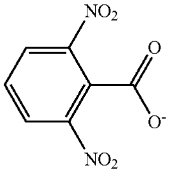
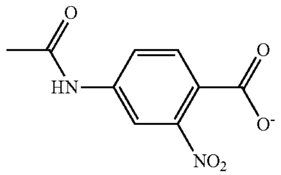
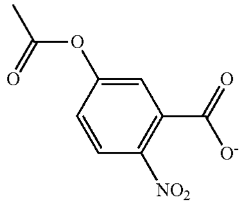
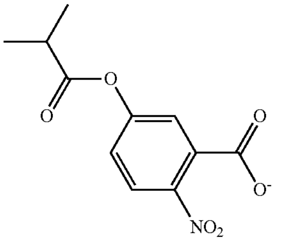
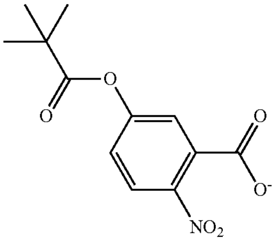
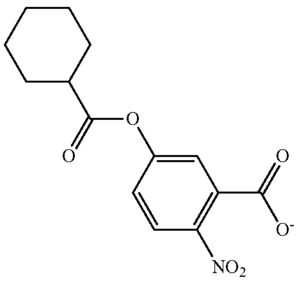
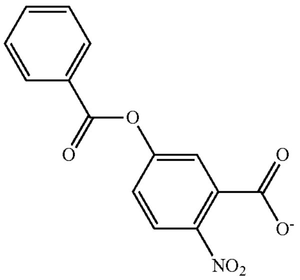

-continued
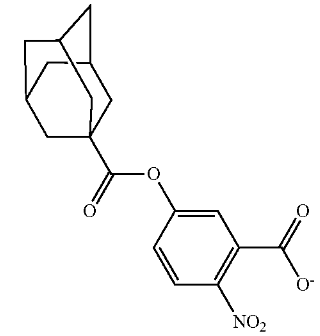
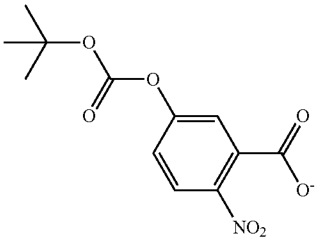
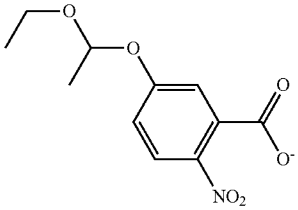
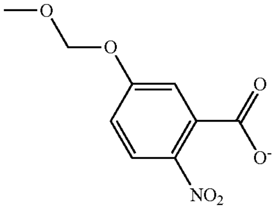
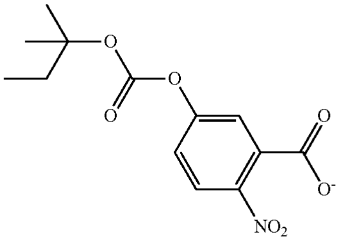
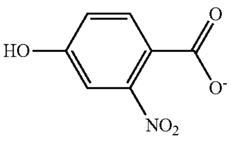
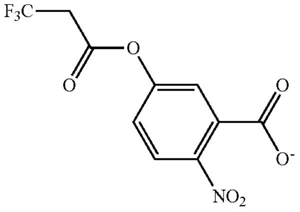
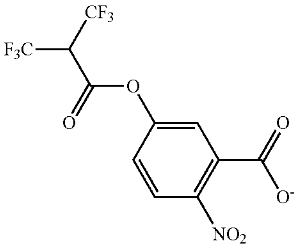
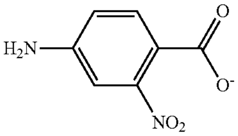
-continued
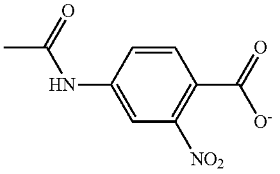
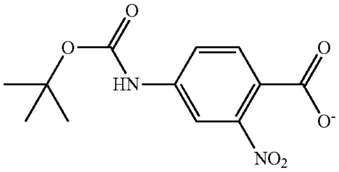
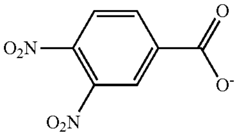
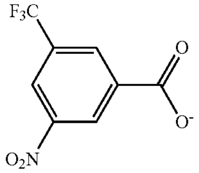
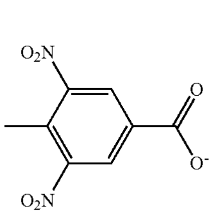
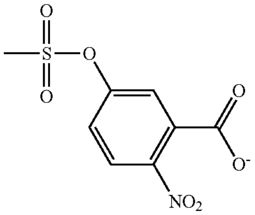
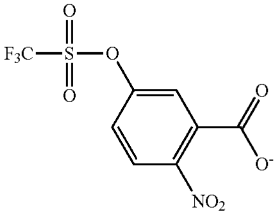
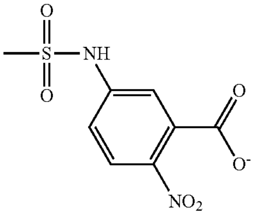
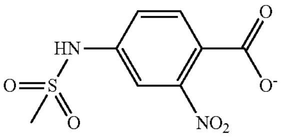
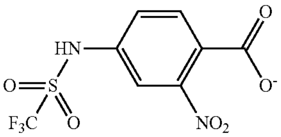
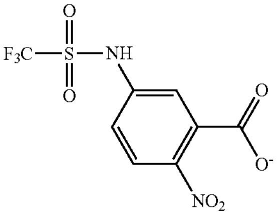
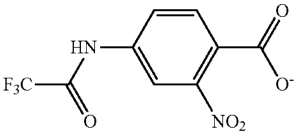
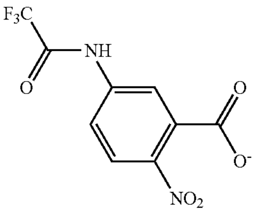

-continued
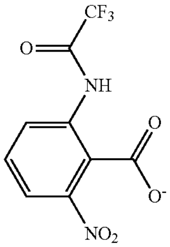
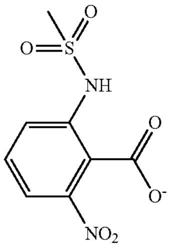
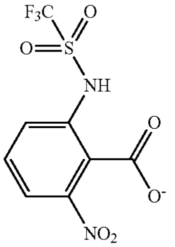
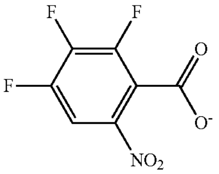
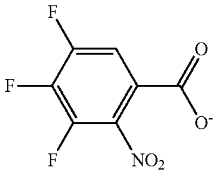
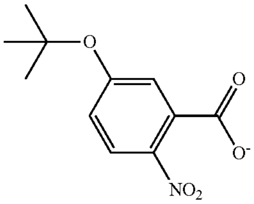
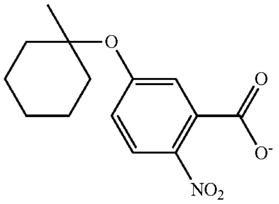
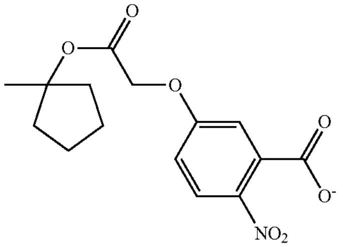
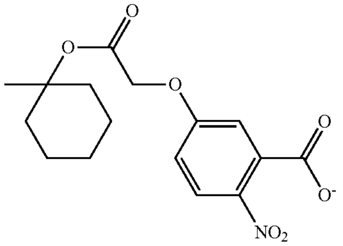
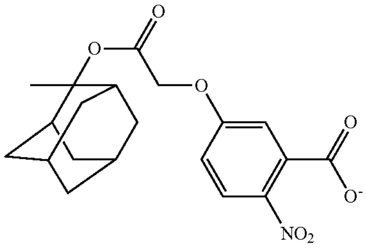
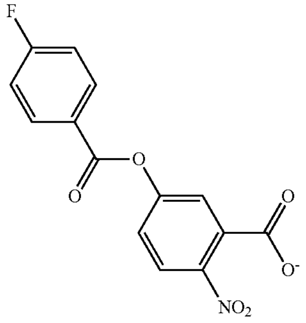
-continued
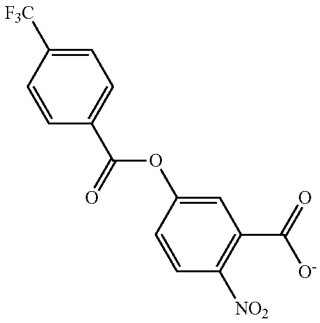
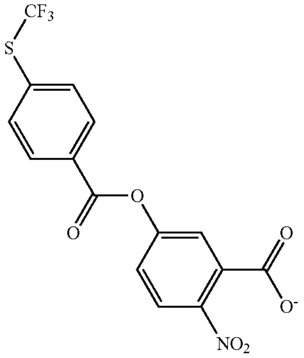
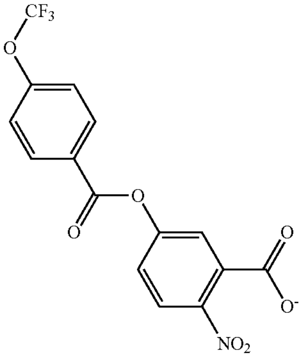
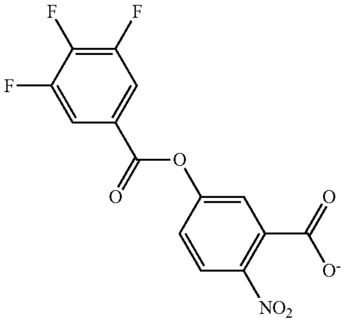
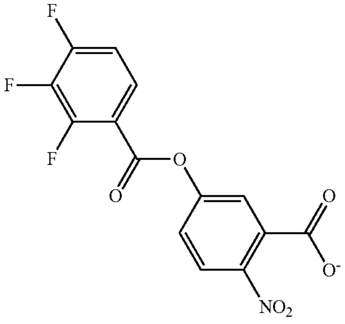

-continued
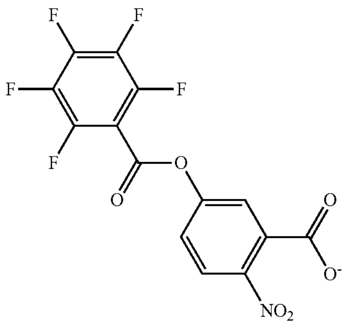
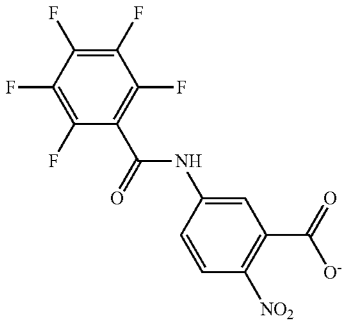
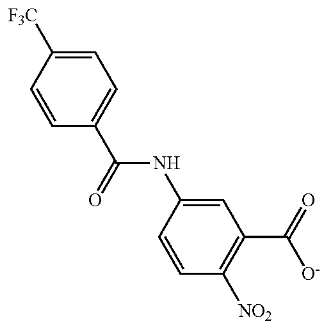
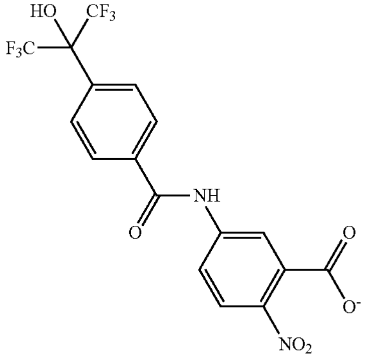
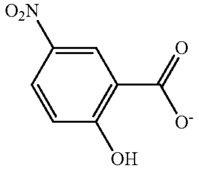
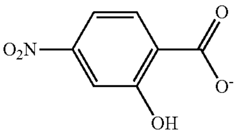
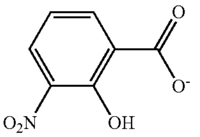
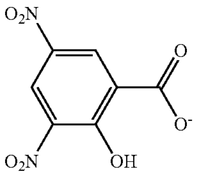
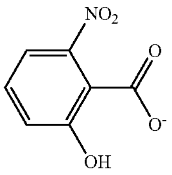
-continued
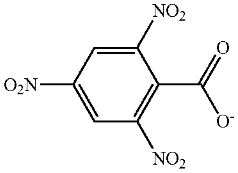
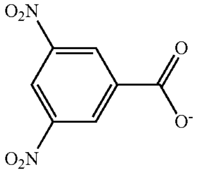
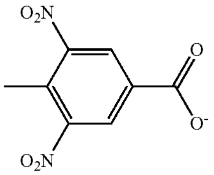
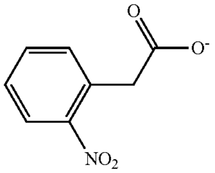
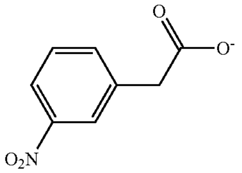
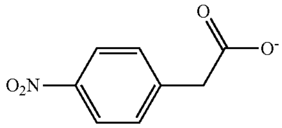
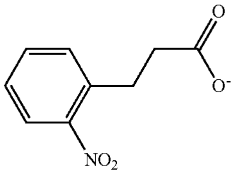
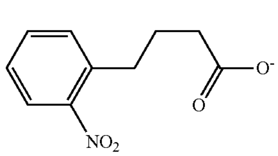
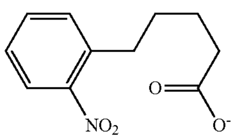
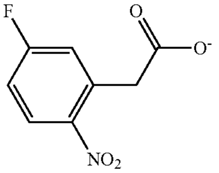
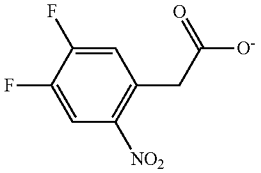
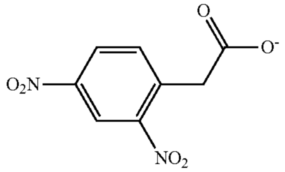
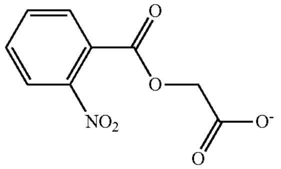
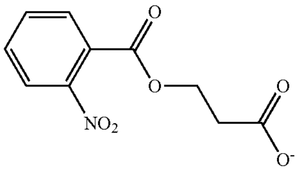
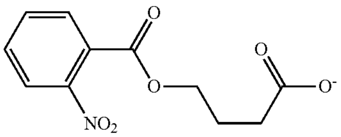
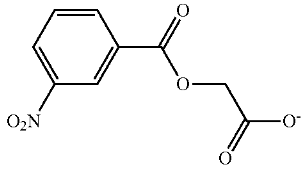

-continued
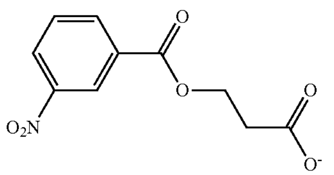
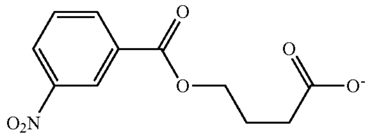
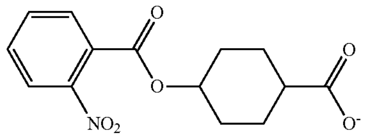
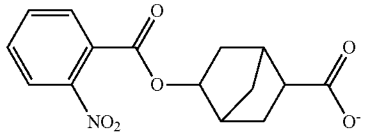
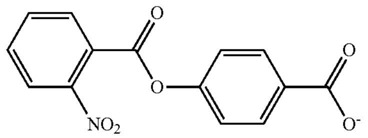
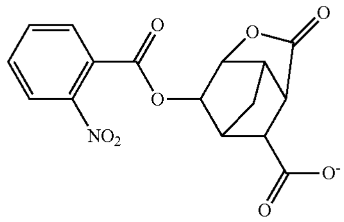
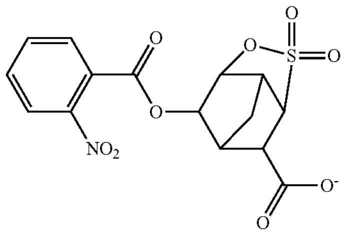
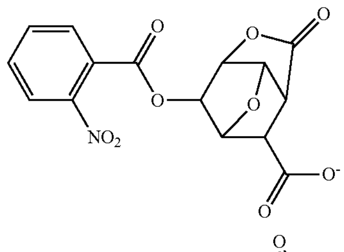
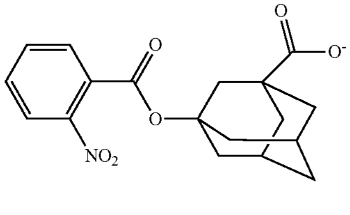
-continued
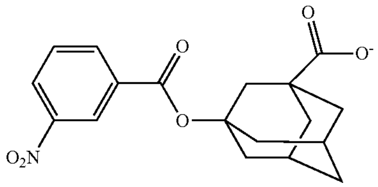
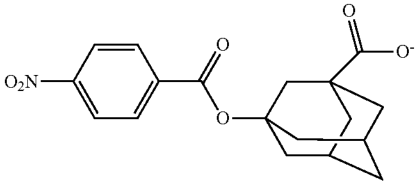
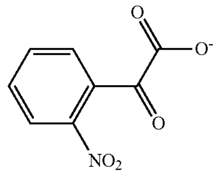
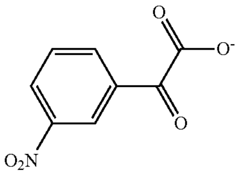
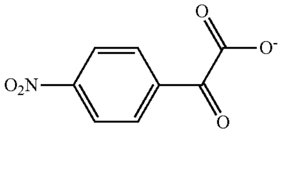
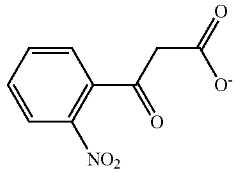
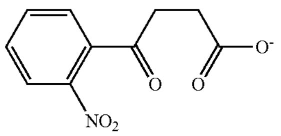
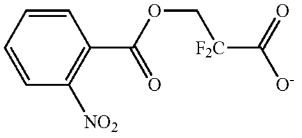
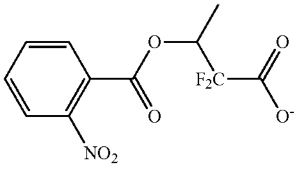
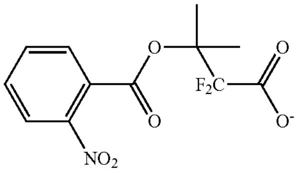
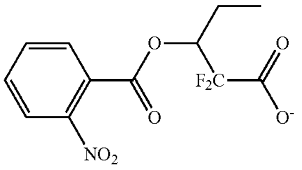
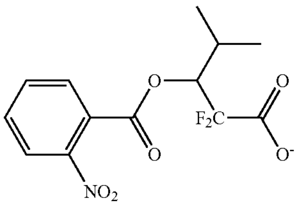

-continued
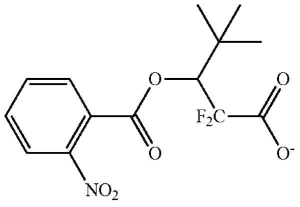
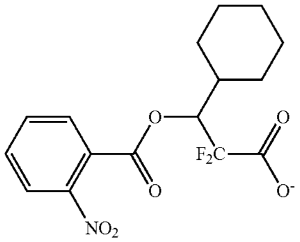
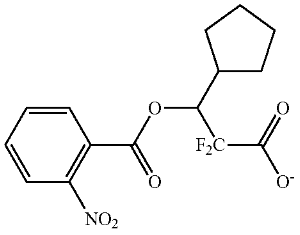
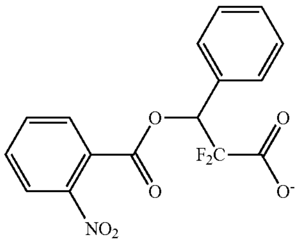
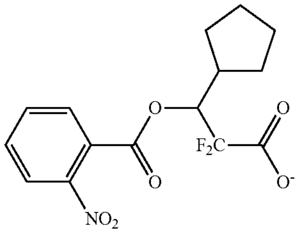
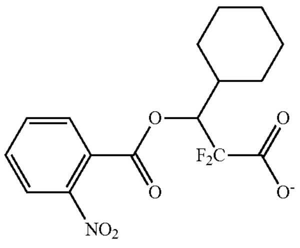
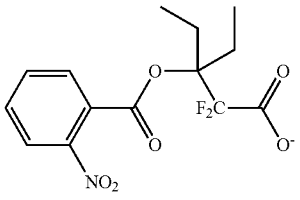
-continued
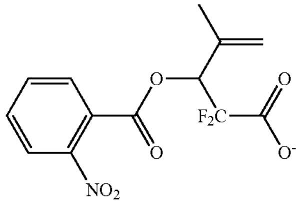
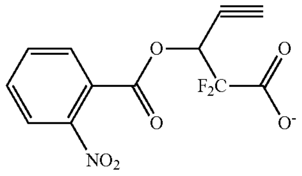
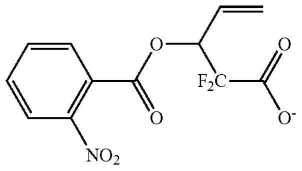
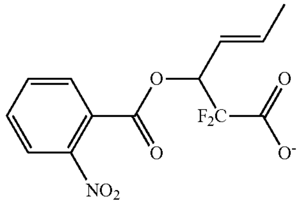
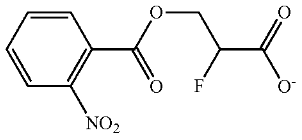 [SMILES: O=C(OCC(F)C(=O)[O-])c1ccccc1[N+](=O)[O-]]
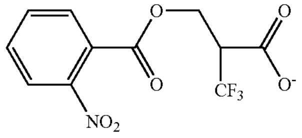
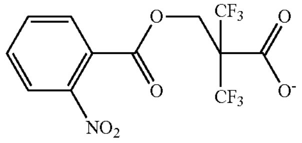
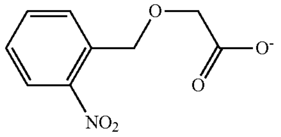
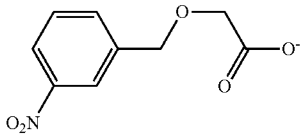
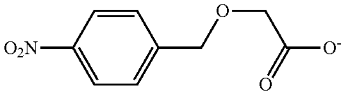
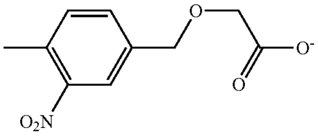

-continued

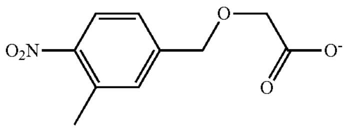

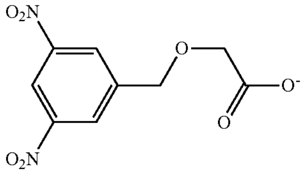

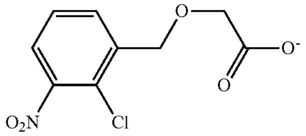

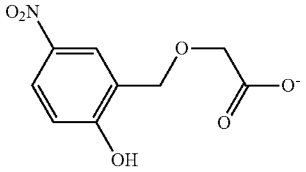

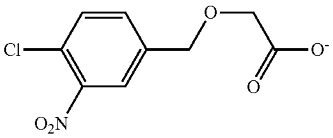

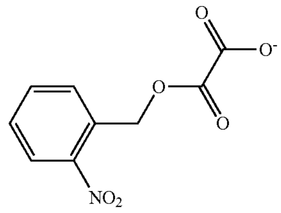

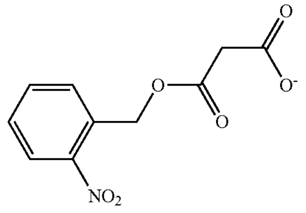

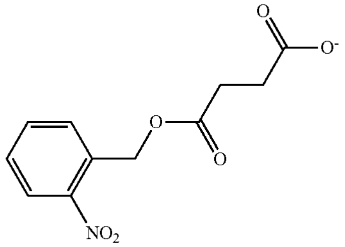

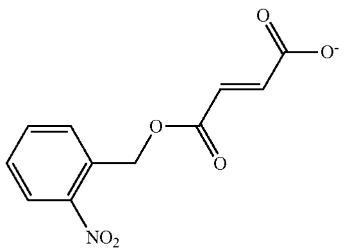

-continued

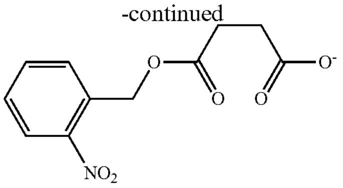

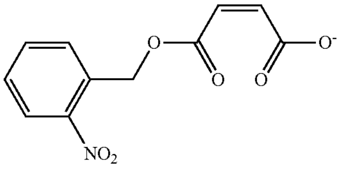

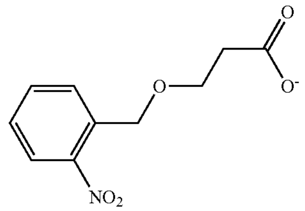

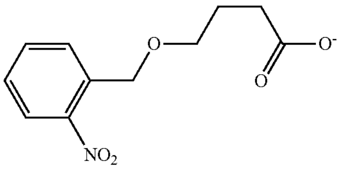

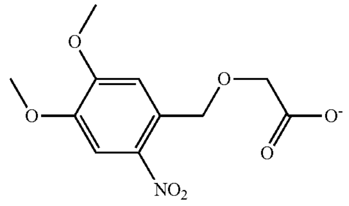

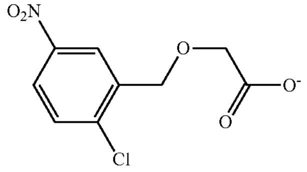

In formula (A), $R^3$ to $R^5$ are each independently halogen or a $C_1$-$C_{20}$ hydrocarbyl group which may contain a heteroatom.

Suitable halogen atoms include fluorine, chlorine, bromine and iodine.

The $C_1$-$C_{20}$ hydrocarbyl group represented by $R^3$ to $R^5$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl: $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl; $C_7$-$C_{20}$ aralkyl groups such as benzyl and phenethyl; and combinations thereof.

In the foregoing hydrocarbyl groups, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride or haloalkyl moiety.

$R^3$ and $R^4$ may bond together to form a ring with the sulfur atom to which they are attached. Examples of the ring are shown below.

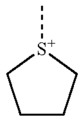
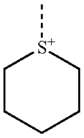
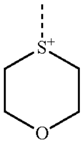
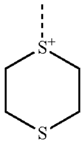
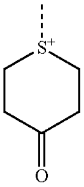
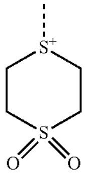
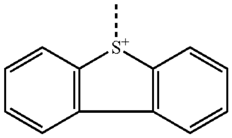
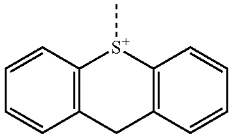
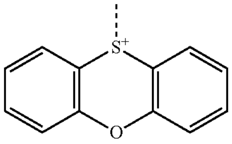

-continued

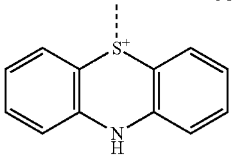
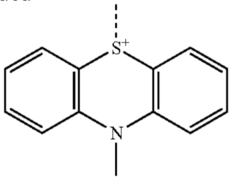
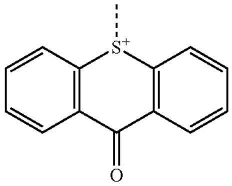
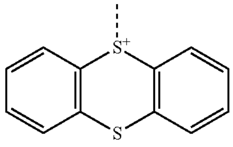
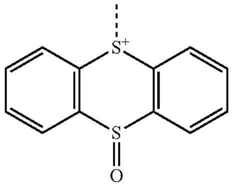
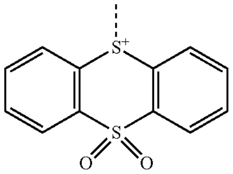
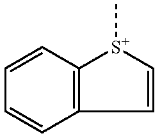

Herein the broken line designates a point of attachment to $R^5$.

Examples of the cation in the sulfonium salt having formula (A) are shown below, but not limited thereto.

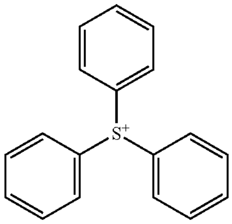
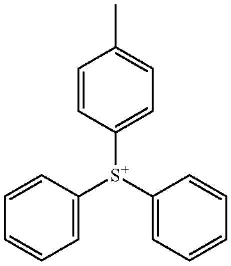
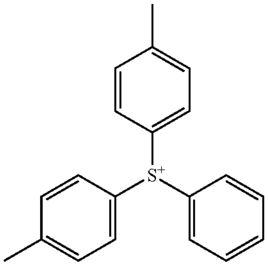
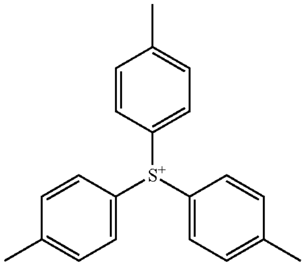
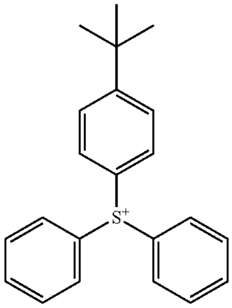
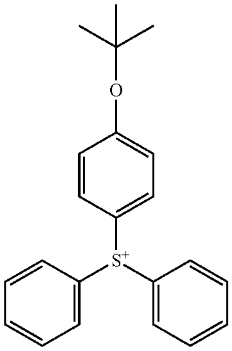
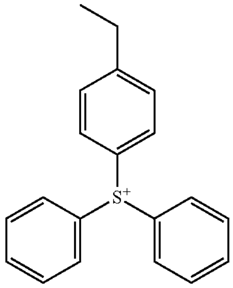
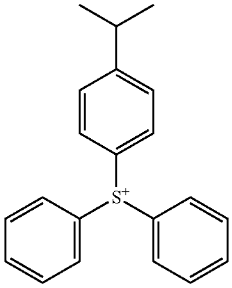

-continued
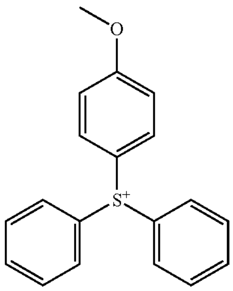
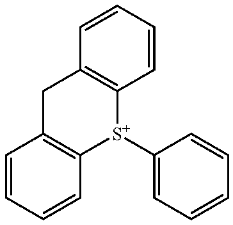
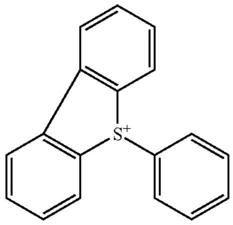
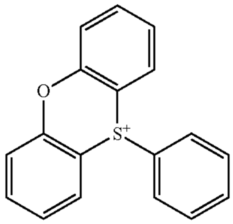
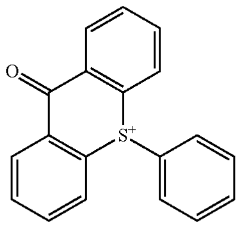
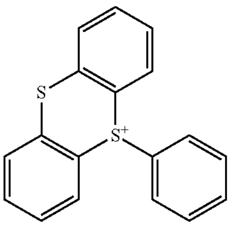
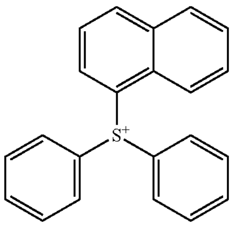
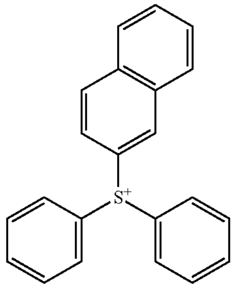
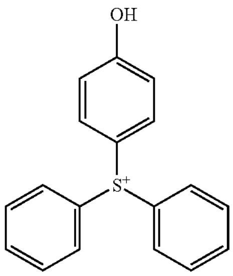
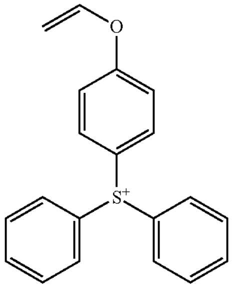
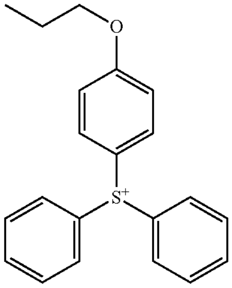
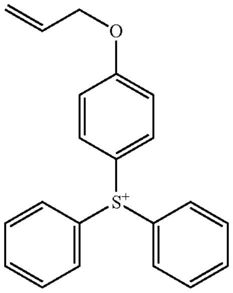
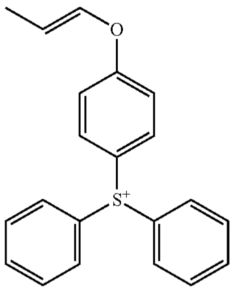
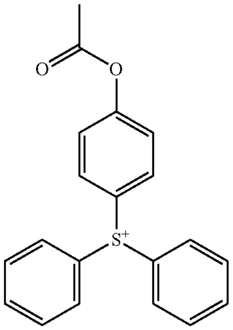
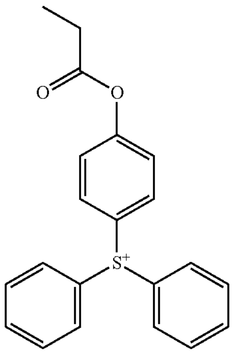
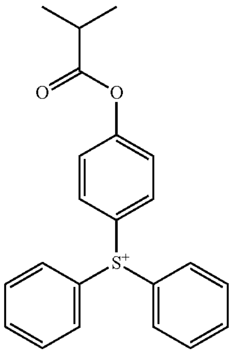
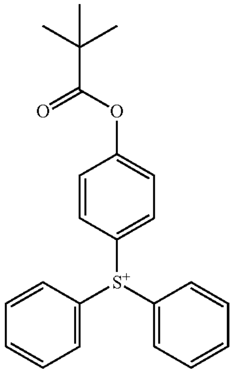
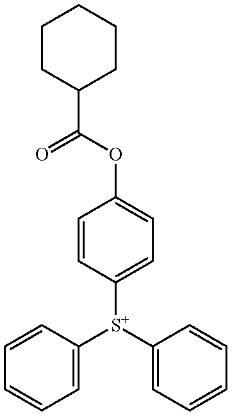
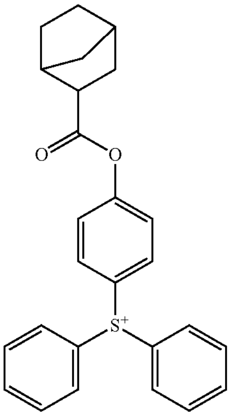
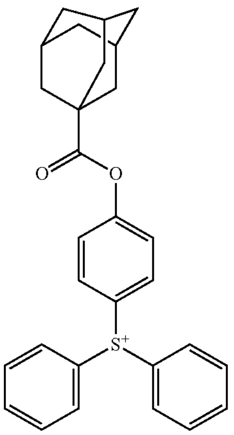

-continued
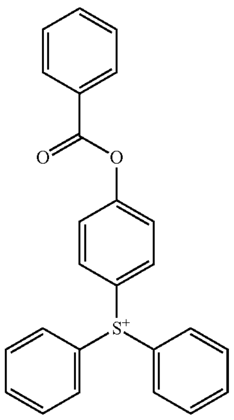
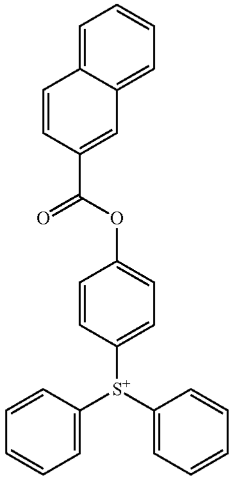
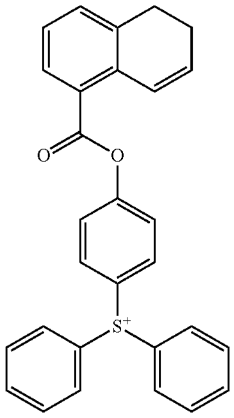
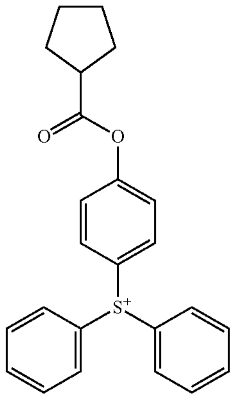
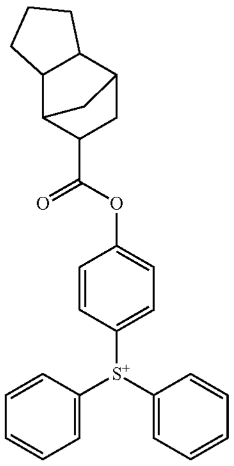
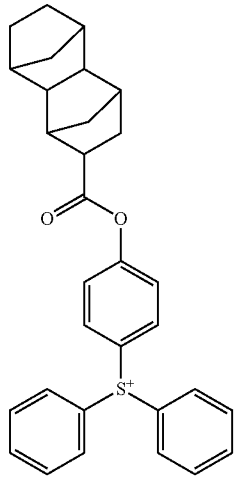
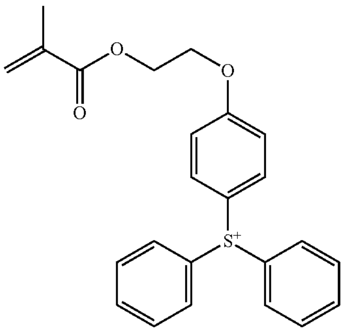
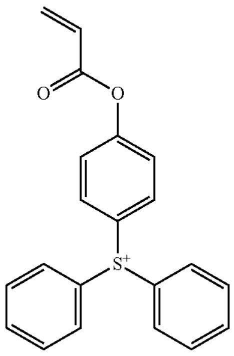
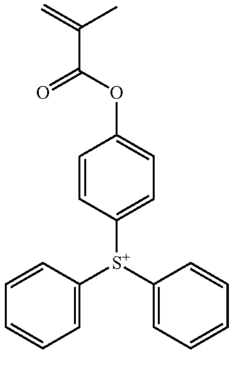
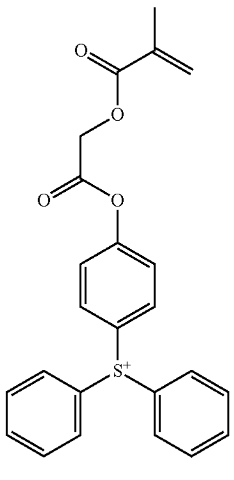
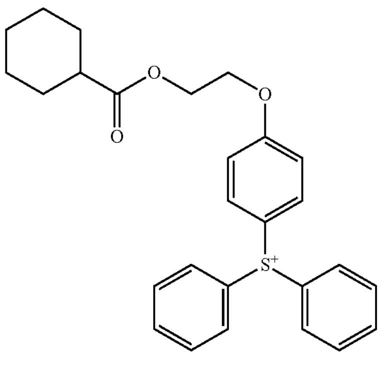

-continued
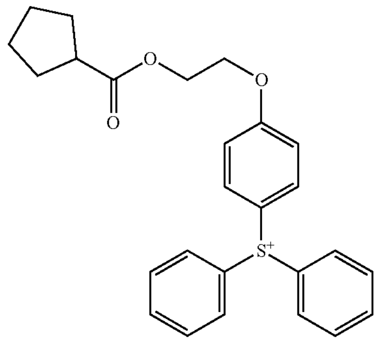
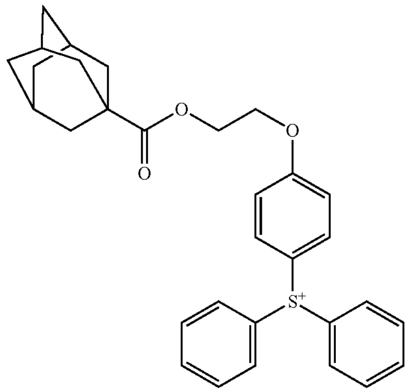
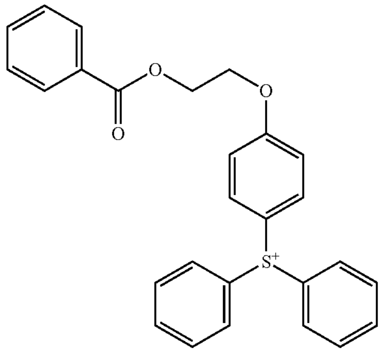
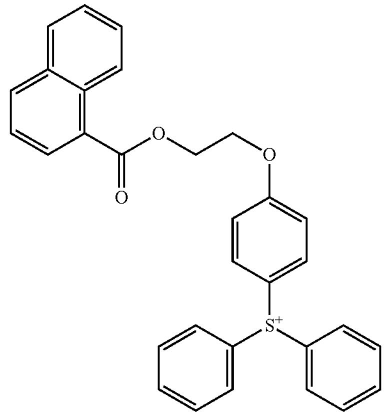
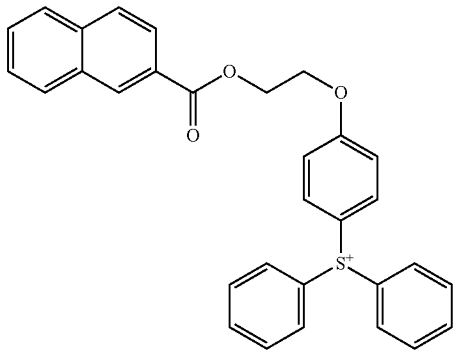
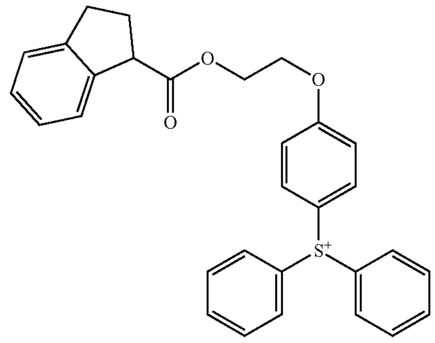
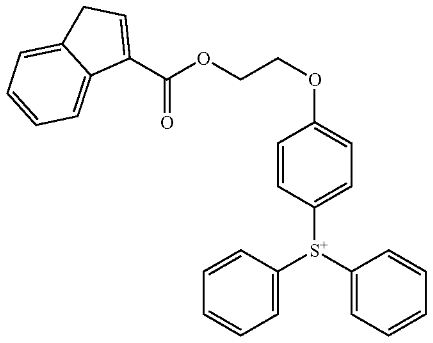
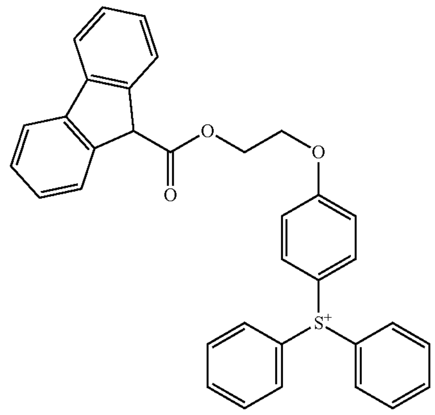
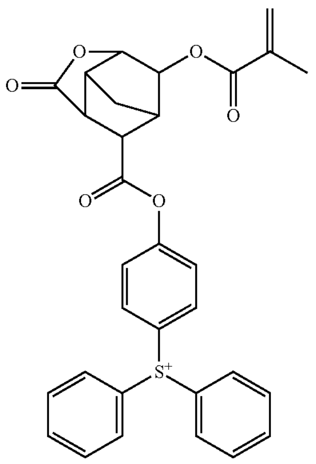
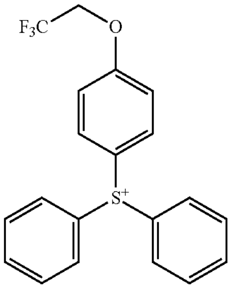

-continued
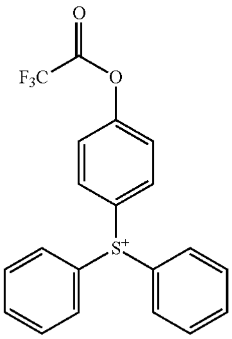
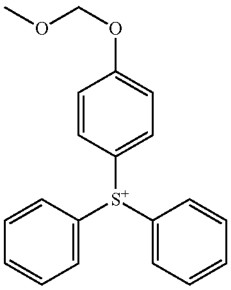
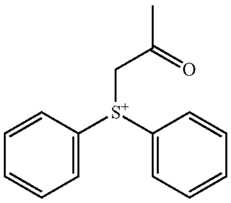
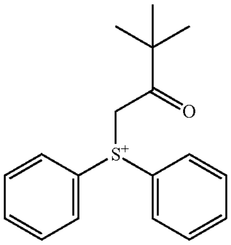
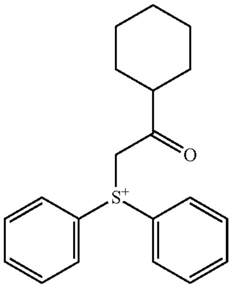
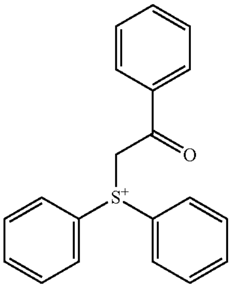
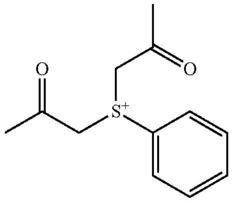
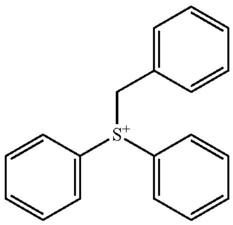
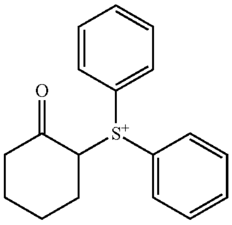
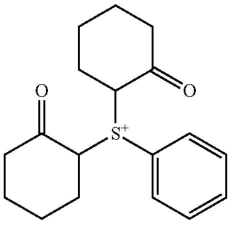
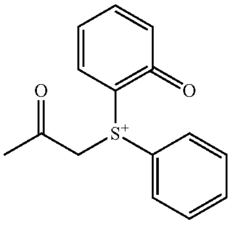
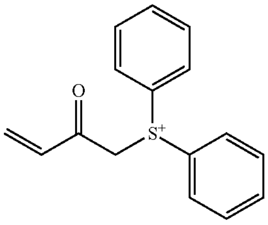
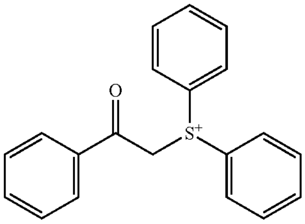
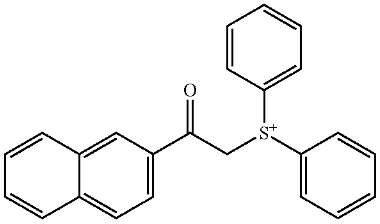
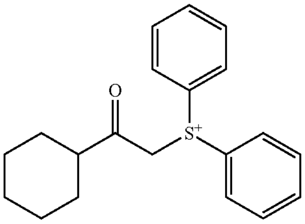
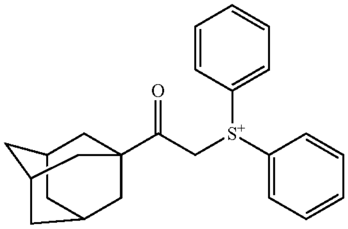
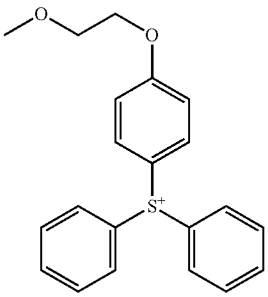
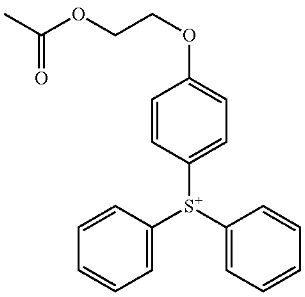
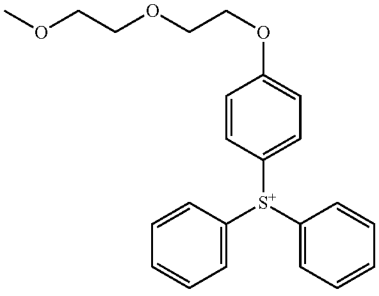
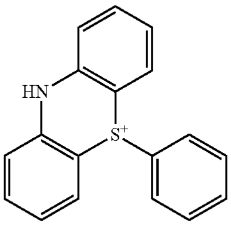
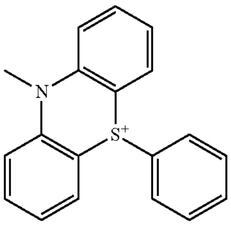

-continued
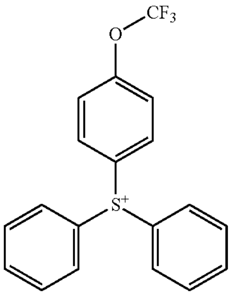
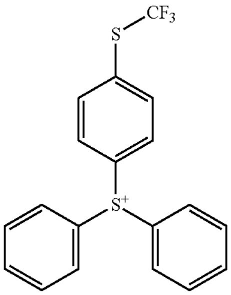
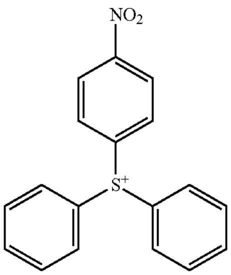
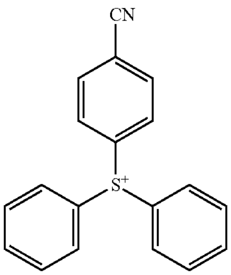
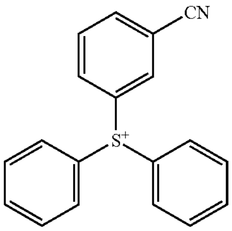
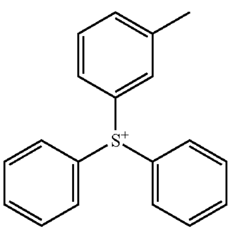
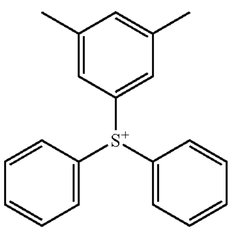
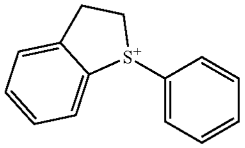
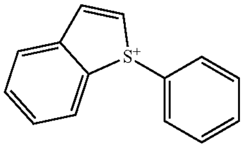
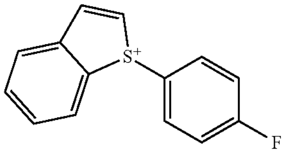
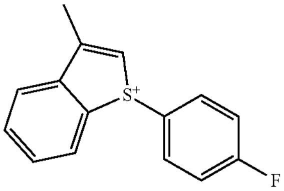
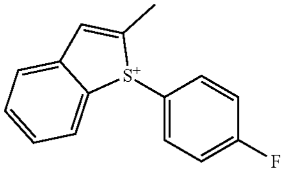
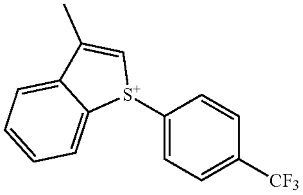
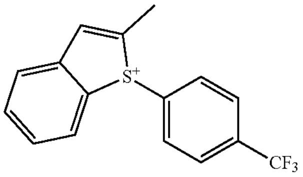
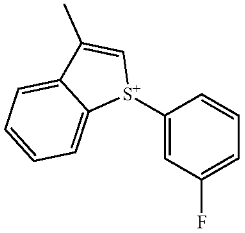
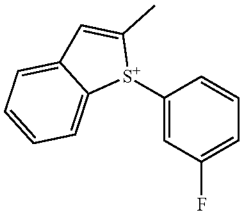
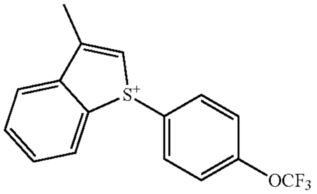
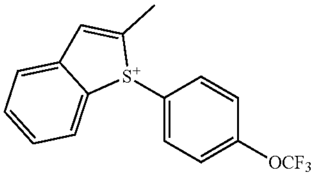
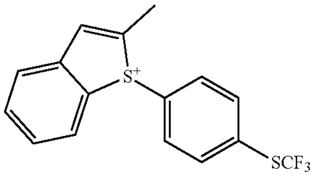
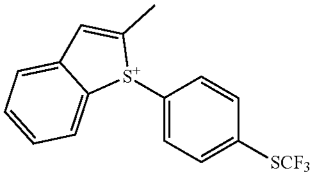
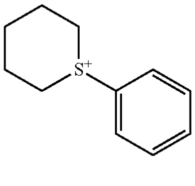
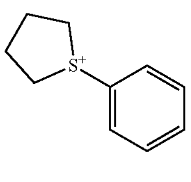
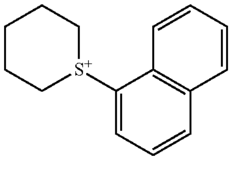
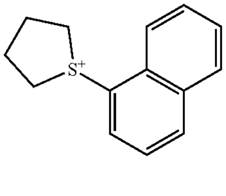
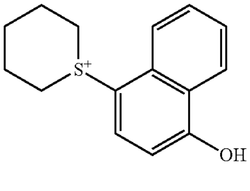
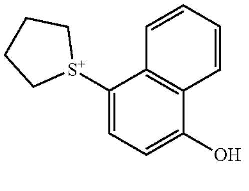
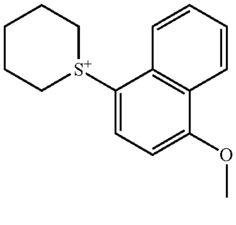

-continued
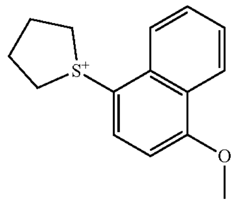
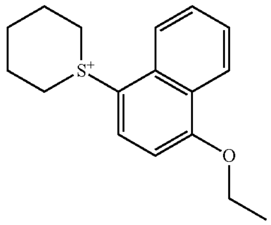
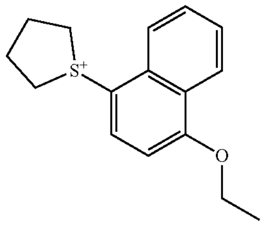
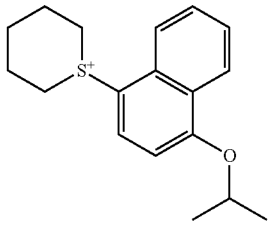
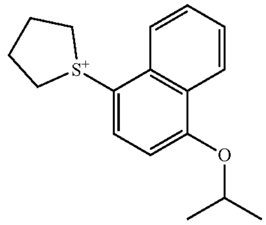
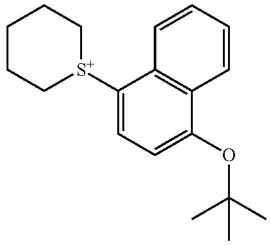
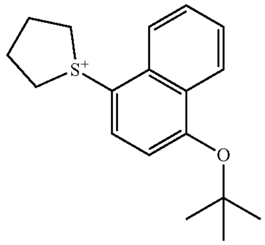
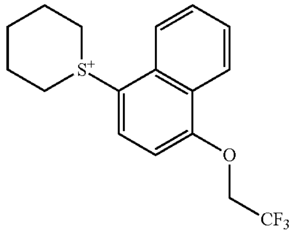
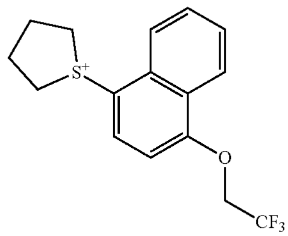
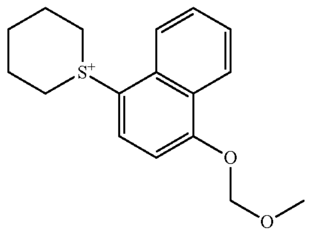
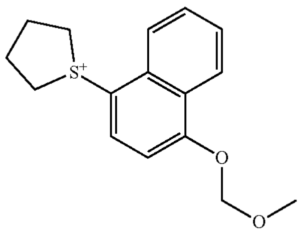
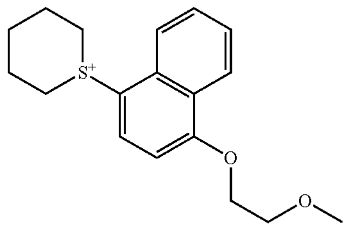
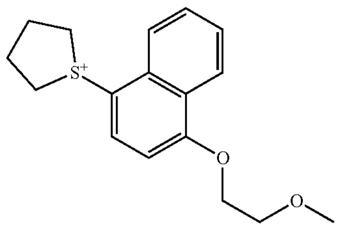
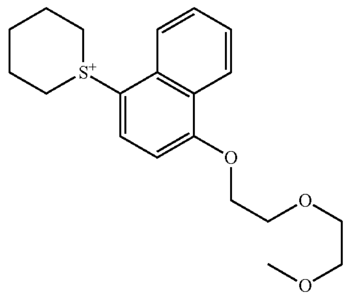
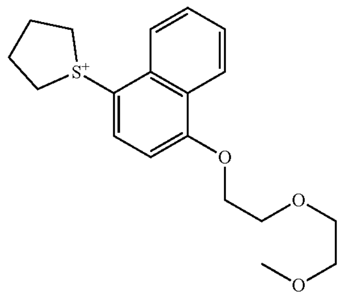
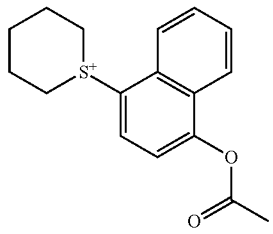
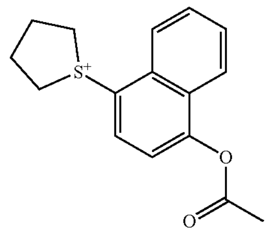
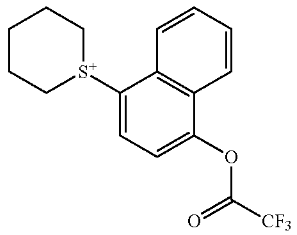
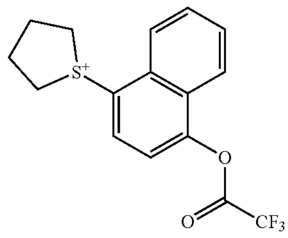
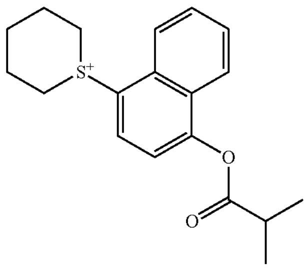
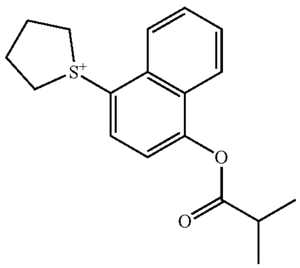
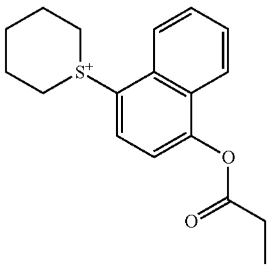

-continued
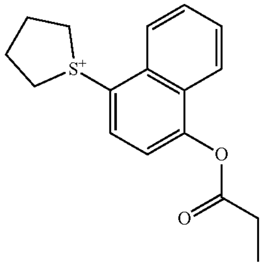
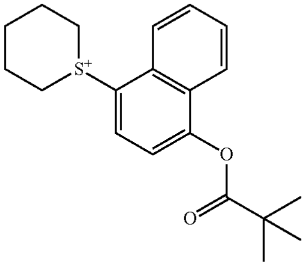
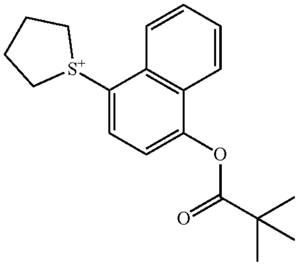
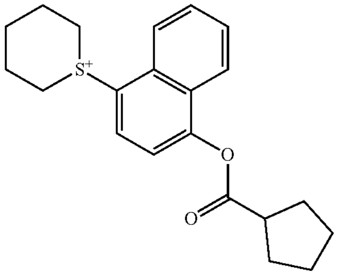
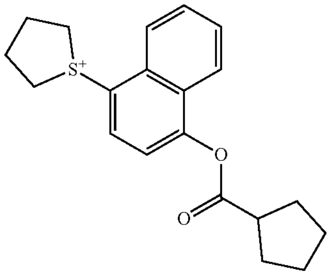
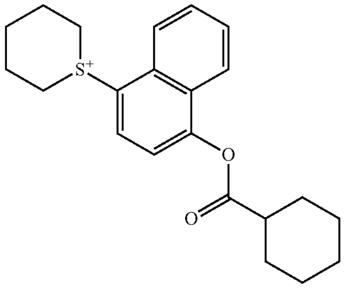
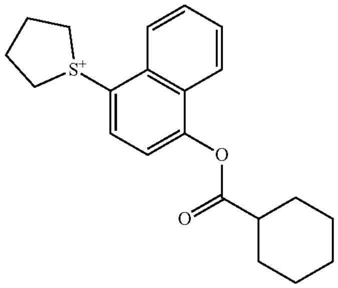
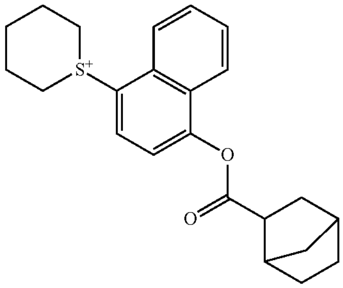
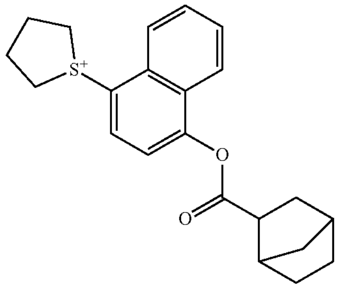
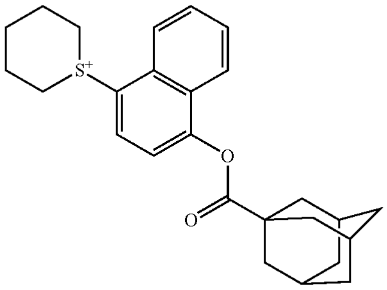
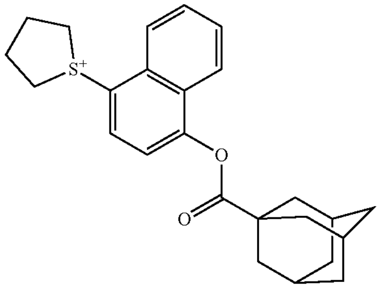
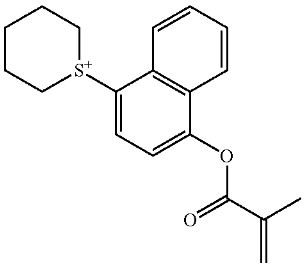
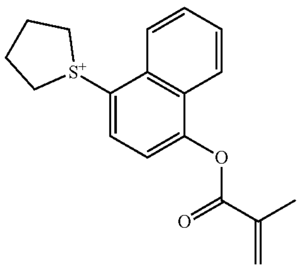
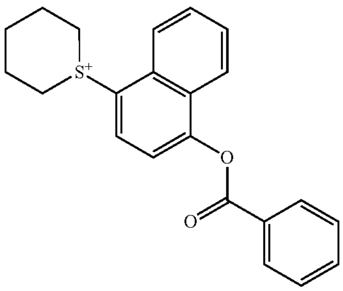
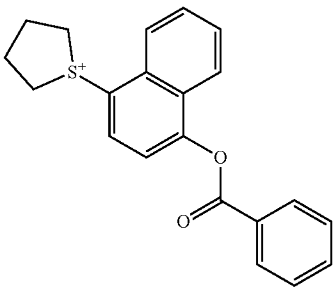
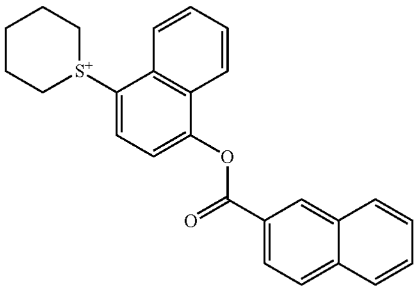
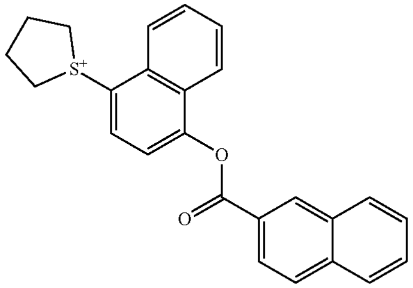

-continued
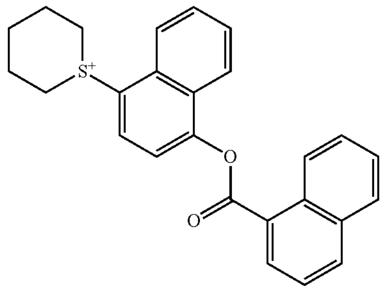
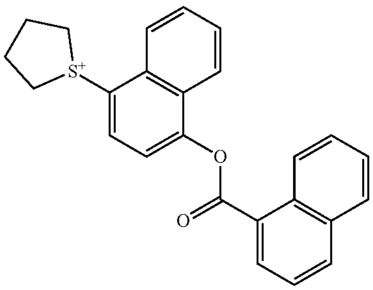
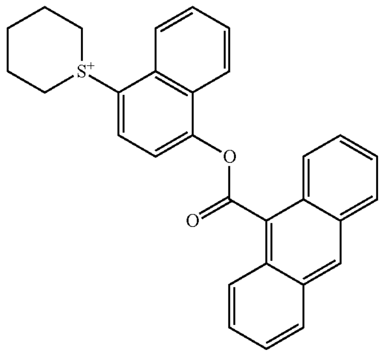
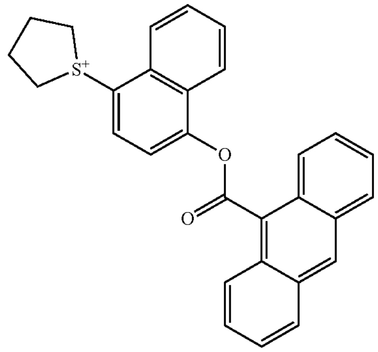
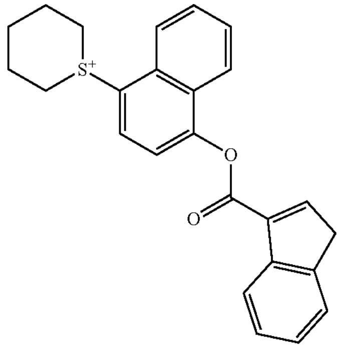
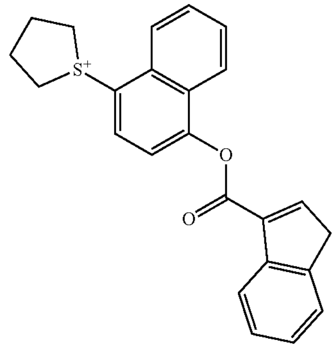
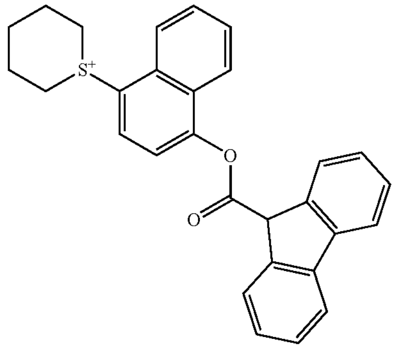
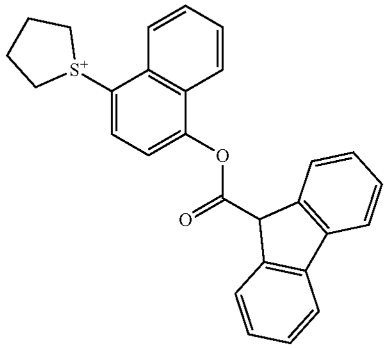
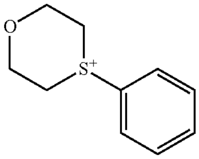
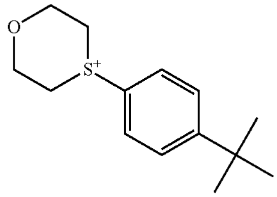
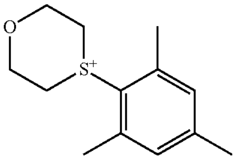
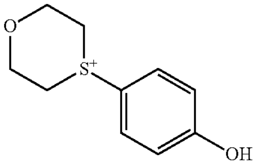
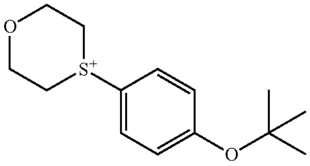
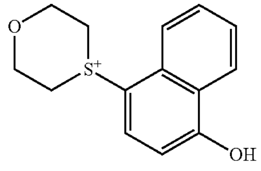
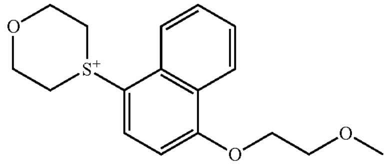
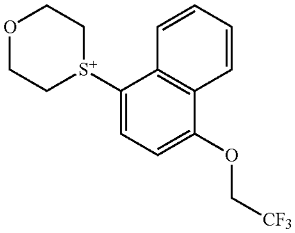
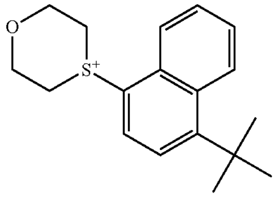
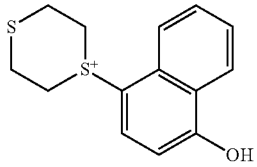

-continued
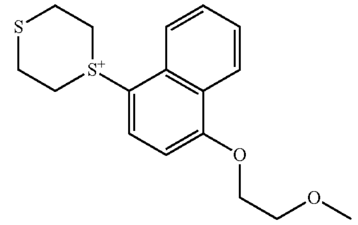
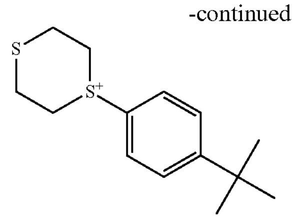
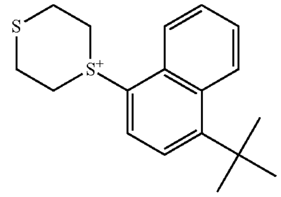
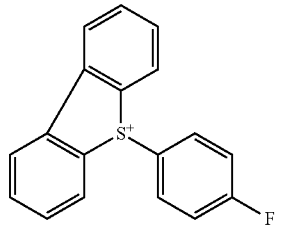
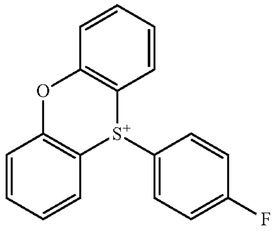
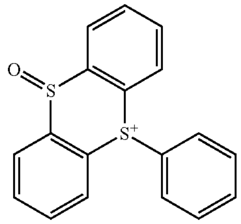
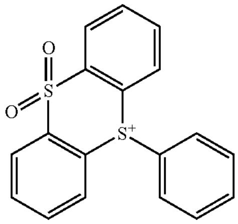
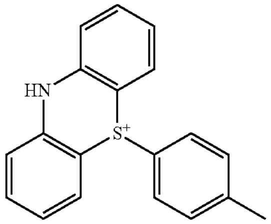
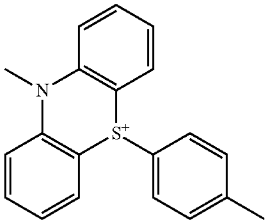
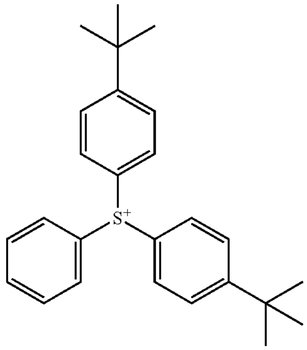
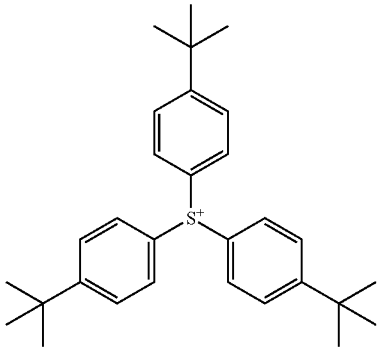
-continued
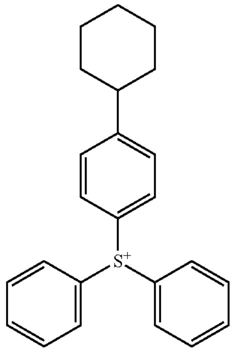
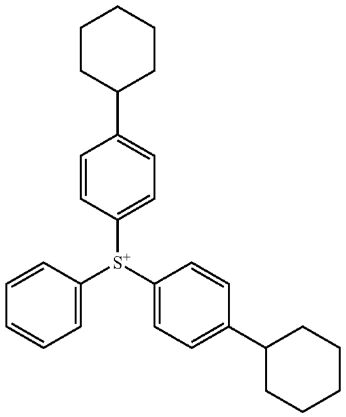
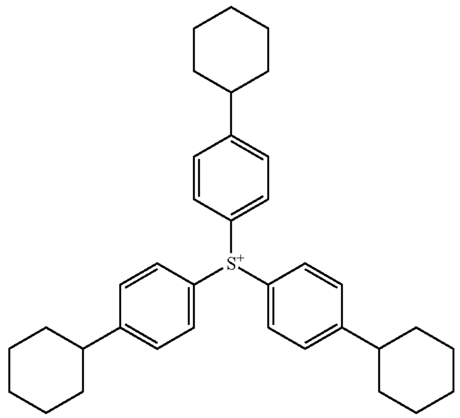

-continued
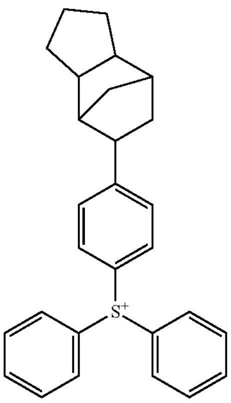
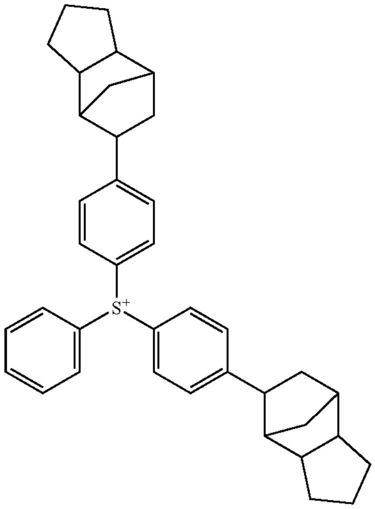
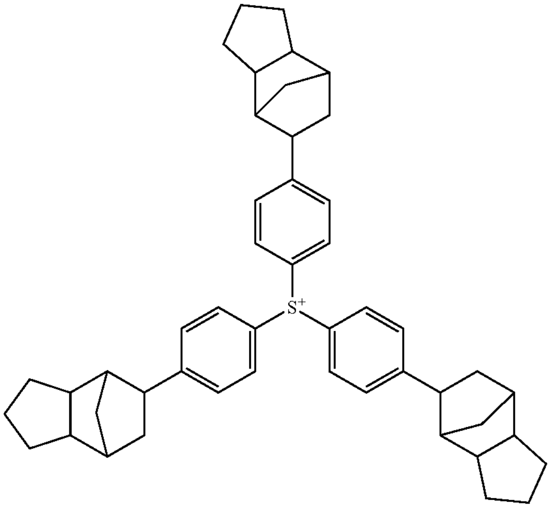
-continued
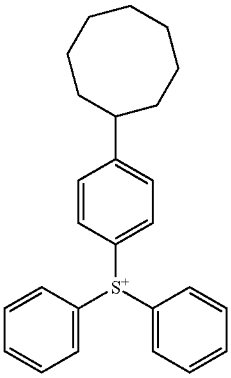
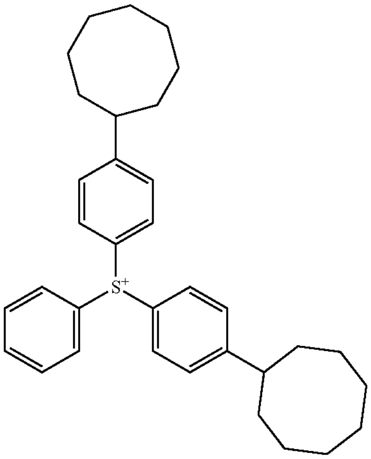
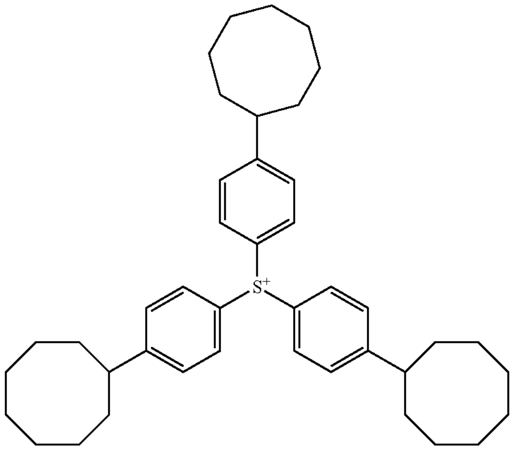
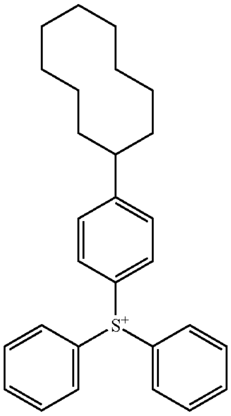

-continued
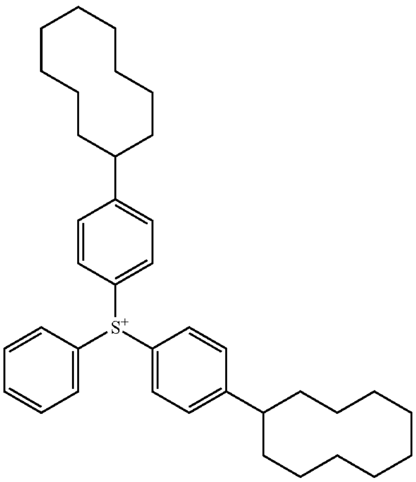
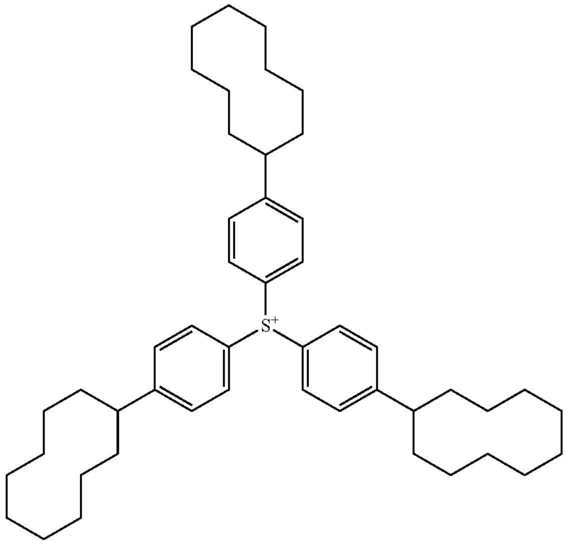
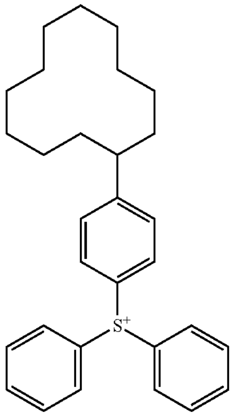
-continued
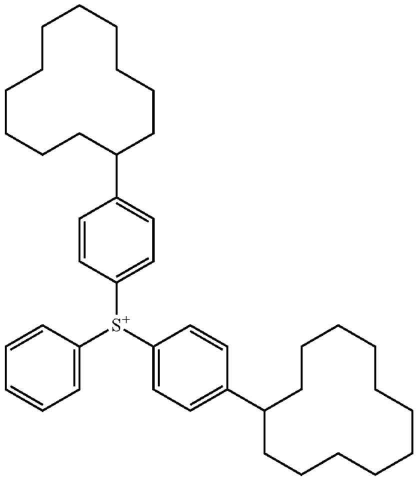
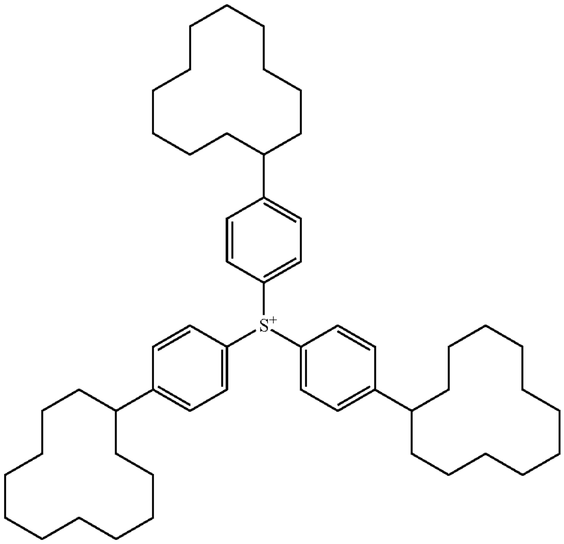
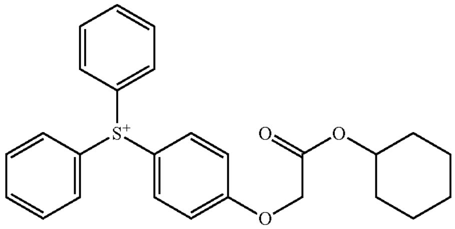
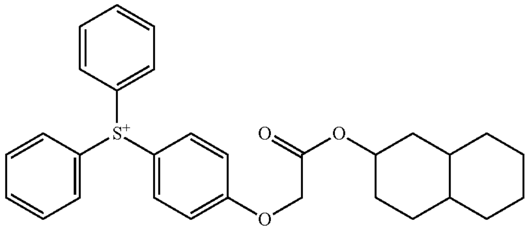
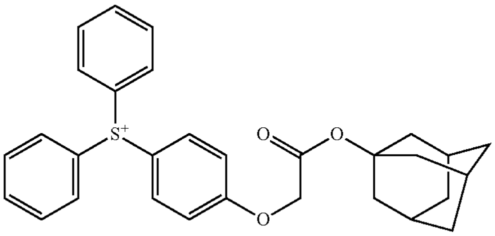

-continued
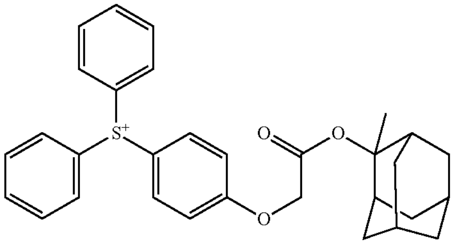
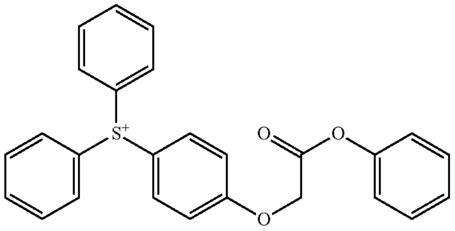
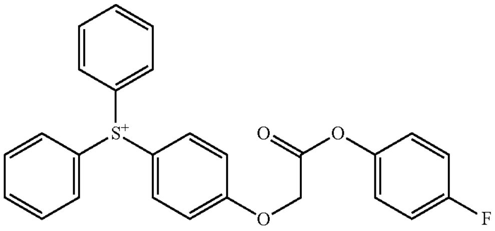
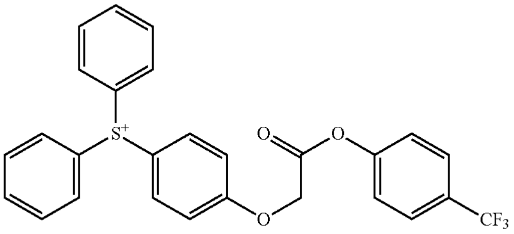
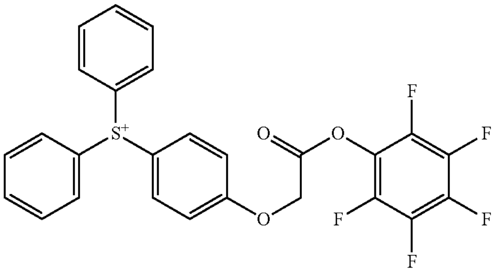
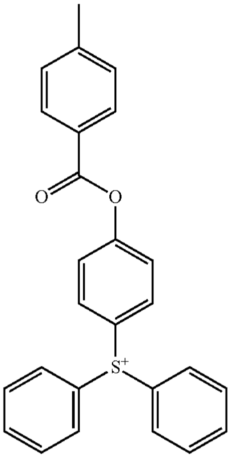
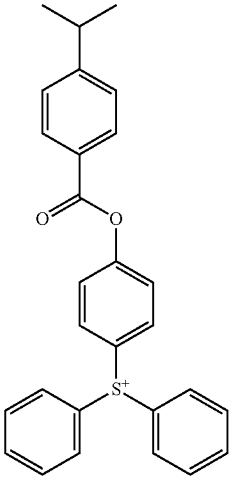
-continued
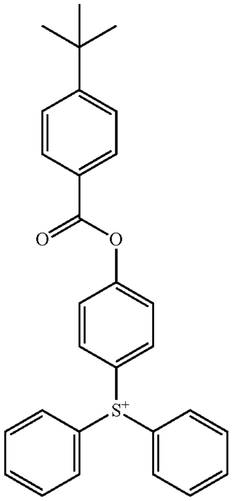
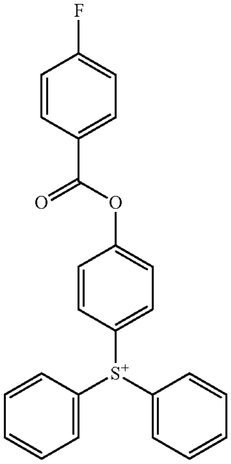
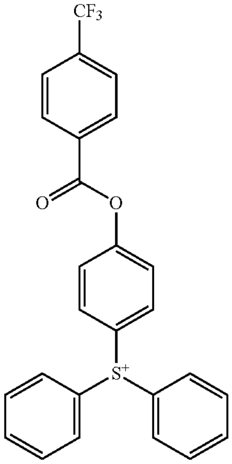
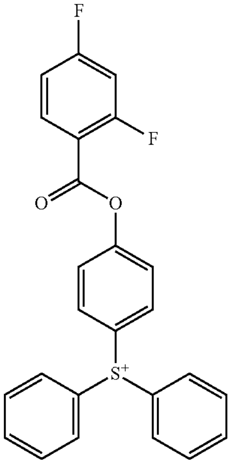
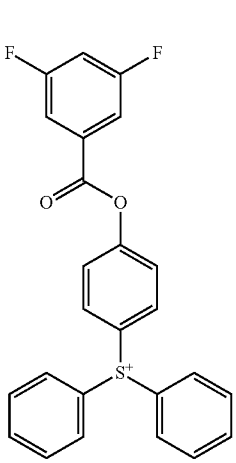
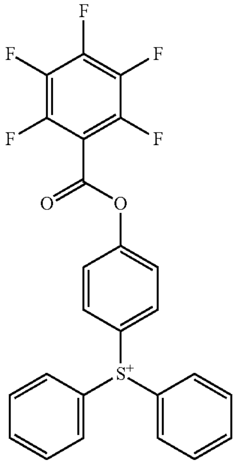
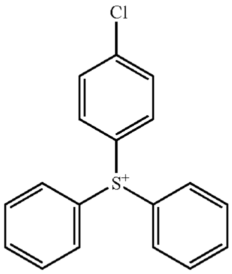
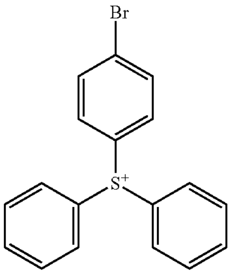

-continued
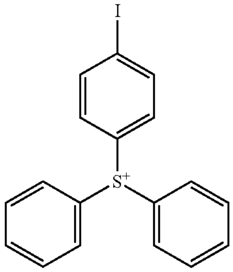
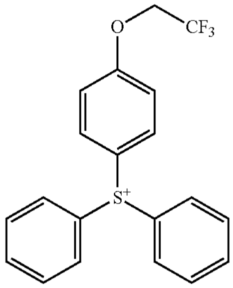
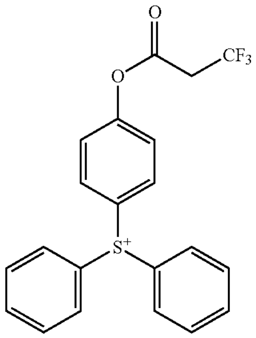
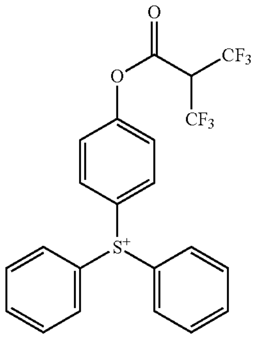
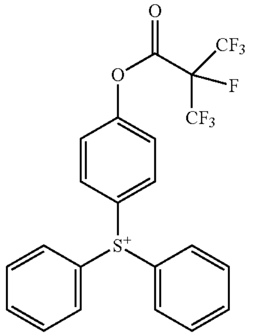
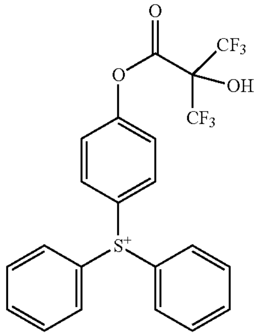
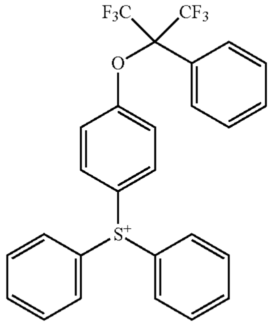
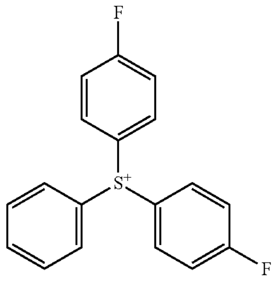
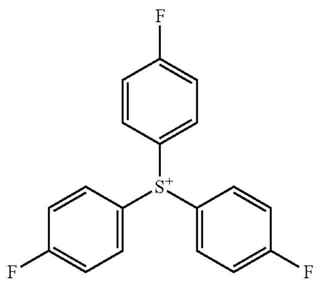
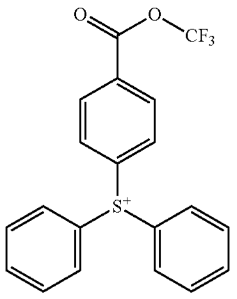
-continued
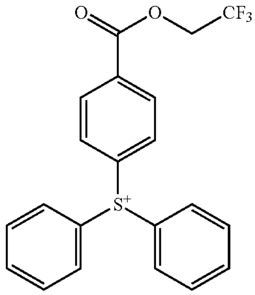
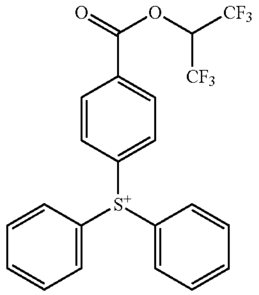
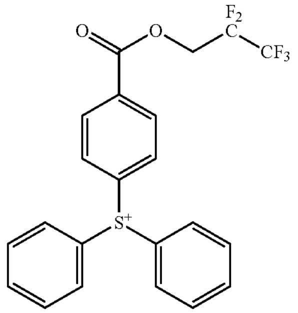
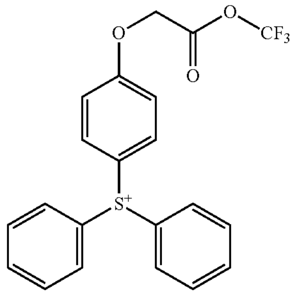
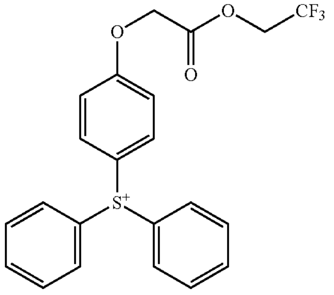
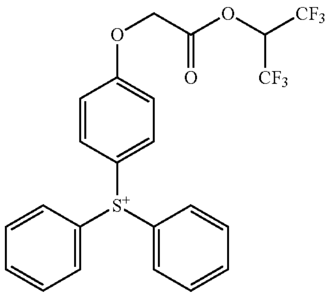

-continued
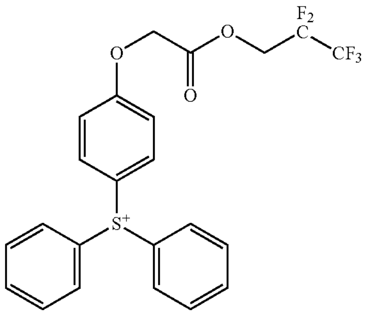
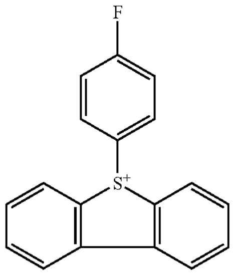
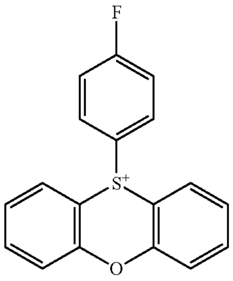
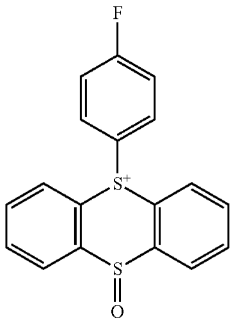
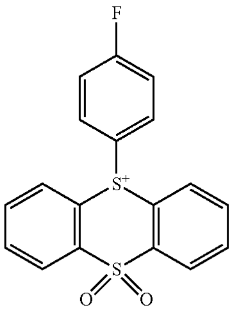
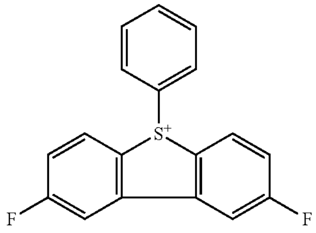
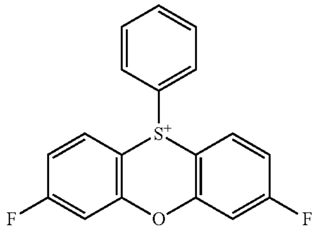
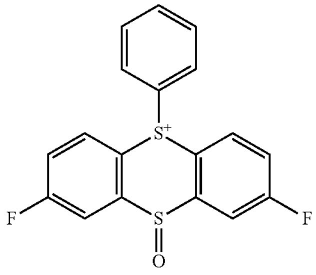
-continued
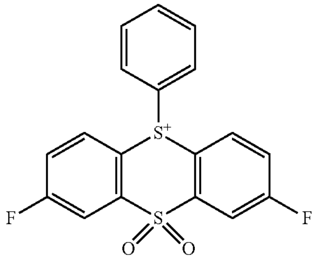
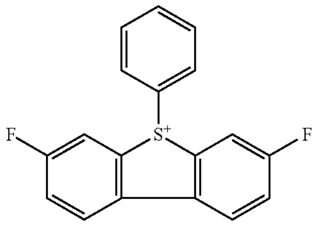
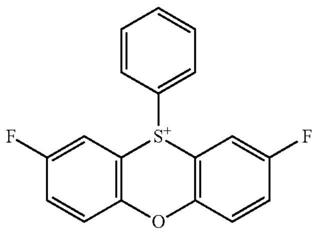
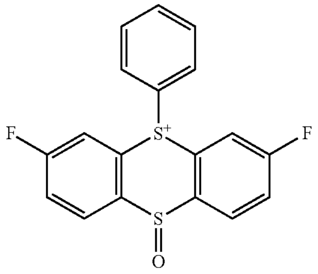
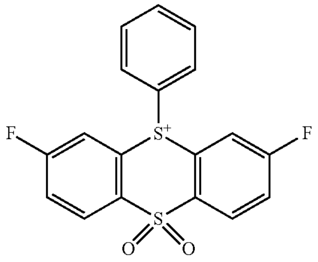
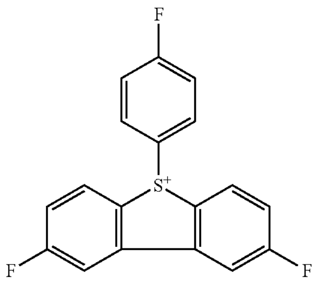

-continued
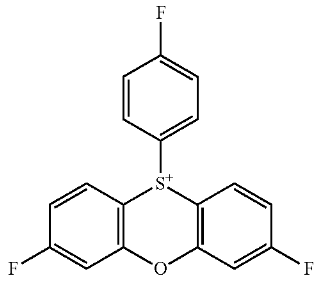
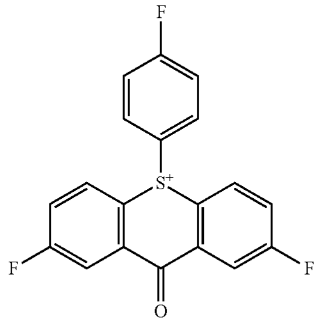
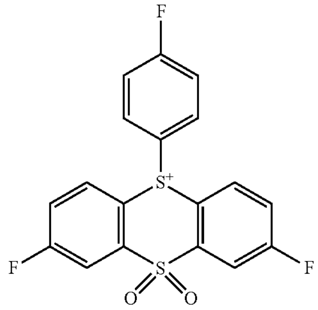
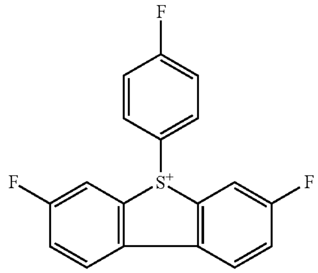
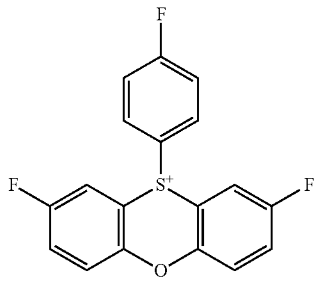
-continued
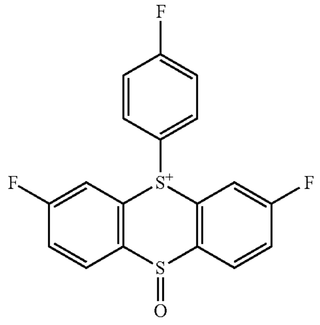
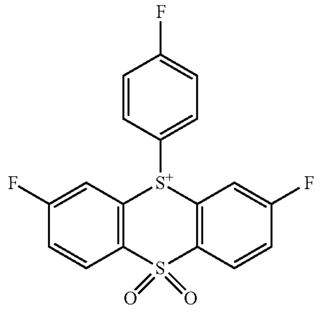
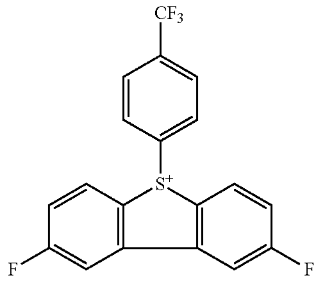
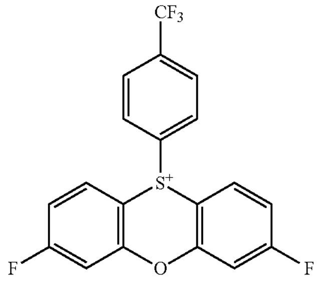
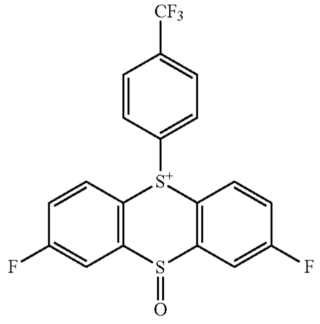

-continued
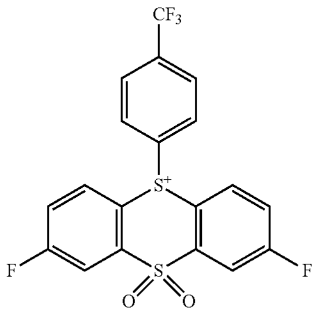
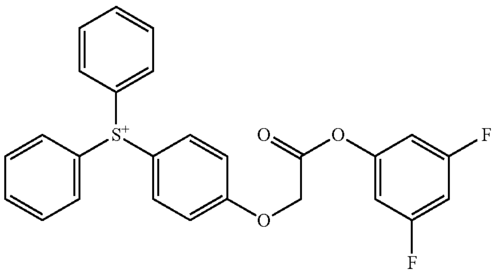
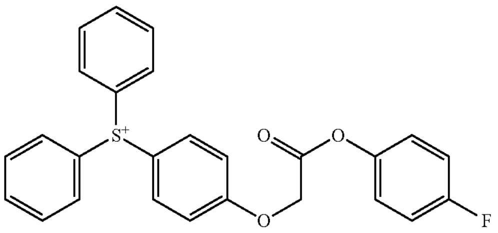
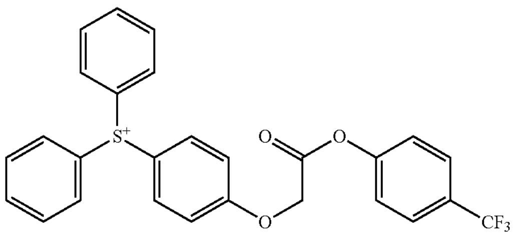
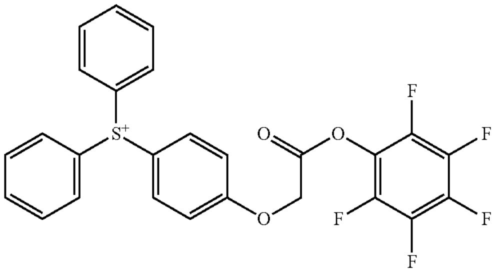
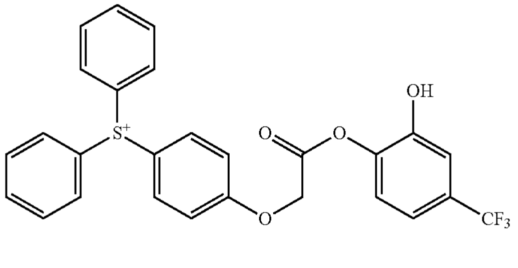
-continued
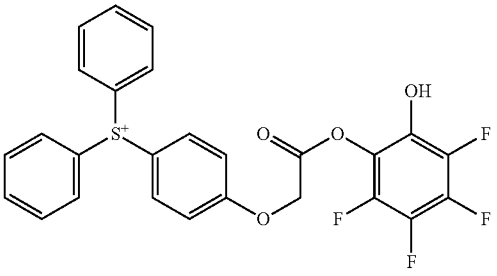
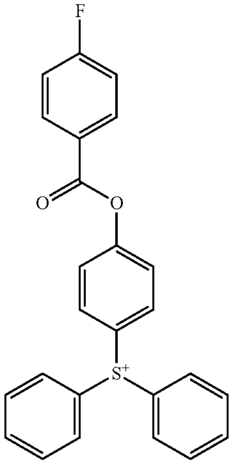
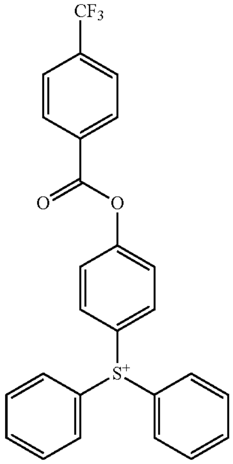
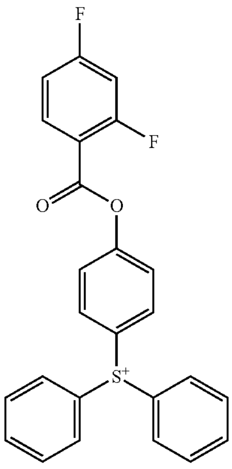
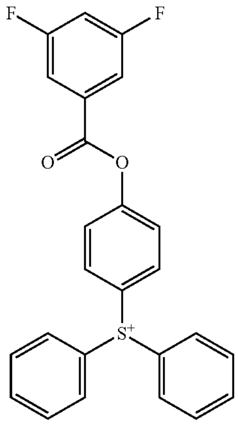
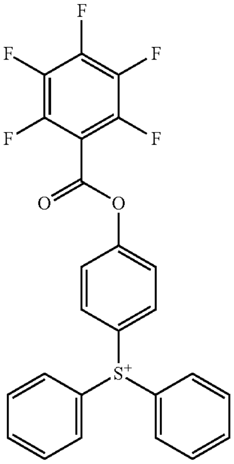
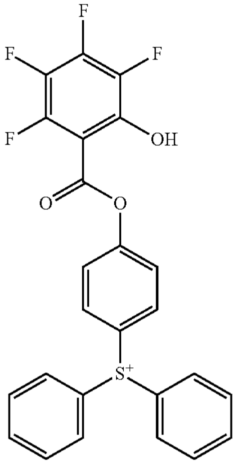

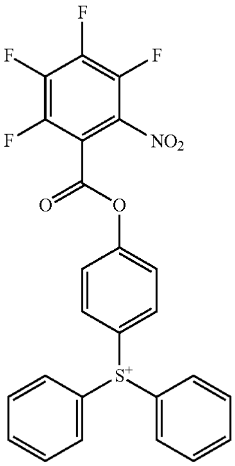
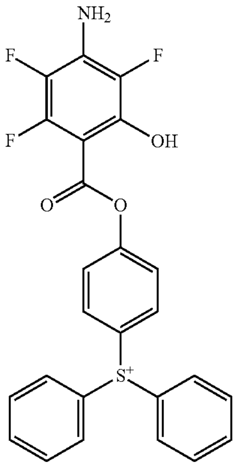
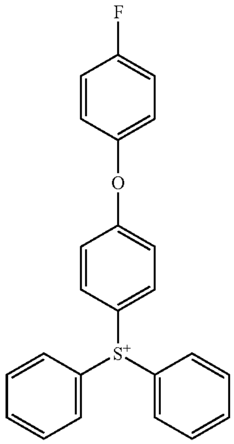
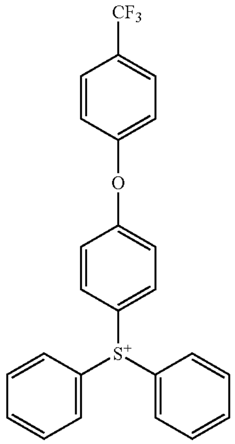
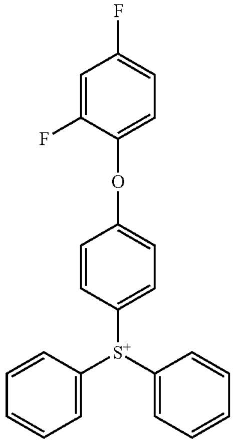
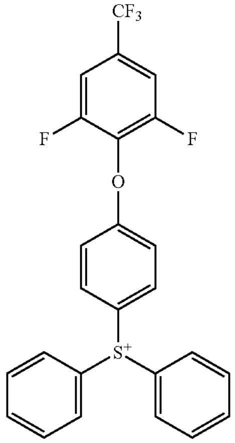
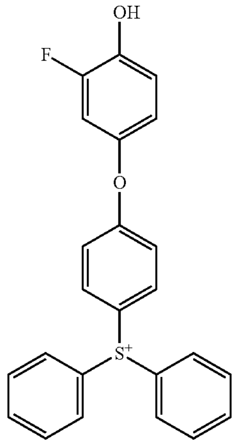
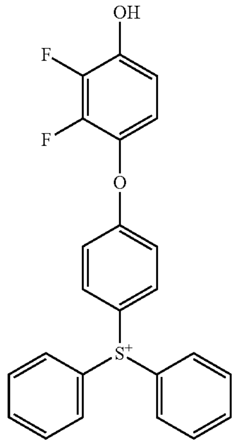
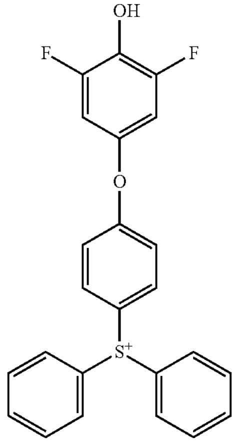
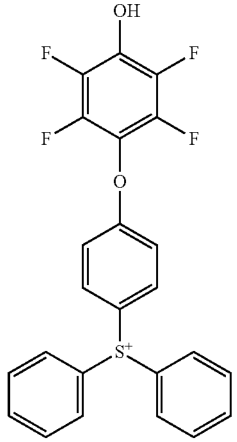
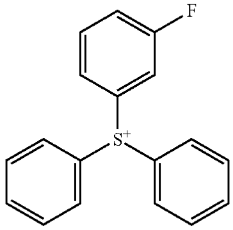
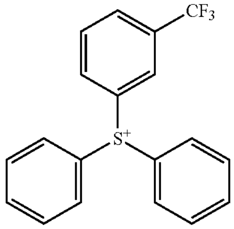
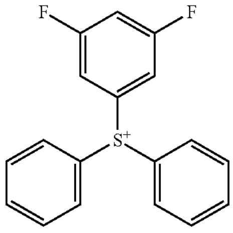
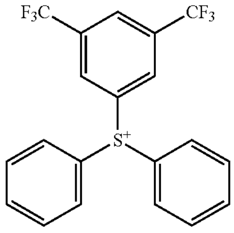
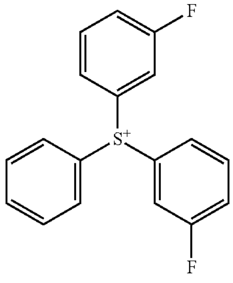
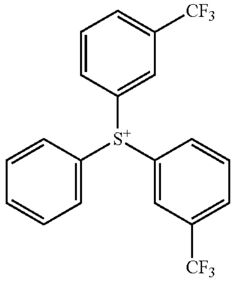

-continued
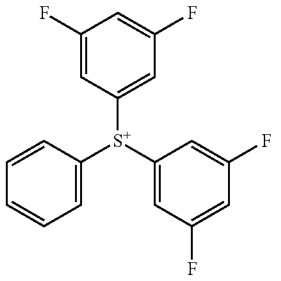
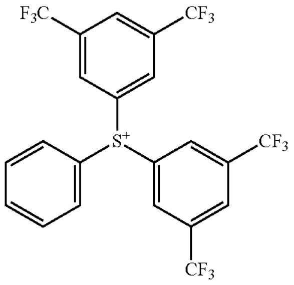
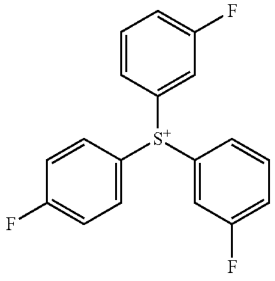
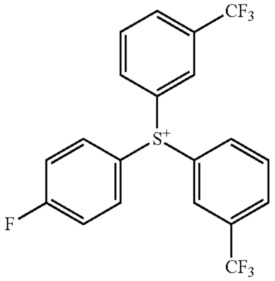
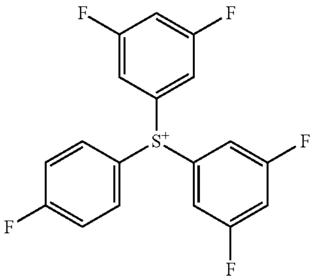
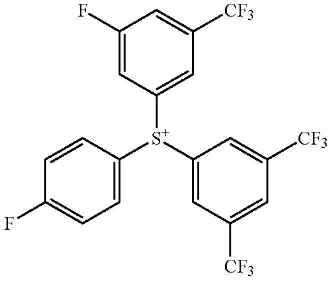
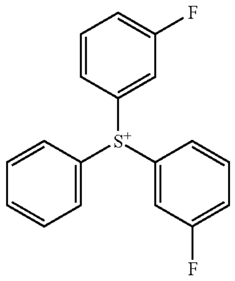
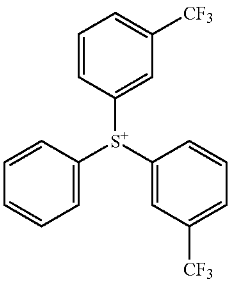
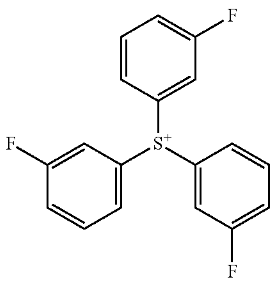
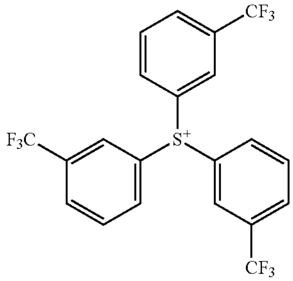
-continued
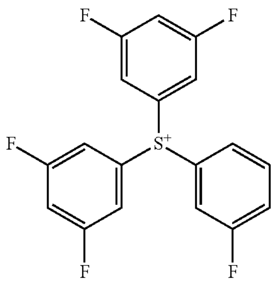
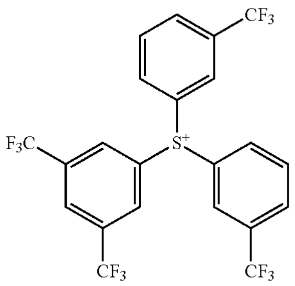
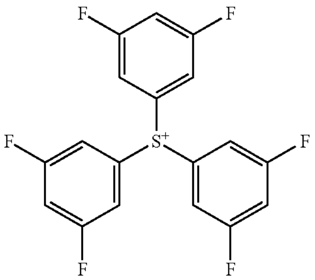
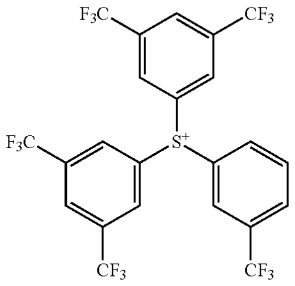
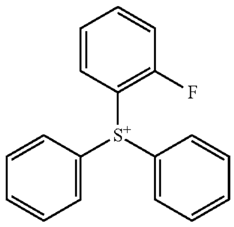
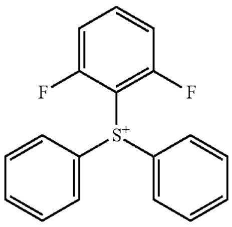
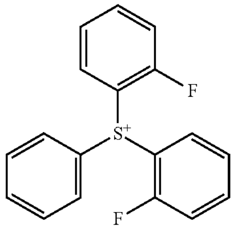
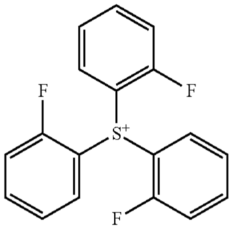
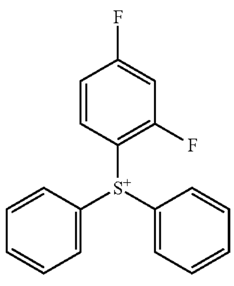
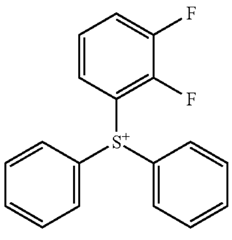

-continued
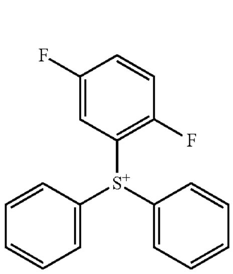
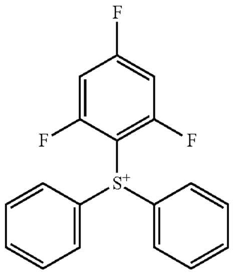
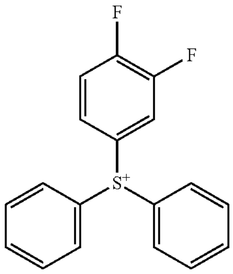
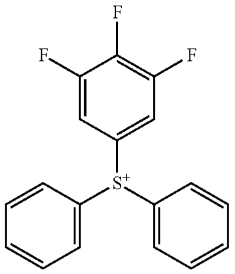
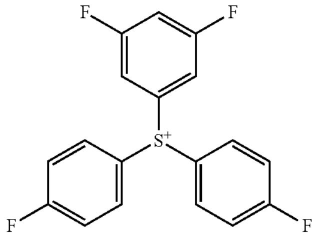
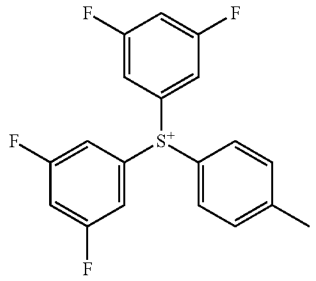
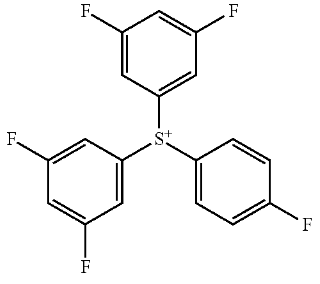
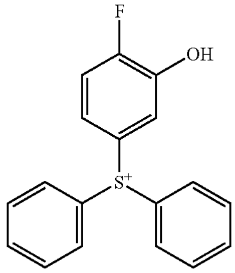
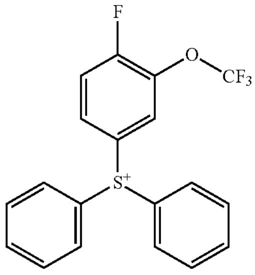
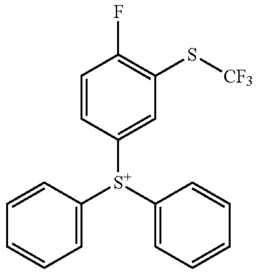
-continued
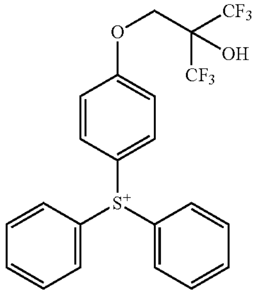
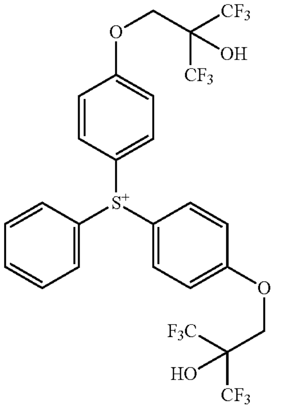
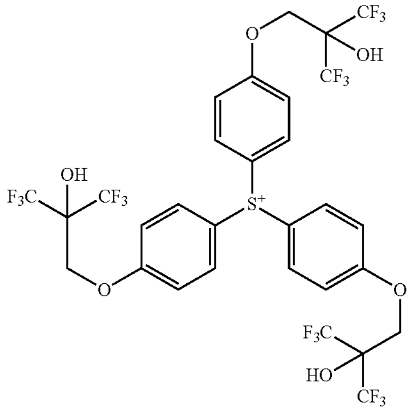
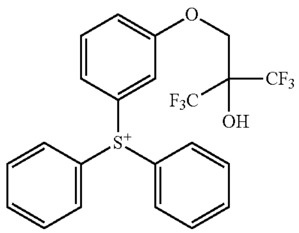
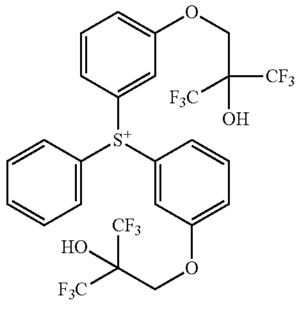
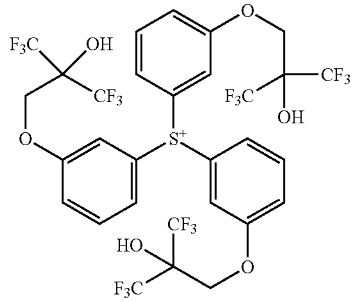

-continued
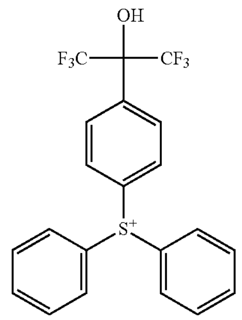
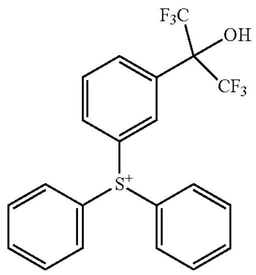
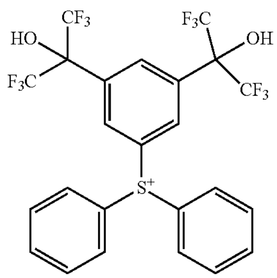
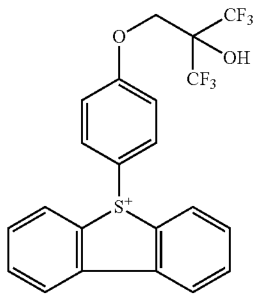
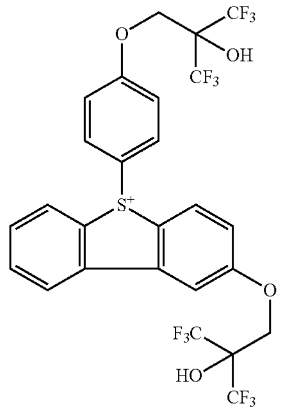
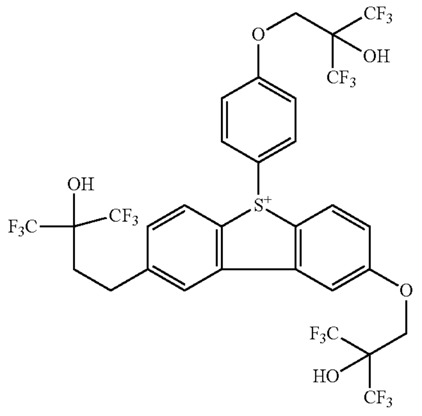
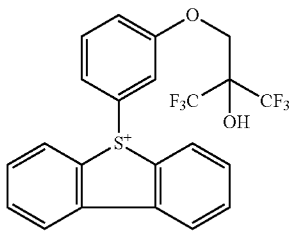
-continued
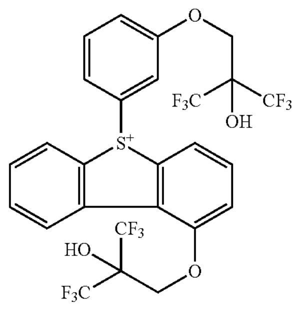
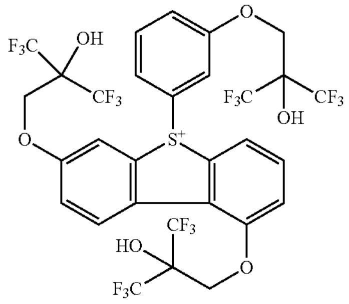
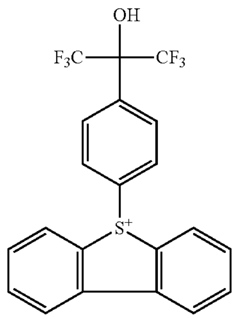
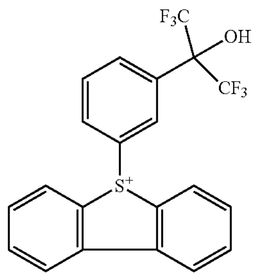
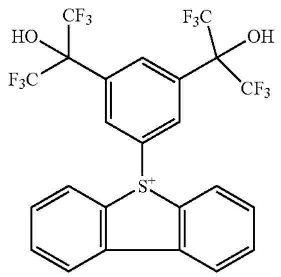
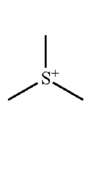
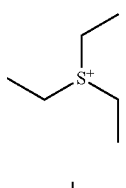
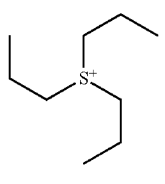
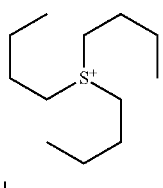
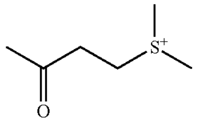
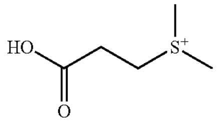
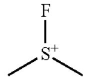
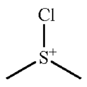
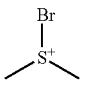
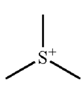
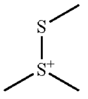
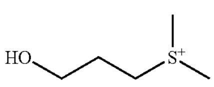

-continued

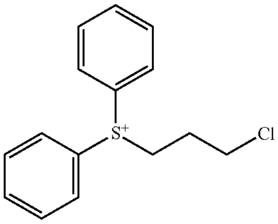

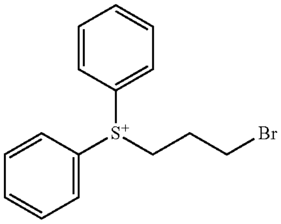

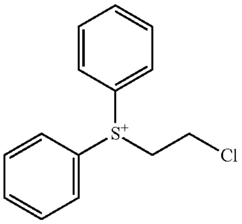

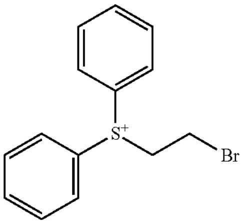

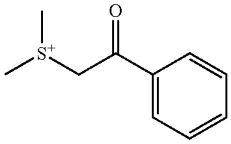

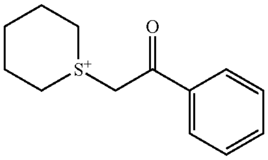

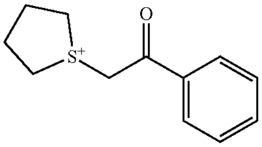

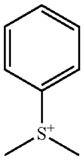

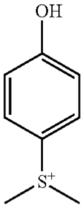

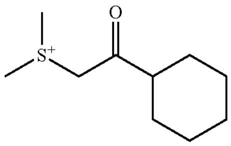

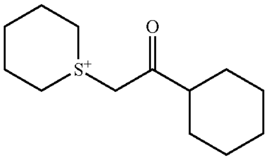

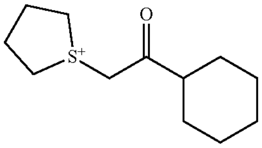

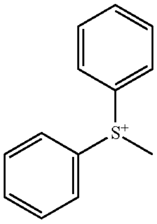

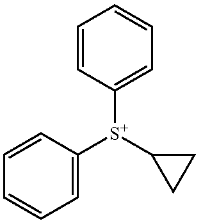

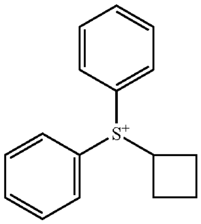

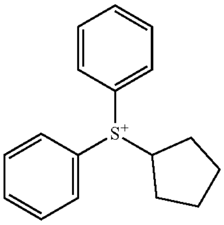

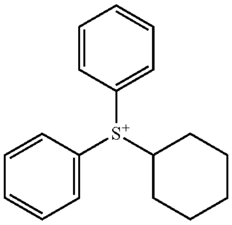

-continued

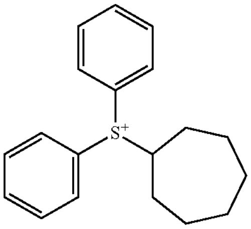

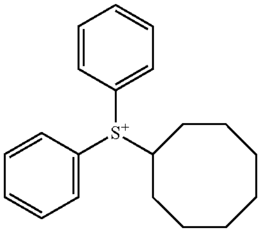

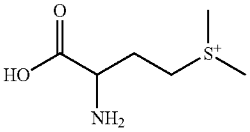

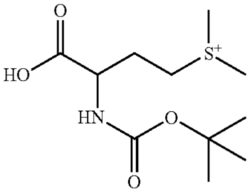

The sulfonium salt of a carboxylic acid having a nitrobenzene ring may be synthesized, for example, by ion exchange between a hydrochloride or carbonate salt of triphenylsulfonium and a carboxylic acid having a specific nitrobenzene ring.

The nitrogen atom on the nitro group has a positive charge, which cooperates with a positive charge of the sulfonium cation in a synergistic way to exert a significant effect of controlling acid diffusion. In addition, the carboxylic acid having the nitrobenzene ring generated upon light exposure is effective for reducing swell and accelerating an alkaline dissolution rate. By virtue of these effects, the resist pattern as developed is improved in LWR and CDU.

In the resist composition, the sulfonium salt having formula (A) is preferably used in an amount of 0.001 to 50 parts by weight, more preferably 0.01 to 40 parts by weight per 100 parts by weight of the base polymer to be described below. The sulfonium salt may be used alone or in admixture of two or more.

Base Polymer

In one embodiment, the resist composition contains a base polymer. In the case of positive resist compositions, the base polymer comprises repeat units containing an acid labile group. The preferred repeat units containing an acid labile group are repeat units having the formula (a1) or repeat units having the formula (a2), which are also referred to as repeat units (a1) or (a2).

(a1)

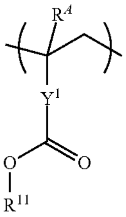

-continued (a2)

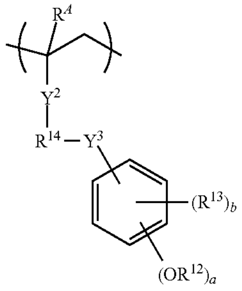

In formulae (a1) and (a2), $R^A$ is each independently hydrogen or methyl. $Y^1$ is a single bond, phenylene group, naphthylene group, or a $C_1$-$C_{12}$ linking group containing an ester bond and/or lactone ring. $Y^2$ is a single bond or ester bond. $Y^3$ is a single bond, ether bond or ester bond. $R^{11}$ and $R^{12}$ are each independently an acid labile group. It is noted that when the base polymer contains both repeat units (a1) and (a2), $R^{11}$ and $R^{12}$ may be identical or different. $R^{13}$ is fluorine, trifluoromethyl, cyano or a $C_1$-$C_6$ saturated hydrocarbyl group. $R^{14}$ is a single bond or a $C_1$-$C_6$ alkanediyl group in which some carbon may be replaced by an ether bond or ester bond. The subscript "a" is 1 or 2, b is an integer of 0 to 4, and the sum of a+b is from 1 to 5.

Examples of the monomer from which repeat units (a1) are derived are shown below, but not limited thereto. Herein $R^A$ and $R^{11}$ are as defined above.

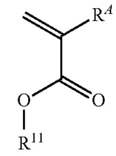
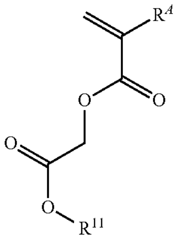
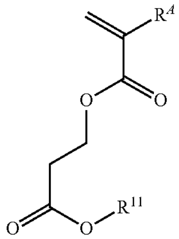

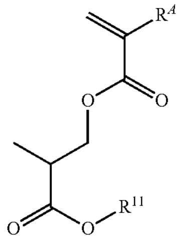
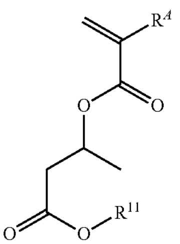

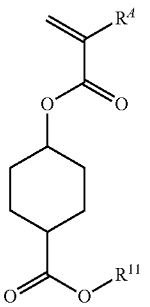
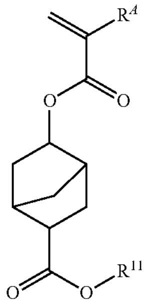
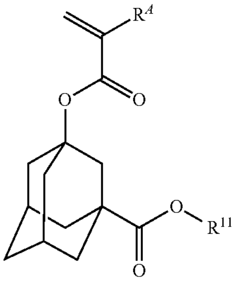

-continued

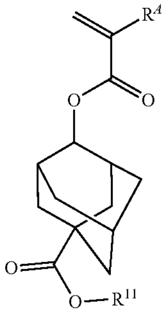
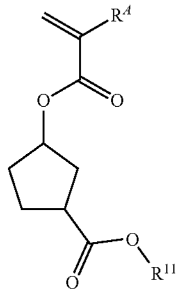

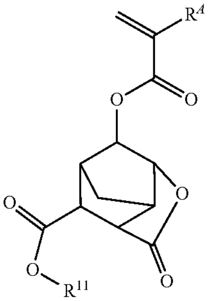
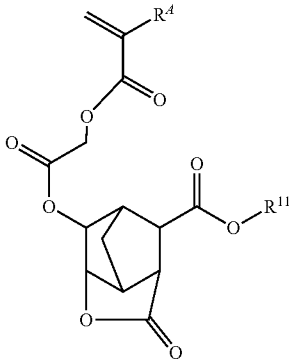

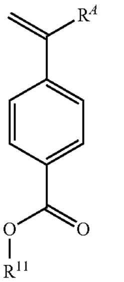
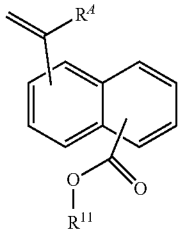

Examples of the monomer from which repeat units (a2) are derived are shown below, but not limited thereto. Herein $R^A$ and $R^{12}$ are as defined above.

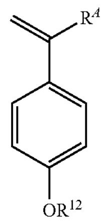
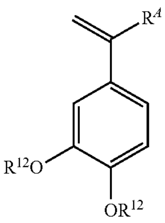
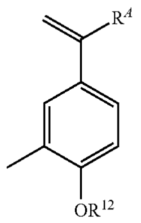

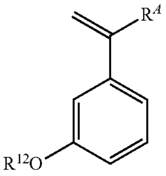
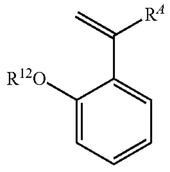
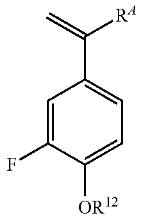

-continued

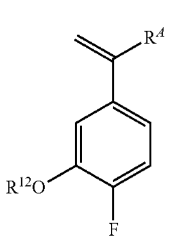
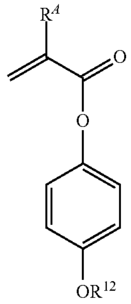
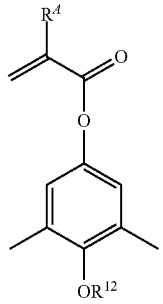

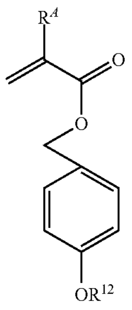
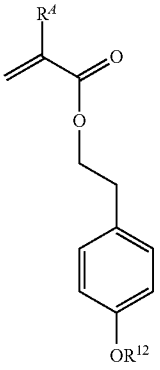
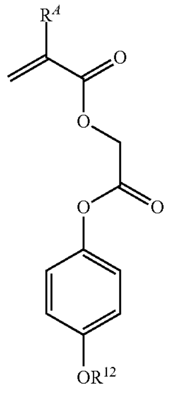

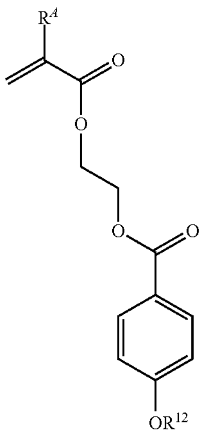
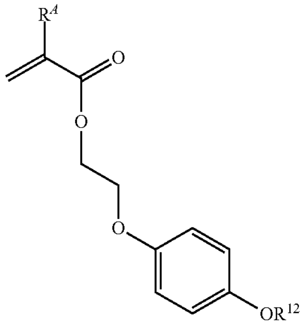

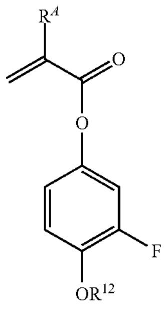
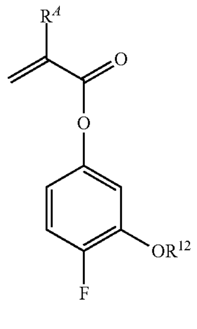
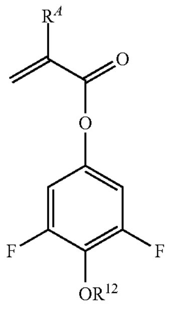

-continued

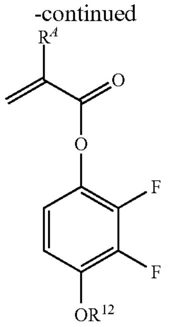

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

(AL-1)

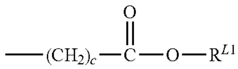

(AL-2)

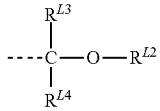

(AL-3)

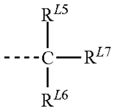

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{40}$ saturated hydrocarbyl groups are preferred, and $C_1$-$C_{20}$ saturated hydrocarbyl groups are more preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$ and $R^{L4}$ may bond together to form a $C_3$-$C_{20}$ ring with the carbon atom or carbon and oxygen atoms to which they are attached. The ring preferably contains 4 to 16 carbon atoms and is typically alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia. $C_1$-$C_{20}$ saturated hydrocarbyl groups are preferred. Any two of $R^{L5}$, $R^{L6}$ and $R^{L7}$ may bond together to form a $C_3$-$C_{20}$ ring with the carbon atom to which they are attached. The ring preferably contains 4 to 16 carbon atoms and is typically alicyclic.

The base polymer may further comprise repeat units (b) having a phenolic hydroxy group as an adhesive group. Examples of suitable monomers from which repeat units (b) are derived are given below, but not limited thereto. Herein $R^A$ is as defined above.
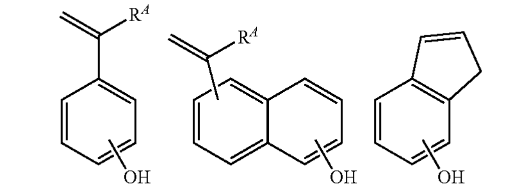
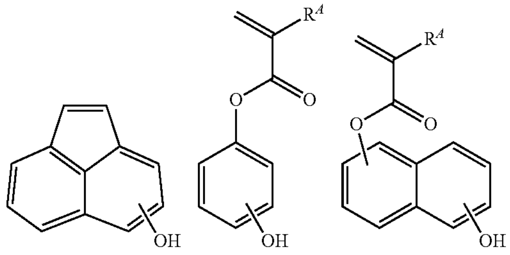
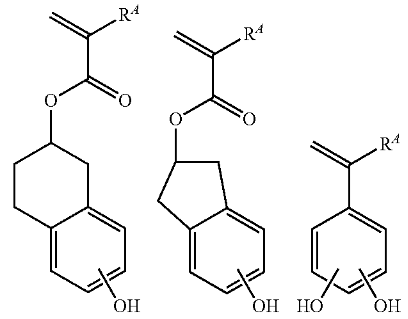
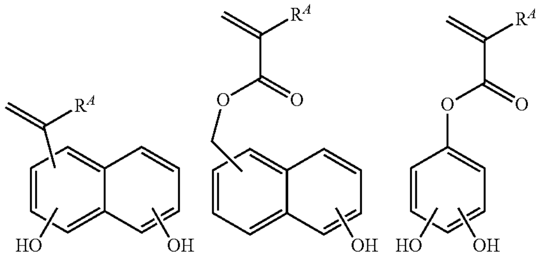
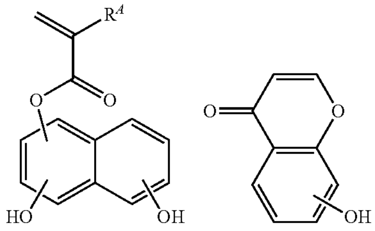
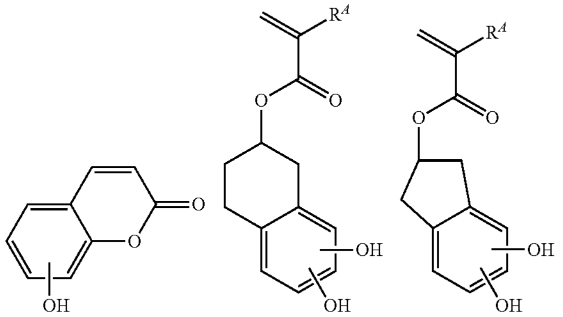
-continued
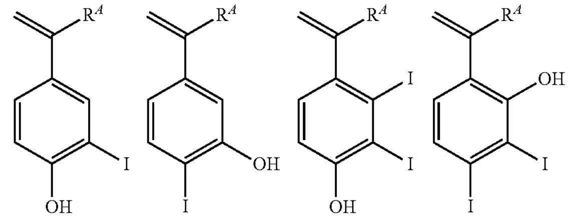
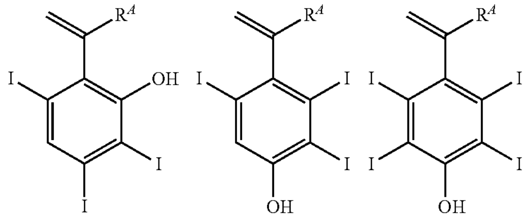
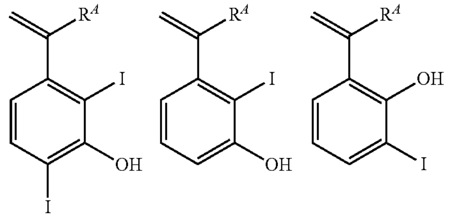
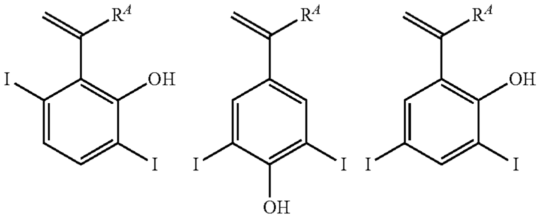
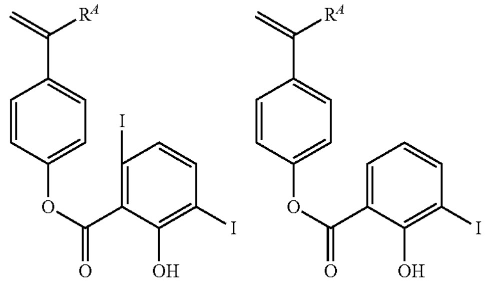
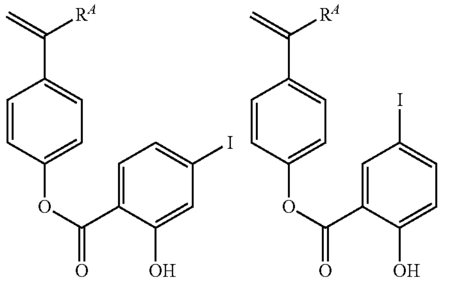
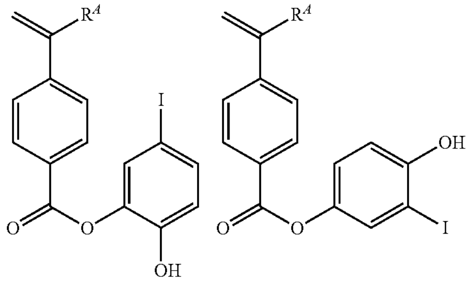

-continued

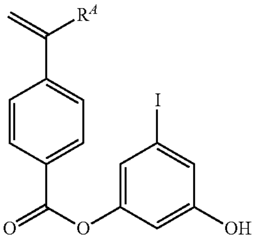

The base polymer may further comprise repeat units (c) having another adhesive group selected from hydroxy group (other than the foregoing phenolic hydroxy), lactone ring, sultone ring, ether bond, ester bond, sulfonate bond, carbonyl group, sulfonyl group, cyano group, and carboxy group. Examples of suitable monomers from which repeat units (c) are derived are given below, but not limited thereto. Herein $R^A$ is as defined above.

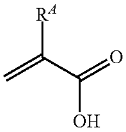
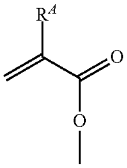
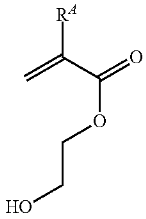
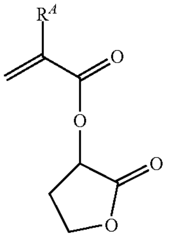
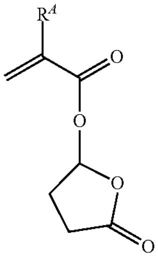
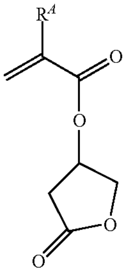
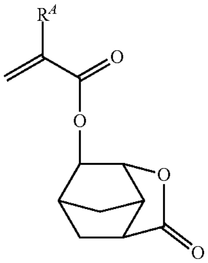
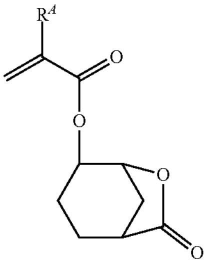
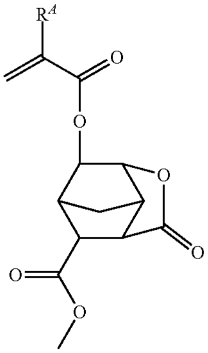
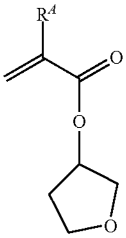
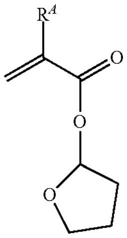

-continued

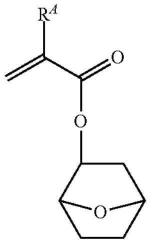
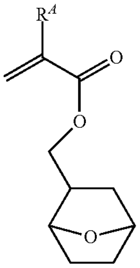
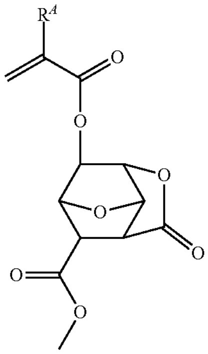
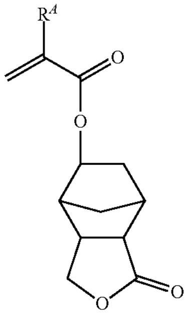
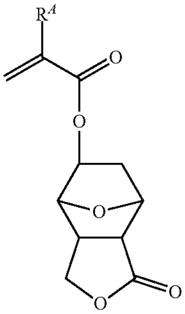
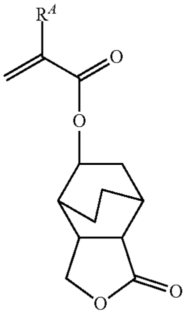
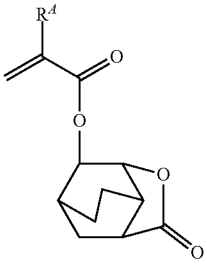
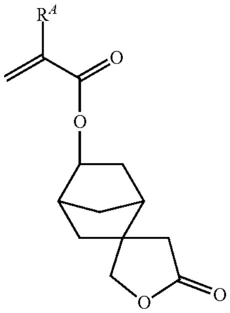
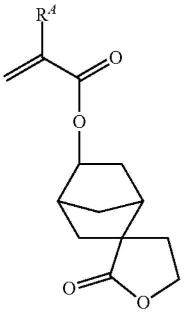
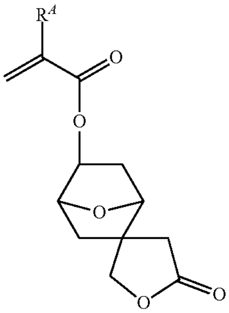
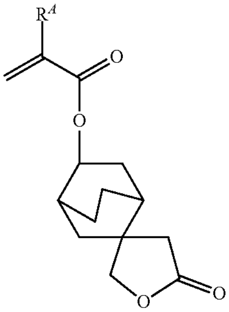

-continued
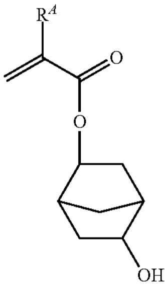
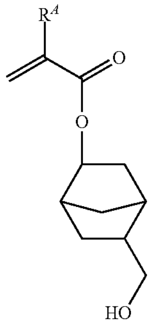
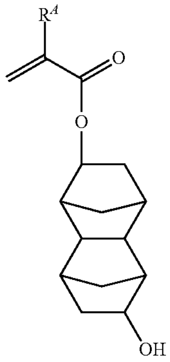
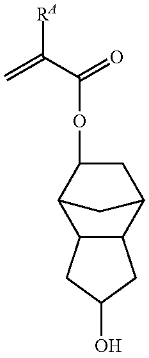
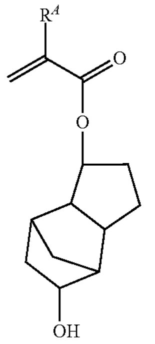
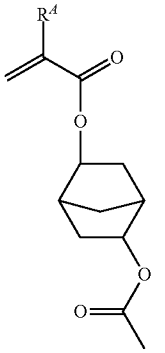
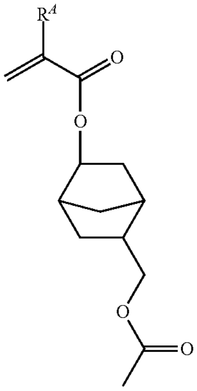
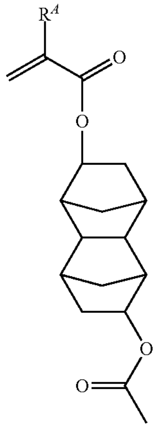
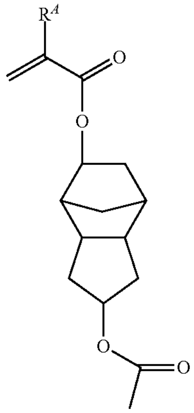
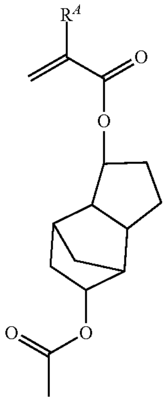
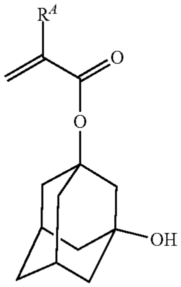
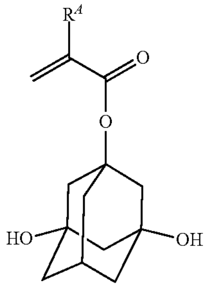
-continued
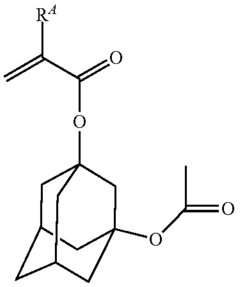
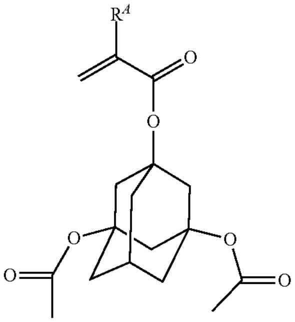
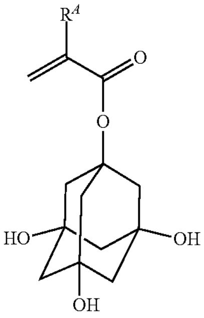
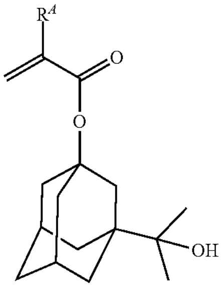
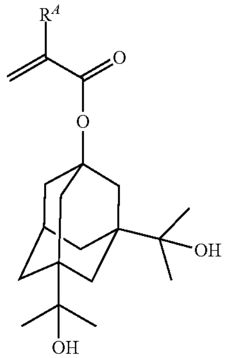
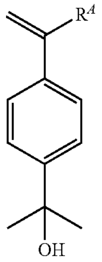
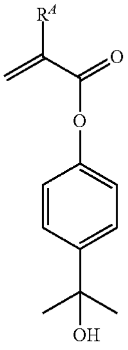
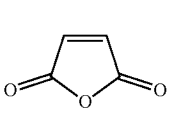
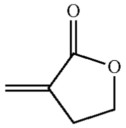
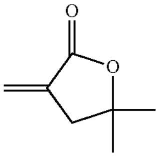
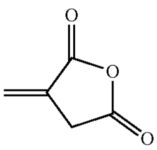
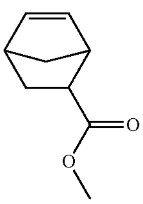
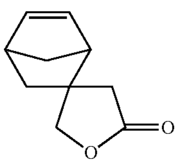
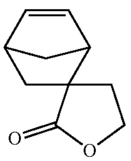
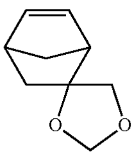
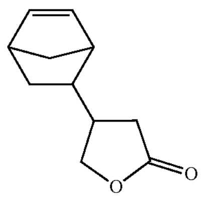

-continued
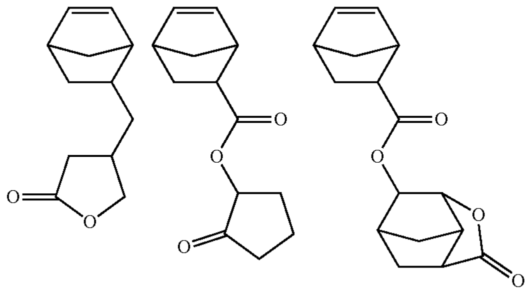
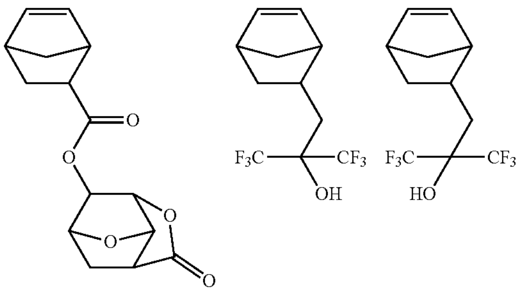
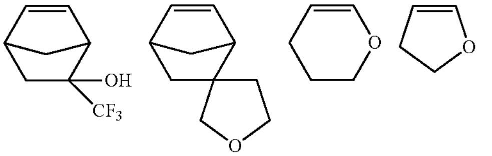
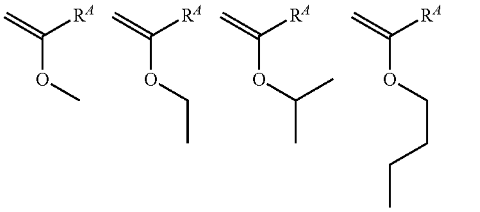
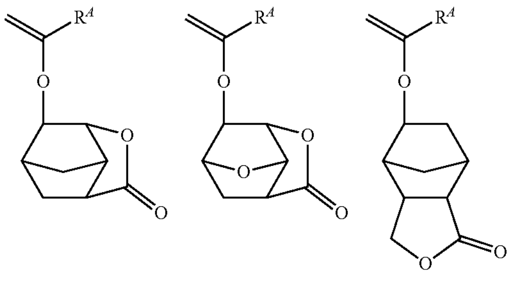
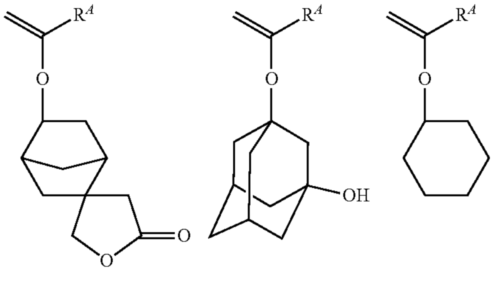
-continued
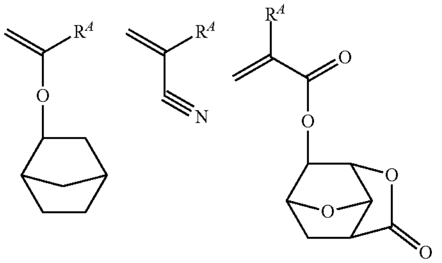
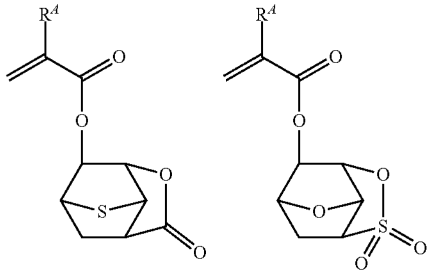
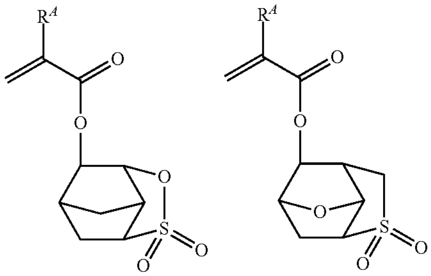
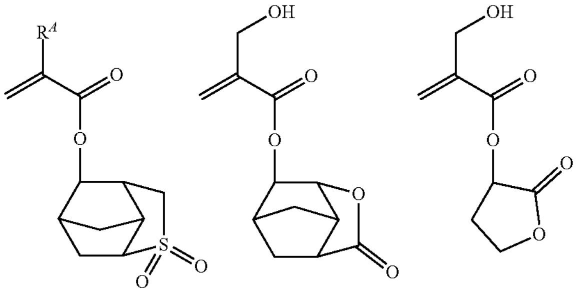
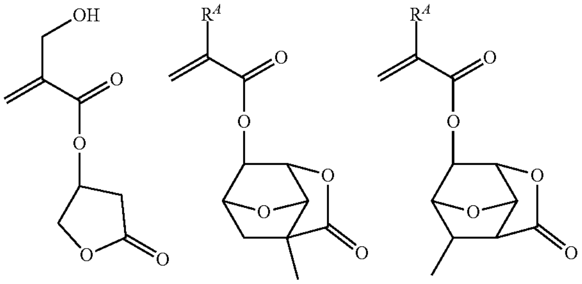
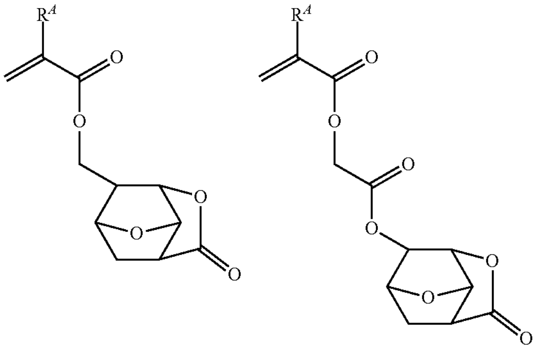

-continued
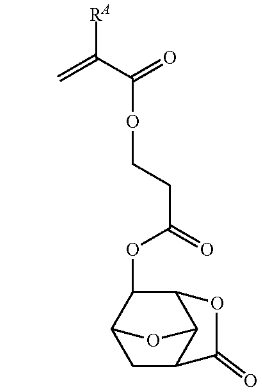
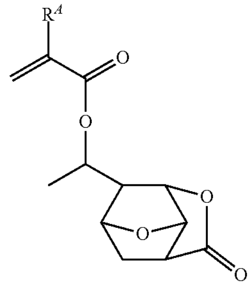
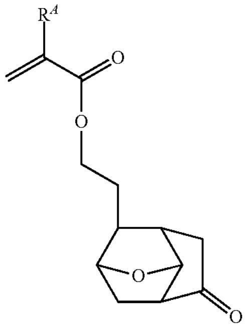
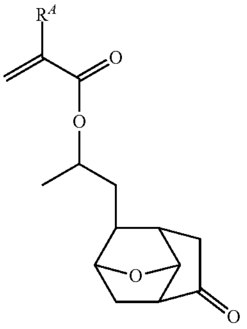
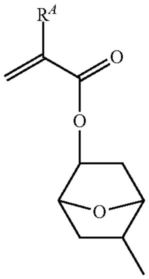
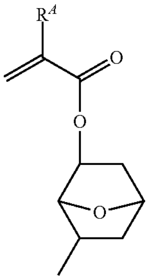
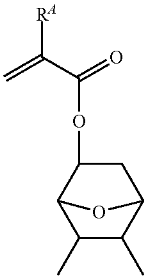
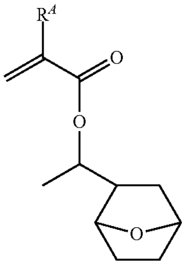
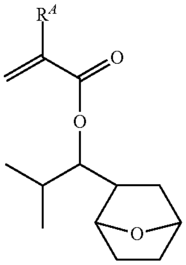
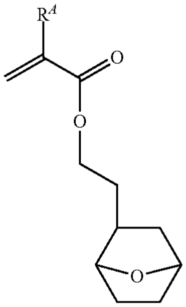
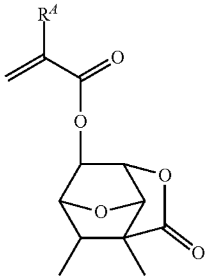
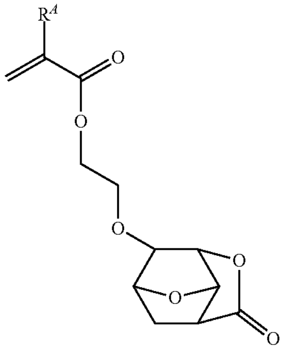
-continued
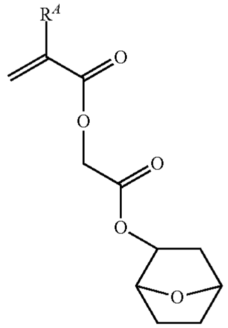
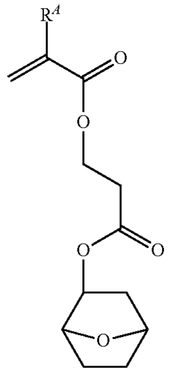
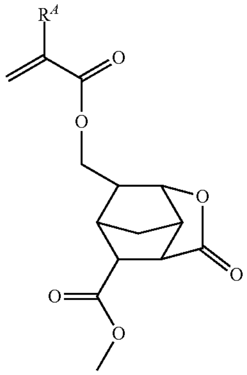
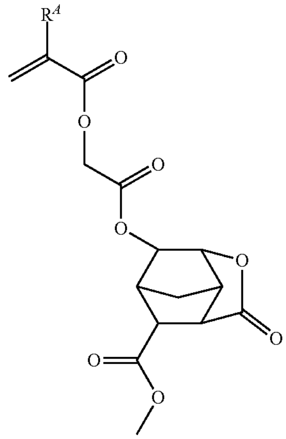
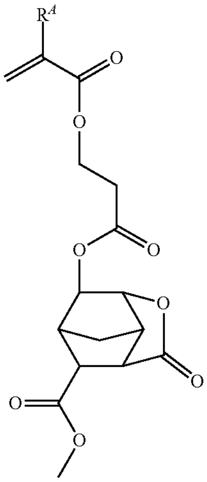
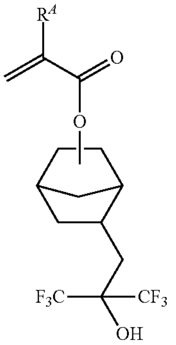
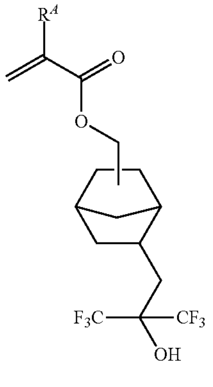
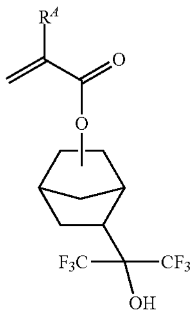

-continued
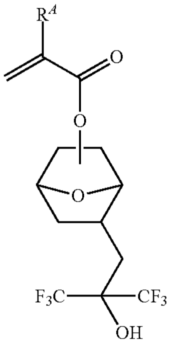
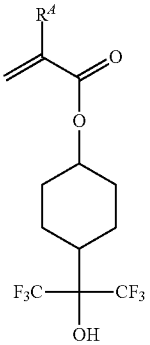
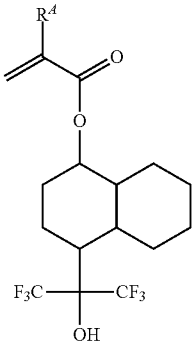
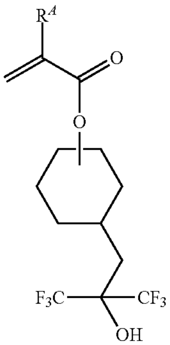
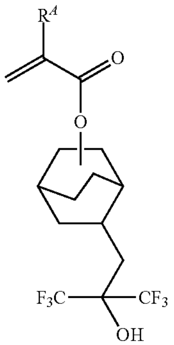
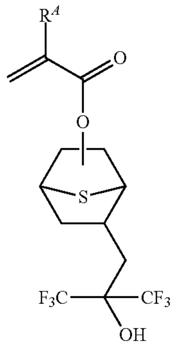
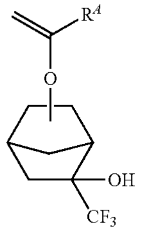
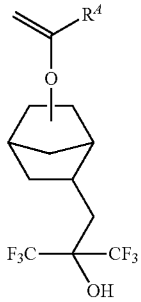
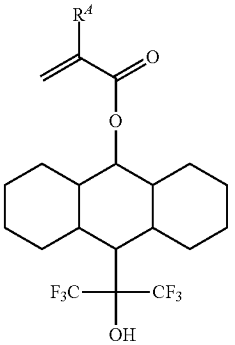
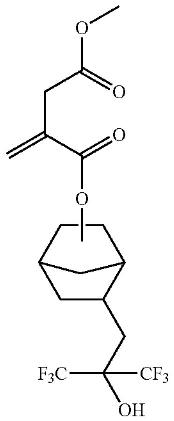
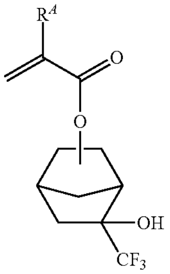
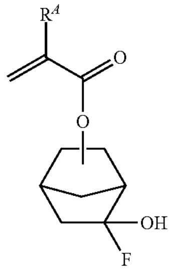
-continued
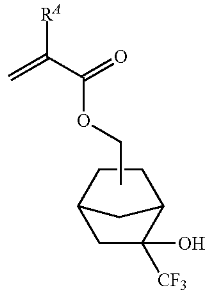
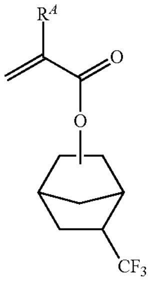
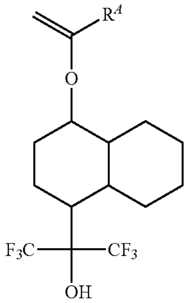
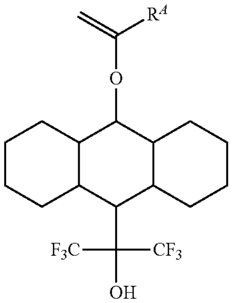
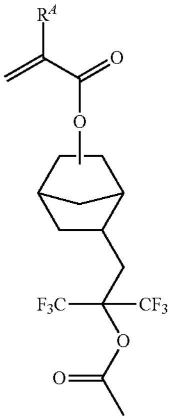
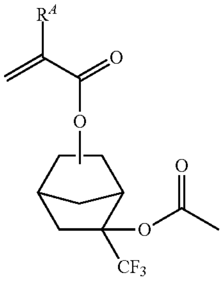
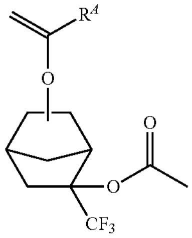
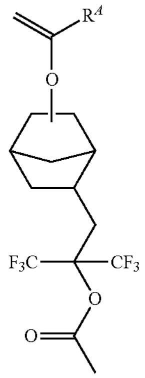
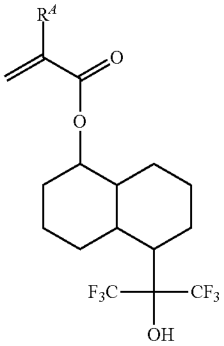
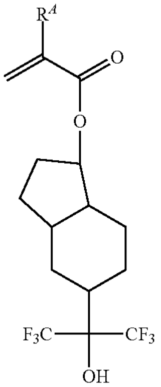
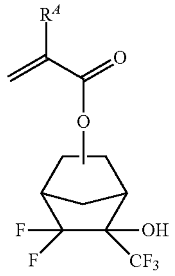
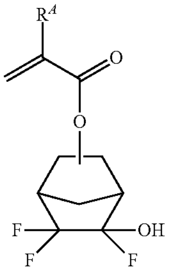
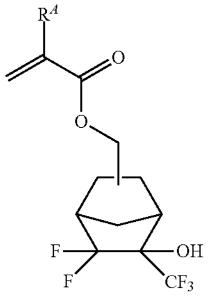

-continued
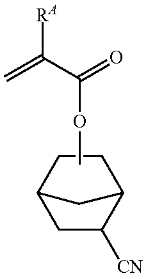
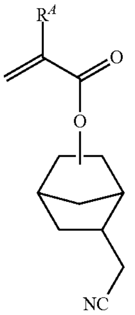
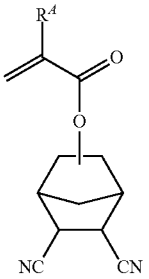
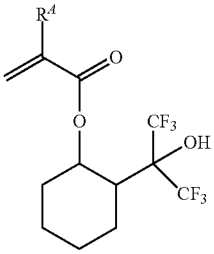
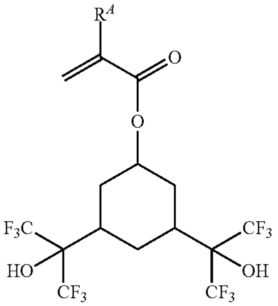
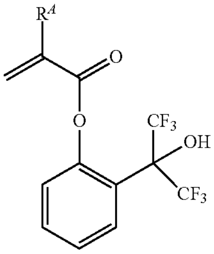
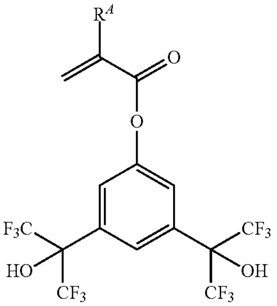
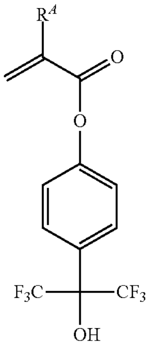
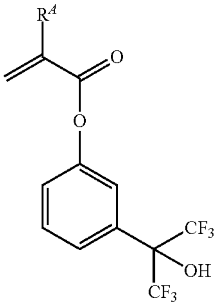
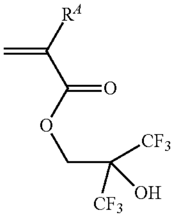
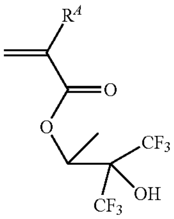
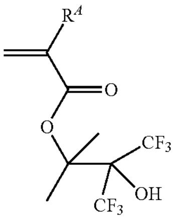
-continued
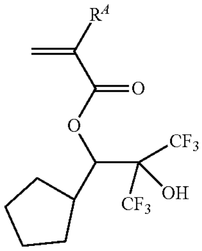
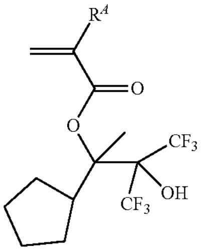
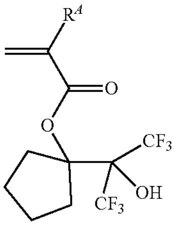
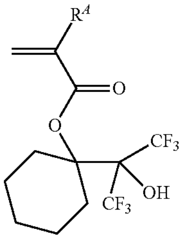
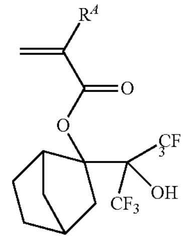
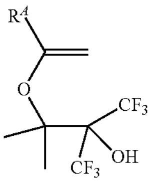
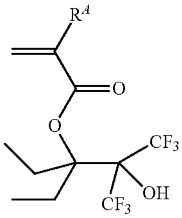
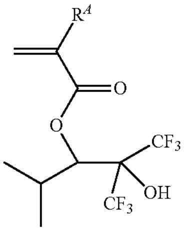
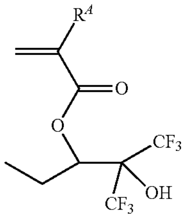
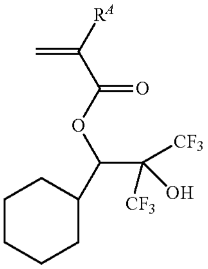
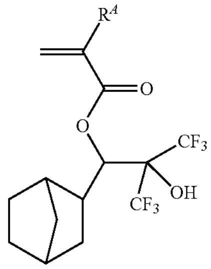
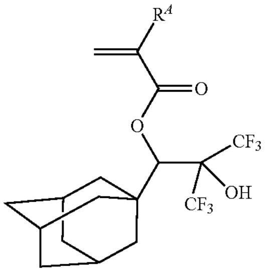
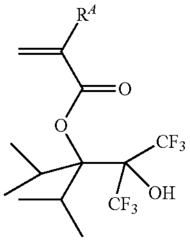
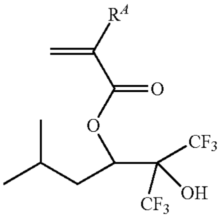
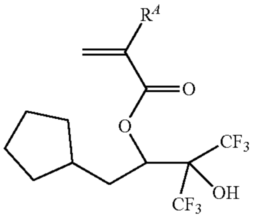
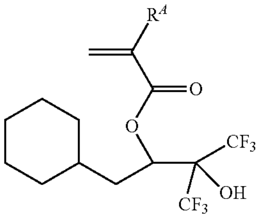

-continued
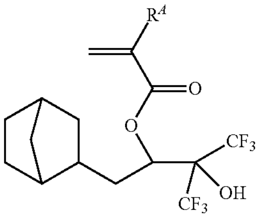
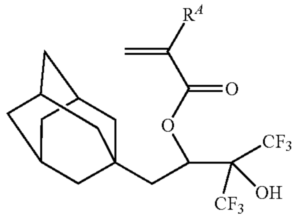
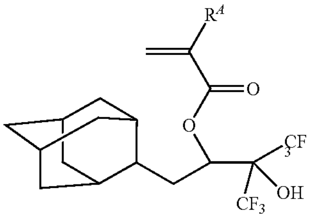
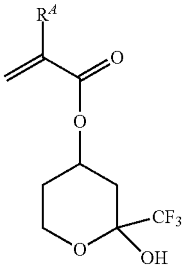
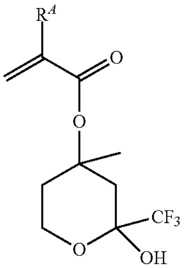
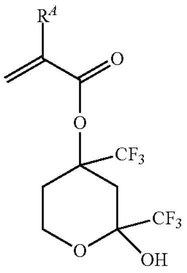
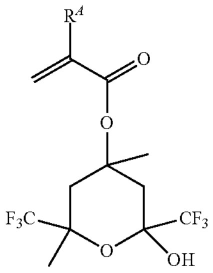
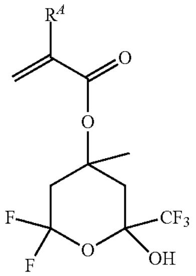
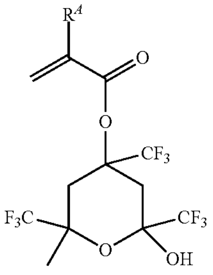
-continued
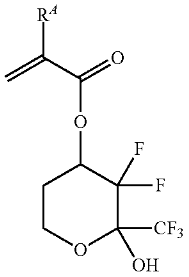
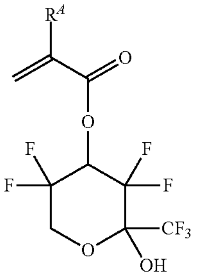
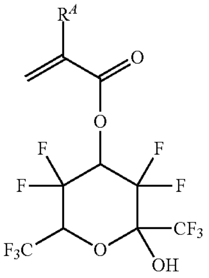
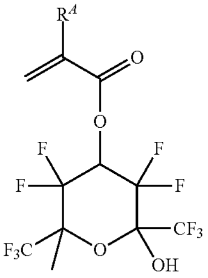
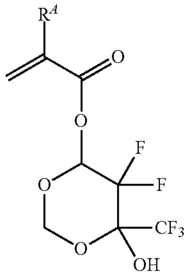
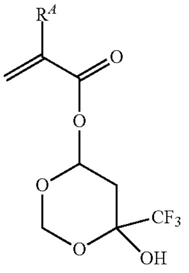
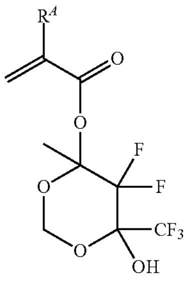
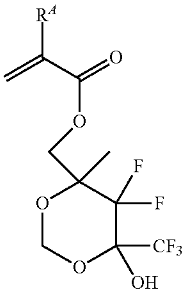
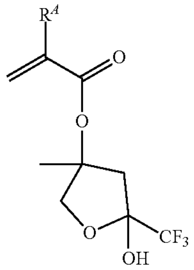
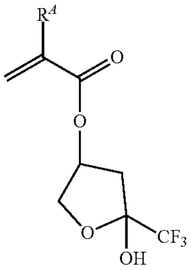
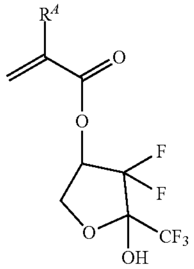
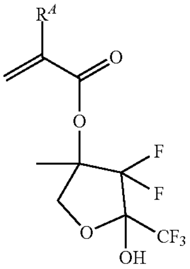

-continued
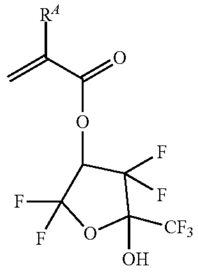
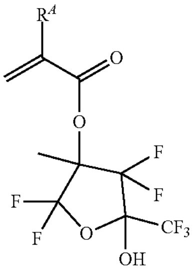
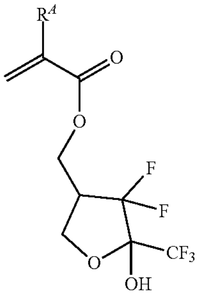
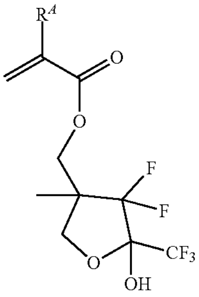
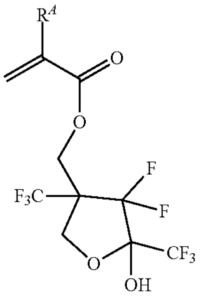
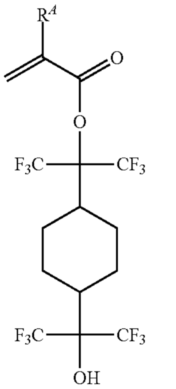
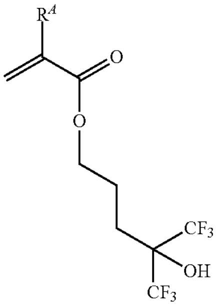
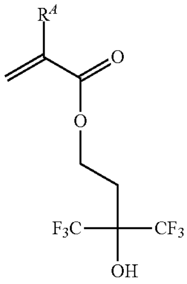
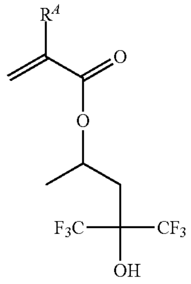
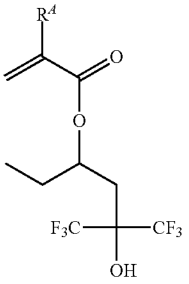
-continued
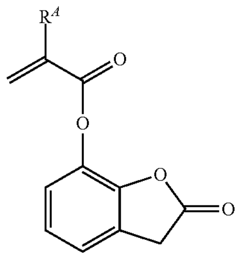
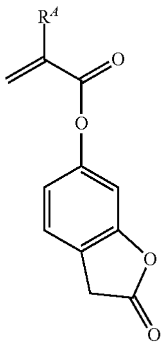
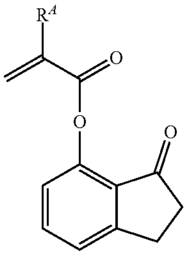
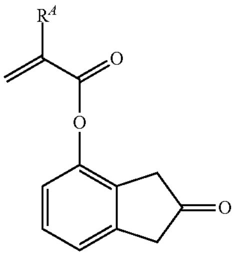
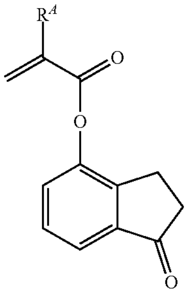
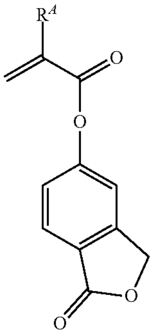
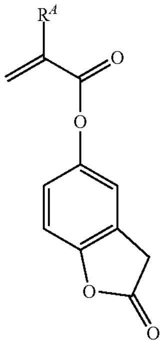
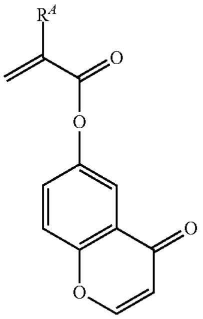
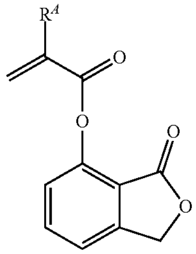
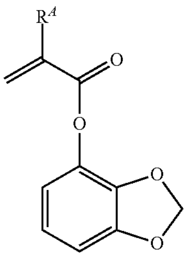
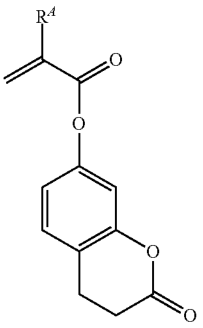

-continued
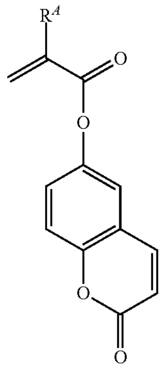
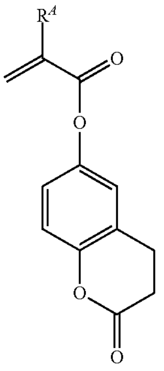
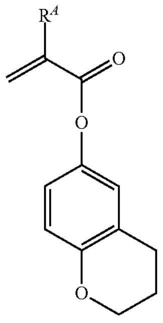
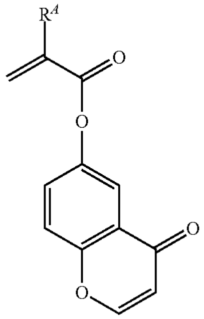
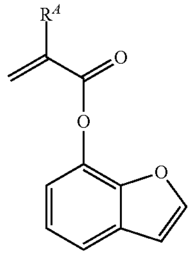
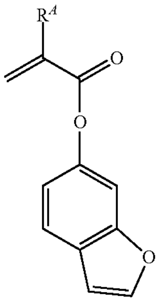
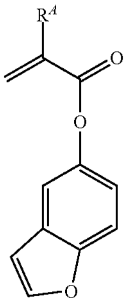
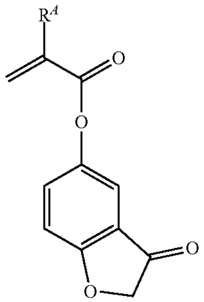
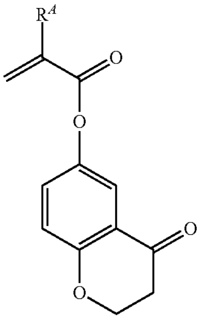
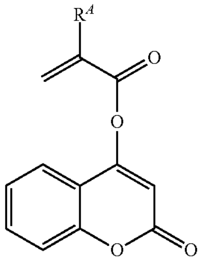
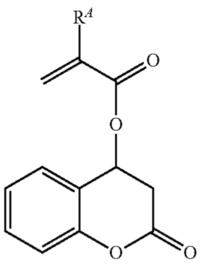
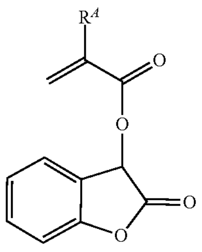
-continued
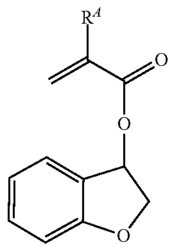
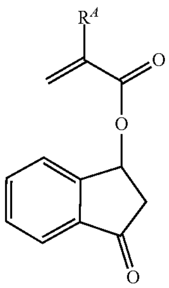
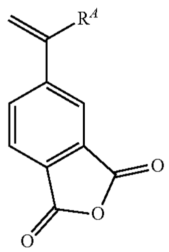
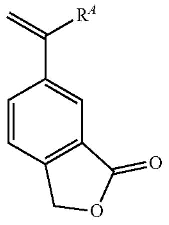
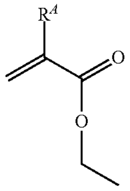
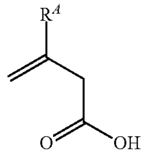
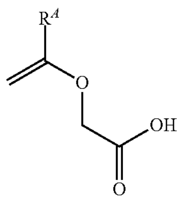
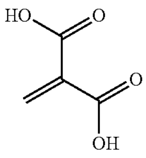
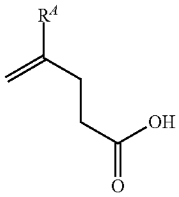
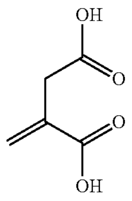
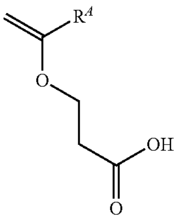
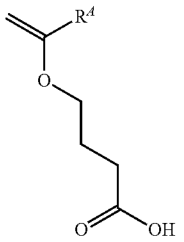
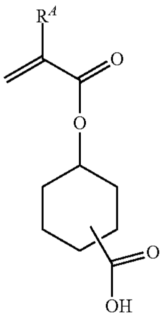
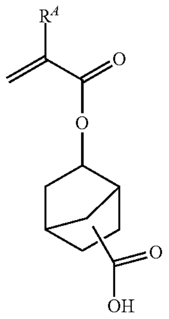
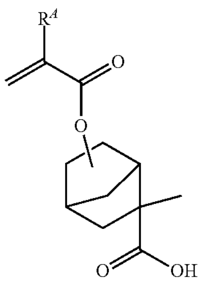
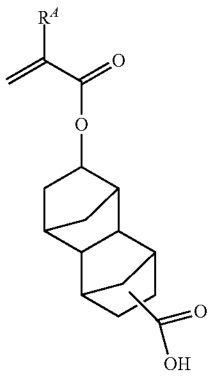
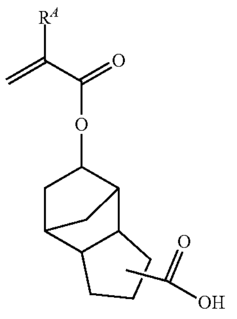

-continued
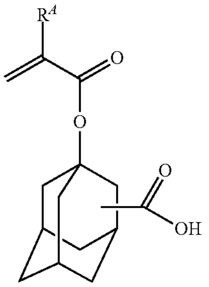
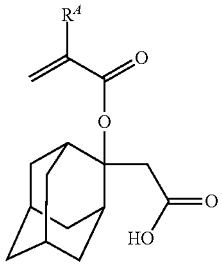
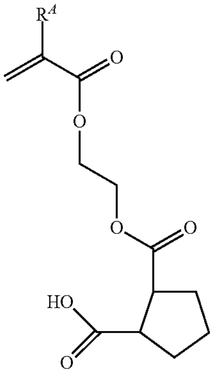
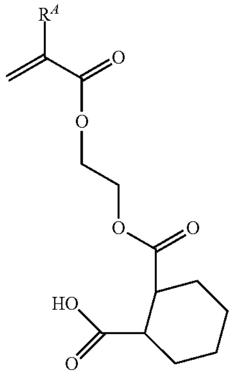
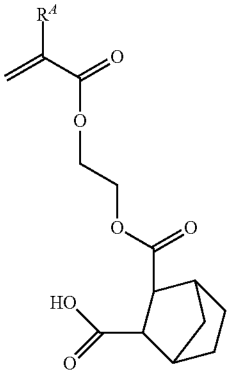
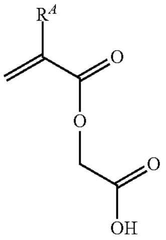
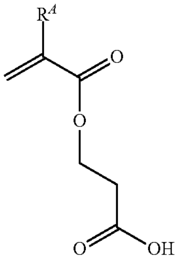
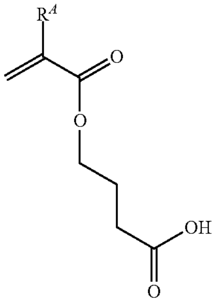
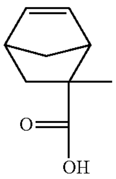
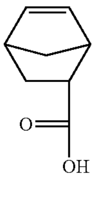
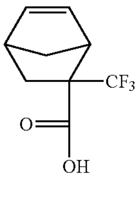
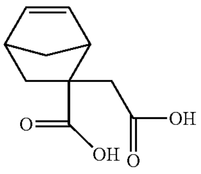
-continued
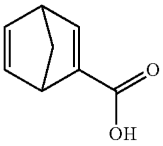
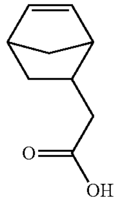
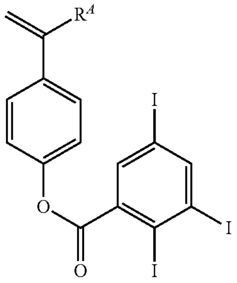
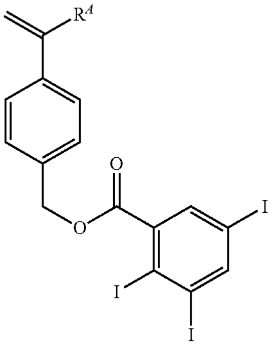
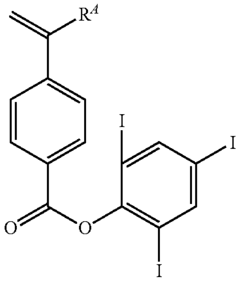
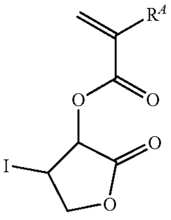
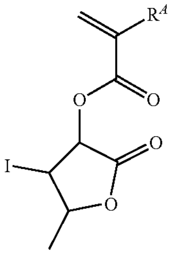
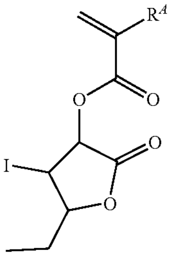
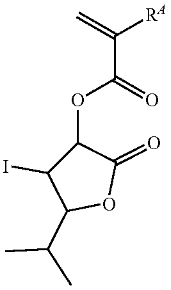
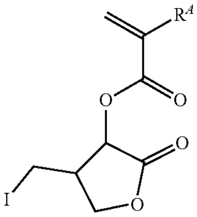
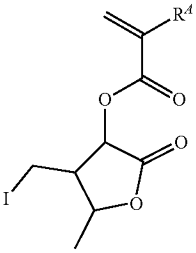
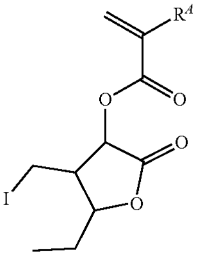
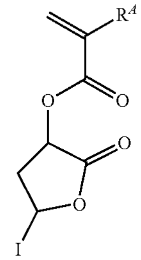
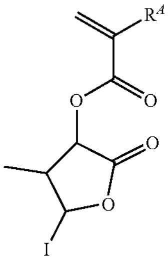
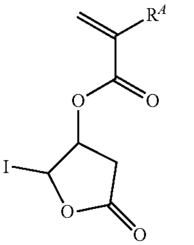

-continued

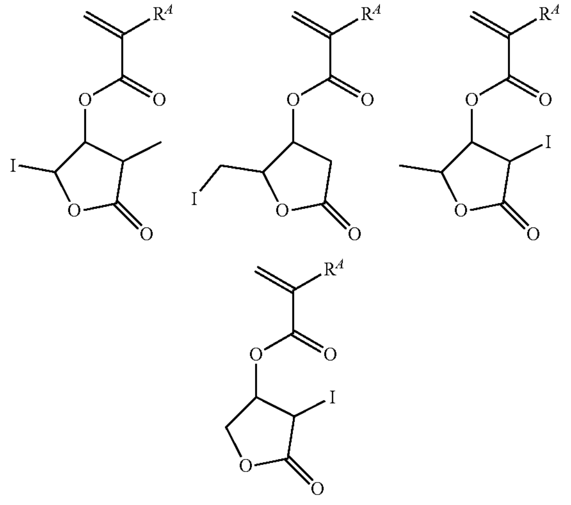

In another preferred embodiment, the base polymer may further comprise repeat units (d) derived from indene, benzofuran, benzothiophene, acenaphthylene, chromone, coumarin, and norbornadiene, or derivatives thereof. Suitable monomers are exemplified

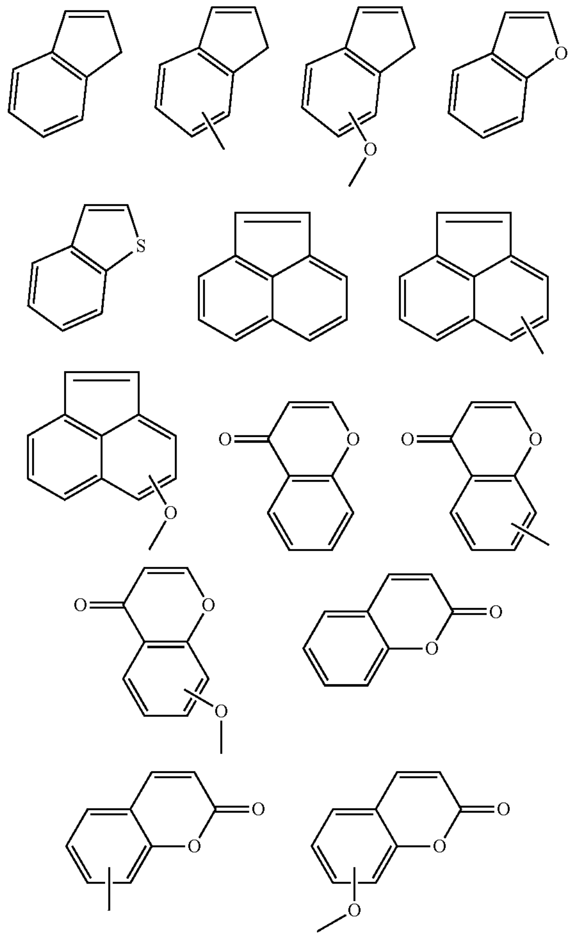

-continued

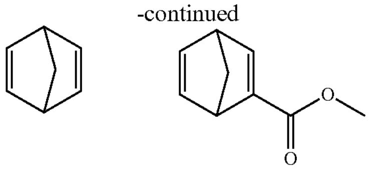

Furthermore, the base polymer may comprise repeat units (e) derived from styrene, vinylnaphthalene, vinylanthracene, vinylpyrene, methyleneindene, vinylpyridine, vinylcarbazole, or derivatives thereof.

In a further embodiment, the base polymer may comprise repeat units (f) derived from an onium salt having a polymerizable unsaturated bond. Specifically, the base polymer may comprise repeat units of at least one type selected from repeat units having formula (f1), repeat units having formula (f2), and repeat units having formula (f3). These units are simply referred to as repeat units (f1). (f2) and (f3), which may be used alone or in combination of two or more types.

(f1)

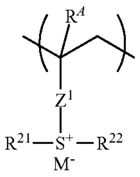

(f2)

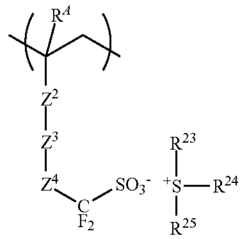

(f3)

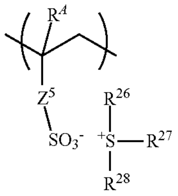

In formulae (f1) to (f3). $R^A$ is each independently hydrogen or methyl. Z is a single bond, $C_1$-$C_6$ aliphatic hydrocarbylene group, phenylene group, naphthylene group, or $C_7$-$C_{18}$ group obtained by combining the foregoing, —O—$Z^{11}$—, —C(=O)—O—$Z^1$—, or —C(=O)—NH—$Z^{11}$—. $Z^{11}$ is a $C_1$-$C_6$ aliphatic hydrocarbylene group, phenylene group, naphthylene group, or $C_{7-18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(=O)—O)—, —$Z^{31}$—O— or —$Z^{31}$—O—C(=O)—. $Z^{31}$ is a $C_1$-$C_2$ saturated hydrocarbylene group, phenylene group, or $C_7$-$C_{18}$ group obtained by combining the foregoing, which may contain a carbonyl moiety, ester bond, ether bond, iodine or bromine. $Z^4$ is methylene, 2,2,2-trifluoro-1,1-ethanediyl or carbonyl group. Z is a single bond, methylene, ethylene, phenylene, fluorinated phenylene, trifluoromethyl-substituted phenylene, —O—$Z^{11}$—, —C(=O)—

O—$Z^{51}$—, or —C(═O)—NH—$Z^{51}$—. $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety.

In formulae (f1) to (f3), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic. Examples thereof are as will be exemplified later for $R^{101}$ to $R^{105}$ in formulae (1-1) and (1-2). In these hydrocarbyl groups, some or all of the hydrogen atoms may be substituted by a moiety containing a heteroatom such as oxygen, sulfur, nitrogen or halogen and some carbon may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonate bond, carbonate moiety, lactone ring, sultone ring, carboxylic anhydride, or haloalkyl moiety. A pair of $R^{23}$ and $R^{24}$, or $R^{26}$ and $R^{27}$ may bond together to form a ring with the sulfur atom to which they are attached. Examples of the ring are as will be exemplified later for the ring that $R^{101}$ and $R^{10}$ in formula (1-1), taken together, form with the sulfur atom to which they are attached.

In formula (f1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide: methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl at β-position as represented by the formula (f1-2).

(f1-1)

$$R^{31}—CF_2—SO_3^-$$

(f1-2)

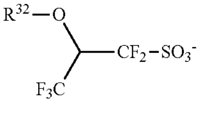

In formula (f1-1), $R^{31}$ is hydrogen, or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples of the hydrocarbyl group are as will be exemplified later for $R^{111}$ in formula (1A').

In formula (f1-2), $R^{32}$ is hydrogen, or a $C_1$-$C_{30}$ hydrocarbyl group or $C_2$-$C_{30}$ hydrocarbylcarbonyl group, which may contain an ether bond, ester bond, carbonyl moiety or lactone ring. The hydrocarbyl group and hydrocarbyl moiety in the hydrocarbylcarbonyl group may be saturated or unsaturated and straight, branched or cyclic. Examples of the hydrocarbyl group are as will be exemplified later for $R^{11}$ in formula (1A').

Examples of the cation in the monomer from which repeat unit (f1) is derived are shown below, but not limited thereto. $R^A$ is as defined above.

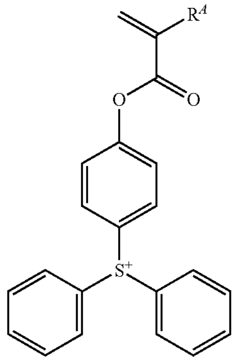

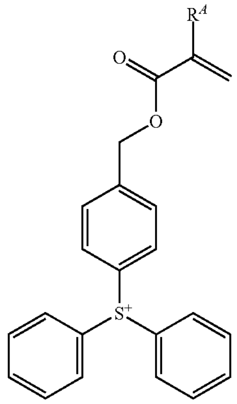

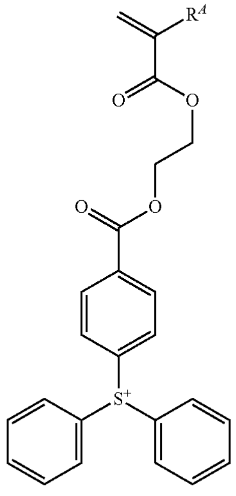

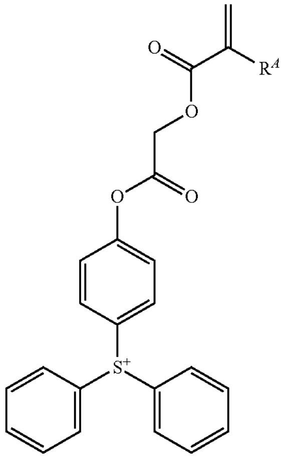

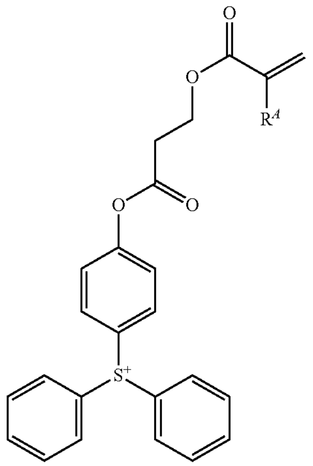

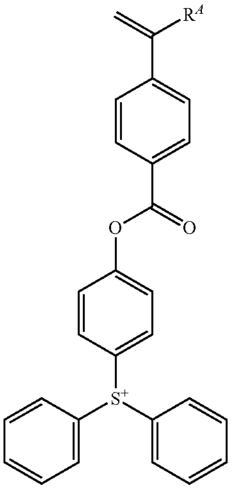

-continued
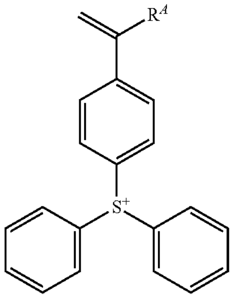
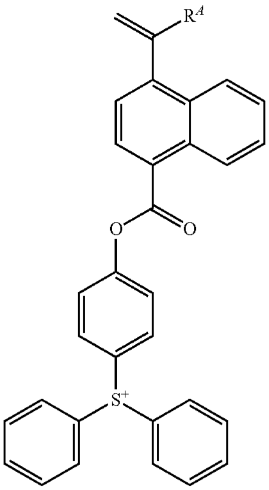
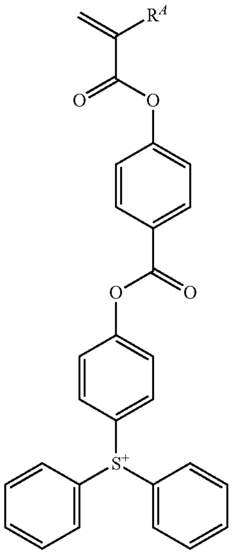
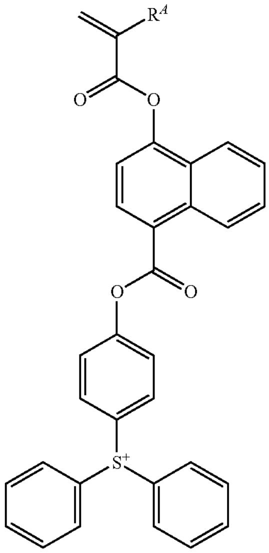
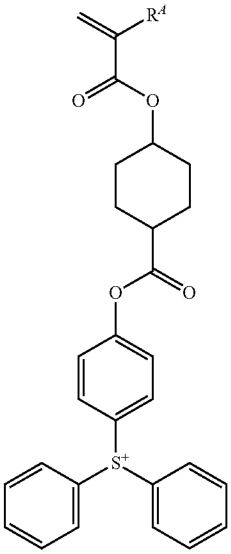
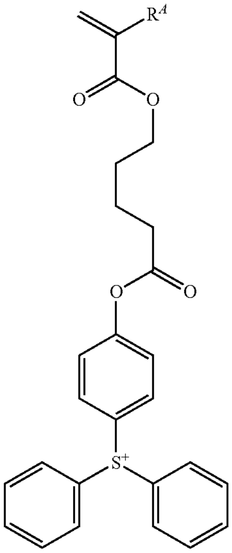
-continued
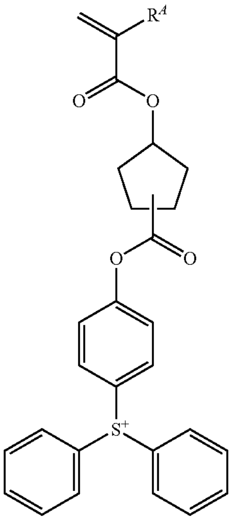
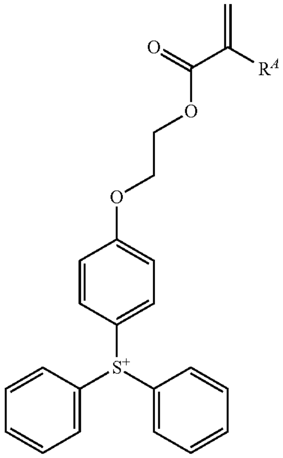
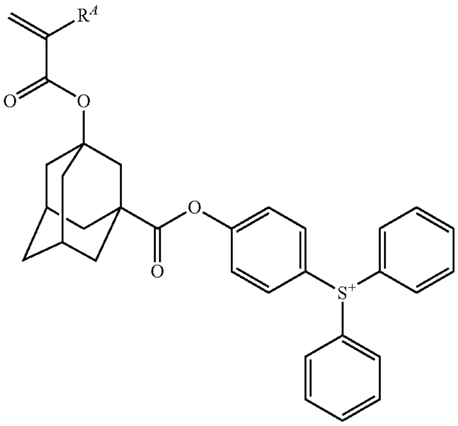
Examples of the cation in the monomer from which repeat unit (f2) or (f3) is derived are as will be exemplified later for the cation in the sulfonium salt having formula (1-1).
Examples of the anion in the monomer from which repeat unit (f2) is derived are shown below, but not limited thereto. $R^A$ is as defined above.
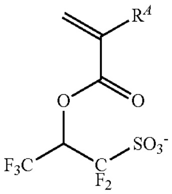
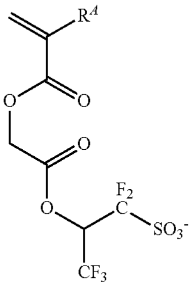
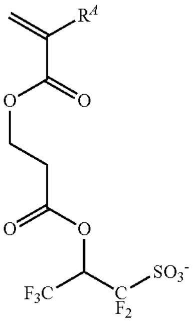

-continued
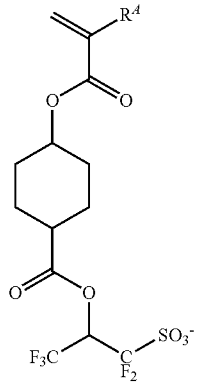
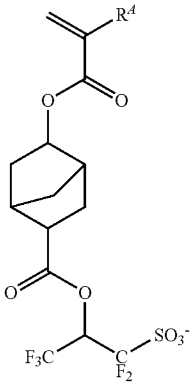
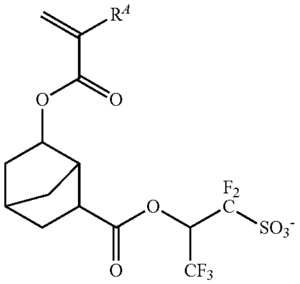
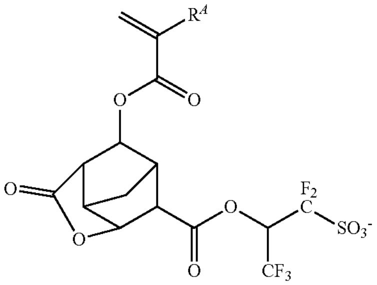
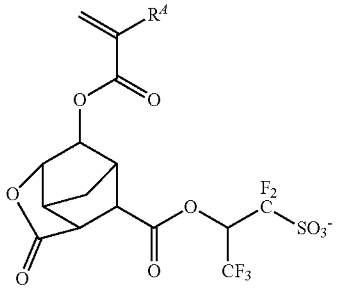
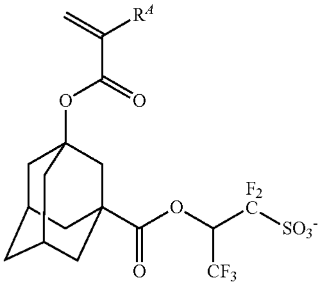
-continued
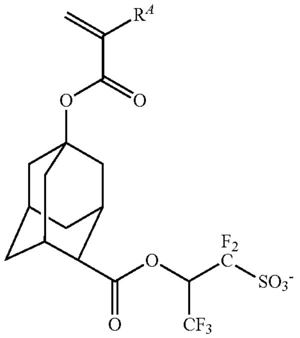
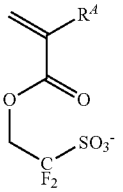
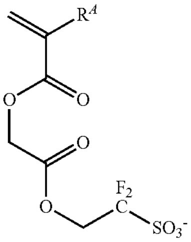
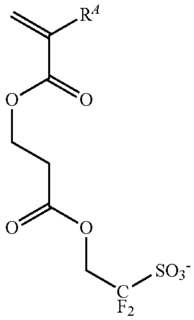
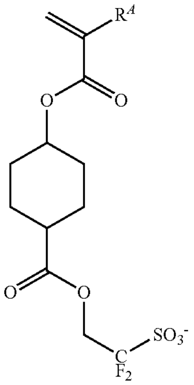
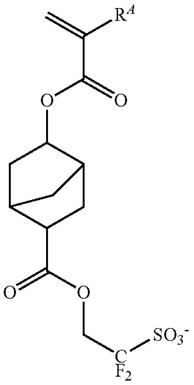
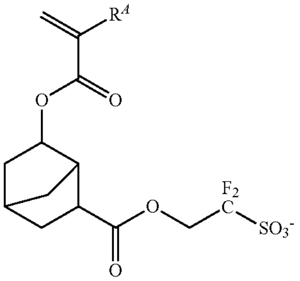
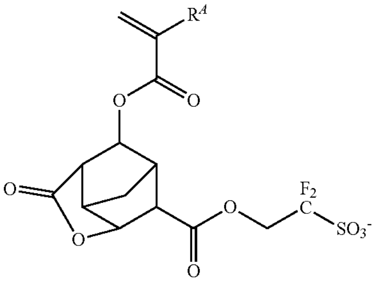

-continued
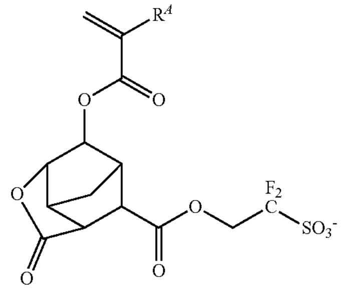
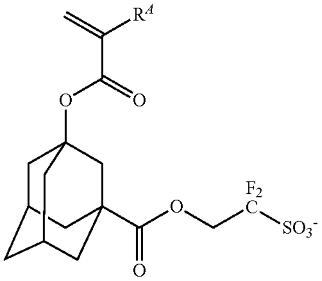
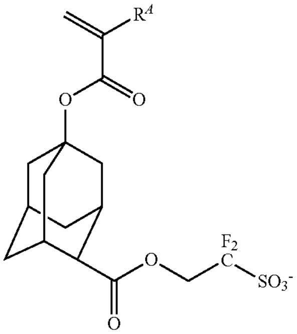
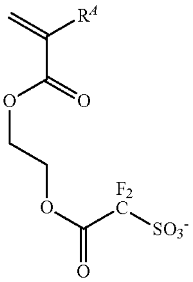
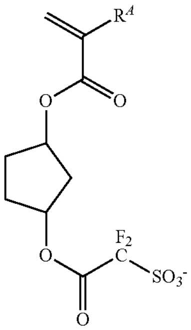
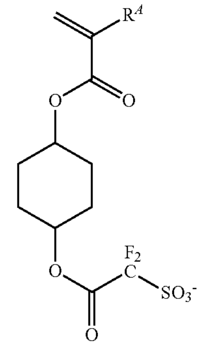
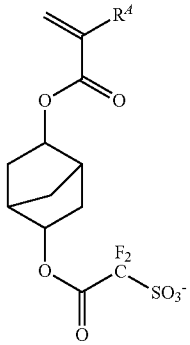
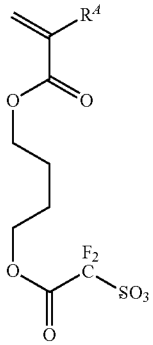
-continued
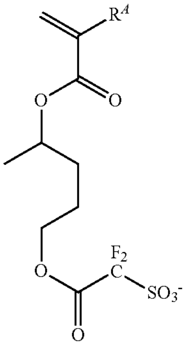
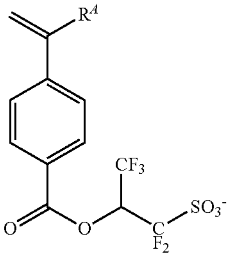
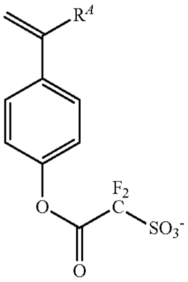
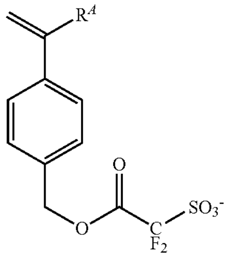
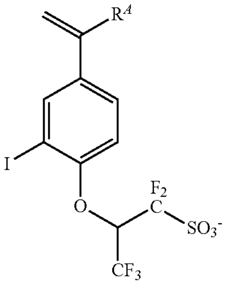
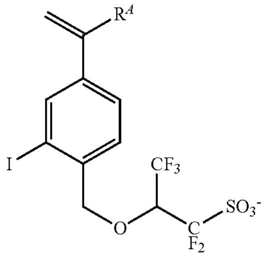
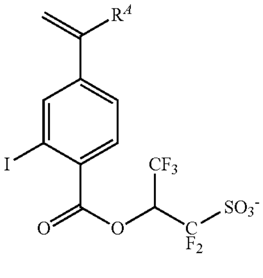
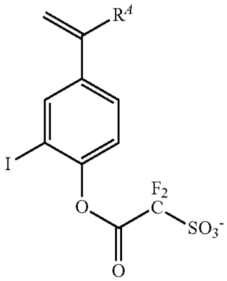
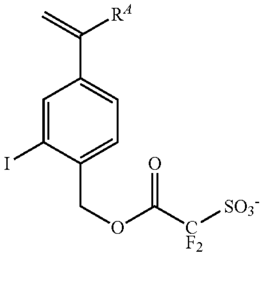
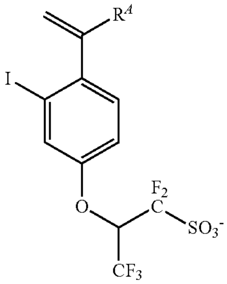

-continued
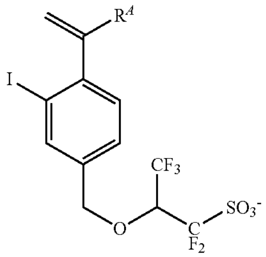
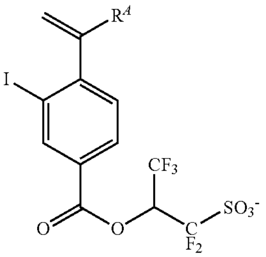
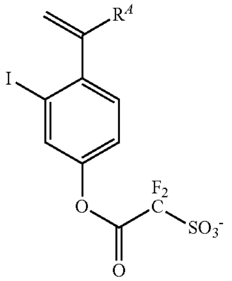
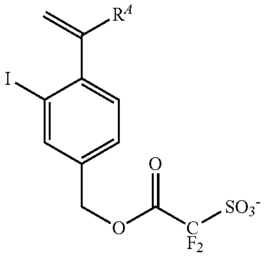
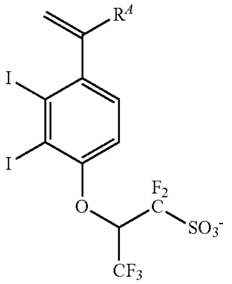
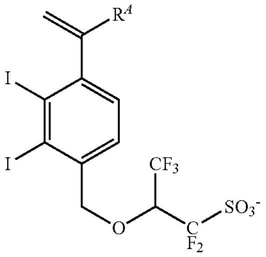
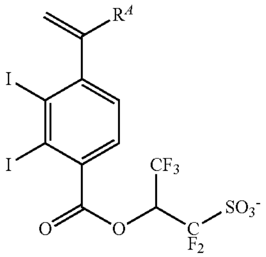
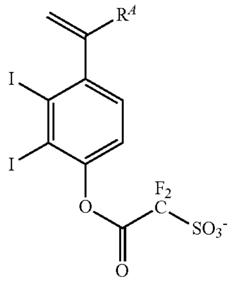
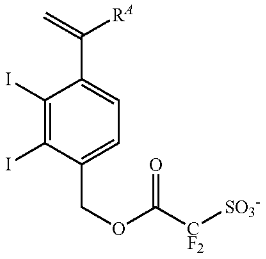
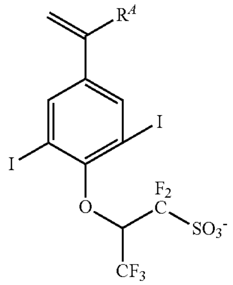
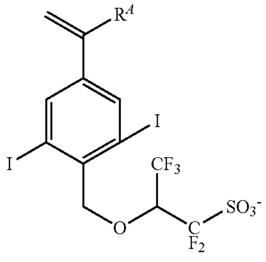
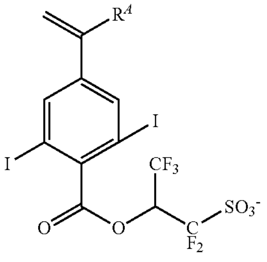
-continued
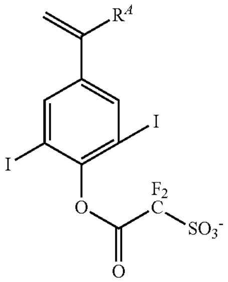
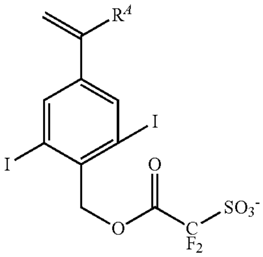
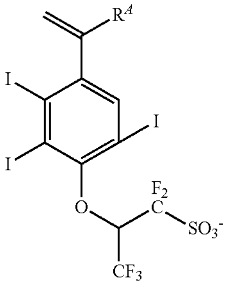
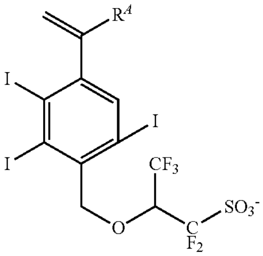
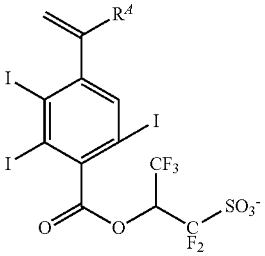
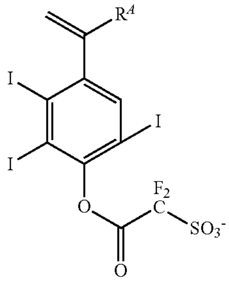
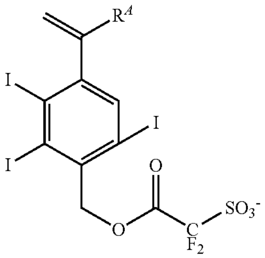
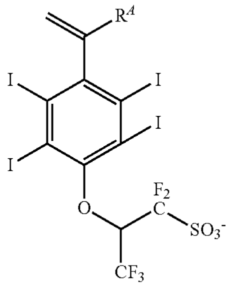
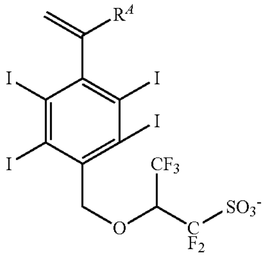
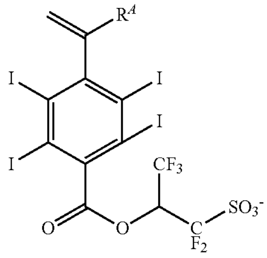
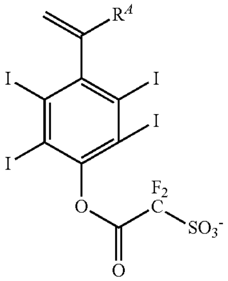
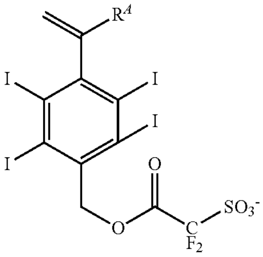

-continued
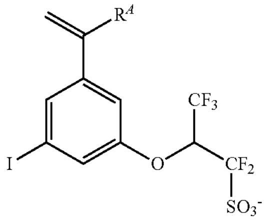
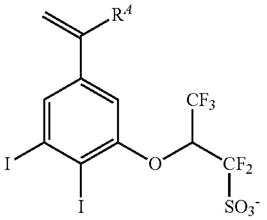
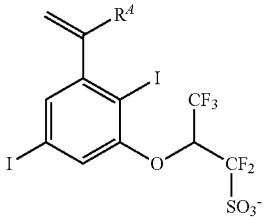
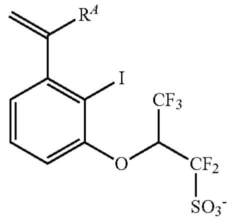
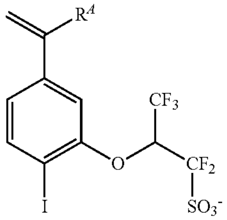
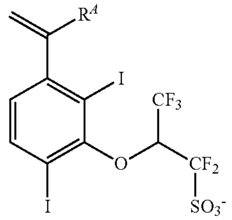
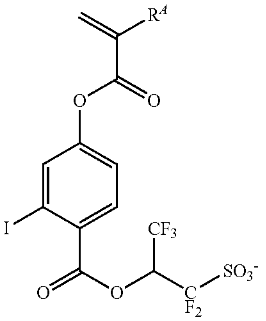
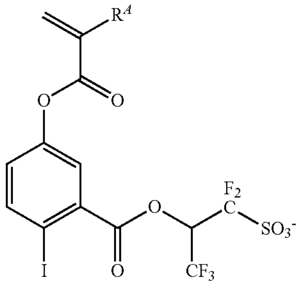
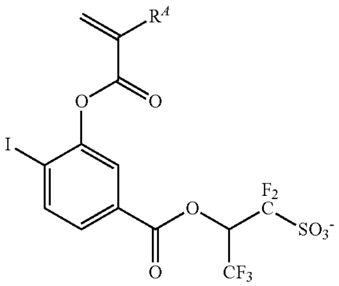
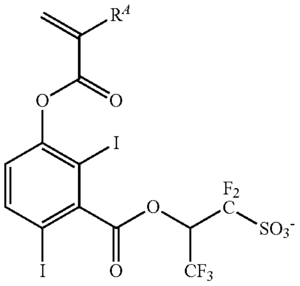
-continued
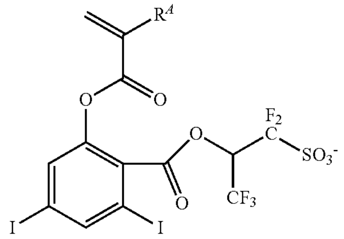
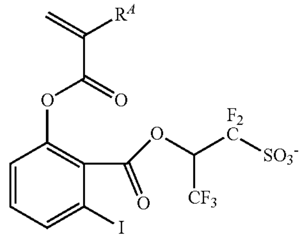
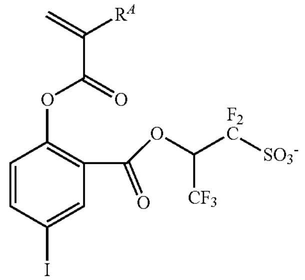
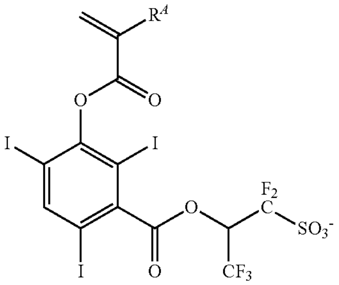
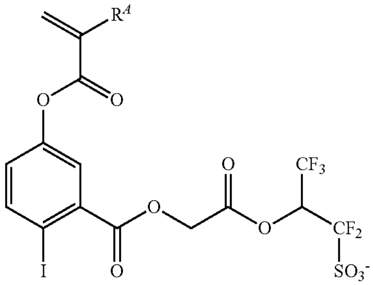
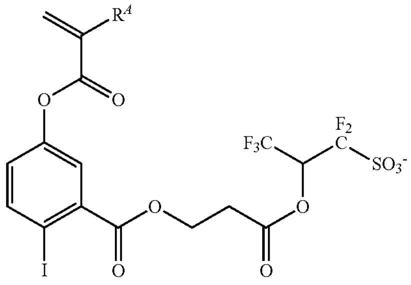

-continued
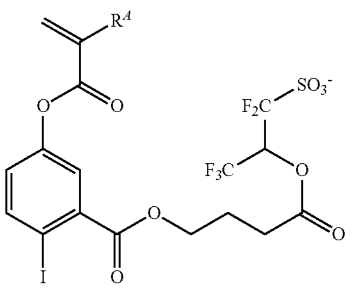
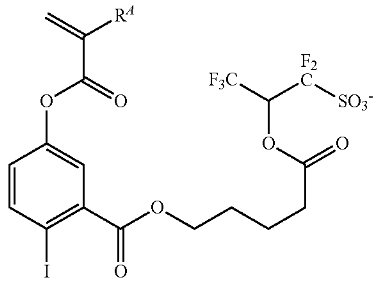
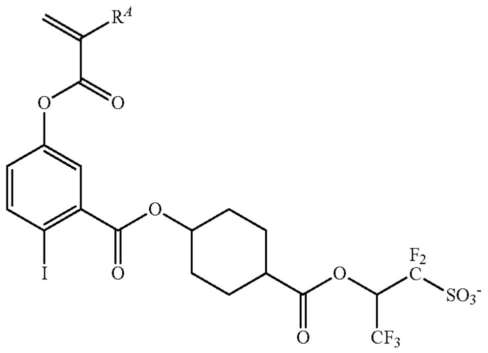
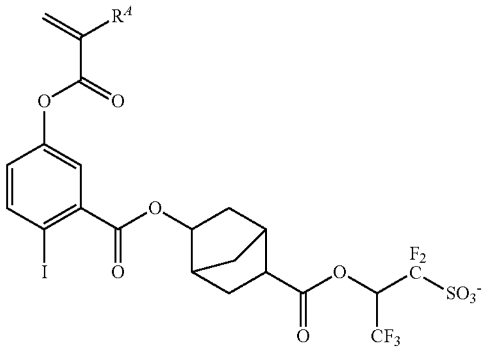
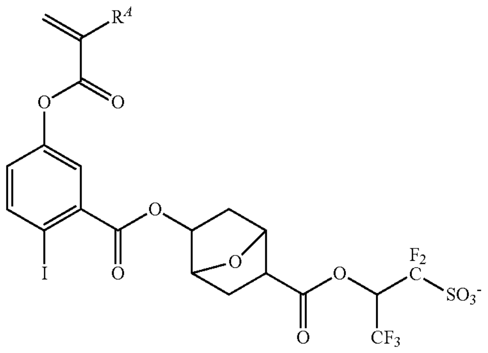
-continued
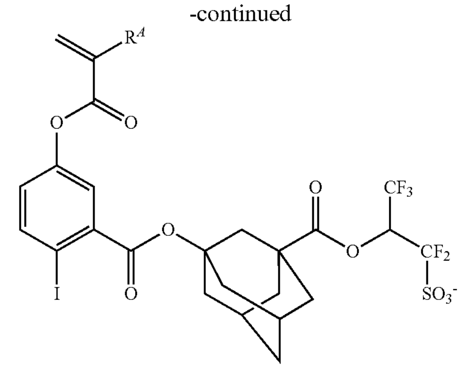
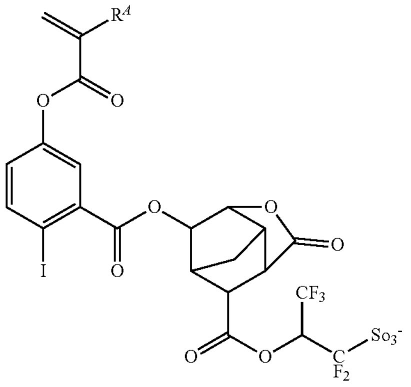
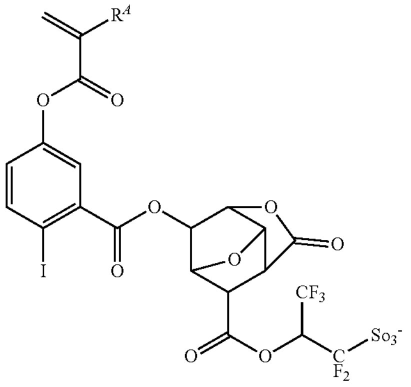
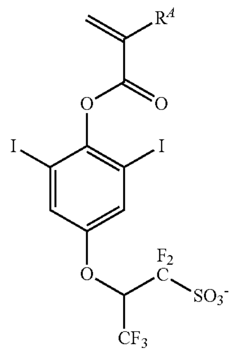
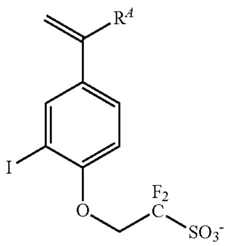
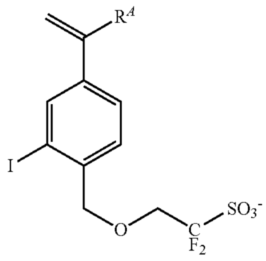
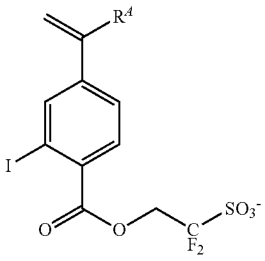

-continued
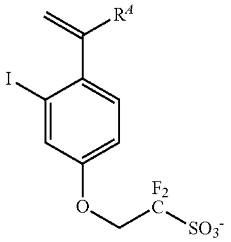
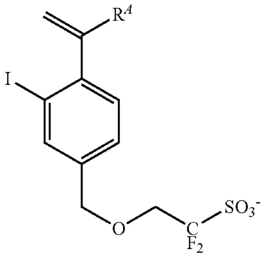
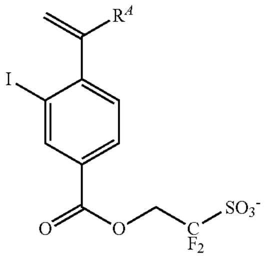
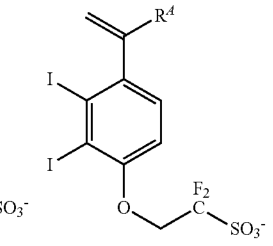
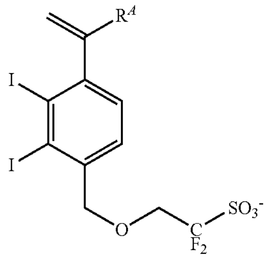
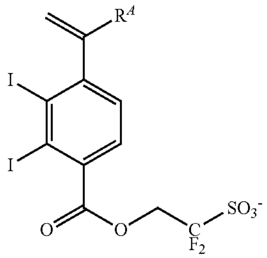
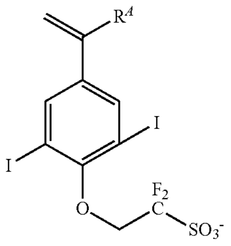
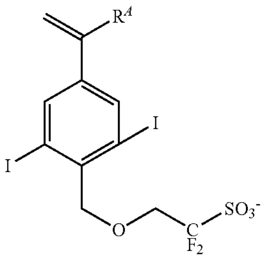
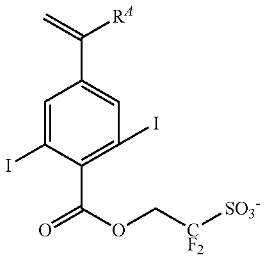
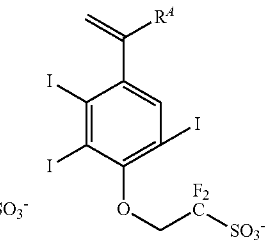
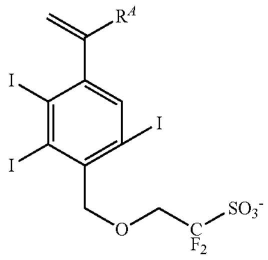
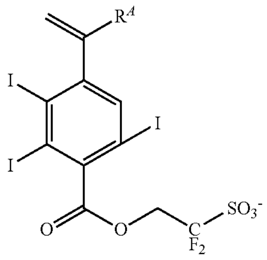
-continued
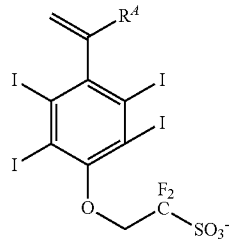
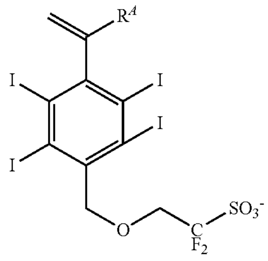
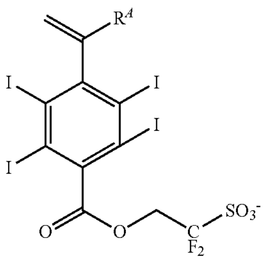
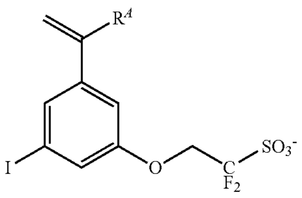
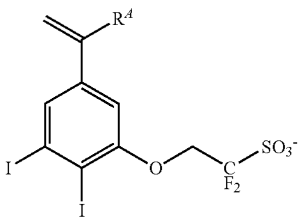
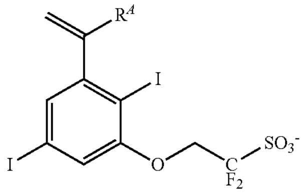
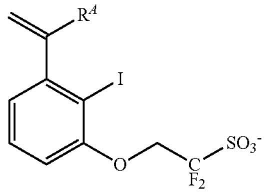
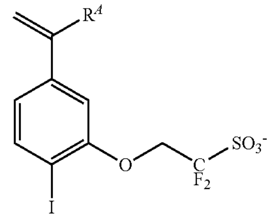
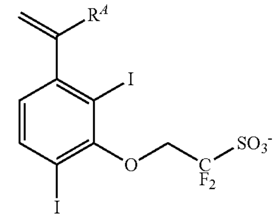
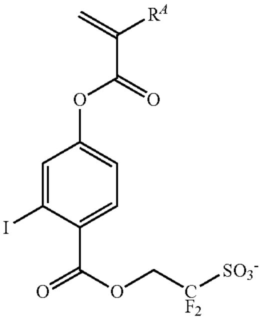
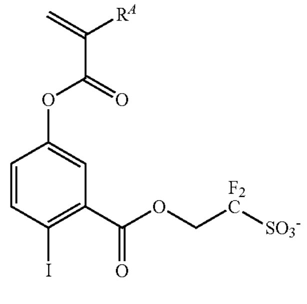

-continued
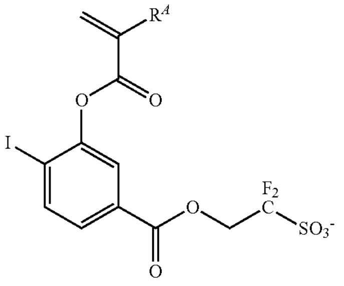
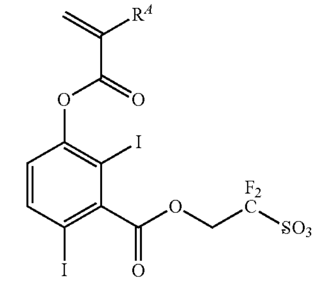
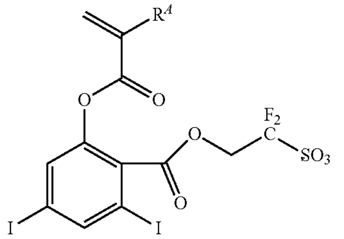
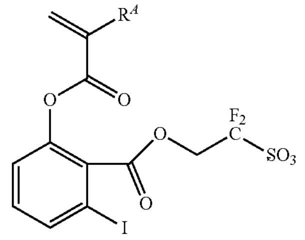
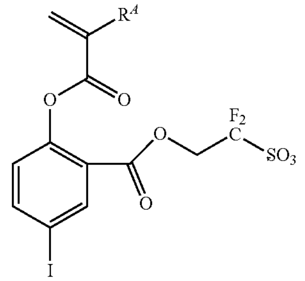
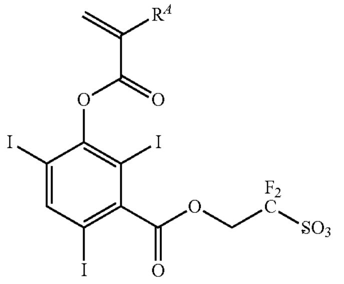
-continued
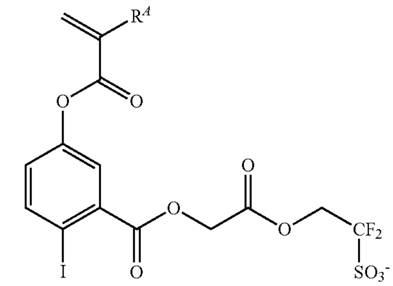
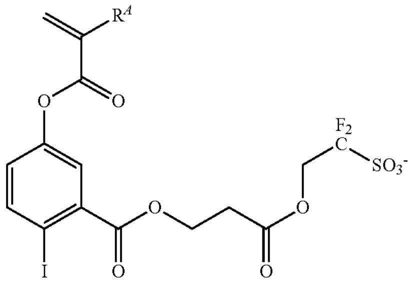
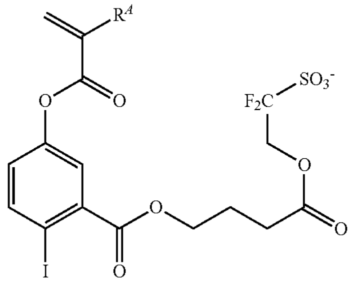
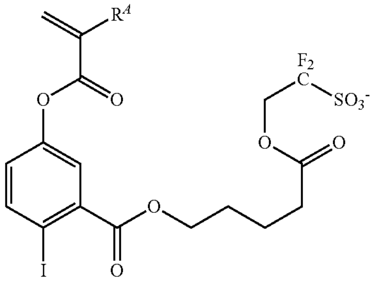
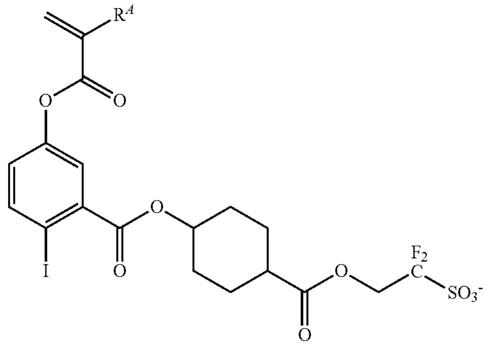

-continued
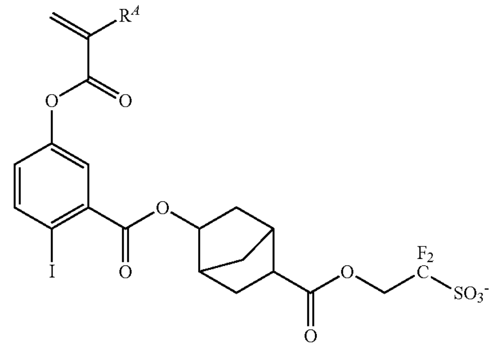
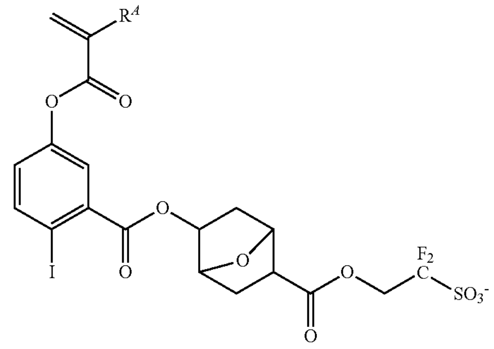
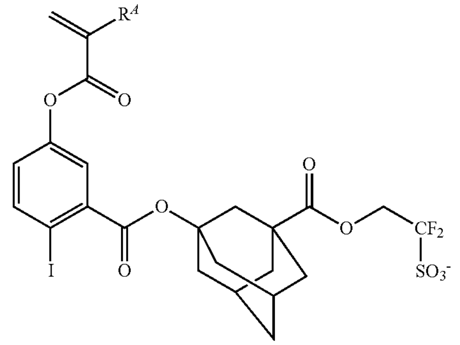
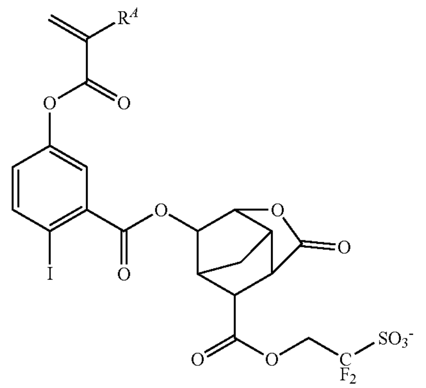
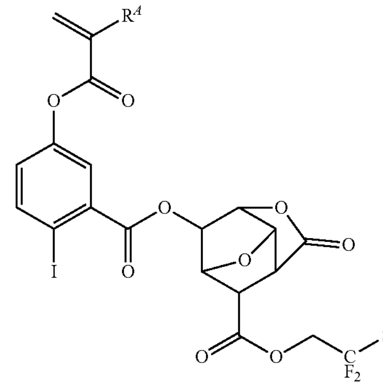
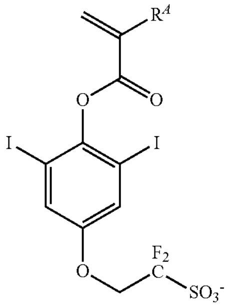
Examples of the anion in the monomer from which repeat unit (f3) is derived are shown below, but not limited thereto. $R^A$ is as defined above.
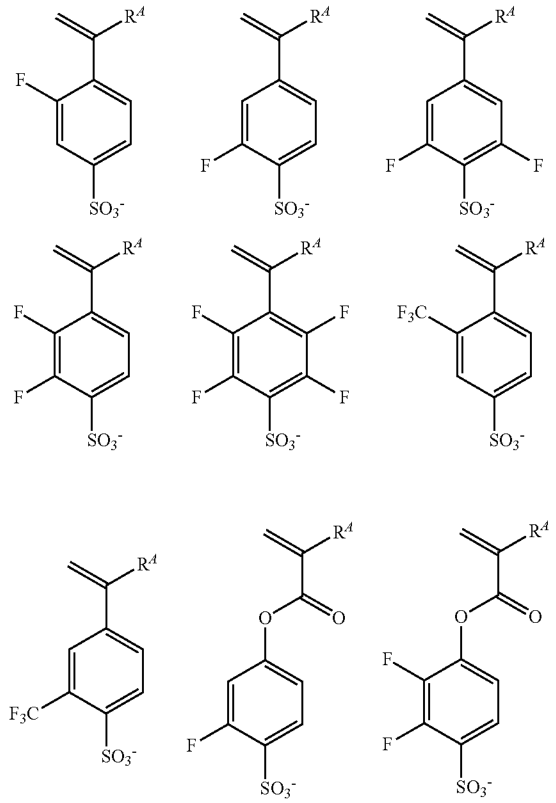

-continued

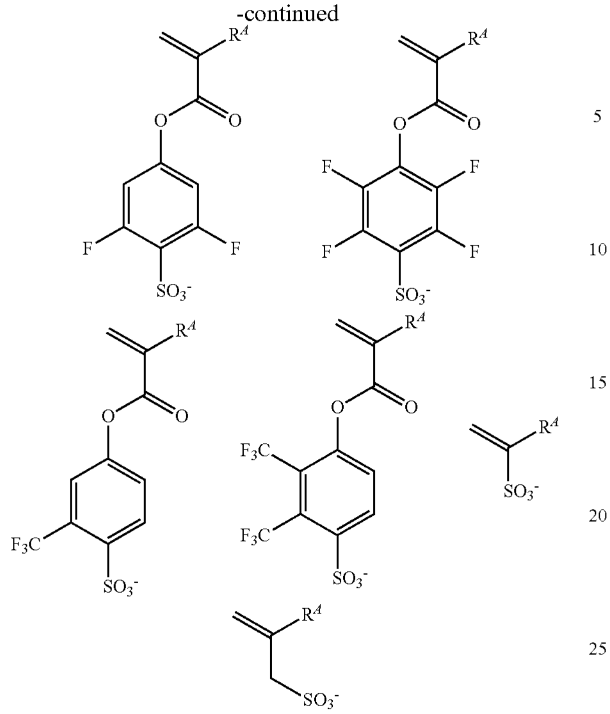

The attachment of an acid generator to the polymer main chain is effective in restraining acid diffusion, thereby preventing a reduction of resolution due to blur by acid diffusion. Also, LWR or CDU is improved since the acid generator is uniformly distributed. Where a base polymer containing repeat units (f), i.e., polymer-bound acid generator is used, the blending of an acid generator of addition type (to be described later) may be omitted.

The base polymer for formulating the positive resist composition comprises repeat units (a1) or (a2) having an acid labile group as essential component and additional repeat units (b), (c), (d), (e), and (f) as optional components. A fraction of units (a1), (a2), (b), (c), (d), (e), and (f) is: preferably $0\leq a1<1.0$, $0\leq a2\leq 1.0$, $0<a1+a2<1.0$, $0.0\leq b\leq 0.9$, $0\leq c\leq 0.9$, $0\leq d\leq 0.8$, $0\leq e\leq 0.8$, and $0\leq f\leq 0.5$; more preferably $0\leq a1\leq 0.9$, $0\leq a\leq 0.9$, $0.1\leq a1+a2\leq 0.9$, $0\leq b\leq 0.8$, $0\leq c\leq 0.8$, $0\leq d\leq 0.7$, $0\leq e\leq 0.7$, and $0\leq f\leq 0.4$; and even more preferably $0\leq a\leq 0.8$, $0\leq a2\leq 0.8$, $0.1\leq a\leq +a2\leq 0.8$, $0\leq b\leq 0.75$, $0\leq c\leq 0.75$, $0\leq d\leq 0.6$, $0\leq e\leq 0.6$, and $0\leq f\leq 0.3$. Notably, $f=f1+f2+f3$, meaning that unit (f) is at least one of units (f1) to (3), and $a1+a2+b+c+d+e+f=1.0$.

For the base polymer for formulating the negative resist composition, an acid labile group is not necessarily essential. The base polymer comprises repeat units (b), and optionally repeat units (c), (d), (e), and/or (f). A fraction of these units is: preferably $0<b\leq 1.0$, $0\leq c\leq 0.9$, $0\leq d\leq 0.8$, $0\leq e\leq 0.8$, and $0\leq f\leq 0.5$; more preferably $0.2\leq b\leq 1.0$, $0\leq c\leq 0.8$, $0\leq d\leq 0.7$, $0\leq e\leq 0.7$, and $0\leq f\leq 0.4$; and even more preferably $0.3\leq b\leq 1.0$, $0\leq c\leq 0.75$, $0\leq d\leq 0.6$, $0\leq e\leq 0.6$, and $0\leq f\leq 0.3$. Notably, $f=f1+f2+f$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing repeat units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

Where a monomer having a hydroxy group is copolymerized, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyne or acetoxyvinyinaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500.000, and more preferably 2,000 to 30.000, as measured by GPC versus polystyrene standards using tetrahydrofuran (THF) solvent. A Mw in the range ensures that the resist film is fully heat resistant and dissolvable in alkaline developer.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the sulfonium salt of a carboxylic acid having a nitro-substituted benzene ring functions as a quencher and the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, sulfonium salts having the formula (1-1) and iodonium salts having the formula (1-2) are also preferred.

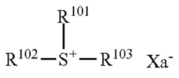

(1-1)

$$R^{104}—I^{+}—R^{105}\quad Xa^{-}$$

(1-2)

In formulae (1-1) and (1-2), $R^{101}$ to $R^{105}$ are each independently halogen or a $C_1$-$C_{20}$ hydrocarbyl group which may contain a heteroatom.

Suitable halogen atoms include fluorine, chlorine, bromine and iodine.

The $C_1$-$C_{20}$ hydrocarbyl group represented by $R^{101}$ to $R^{105}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexyhnethyl, norbornyl and adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl and tert-butylnaphthyl; $C_7$-$C_{20}$ aralkyl groups such as benzyl and phenethyl; and combinations thereof.

Also included are substituted forms of the foregoing groups in which some or all of the hydrogen atoms are substituted by a moiety containing a heteroatom such as oxygen, sulfur, nitrogen or halogen, or some carbon is replaced by a moiety containing a heteratom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic ester bond, carbonate moiety, lactone ring, sultone ring, carboxylic anhydride or haloalkyl moiety.

A pair of $R^{101}$ and $R^{102}$ may bond together to form a ring with the sulfur atom to which they are attached. Preferred are those rings of the structure shown below.

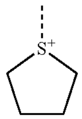
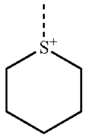
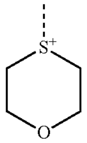
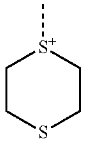
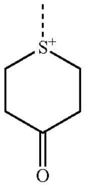

-continued

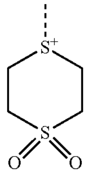
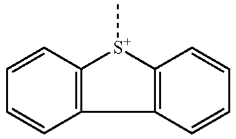
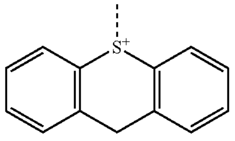
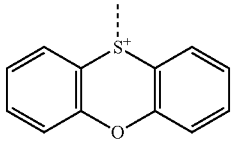
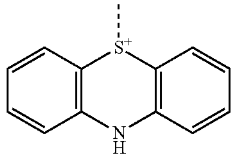
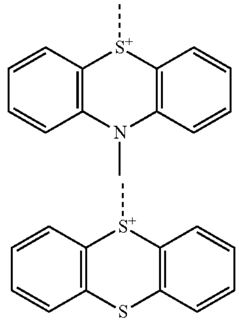
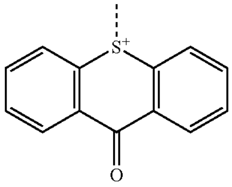
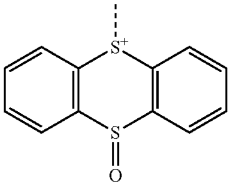
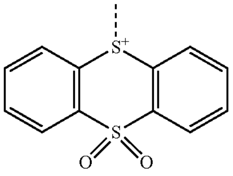
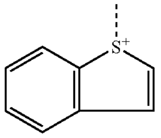

Herein, the broken line denotes a point of attachment to $R^{103}$.

Examples of the cation in the sulfonium salt having formula (1-1) are as exemplified above for the cation in the sulfonium salt having formula (A).

Examples of the cation in the iodonium salt having formula (1-2) are shown below, but not limited thereto.

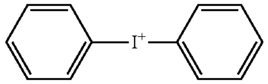
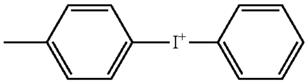
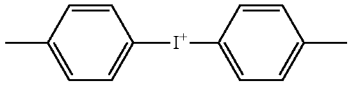
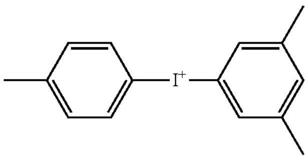

-continued
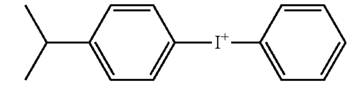
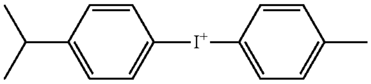
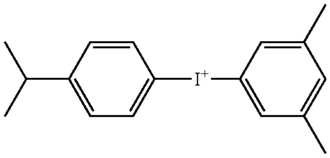
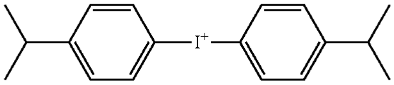
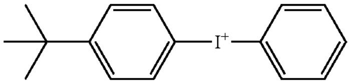
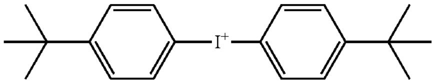
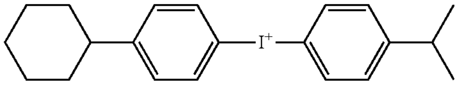
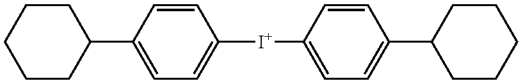
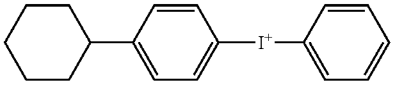
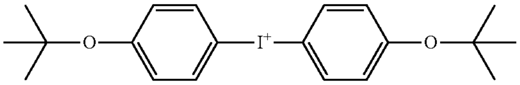
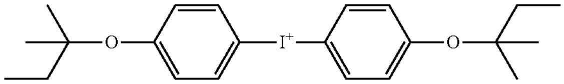
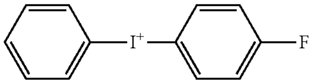
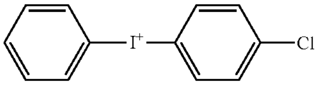
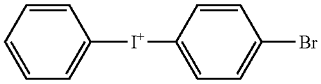
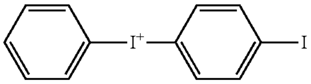
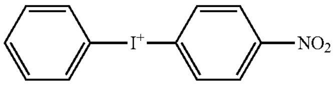
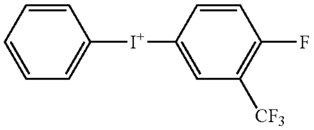
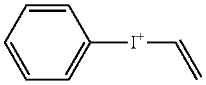
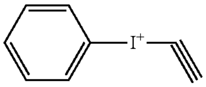
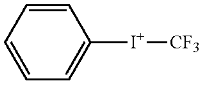
-continued
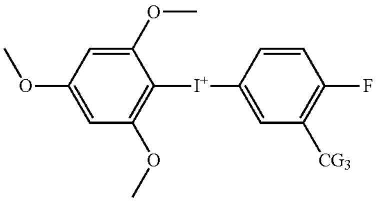
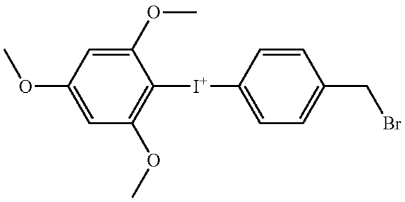
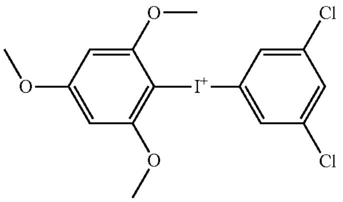
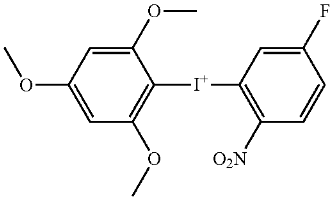
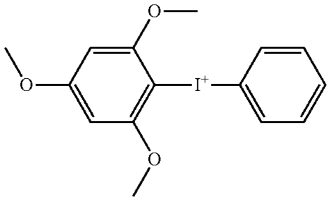
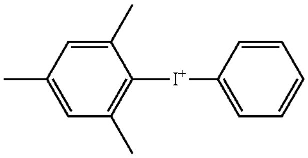
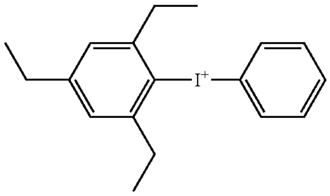
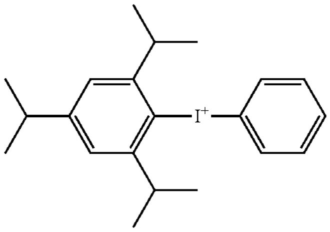

-continued

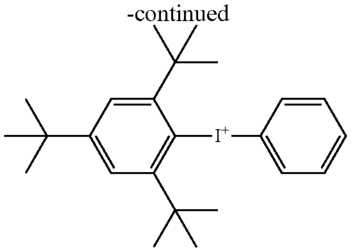

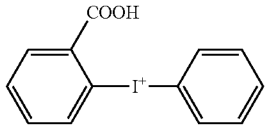

In formulae (1-1) and (1-2), $Xa^-$ is an anion of the following formula (1A), (1B), (1C) or (1D).

(1A)

$R^{fa}—CF_2—SO_3^-$ (1B)

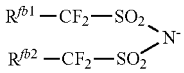

(1C)

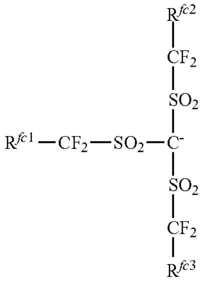

(1D)

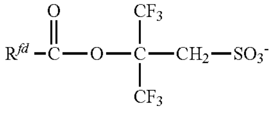

In formula (1A), $R^{fa}$ is fluorine or a $C_1$-$C_{40}$ hydrocarbyl group which may contain a heteroatom. The hydrocarbyl group may be saturated or unsaturated and straight, branched or cyclic. Examples thereof are as will be exemplified later for hydrocarbyl group $R^{111}$ in formula (1A').

Of the anions of formula (1A), a structure having formula (1A') is preferred.

(1A')

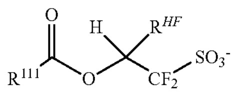

In formula (1A'), $R^{HF}$ is hydrogen or trifluoromethyl, preferably trifluoromethyl.

$R^{111}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation. The hydrocarbyl group $R^{111}$ may be saturated or unsaturated and straight, branched or cyclic.

Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{39}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexyhnethyl: $C_2$-$C_{38}$ unsaturated aliphatic hydrocarbyl groups such as allyl and 3-cyclohexenyl; $C_6$-$C_{38}$ aryl groups such as phenyl, 1-naphthyl, 2-naphthyl; $C_7$-$C_{38}$ aralkyl groups such as benzyl and diphenylmethyl; and combinations thereof.

In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic acid ester bond, carbonate, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608. JP-A 2012-041320, JP-A 2012-106986, and JP-A 2012-153644.

Examples of the anion having formula (1A) are as exemplified for the anion having formula (1A) in US 20180335696 (JP-A 2018-197853).

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage ($—CF_2—SO_2—N^-—SO_2—CF_2—$) to which they are attached, and the ring-forming pair is preferably a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fc1}$, $R^{fc2}$ and $R^{fc3}$, each are fluorine or a straight $C_1$-$C_4$ fluorinated alkyl group. A pair of $R^{fc1}$ and $R^{fc2}$ may bond together to form a ring with the linkage ($—CF_2—SO_2—C^-—SO_2—CF_2—$) to which they are attached, and the ring-forming pair is preferably a fluorinated ethylene or fluorinated propylene group.

In formula (1D), $R^{fd}$ is a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$.

With respect to the synthesis of the sulfonium salt having an anion of formula (1D), reference is made to JP-A 2010-215608 and JP-A 2014-133723.

Examples of the anion having formula (1D) are as exemplified for the anion having formula (1D) in US 20180335696 (JP-A 2018-197853).

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Also compounds having the formula (2) are useful as the PAG.

(2)

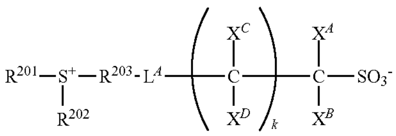

In formula (2), $R^{201}$ and $R^{202}$ are each independently halogen or a $C_1$-$C_{30}$ hydrocarbyl group which may contain a heteroatom. R is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl: $C_3$-$C_{30}$ cyclic saturated hydrocarbyl groups such as cyclopentyl, cyclohexyl, cyclopentyhnethyl, cyclopentylethyl, cyclopentylbutyl, cyclohexyhnethyl, cyclohexylethyl, cyclohexylbutyl, norbornyl, oxanorbornyl, tricyclo[5.2.1.0$^{2,6}$]decanyl, and adamantyl; $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl, and anthracenyl; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate moiety, lactone ring, sultone ring, carboxylic anhydride or haloalkyl moiety.

The hydrocarbylene group $R^{203}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl and adamantanediyl; $C_6$-$C_{30}$ arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, sec-butylnaphthylene and tert-butylnaphthylene; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy, fluorine, chlorine, bromine, iodine, cyano, nitro, carbonyl, ether bond, ester bond, sulfonic ester bond, carbonate bond, lactone ring, sultone ring, carboxylic anhydride or haloalkyl moiety. Of the heteroatoms, oxygen is preferred.

In formula (2), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for R.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

In formula (2), k is an integer of 0 to 3.

Of the PAGs having formula (2), those having formula (2') are preferred.

(2')

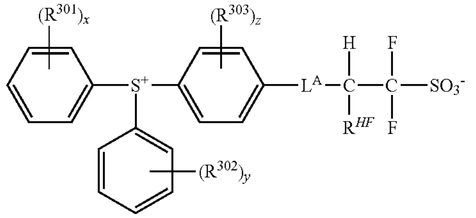

In formula (2'), $L^A$ is as defined above. $R^F$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified for the PAG having formula (2) in JP-A 2017-026980.

Of the foregoing PAGs, those having an anion of formula (1A') or (1D) are especially preferred because of reduced acid diffusion and high solubility in the solvent. Also those having formula (2') are especially preferred because of extremely reduced acid diffusion.

Also a sulfonium or iodonium salt having an anion containing an iodized or brominated aromatic ring may be used as the PAG. Suitable are sulfonium and iodonium salts having the formulae (3-1) and (3-2).

(3-1)

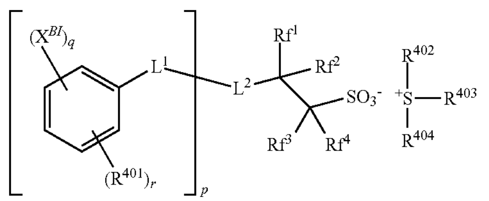

(3-2)

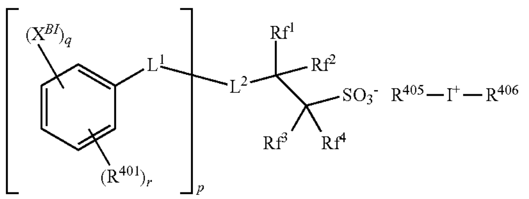

In formulae (3-1) and (3-2), p is an integer of 1 to 3, q is an integer of 1 to 5, and r is an integer of 0 to 3, and $1 \le q+r \le 5$. Preferably, q is 1, 2 or 3, more preferably 2 or 3, and r is 0, 1 or 2.

In formulae (3-1) and (3-2), $X^{BI}$ is iodine or bromine, and may be the same or different when p and/or q is 2 or more.

$L^1$ is a single bond, ether bond, ester bond, or a $C_1$-$C_6$ saturated hydrocarbylene group which may contain an ether bond or ester bond. The saturated hydrocarbylene group may be straight, branched or cyclic.

$L^2$ is a single bond or a $C_1$-$C_{20}$ divalent linking group when p is 1, and a $C_1$-$C_{20}$ (p+1)-valent linking group which may contain oxygen, sulfur or nitrogen when p is 2 or 3.

$R^{401}$ is a hydroxy group, carboxy group, fluorine, chlorine, bromine, amino group, or a $C_1$-$C_{20}$ hydrocarbyl, $C_1$-$C_{20}$ hydrocarbyloxy, $C_2$-$C_{20}$ hydrocarbylcarbonyl, $C_2$-$C_{20}$ hydrocarbyloxycarbonyl, $C_2$-$C_{20}$ hydrocarbylcarbonyloxy or $C_1$-$C_{20}$ hydrocarbylsulfonyloxy group, which may contain fluorine, chlorine, bromine, hydroxy, amino or ether bond, or $-N(R^{401A})(R^{401B})$, $-N(R^{401C})-(=O)-R^{401D}$ or $-N(R^{401C})-C(=O)-O-R^{401D}$. $R^{401A}$ and $R^{401B}$ are each independently hydrogen or a $C_1$-$C_6$ saturated hydrocarbyl group. $R^{401C}$ is hydrogen or a $C_1$-$C_6$ saturated hydrocarbyl group which may contain halogen, hydroxy. $C_1$-$C_6$ saturated hydrocarbyloxy, $C_2$-$C_6$ saturated hydrocarbylcarbonyl or $C_2$-$C_6$ saturated hydrocarbylcarbonyloxy moiety. $R^{401D}$ is a $C_1$-$C_{16}$ aliphatic hydrocarbyl group, $C_6$-$C_{14}$ aryl group or $C_7$-$C_{15}$ aralkyl group, which may contain halogen, hydroxy, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. The aliphatic hydrocarbyl group may be saturated or unsaturated and straight, branched or cyclic. The saturated hydrocarbyl, saturated hydrocarbyloxy, saturated hydrocarbyloxycarbonyl, saturated hydrocarbylcarbonyl, and saturated hydrocarbylcarbonyloxy groups may be straight, branched or cyclic. Groups $R^{401}$ may be the same or different when p and/or r is 2 or more. Of these, $R^{401}$ is preferably hydroxy, $-N(R^{401C})-C(=O)-R^{401D}$, $-N(R^{401C})-C(=O)-O-R^{401D}$, fluorine, chlorine, bromine, methyl or methoxy.

In formulae (3-1) and (3-2), $R^{f1}$ to $R^{f4}$ are each independently hydrogen, fluorine or trifluoromethyl, at least one of $Rf^1$ to $Rf^4$ is fluorine or trifluoromethyl, or $Rf^1$ and $Rf^2$, taken together, may form a carbonyl group. Preferably, both $Rf^3$ and $Rf^4$ are fluorine.

$R^{402}$ to $R^{406}$ are each independently halogen or a $C_1$-$C_{20}$ hydrocarbyl group which may contain a heteroatom. The hydrocarbyl group may be saturated or unsaturated and straight, branched or cyclic. Examples thereof include those exemplified above for the hydrocarbyl groups $R^{101}$ to $R^{105}$ in formulae (1-1) and (1-2). In these groups, some or all of the hydrogen atoms may be substituted by hydroxy, carboxy, halogen, cyano, nitro, mercapto, sultone, sulfone, or sulfonium salt-containing moieties, and some carbon may be replaced by an ether bond, ester bond, carbonyl moiety, amide bond, carbonate bond or sulfonic ester bond. $R^{101}$ and $R^{105}$ may bond together to form a ring with the sulfur atom to which they are attached. Exemplary rings are the same as described above for the ring that $R^{101}$ and $R^{102}$ in formula (I-1), taken together, form with the sulfur atom to which they are attached.

Examples of the cation in the sulfonium salt having formula (3-1) include those exemplified above as the cation in the sulfonium salt having formula (1-1). Examples of the cation in the iodonium salt having formula (3-2) include those exemplified above as the cation in the iodonium salt having formula (1-2).

Examples of the anion in the onium salts having formulae (3-1) and (3-2) are shown below, but not limited thereto. Herein $X^{BI}$ is as defined above.

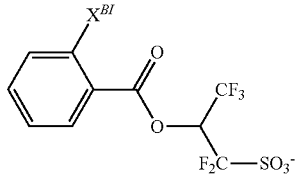

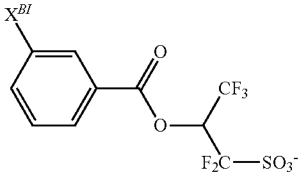

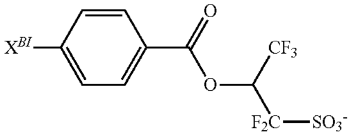

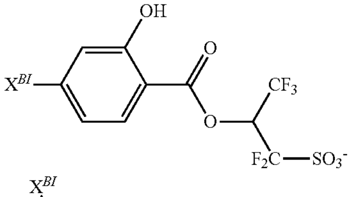

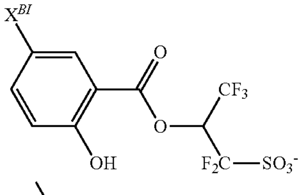

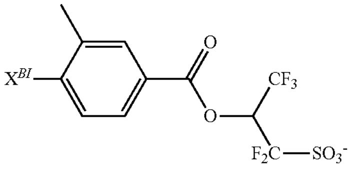

-continued
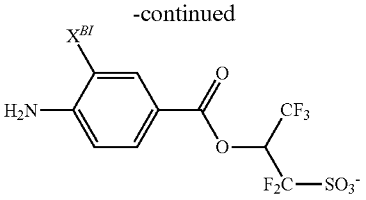
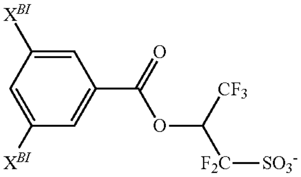
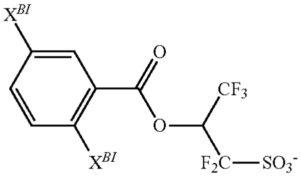
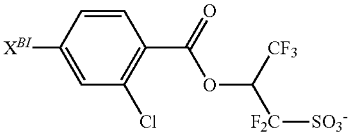
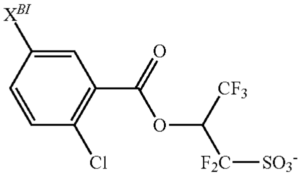
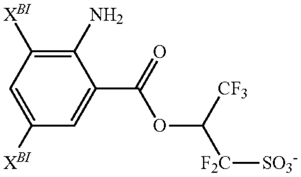
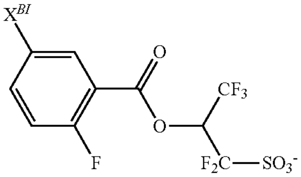
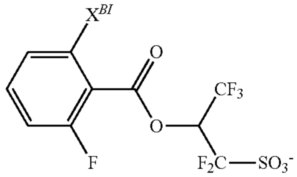
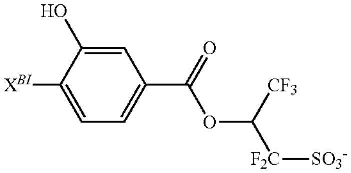
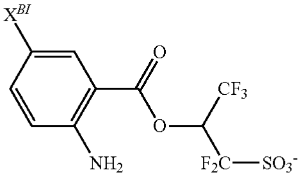
-continued
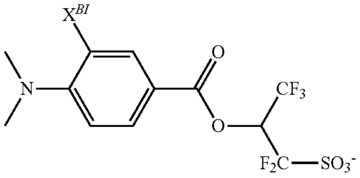
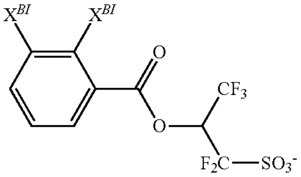
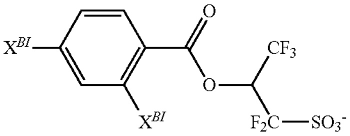
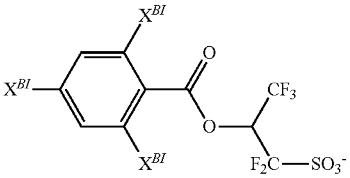
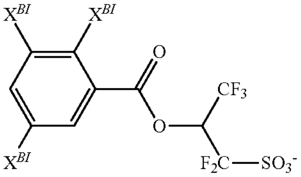
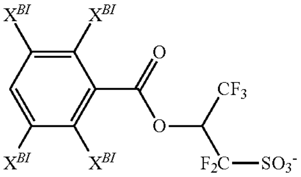
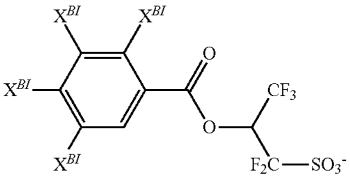
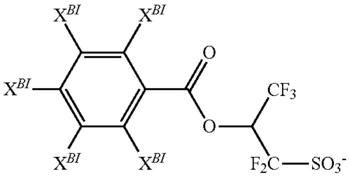
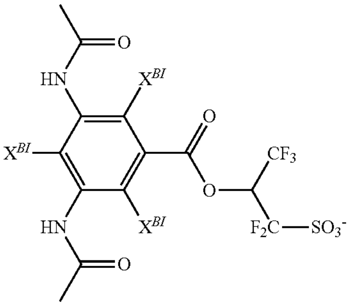

-continued
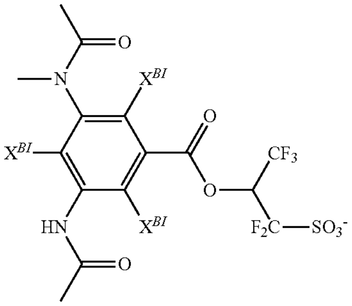
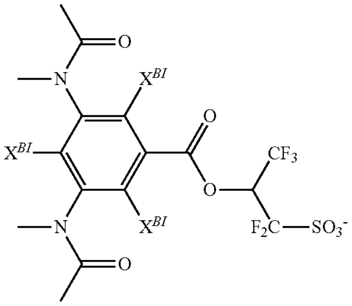
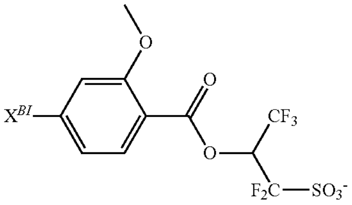
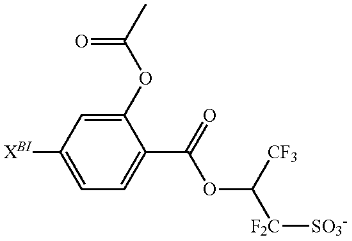
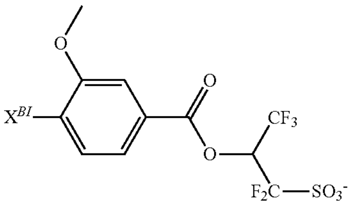
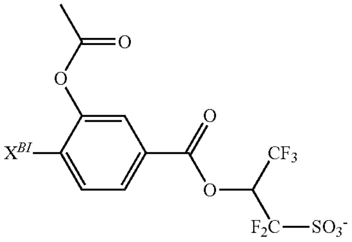
-continued
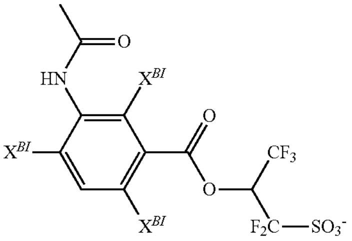
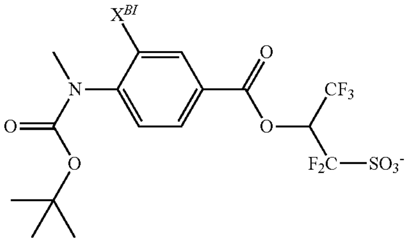
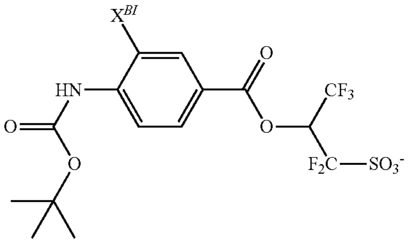
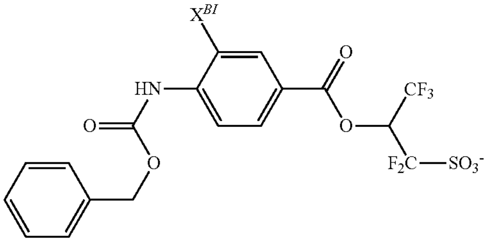
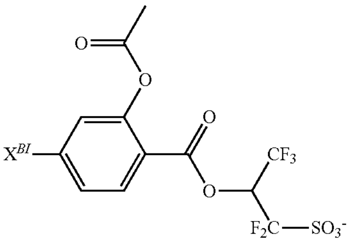
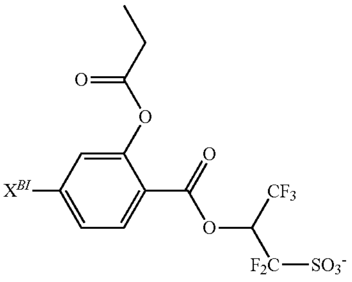

-continued
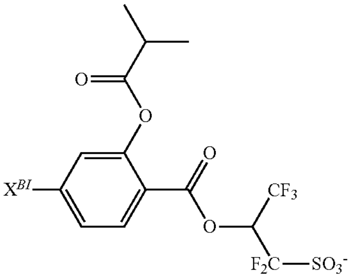
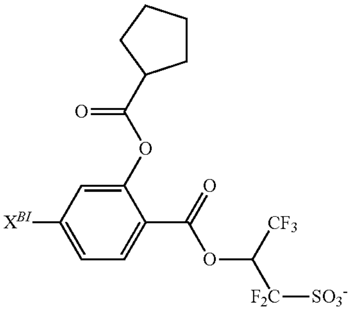
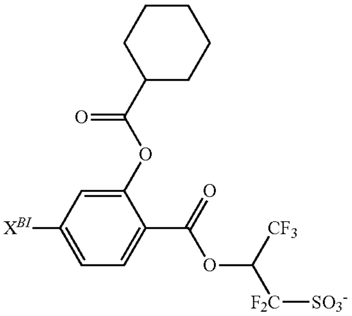
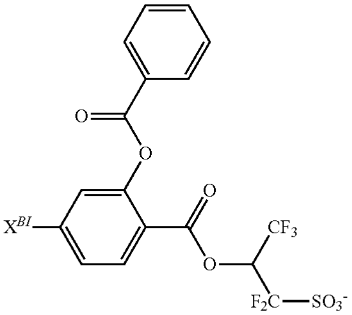
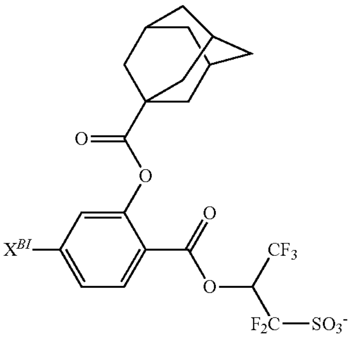
-continued
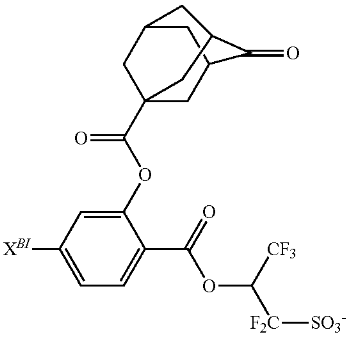
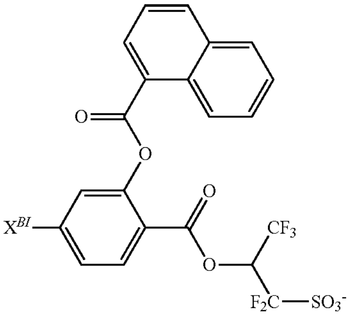
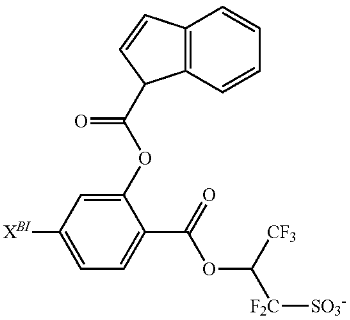
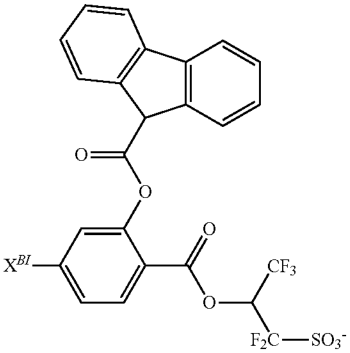
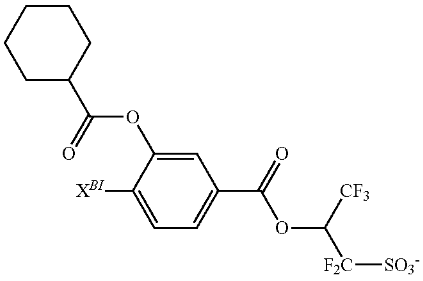

-continued
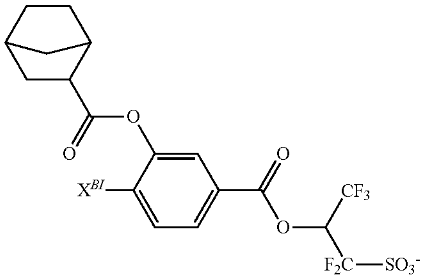
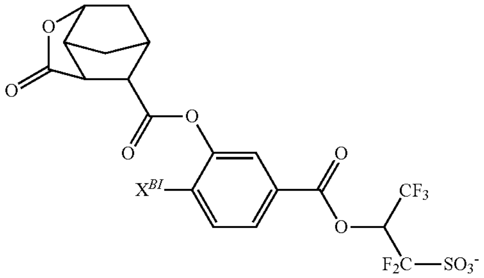
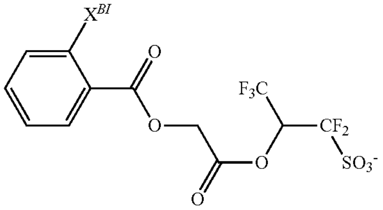
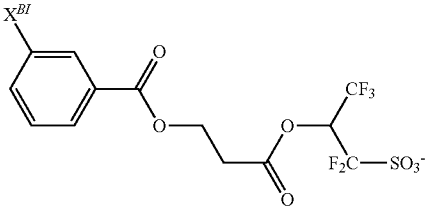
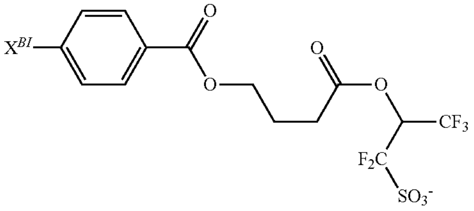
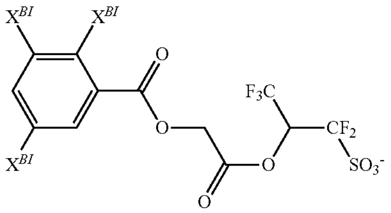
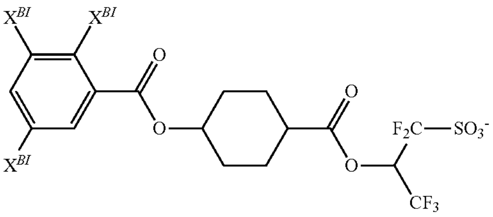
-continued
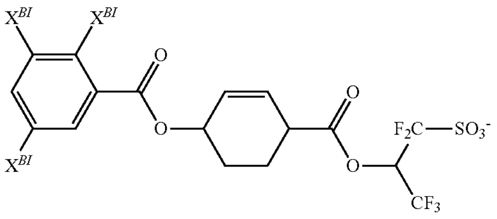
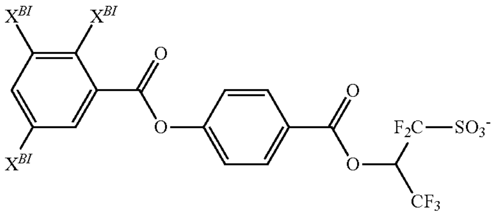
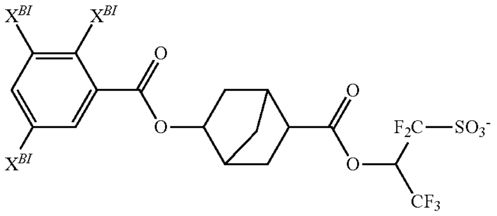
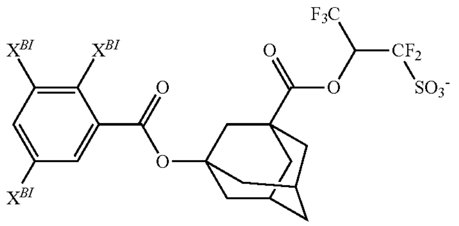
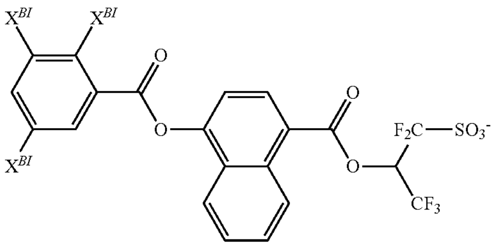
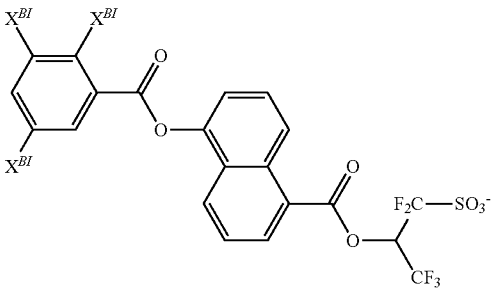
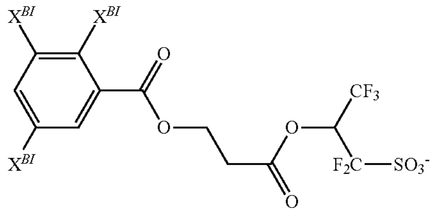

-continued
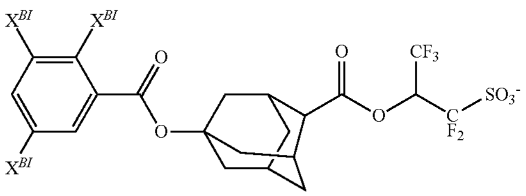
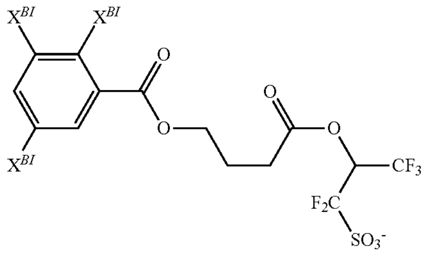
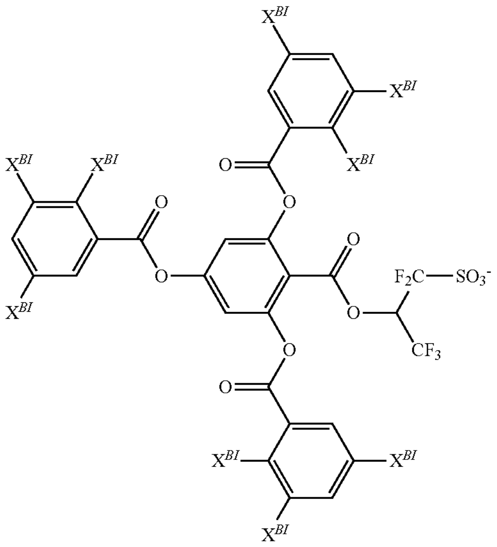
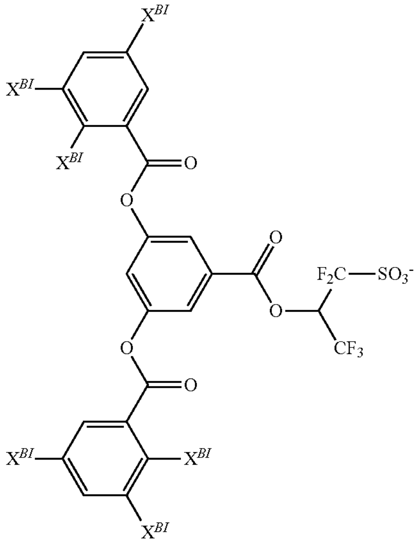
-continued
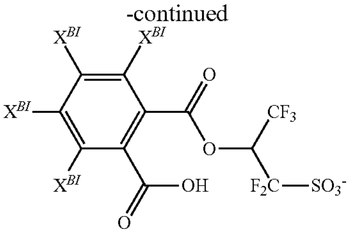
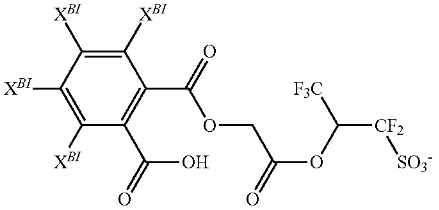
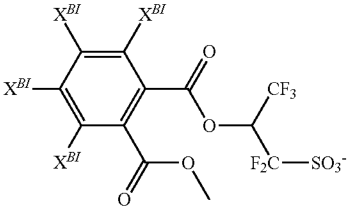
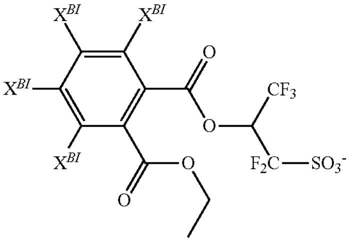
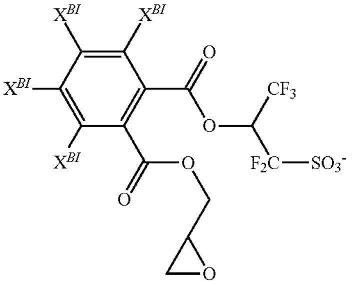
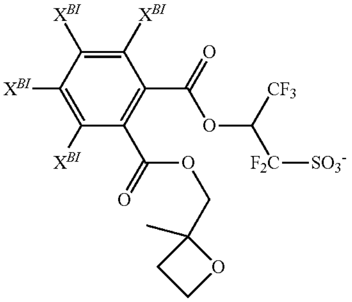
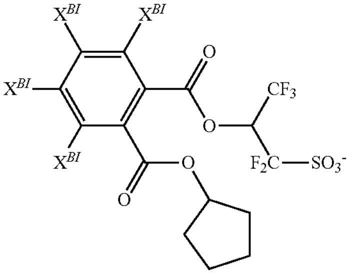

-continued
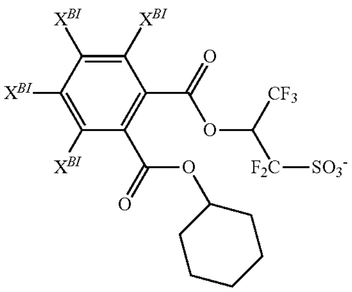
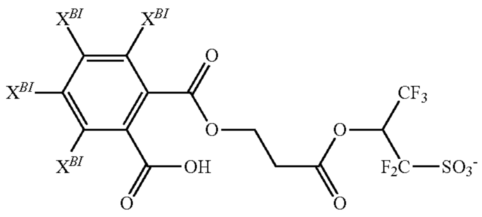
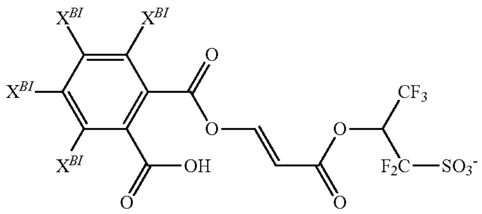
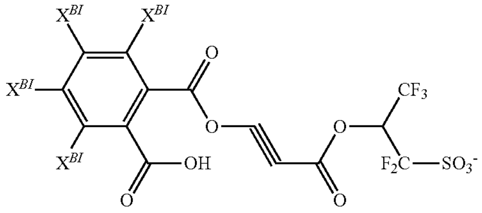
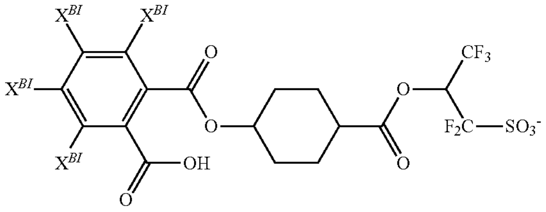
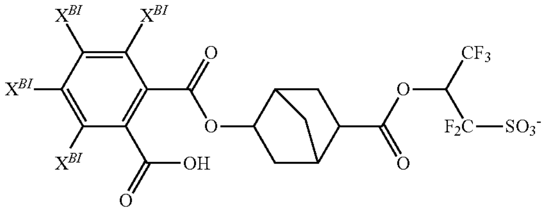
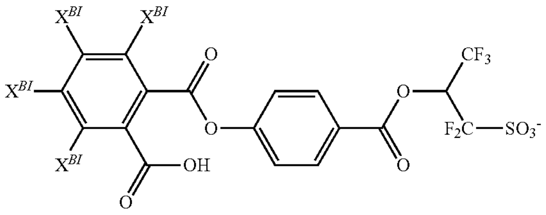
-continued
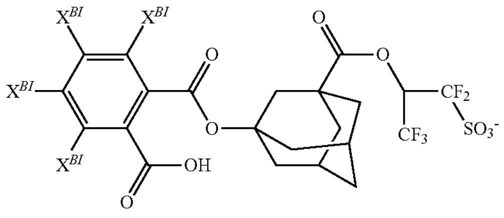
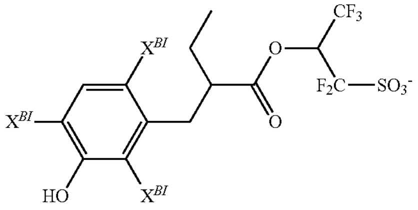
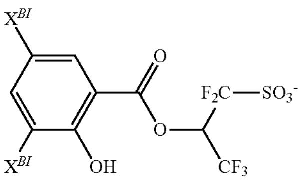
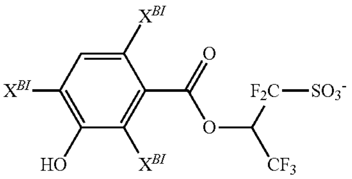
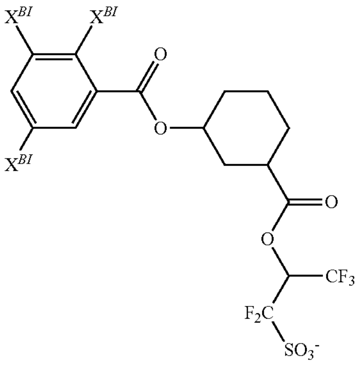
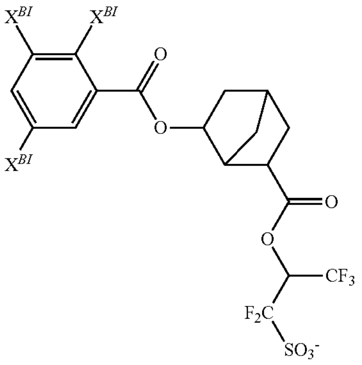

-continued
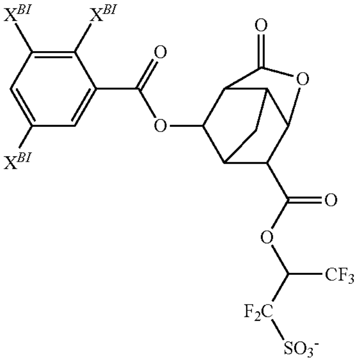
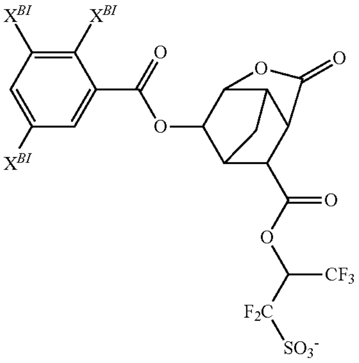
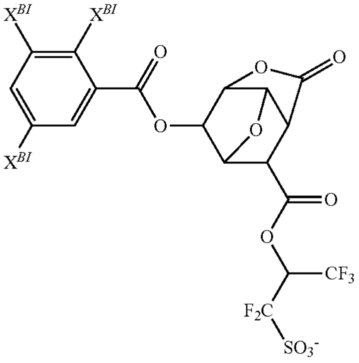
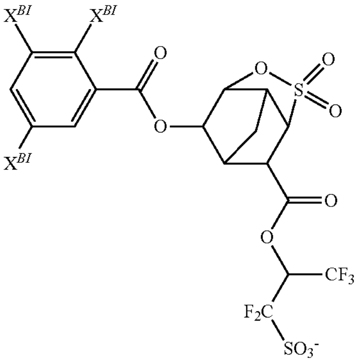
-continued
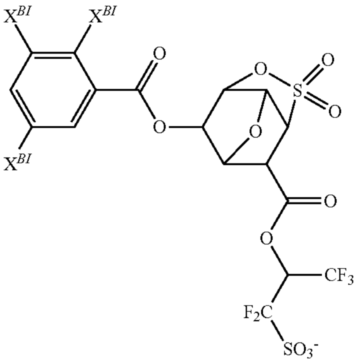
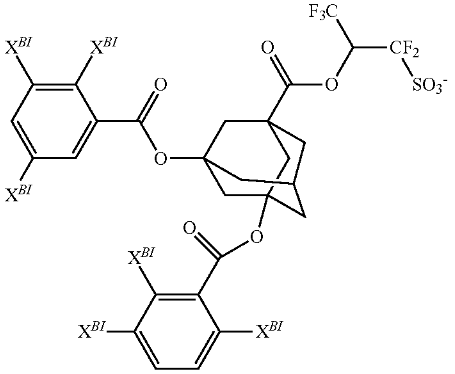
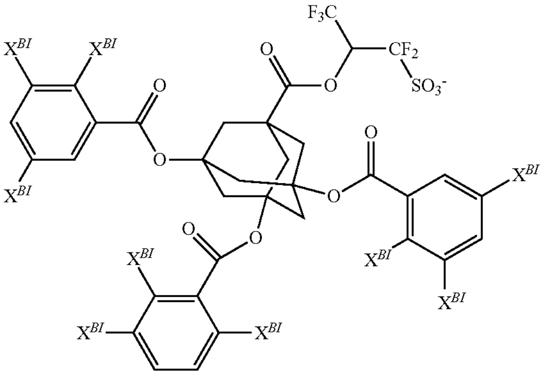
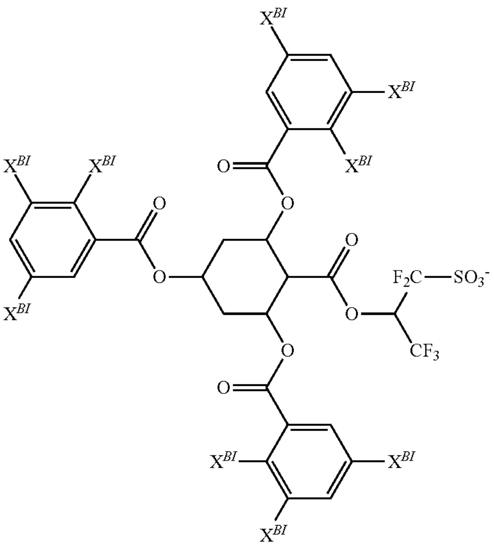

-continued
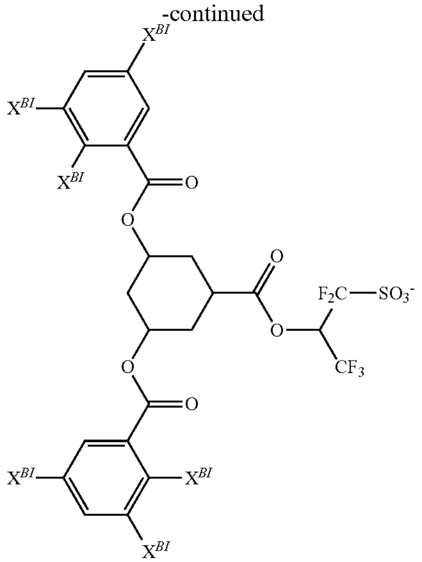
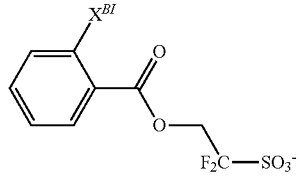
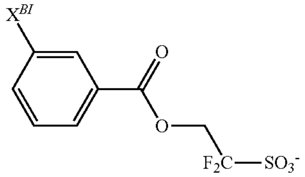
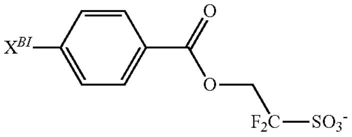
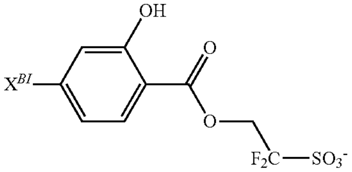
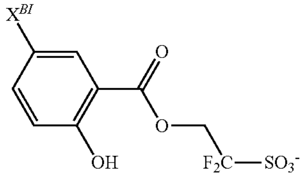
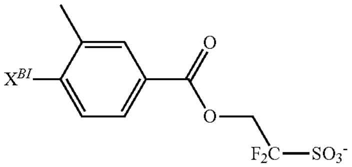
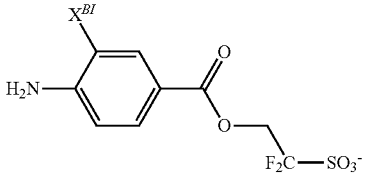
-continued
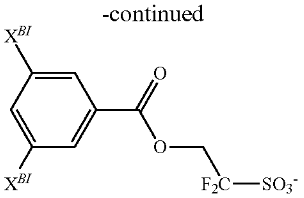
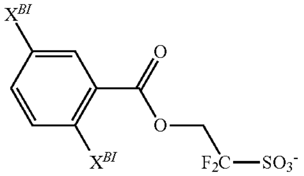
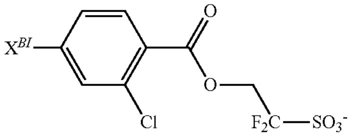
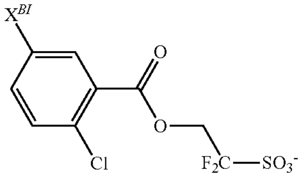
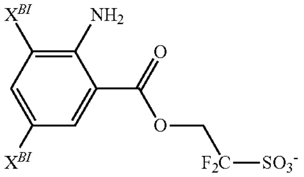
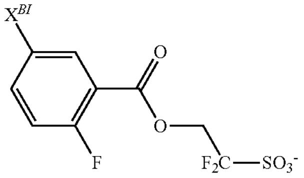
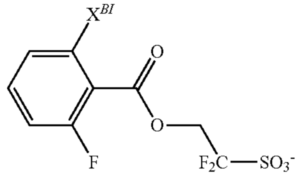
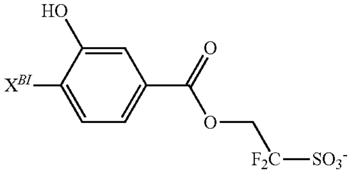
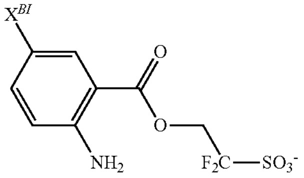
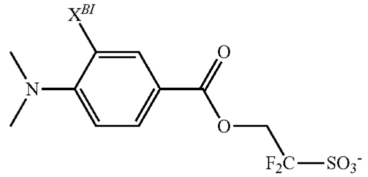

-continued
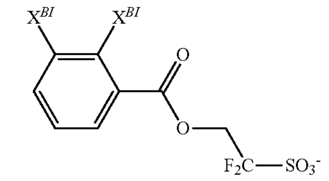
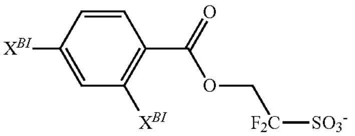
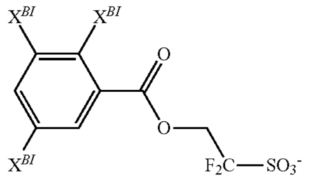
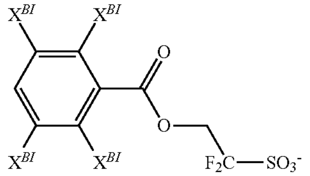
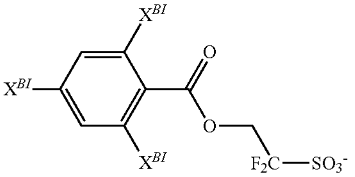
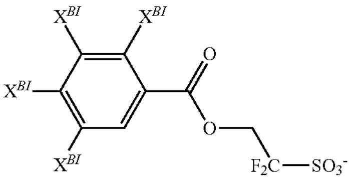
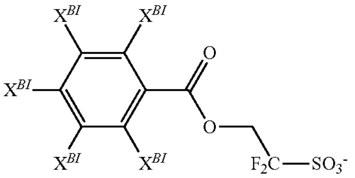
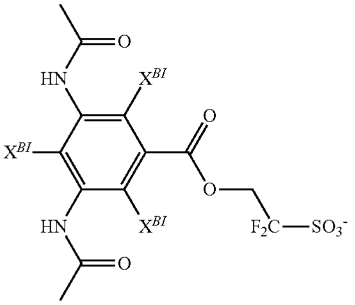
-continued
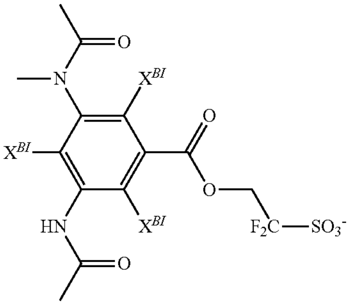
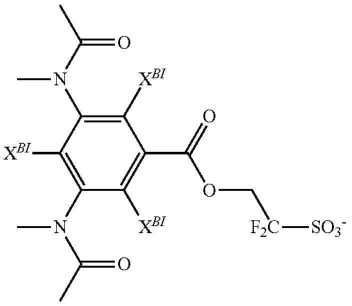
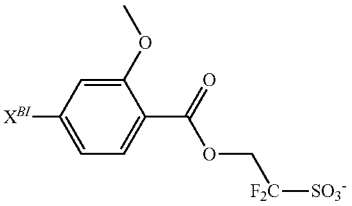
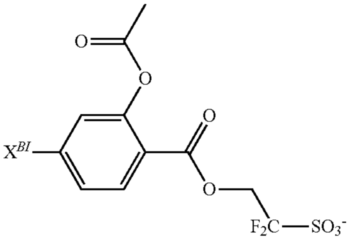
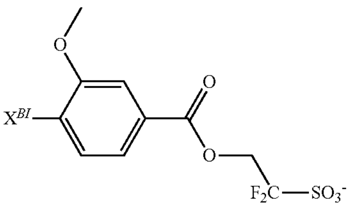
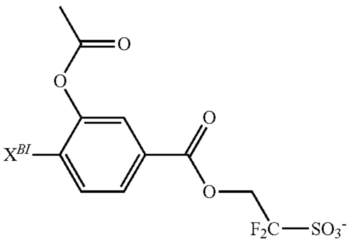

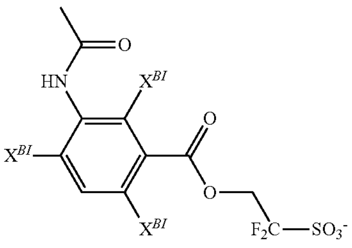
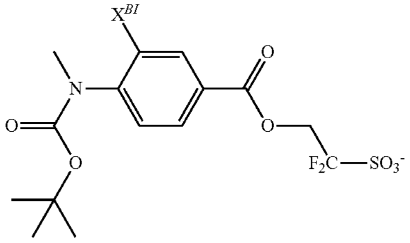
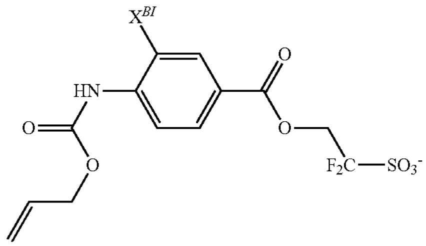
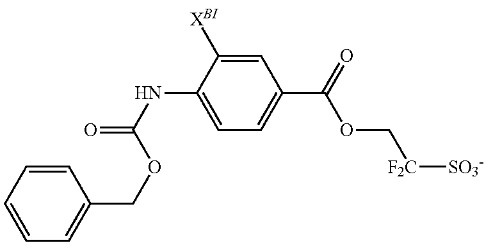
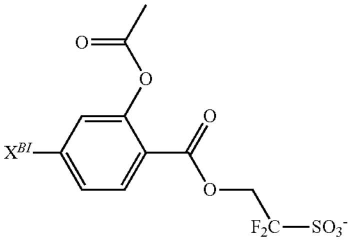
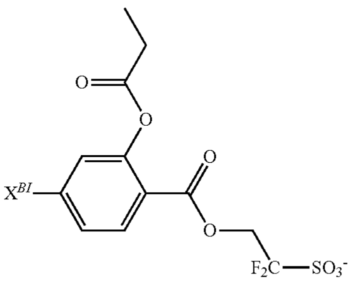
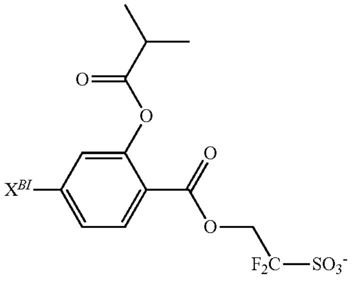
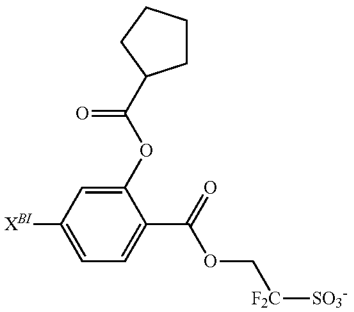
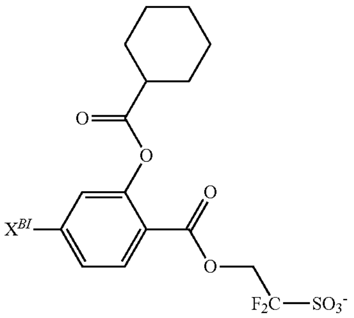
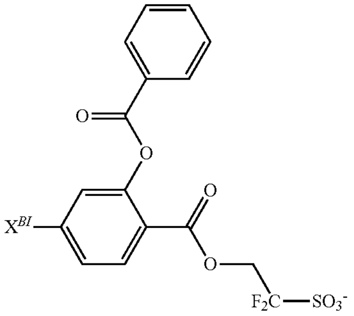
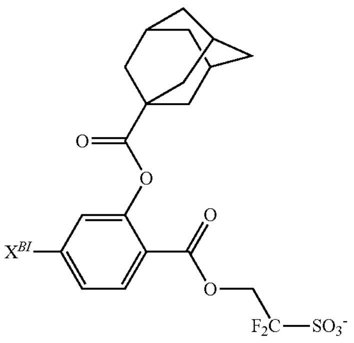

-continued
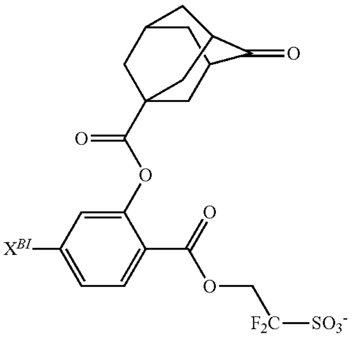
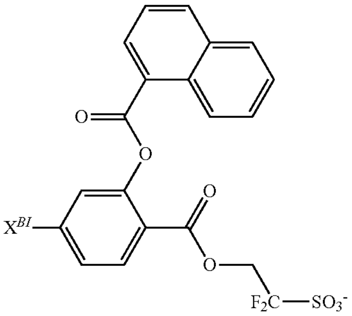
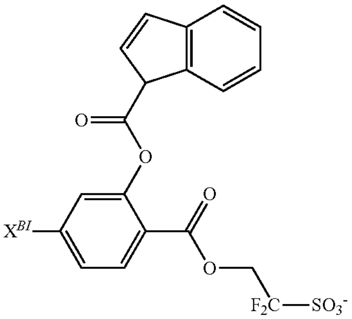
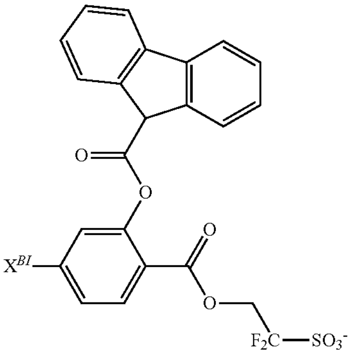
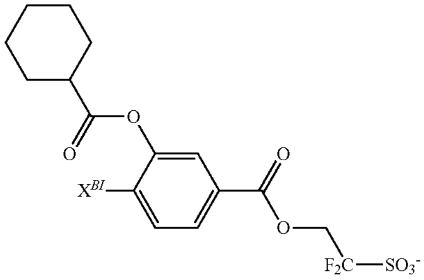
-continued
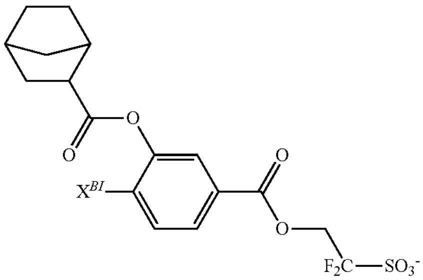
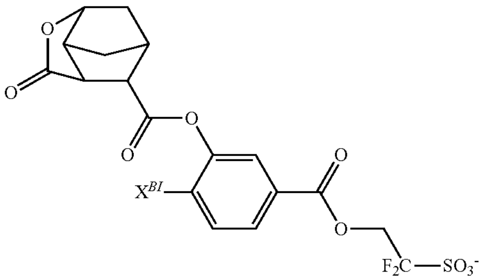
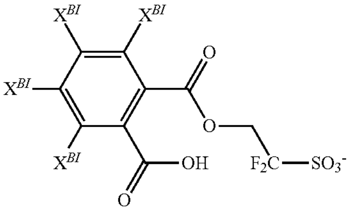
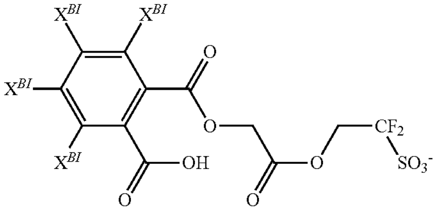
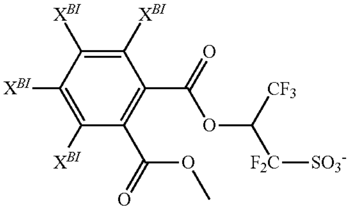
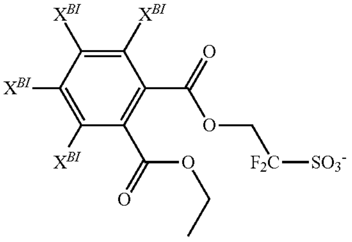
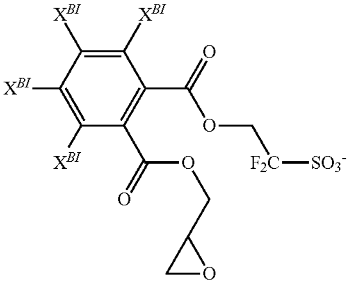

-continued
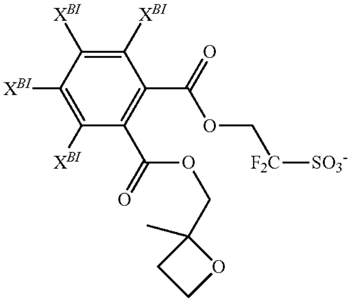
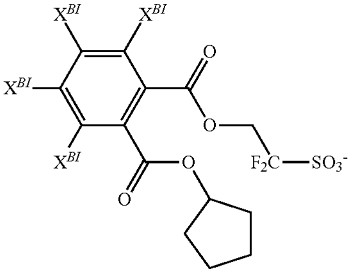
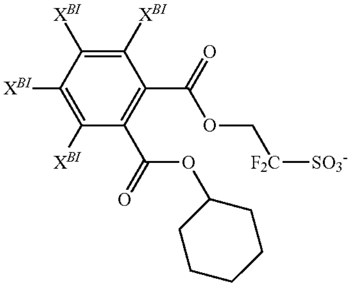
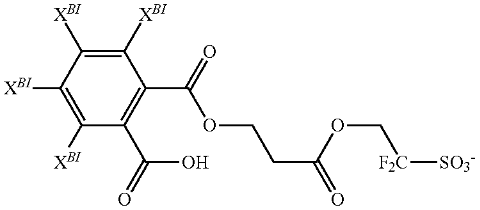
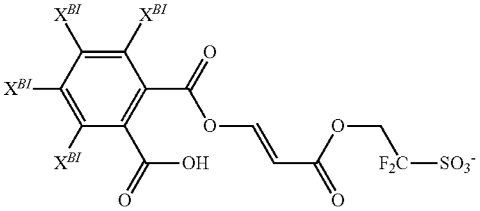
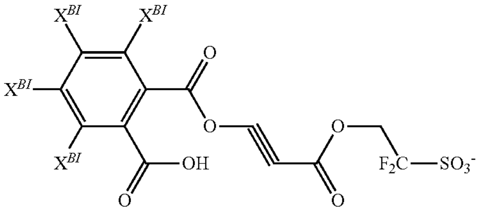
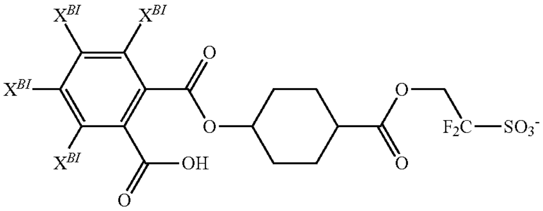
-continued
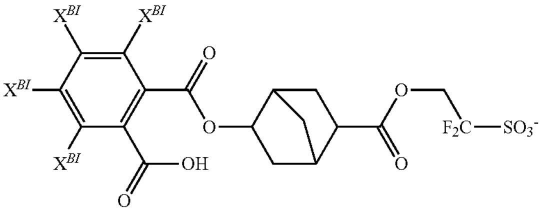
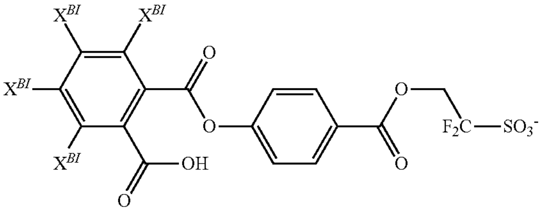
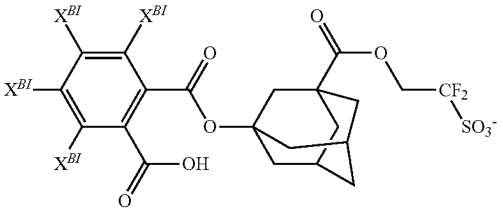
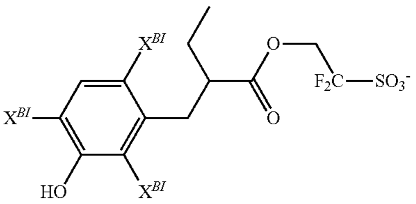
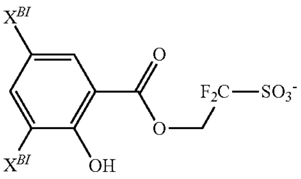
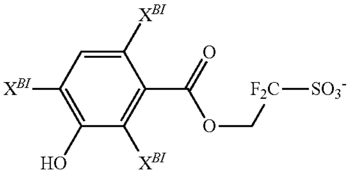
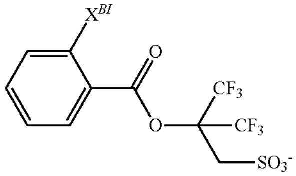
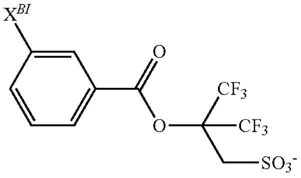

-continued
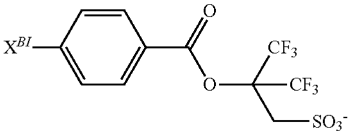
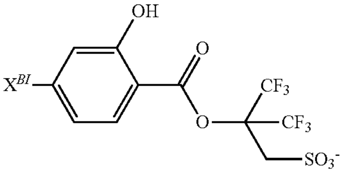
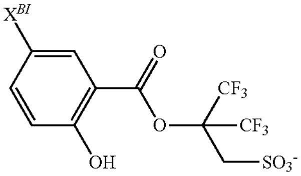
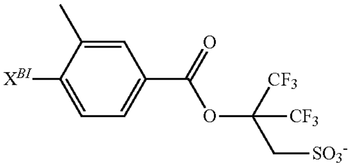
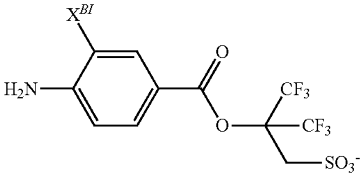
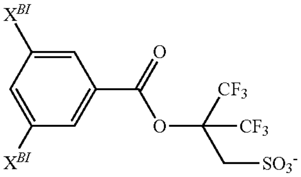
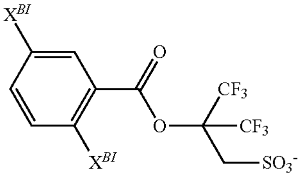
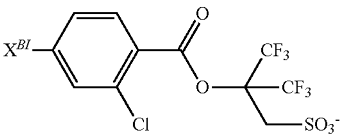
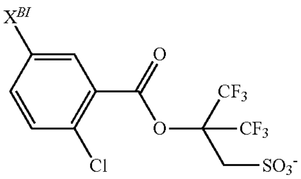
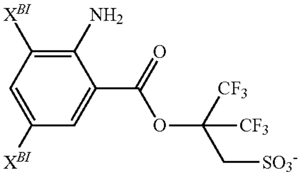
-continued
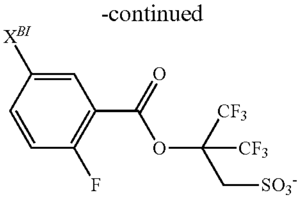
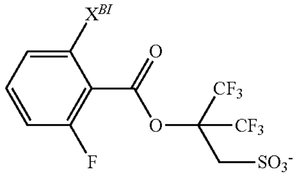
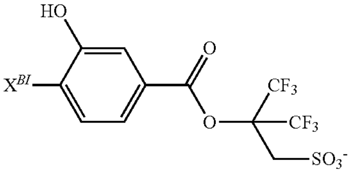
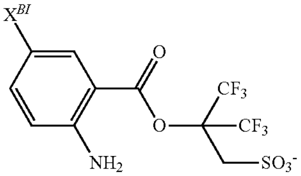
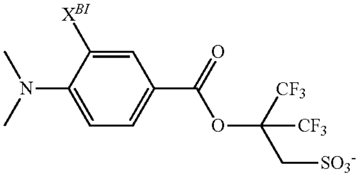
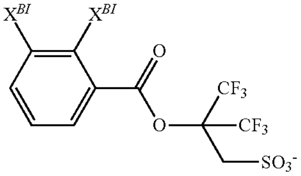
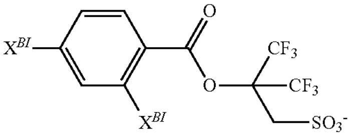
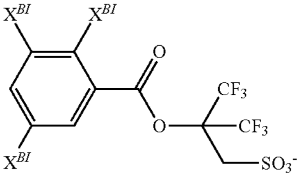
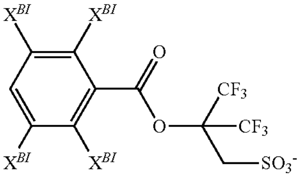
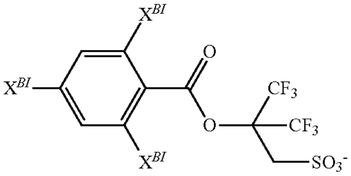

-continued
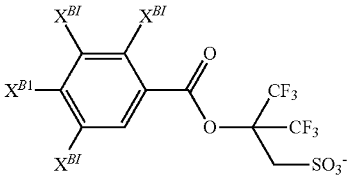
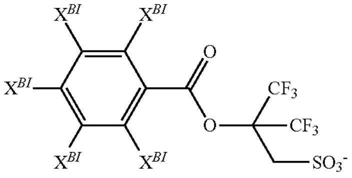
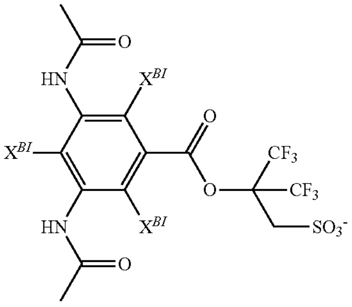
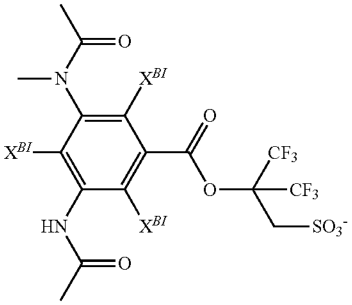
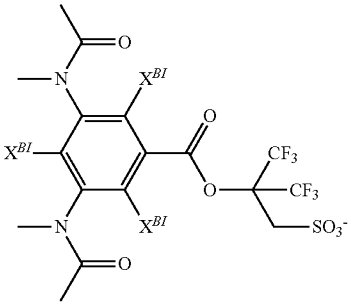
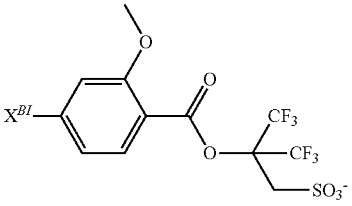
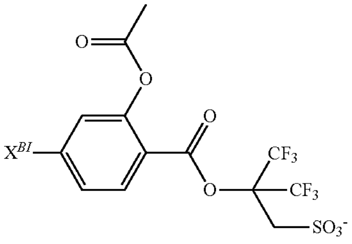
-continued
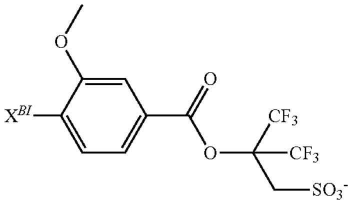
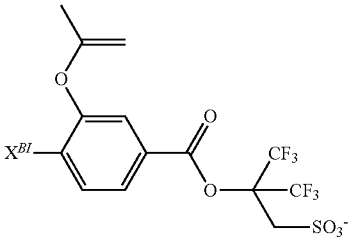
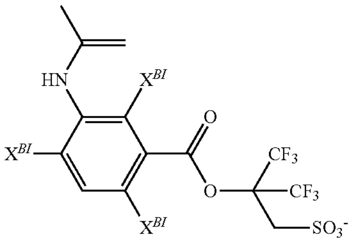
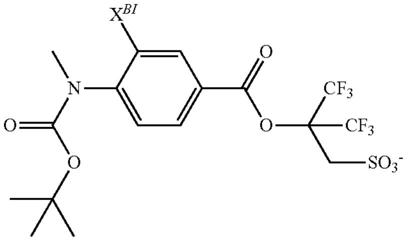
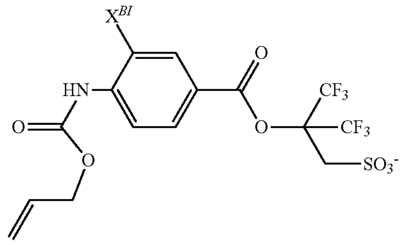
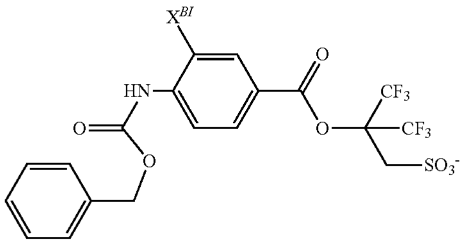
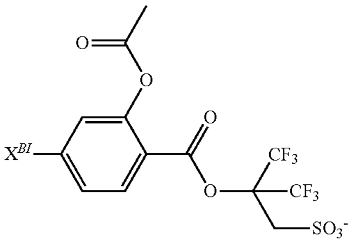

-continued
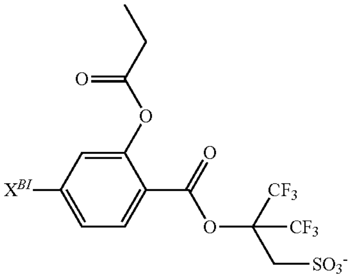
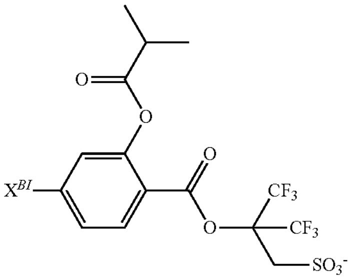
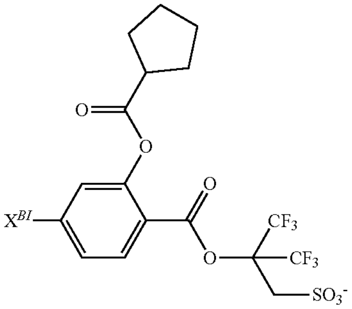
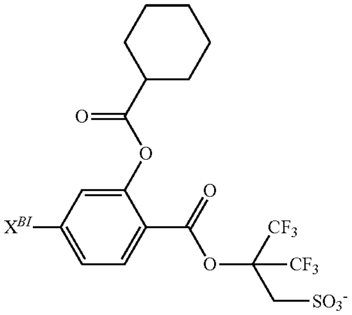
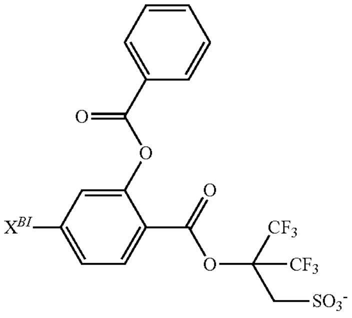
-continued
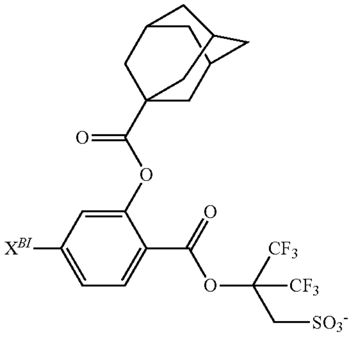
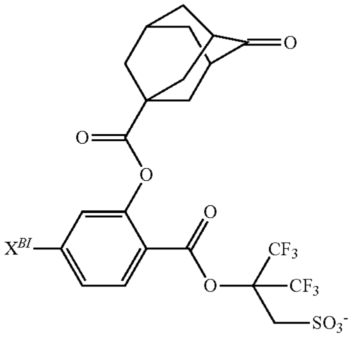
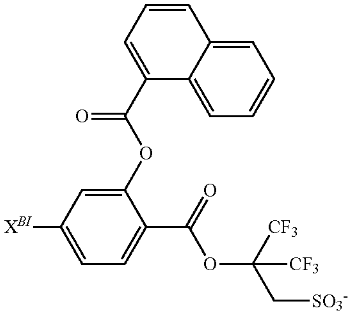
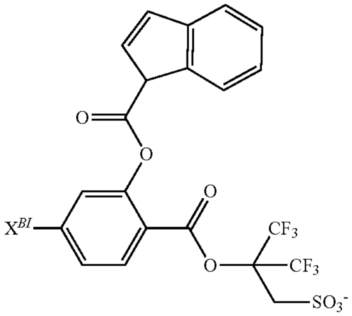
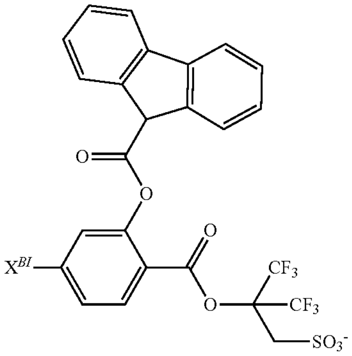

-continued
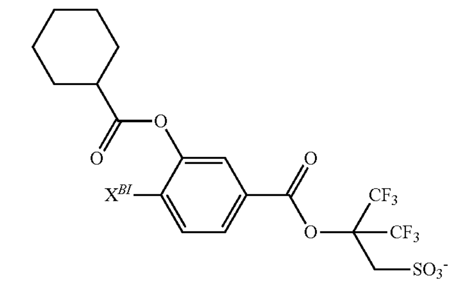
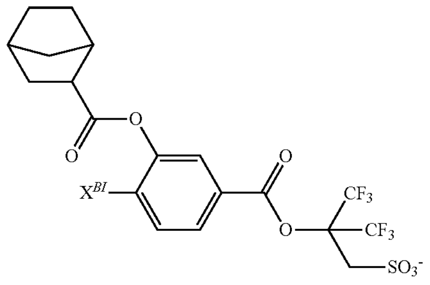
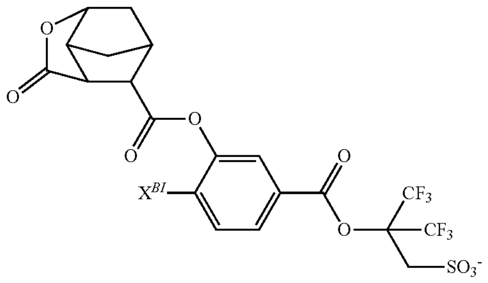
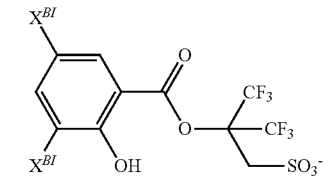
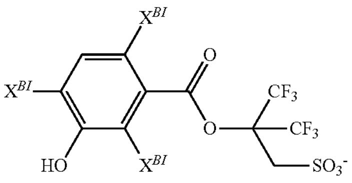
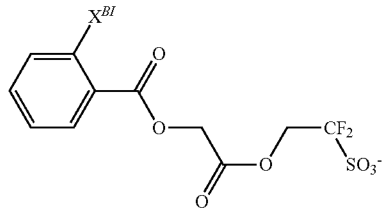
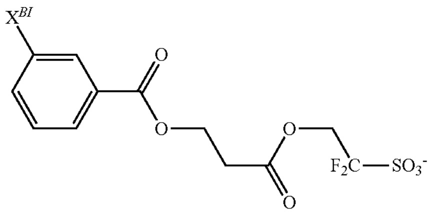
-continued
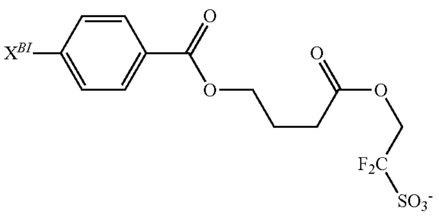
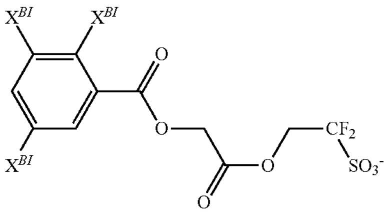
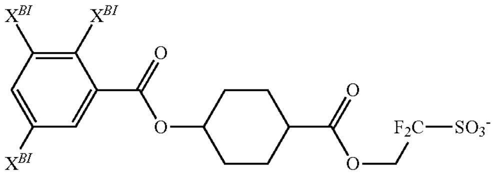
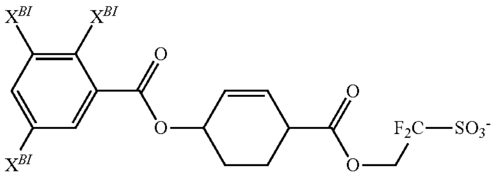
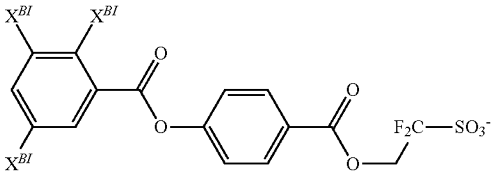
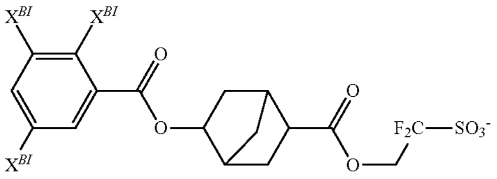
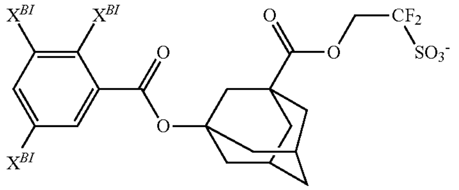
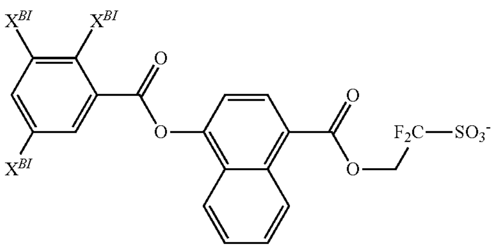

-continued
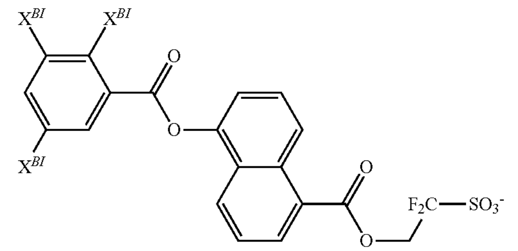
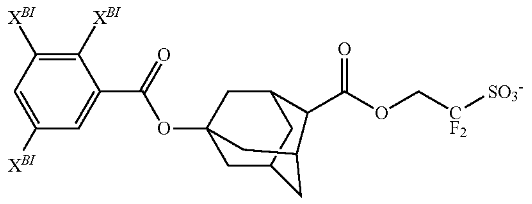
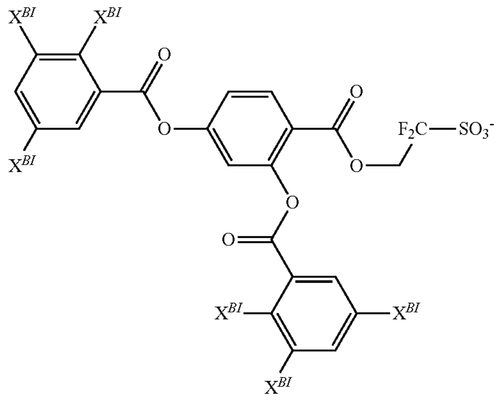
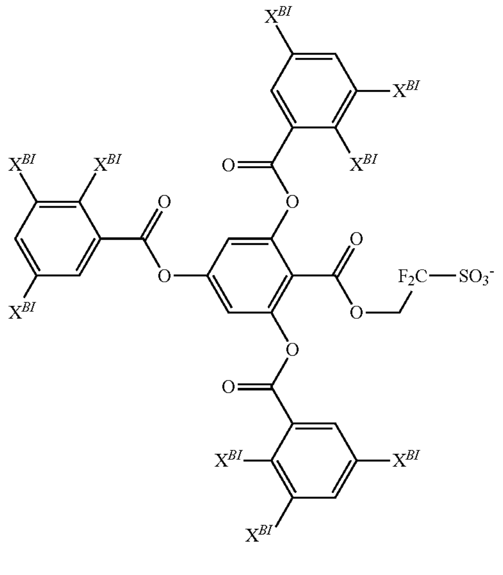
-continued
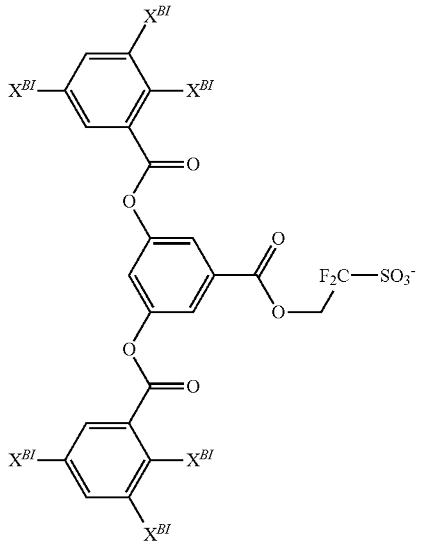
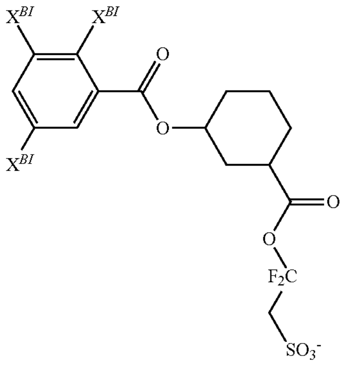
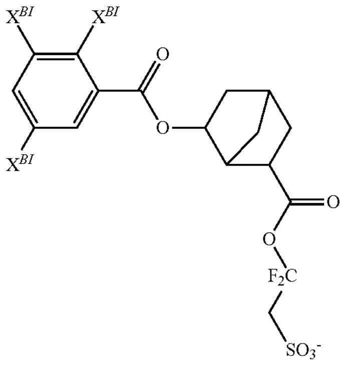
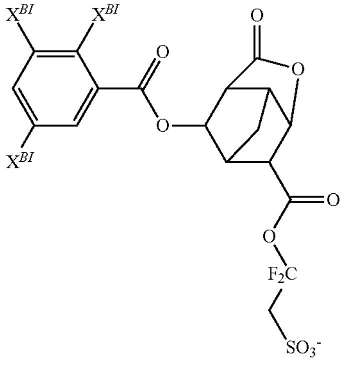

-continued
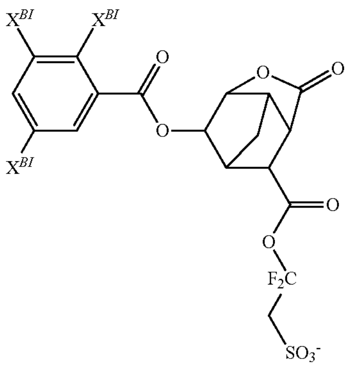
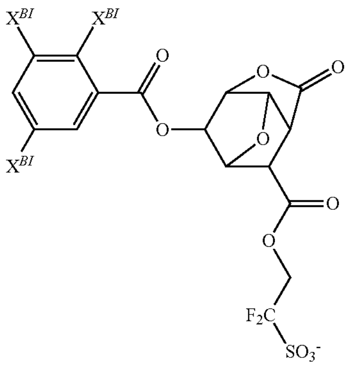
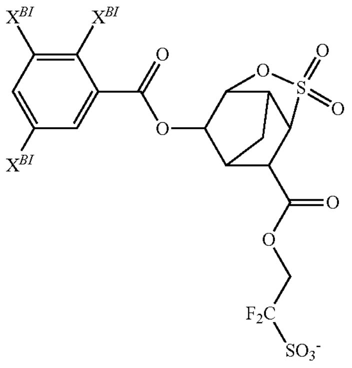
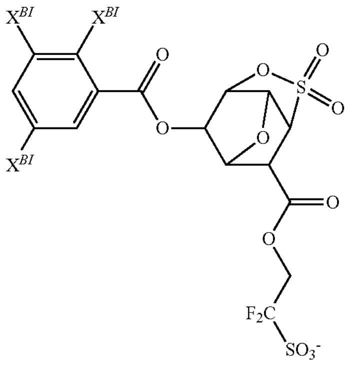
-continued
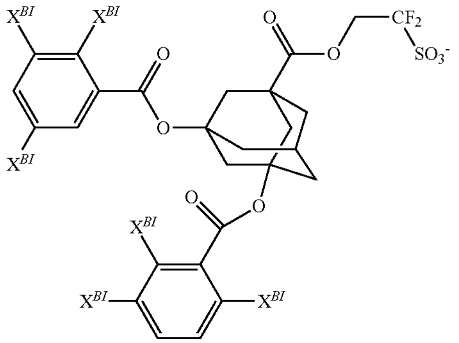
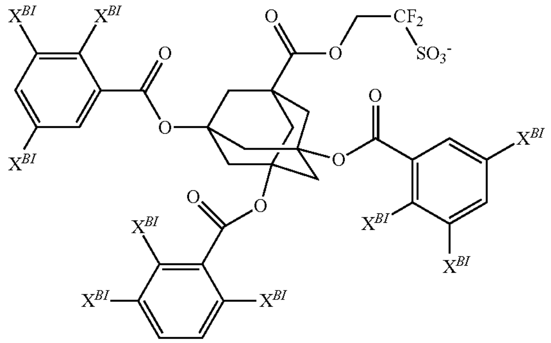
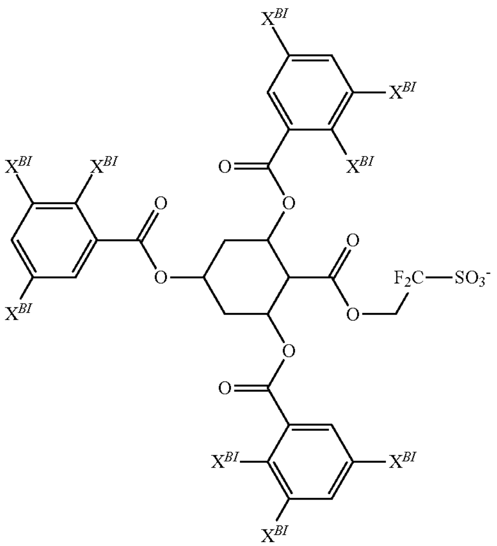

-continued
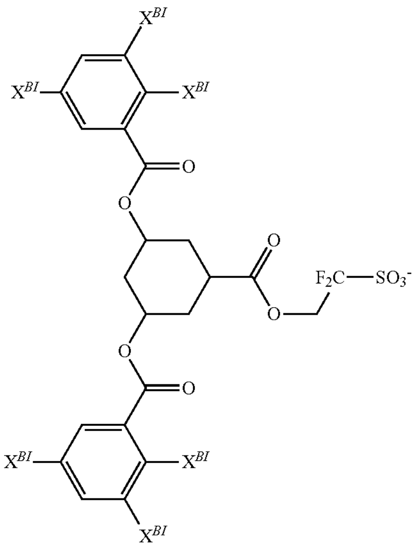
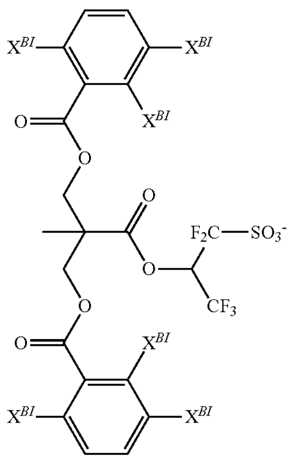
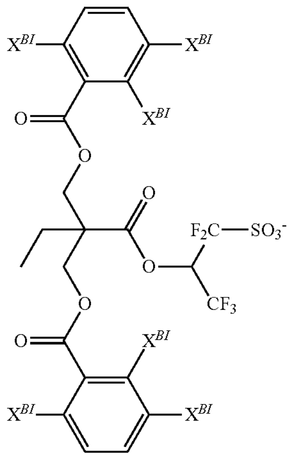
-continued
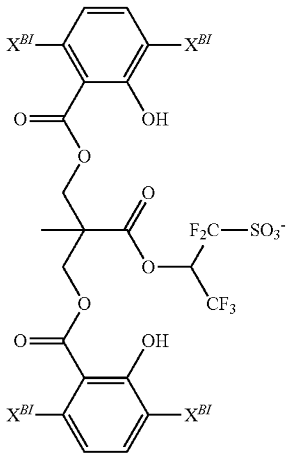
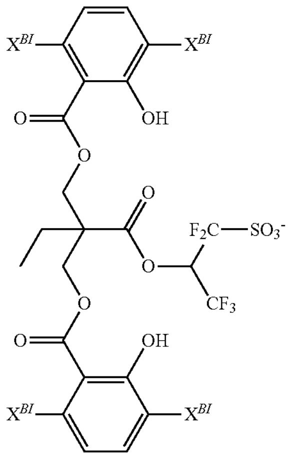
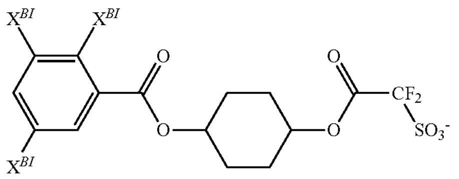
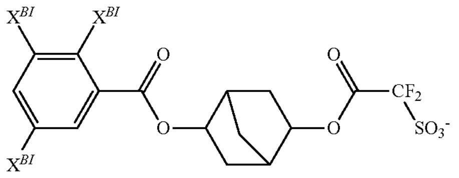
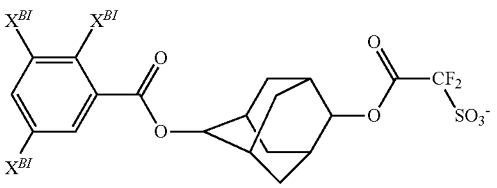
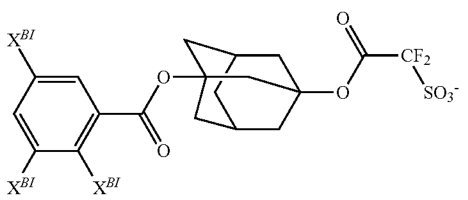

-continued
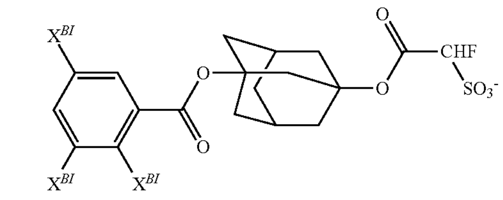
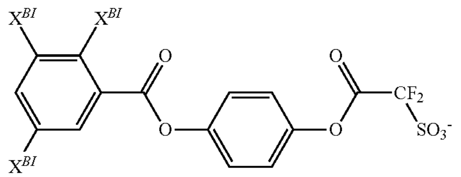
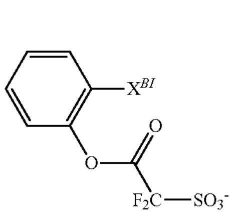
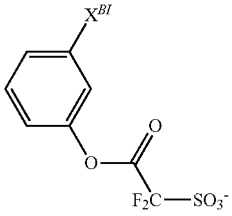
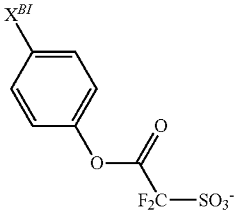
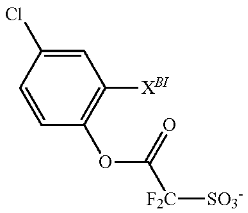
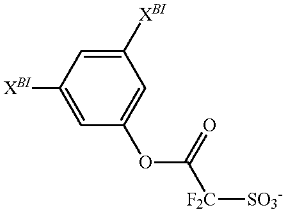
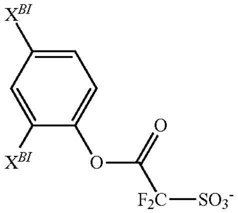
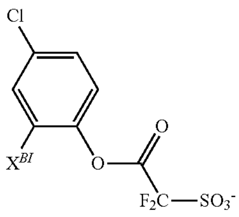
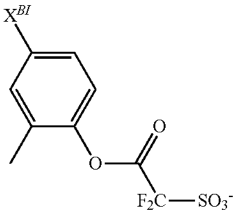
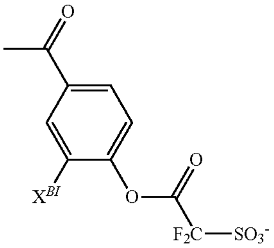
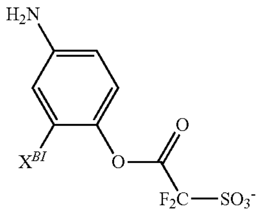
-continued
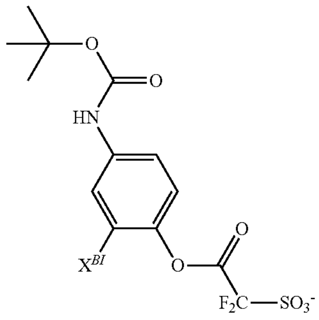
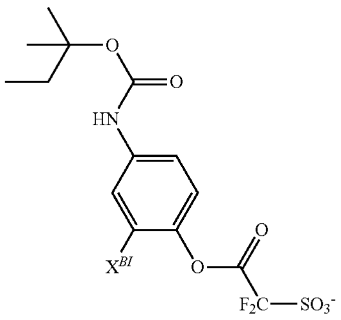
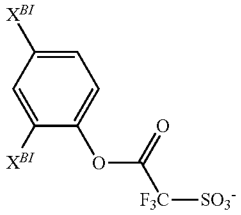
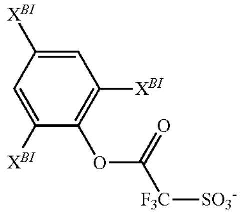
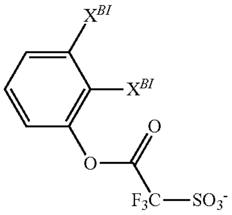
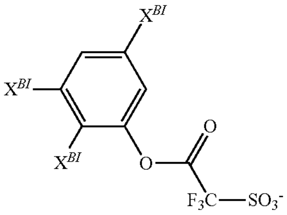
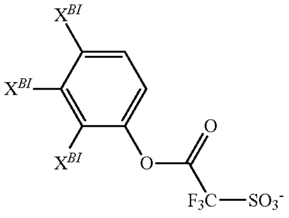
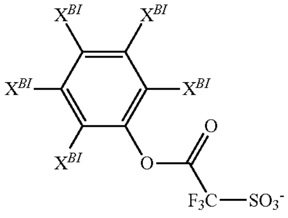
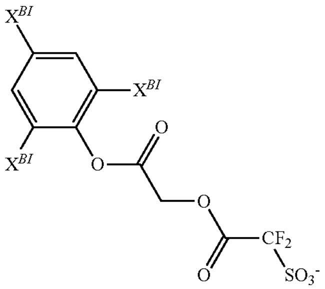

-continued
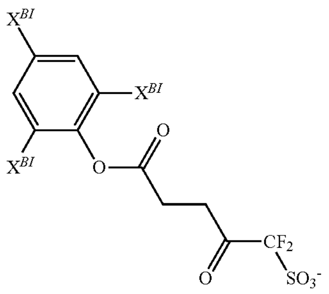
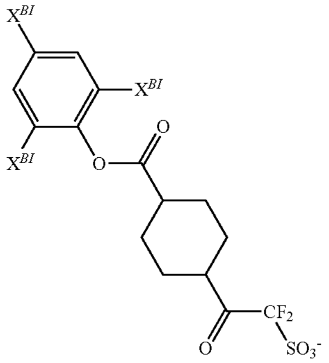
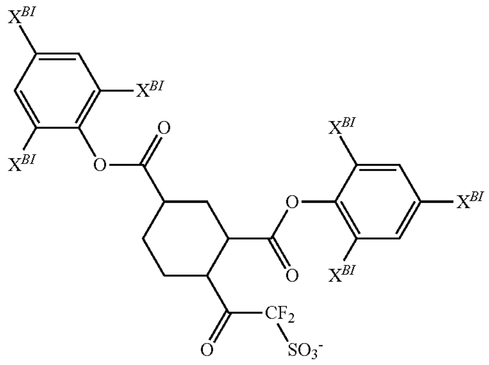
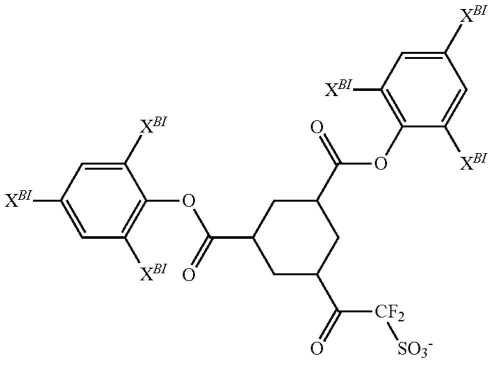
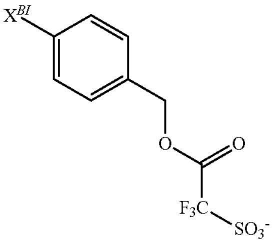
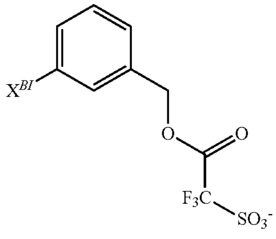
-continued
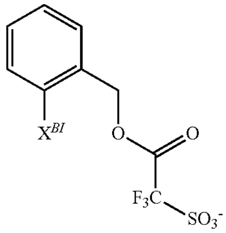
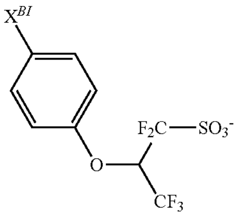
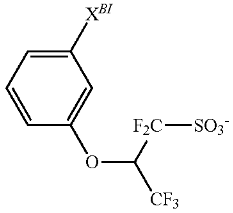
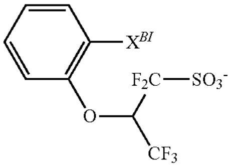
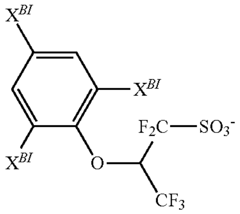
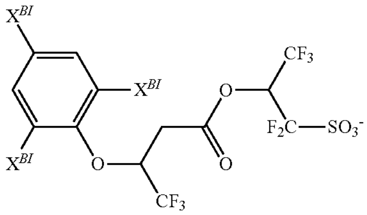
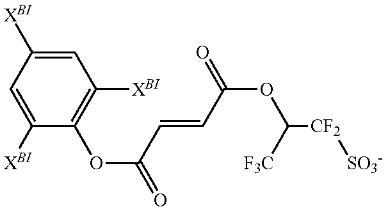
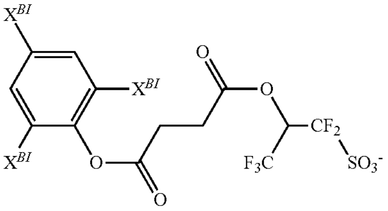
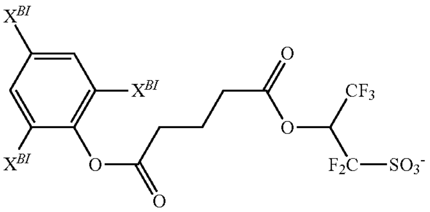
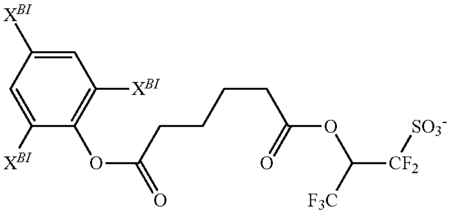

-continued
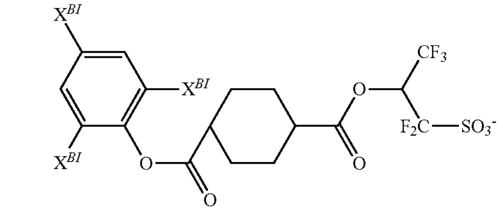
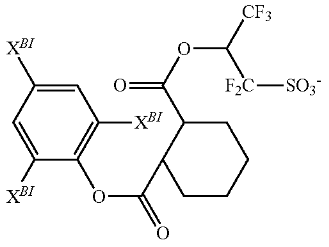
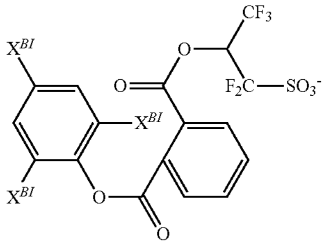
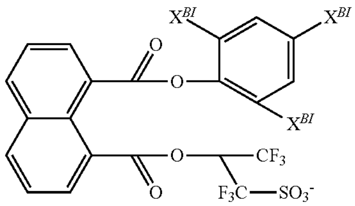
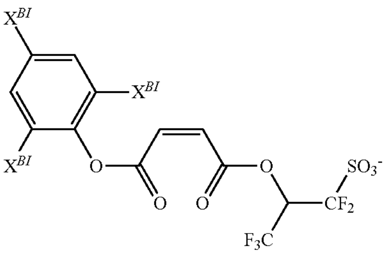
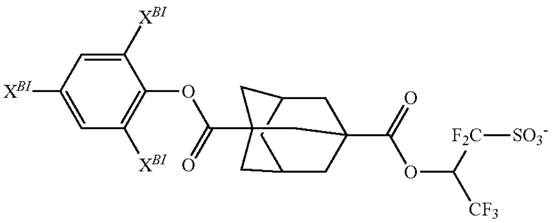
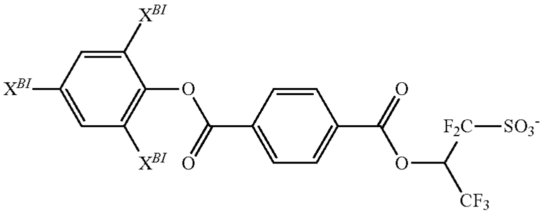
-continued
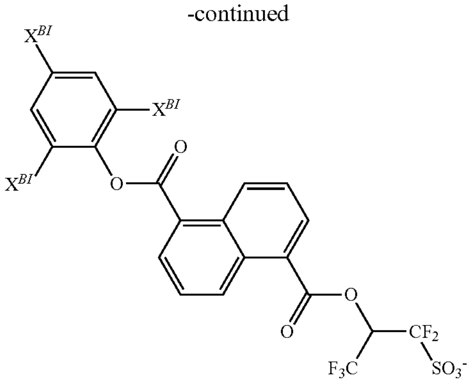
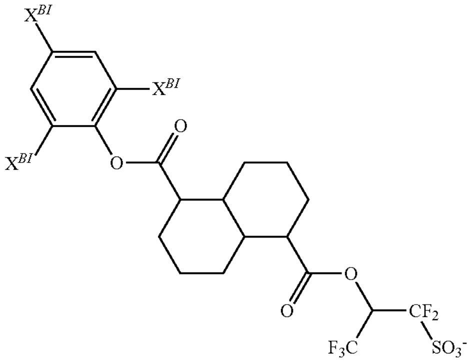
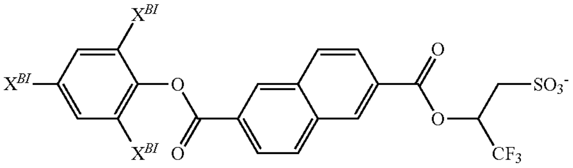
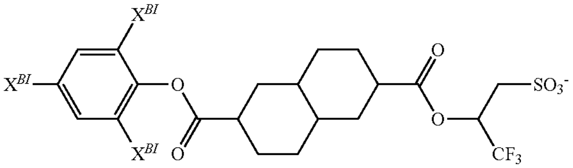
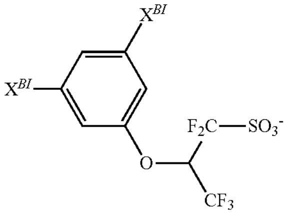
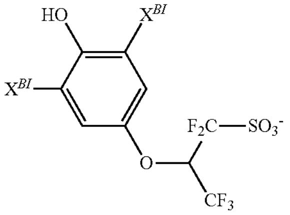
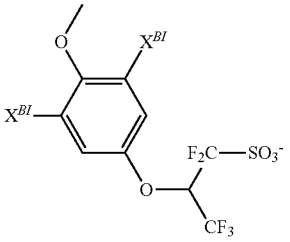

-continued
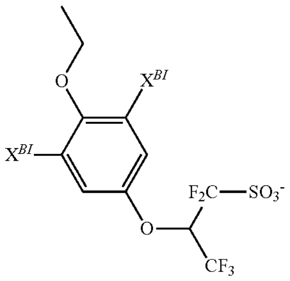
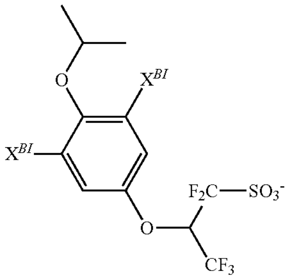
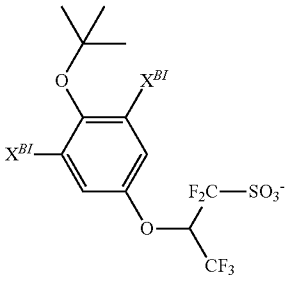
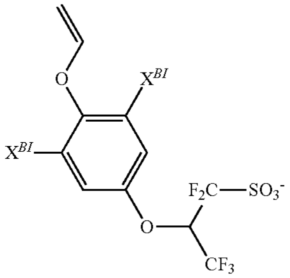
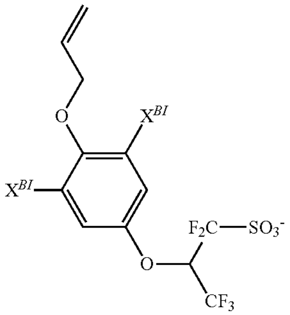
-continued
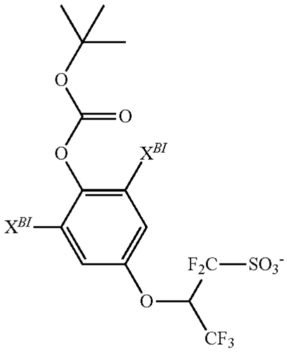
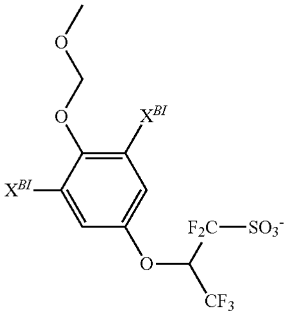
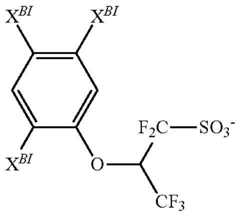
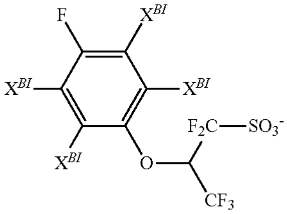
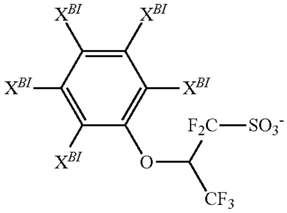
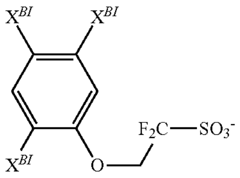
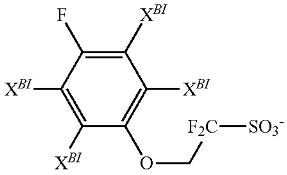

-continued
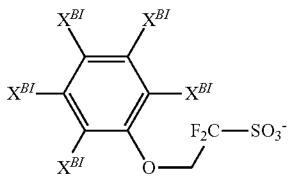
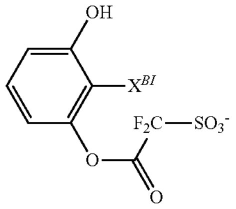
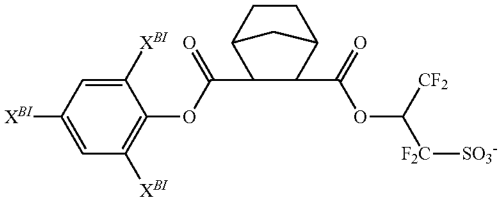
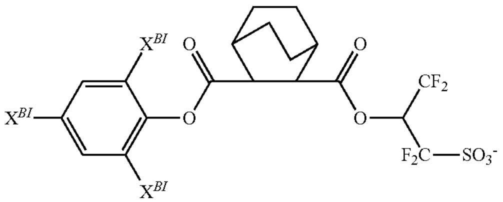
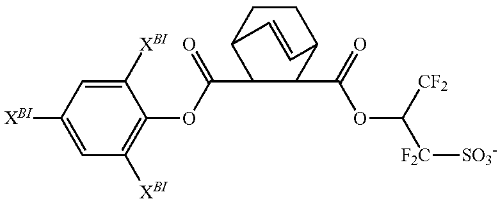
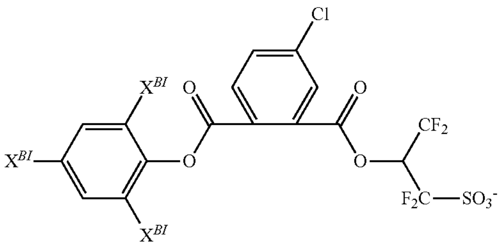
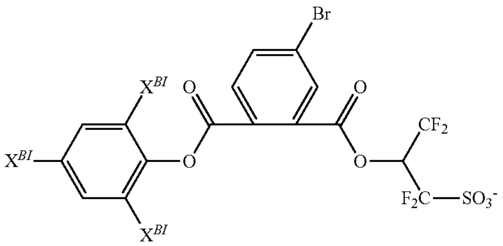
-continued
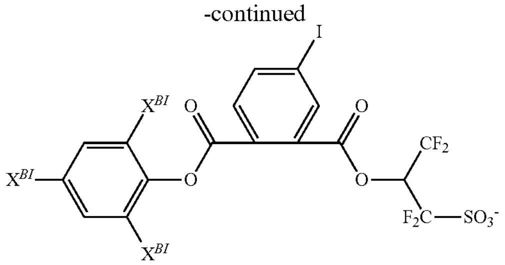
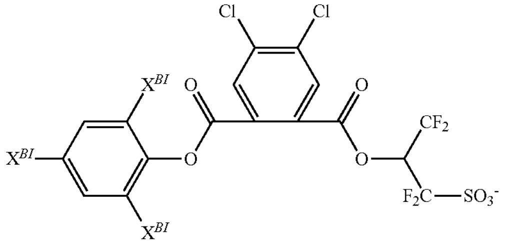
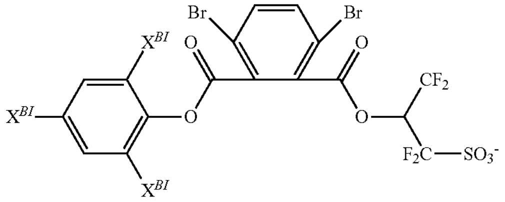
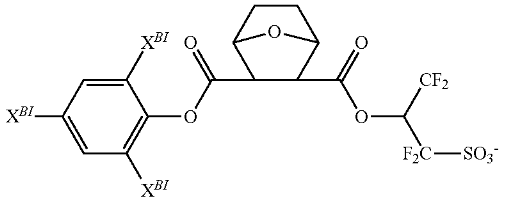
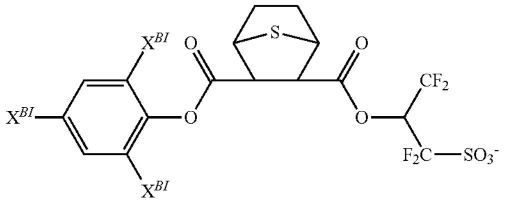
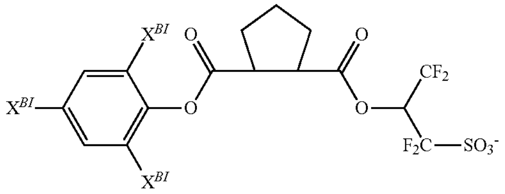
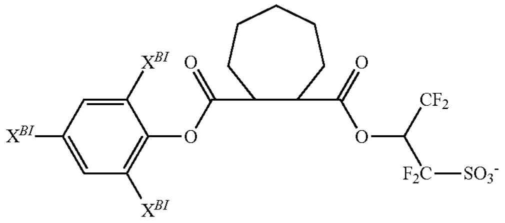
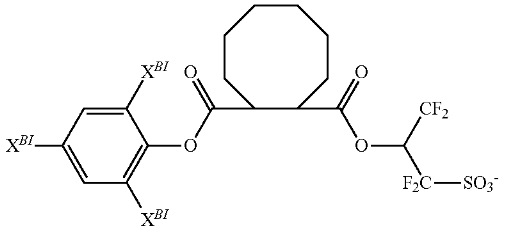

-continued
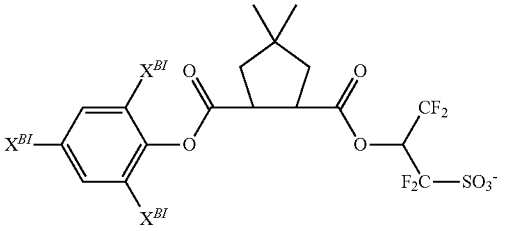
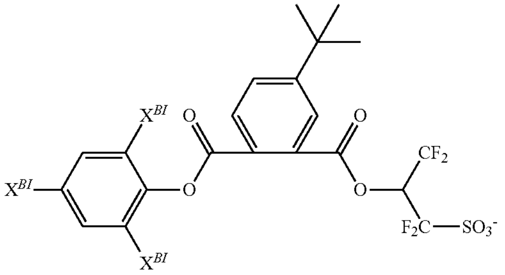
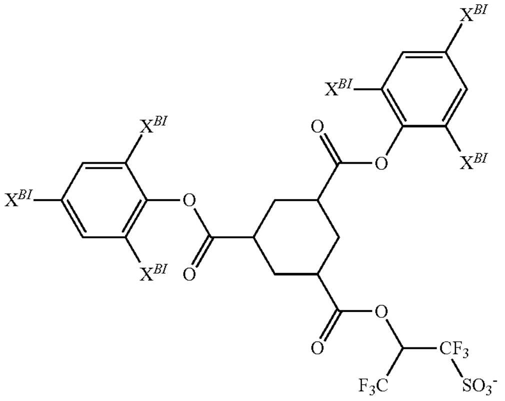
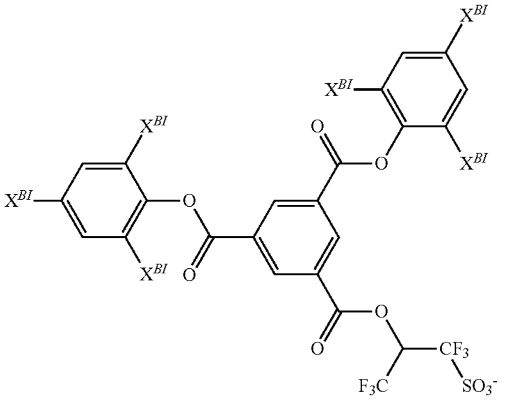
-continued
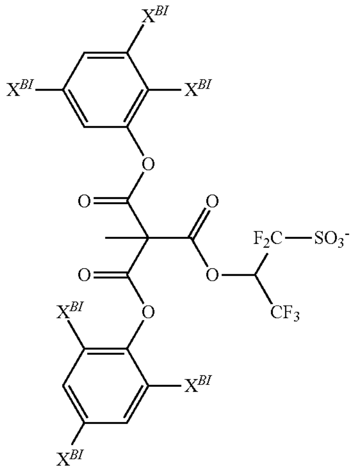
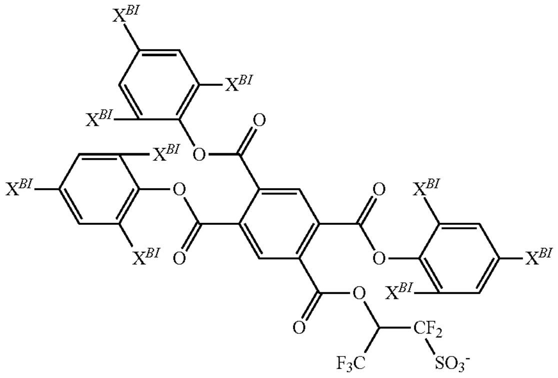
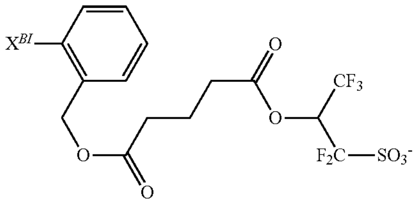
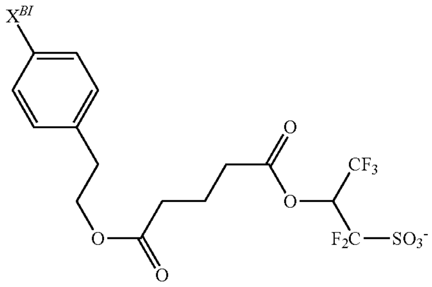
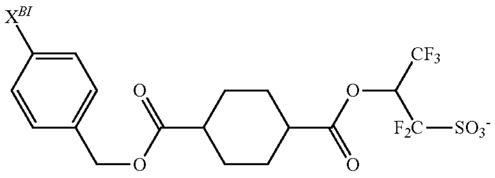

-continued
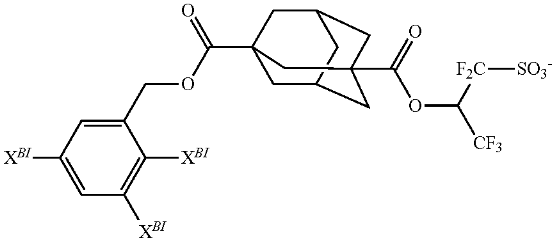
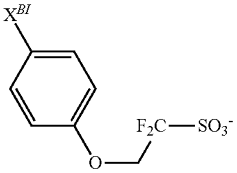
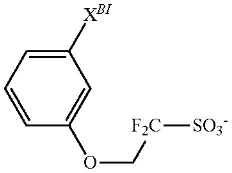
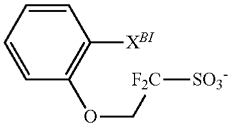
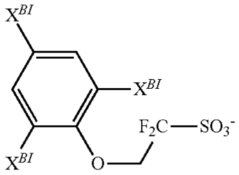
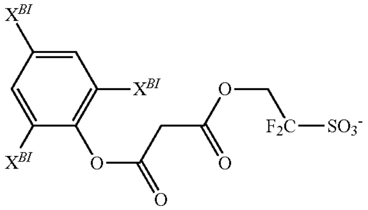
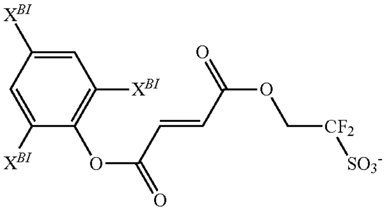
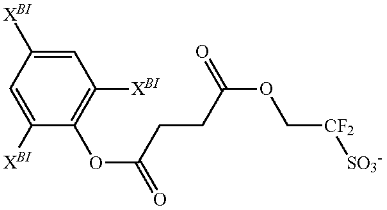
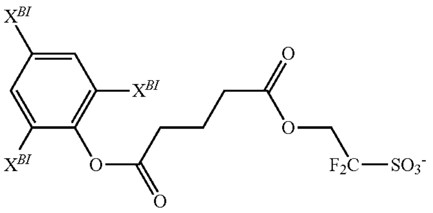
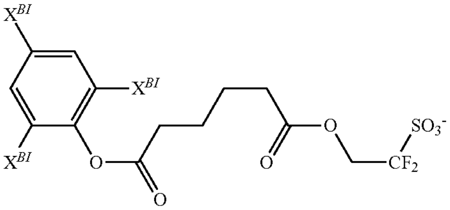
-continued
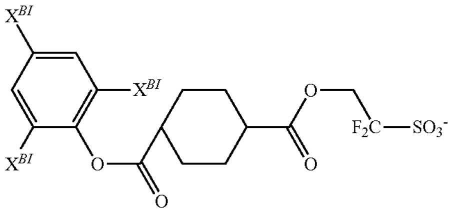
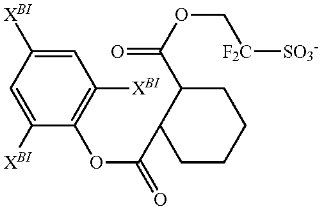
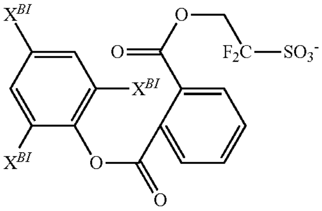
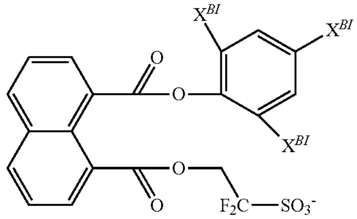
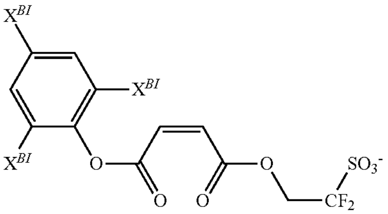
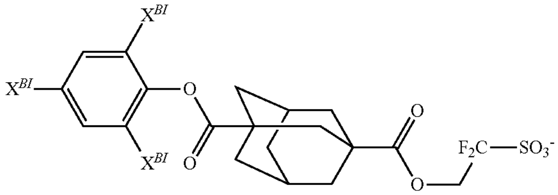
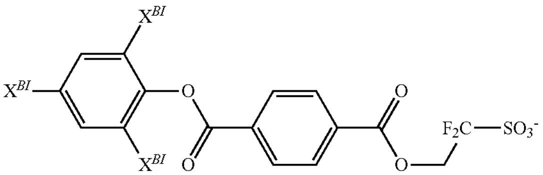
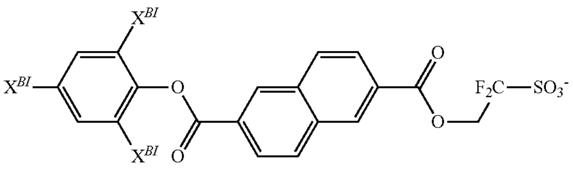

-continued
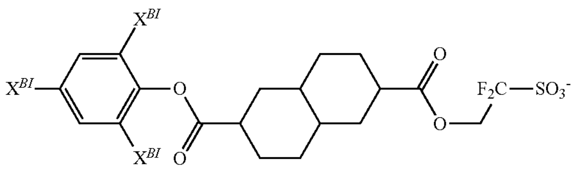
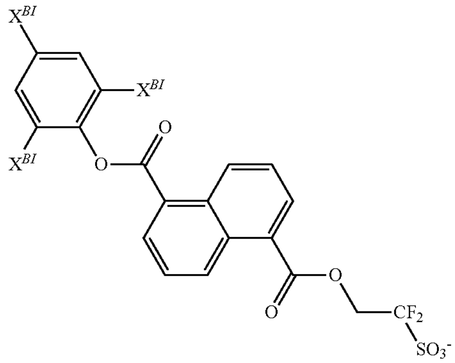
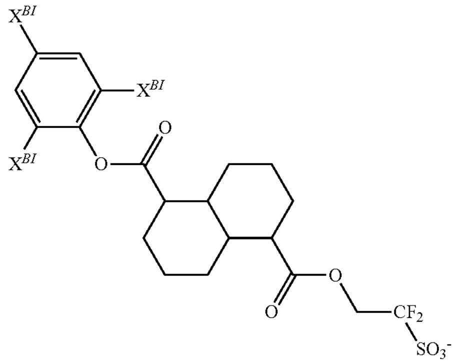
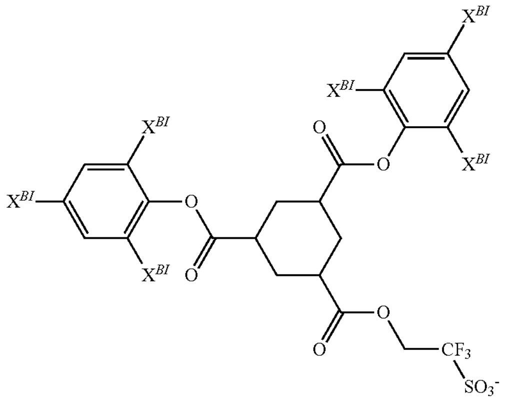
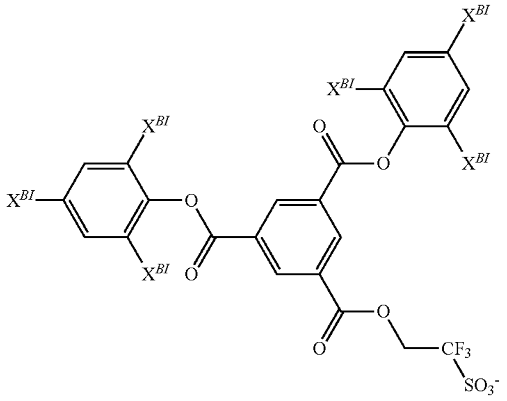
-continued
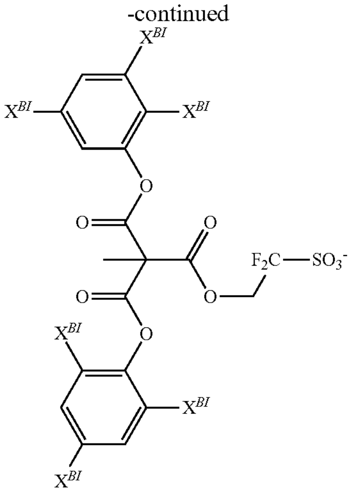
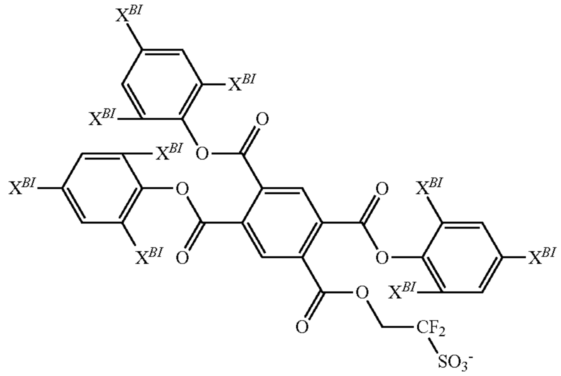
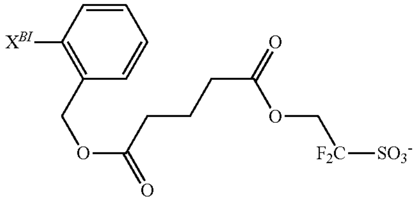
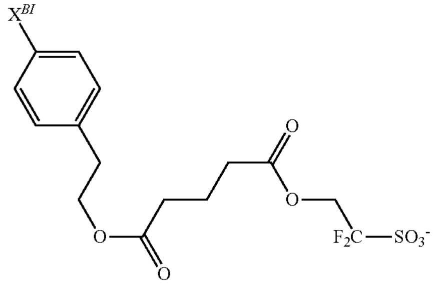
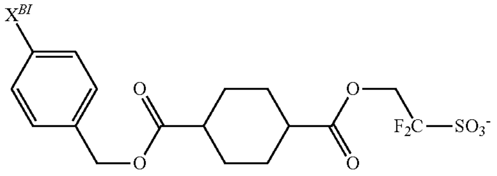
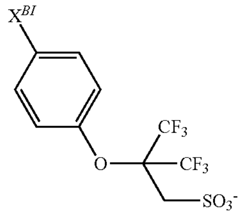
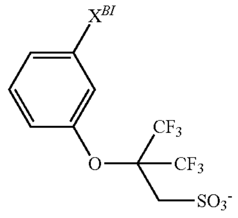

-continued
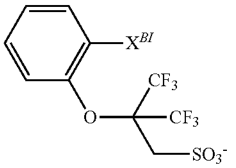
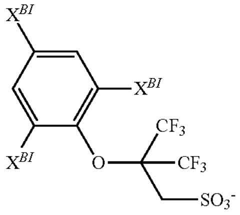
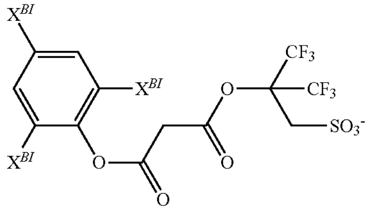
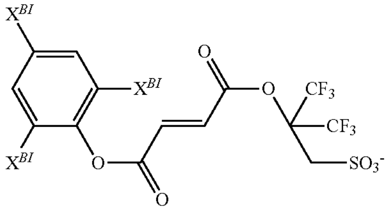
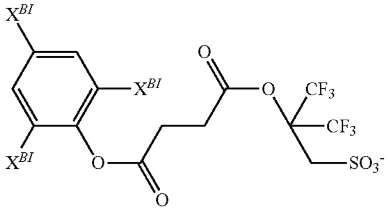
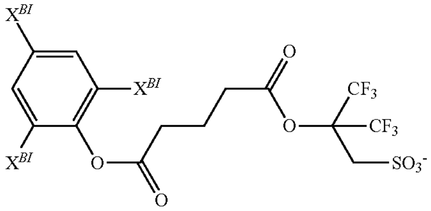
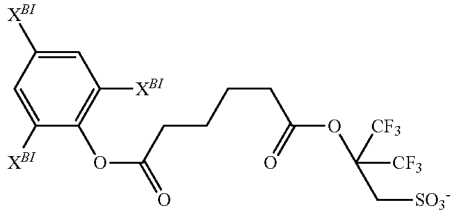
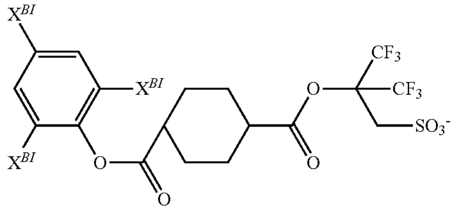
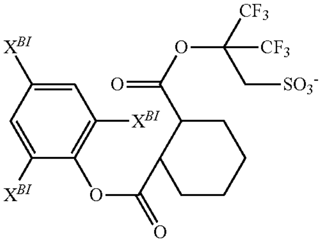
-continued
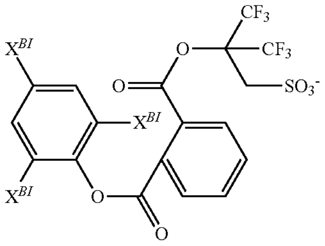
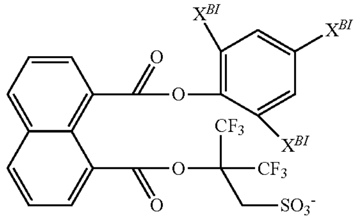
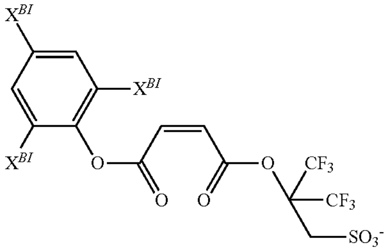
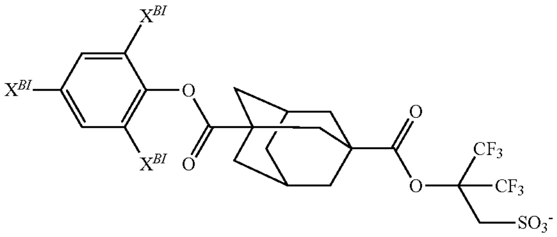
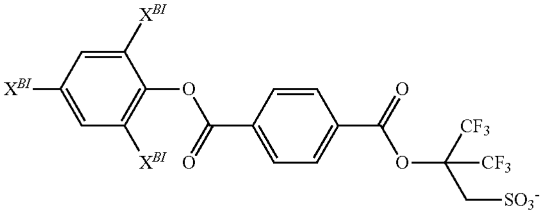
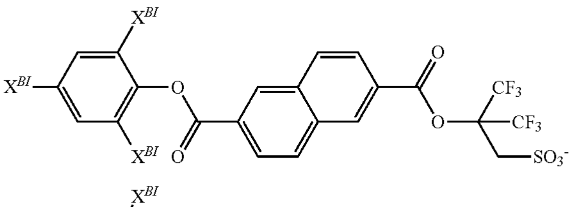
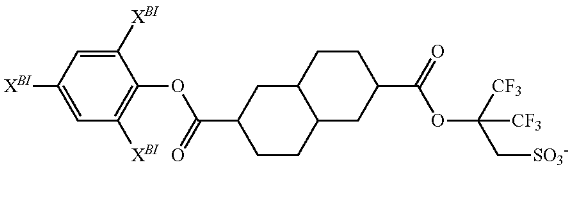

-continued

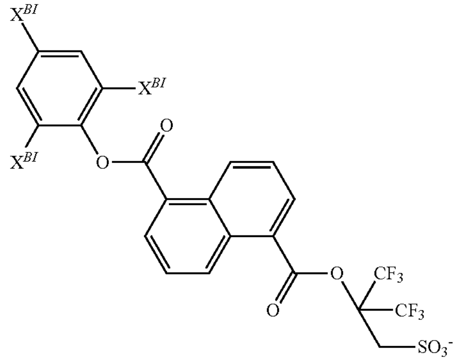

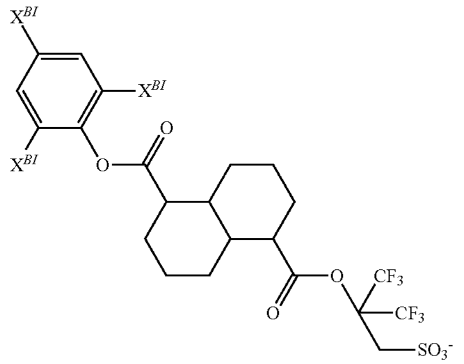

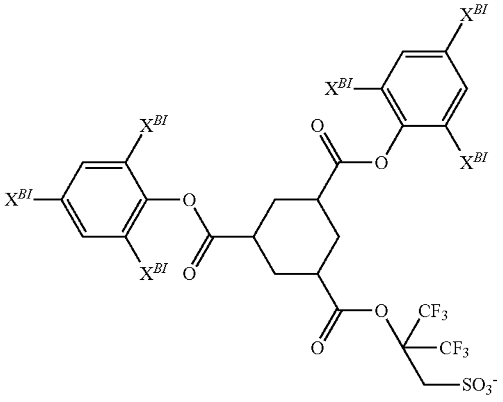

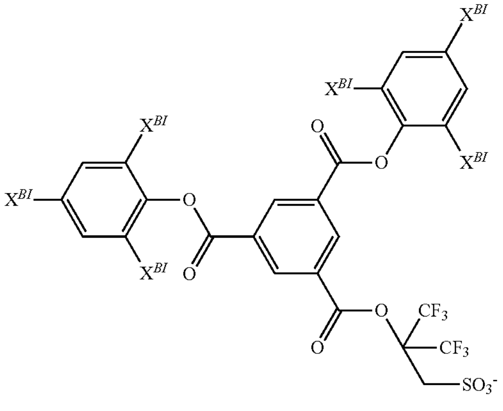

-continued

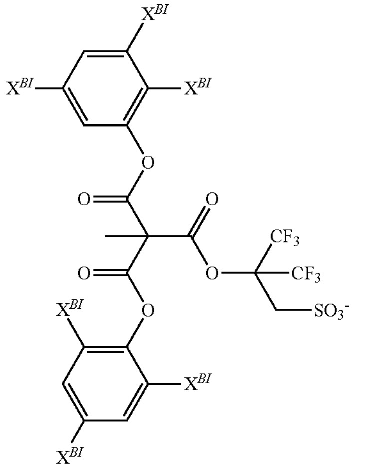

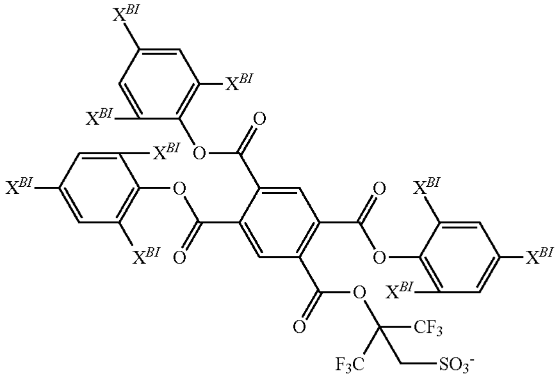

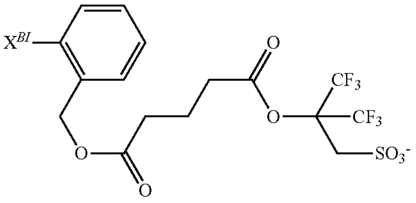

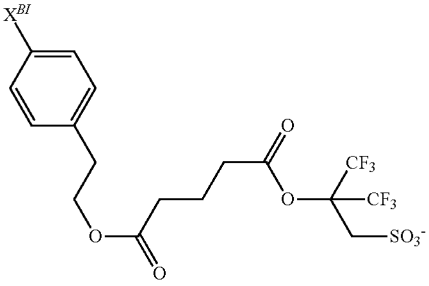

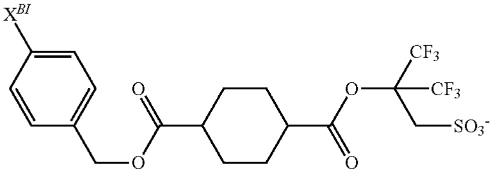

When used, the acid generator of addition type is preferably added in an amount of 0.1 to 50 parts, and more preferably 1 to 40 parts by weight per 100 parts by weight of the base polymer. The resist composition functions as a chemically amplified resist composition when the base polymer includes repeat units (f) and/or the acid generator of addition type is contained.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate: and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a surfactant, dissolution inhibitor, crosslinker, and quencher other than the sulfonium salt having formula (A) may be blended in any desired combination to formulate a positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. When used, the surfactant is preferably added in an amount of 0.0001 to 10 parts by weight per 100 parts by weight of the base polymer. The surfactant may be used alone or in admixture.

When the resist composition is of positive tone, the inclusion of a dissolution inhibitor may lead to an increased difference in dissolution rate between exposed and unexposed areas and a further improvement in resolution. The dissolution inhibitor which can be used herein is a compound having at least two phenolic hydroxy groups on the molecule, in which an average of from 0 to 100 mol % of all the hydrogen atoms on the phenolic hydroxy groups are replaced by acid labile groups or a compound having at least one carboxy group on the molecule, in which an average of 50 to 100 mol % of all the hydrogen atoms on the carboxy groups are replaced by acid labile groups, both the compounds having a molecular weight of 100 to 1.000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxy or carboxy group is replaced by an acid labile group, as described in U.S. Pat. No. 7,771,914 (JP-A 2008-122932, paragraphs [0155]-[0178]).

When the resist composition is of positive tone and contains a dissolution inhibitor, the dissolution inhibitor is preferably added in an amount of 0 to 50 parts, more preferably 5 to 40 parts by weight per 100 parts by weight of the base polymer. The dissolution inhibitor may be used alone or in admixture.

When the resist composition is of negative tone, a negative pattern may be formed by adding a crosslinker to reduce the dissolution rate of a resist film in exposed area. Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, tiimethylolmethane triglycidyl ether, trimethylolpropane triglycidyl ether, and trimethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguananmine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethylurea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

When the resist composition is of negative tone and contains a crosslinker, the crosslinker is preferably added in an amount of 0.1 to 50 parts, more preferably 1 to 40 parts by weight per 100 parts by weight of the base polymer. The crosslinker may be used alone or in admixture.

The other quencher is typically selected from conventional basic compounds. Conventional basic compounds include primary, secondary, and tertiary aliphatic amines, mixed amines, aromatic amines, heterocyclic amines, nitrogen-containing compounds with carboxy group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic ester bond as described in JP-A 2008-111103, paragraphs [0146]-[0164], and compounds having a carbamate group as described in JP 3790649. Addition of a basic compound may be effective for further suppressing the diffusion rate of acid in the resist film or connecting the pattern profile.

Onium salts such as sulfonium, iodonium and ammonium salts of sulfonic acids which are not fluorinated at α-position as described in U.S. Pat. No. 8,795,942 (JP-A 2008-158339) and similar onium salts of carboxylic acid may also be used as the quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface and thus enhances the rectangularity of resist pattern. When a protective film is applied as is often the case in the immersion lithography, the polymeric quencher is also effective for preventing a film thickness loss of resist pattern or rounding of pattern top.

When used, the other quencher is preferably added in an amount of 0 to 5 parts, more preferably 0 to 4 parts by weight per 100 parts by weight of the base polymer. The other quencher may be used alone or in admixture.

To the resist composition, a water repellency improver may also be added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver should be soluble in the alkaline developer and organic solvent developer. The water repellency improver of specific structure with a 1,1,1,3,3,3-hexafluoro-2-propanol residue is well soluble in the developer. A polymer comprising repeat units having an amino group or amine salt may serve as the water repellent additive and is effective for preventing evaporation of acid during PEB, thus preventing any hole pattern opening failure after development. An appropriate amount of the water repellency improver is 0 to 20 parts, more preferably 0.5 to 10 parts by weight per 100 parts by weight of the base polymer. The water repellency improver may be used alone or in admixture.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer. The acetylene alcohols may be used alone or in admixture.

The resist composition of the invention may be prepared by intimately mixing the selected components to form a solution, adjusting so as to meet a predetermined range of sensitivity and film thickness, and filtering the solution. The filtering step is important for reducing the number of defects in a resist pattern after development. The membrane for filtration or filter has a pore size of preferably up to 1 μm, more preferably up to 10 nm, even more preferably up to 5 mu. As the filter pore size is smaller, the number of defects in a small size pattern is reduced. The membrane is typically made of such materials as tetrafluoroethylene, polyethylene, polypropylene, nylon, polyurethane, polycarbonate, polyimide, polyamide-imide, and polysulfone. Membranes of tetrafluoroethylene, polyethylene and polypropylene which have been surface-modified so as to increase an adsorption ability are also useful. Unlike the membranes of nylon, polyurethane, polycarbonate and polyimide possessing an ability to adsorb gel and metal ions due to their polarity, membranes of tetrafluoroethylene, polyethylene and polypropylene which are non-polar do not possess the gel/metal ion adsorption ability in themselves, but can be endowed with the adsorption ability by surface modification with a functional group having polarity. In particular, filters obtained from surface modification of membranes of polyethylene and polypropylene in which pores of a smaller size can be perforated are effective for removing not only submicron particles, but also polar particles and metal ions. A laminate of membranes of different materials or a laminate of membranes having different pore sizes is also useful.

A membrane having an ion exchange ability may also be used as the filter. For example, an ion-exchange membrane capable of adsorbing cations acts to adsorb metal ions for thereby reducing metal impurities.

In the practice of filtration, a plurality of filters may be connected through serial or parallel pipes. The type and pore size of membranes in the plural filters may be the same or different. The filter may be disposed in a conduit between vessels. Alternatively, the filter is disposed in a conduit between inlet and outlet ports of a single vessel so that the solution is filtered while it is circulated.

Process

The resist composition is used in the fabrication of various integrated circuits. Pattern formation using the resist composition may be performed by well-known lithography processes. The process generally involves the steps of applying the resist composition onto a substrate to form a resist film thereon, exposing the resist film to high-energy radiation, and developing the exposed resist film in a developer. If necessary, any additional steps may be added.

Specifically, the resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate preferably at a temperature of 60 to 150° C. for 10 seconds to 30 minutes, more preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 mJ/cm, more preferably about 10 to 100 mJ/cm. When EB is used as the high-energy radiation, the resist film is exposed thereto directly or through a mask having a desired pattern in a dose of preferably about 0.1 to 100 $\mu C/cm^2$, more preferably about 0.5 to 50 $\mu C/cm^2$. It is appreciated that the inventive resist composition is suited in micropatterning using i-line of wavelength 365 nm, KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hotplate or in an oven preferably at 30 to 150° C. for 10 seconds to 30 minutes, more preferably at 50 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). In the case of positive tone, the resist film in the exposed area is dissolved in the developer whereas the resist film in the unexposed area is not dissolved. In this way, the desired positive pattern is formed on the substrate. In the case of negative tone, inversely the resist film in the exposed area is insolubilized whereas the resist film in the unexposed area is dissolved away.

In an alternative embodiment, a negative pattern can be obtained from the positive resist composition comprising a base polymer containing acid labile groups by effecting organic solvent development. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow. RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. All parts are by weight (pbw). THF stands for tetrahydrofuran.

Quenchers Q-1 to Q-28 used in resist compositions have the structure shown below. Quenchers Q-1 to Q-28 were synthesized by ion exchange between a hydrochloride salt of triphenylsulfonium providing the cation shown below and a carboxylic acid providing the anion shown below.

Q-1

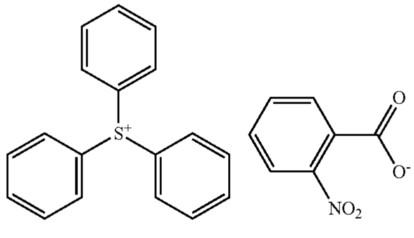

Q-2

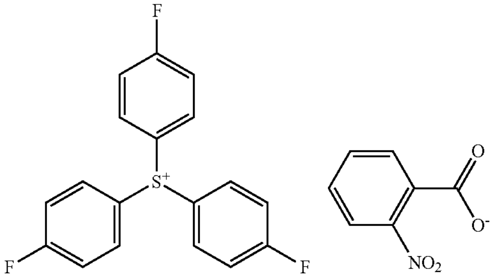

-continued
Q-3
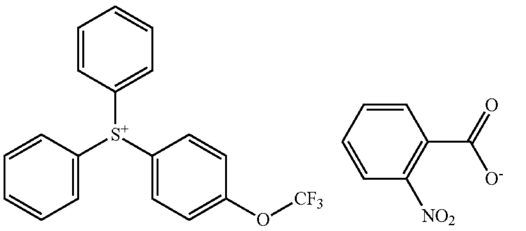
Q-4
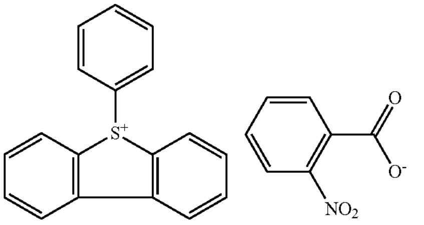
Q-5
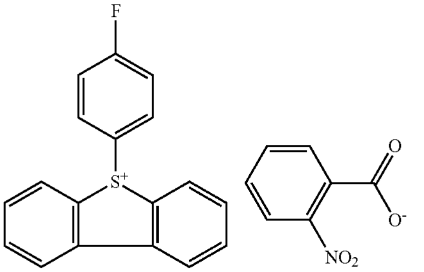
Q-6
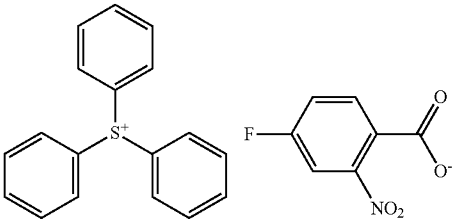
Q-7
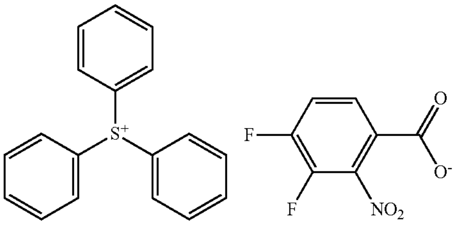
Q-8
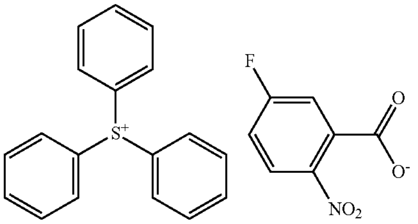
-continued
Q-9
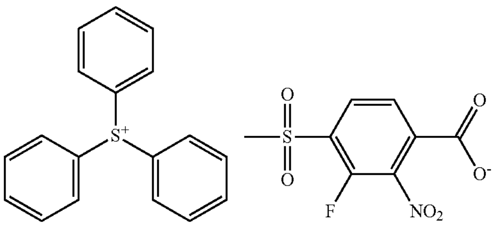
Q-10
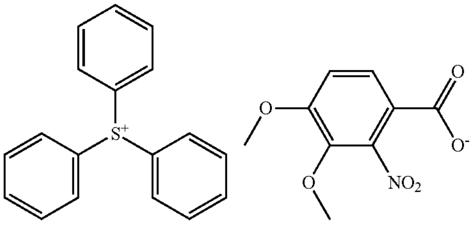
Q-11
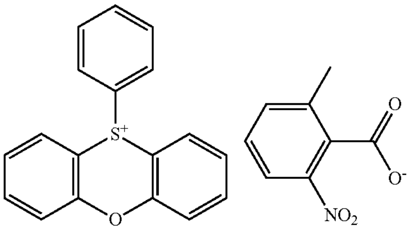
Q-12
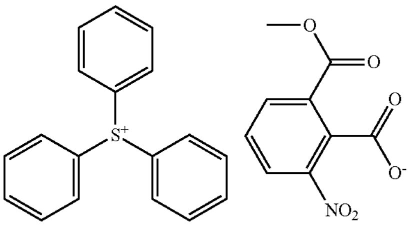
Q-13
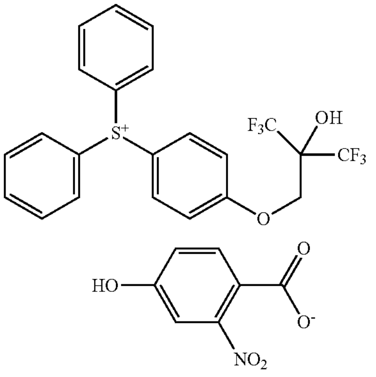
Q-14
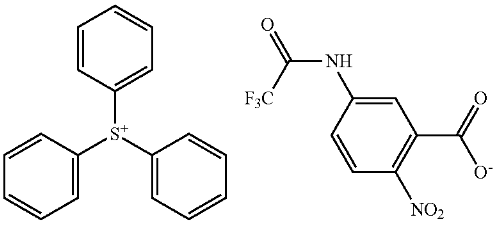

-continued
Q-15
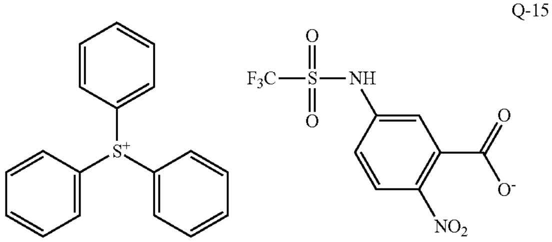
Q-16
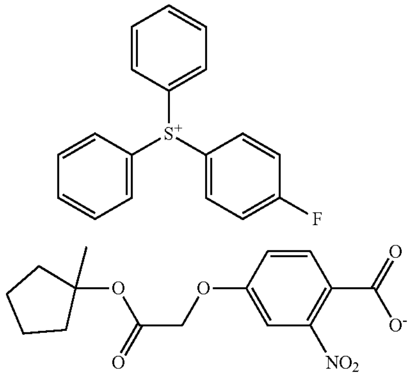
Q-17
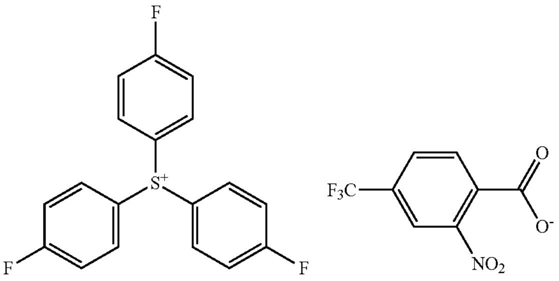
Q-18
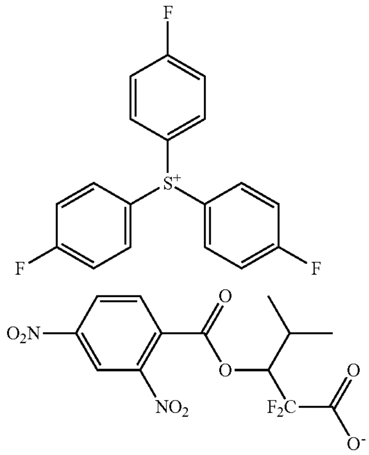
Q-19
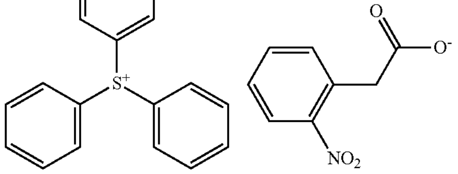
-continued
Q-20
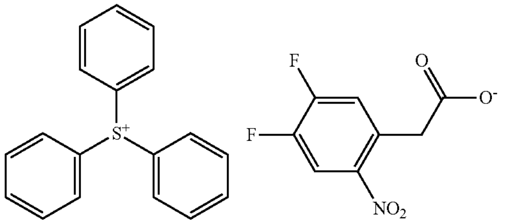
Q-21
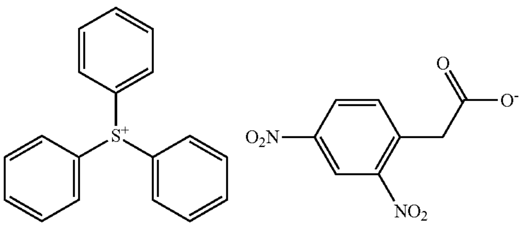
Q-22
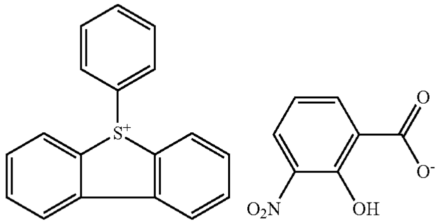
Q-23
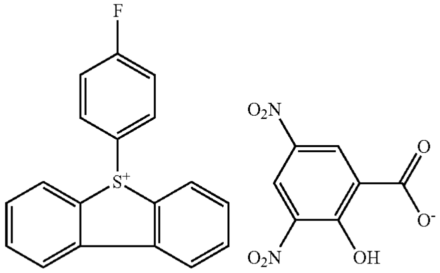
Q-24
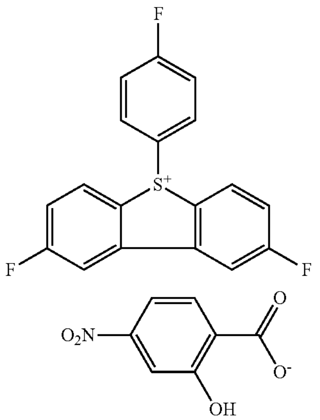

-continued

Q-25

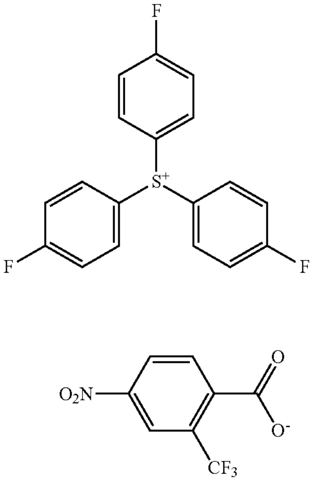

Q-26

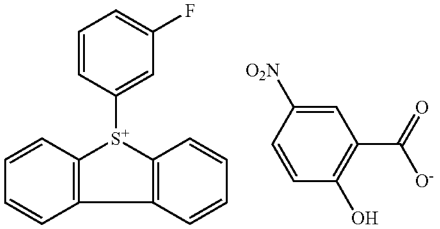

Q-27

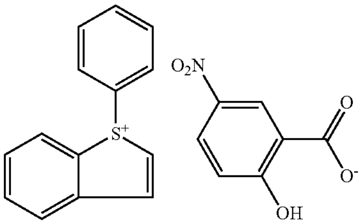

Q-28

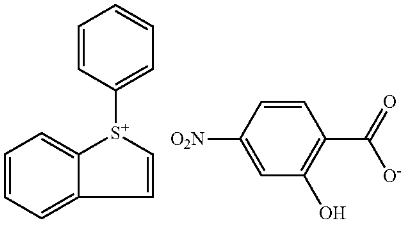

SYNTHESIS EXAMPLE

Synthesis of Base Polymers (Polymers P-1 to P4)

Base polymers (Polymers P-1 to P-4) of the construction shown below were synthesized by combining selected monomers, and effecting copolymerization reaction in THF solvent, followed by crystallization from methanol, repetitive washing with hexane, isolation, and drying. The base polymers were analyzed for composition by $^1$H-NMR spectroscopy and for Mw and Mw/Mn by GPC versus polystyrene standards using THE solvent.

P-1

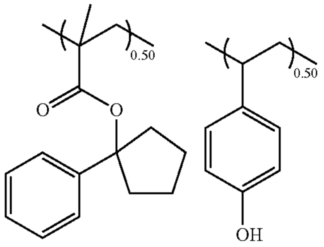

Mw = 4,500
Mw/Mn = 1.41

P-2

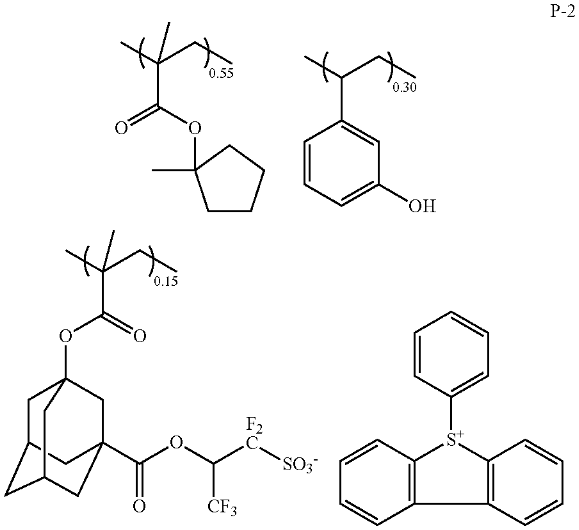

Mw = 8,900
Mw/Mn = 1.89

P-3

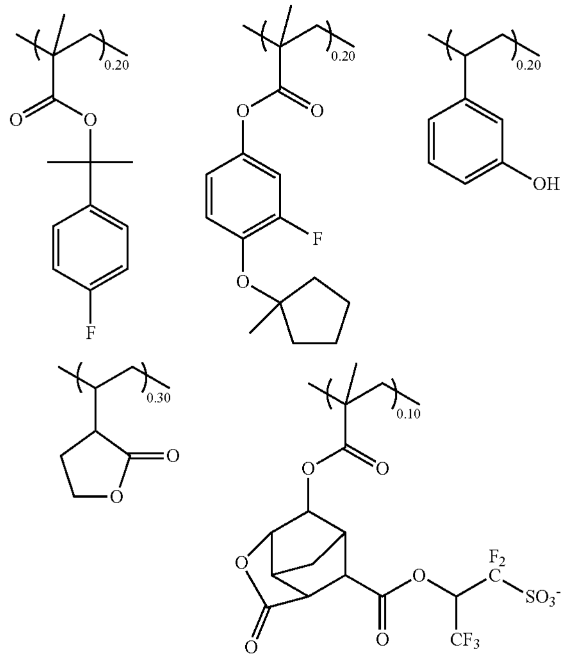

-continued

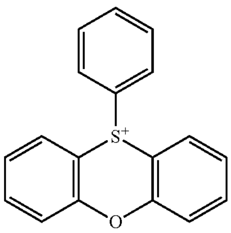

Mw = 7,800
Mw/Mn = 1.75

P-4

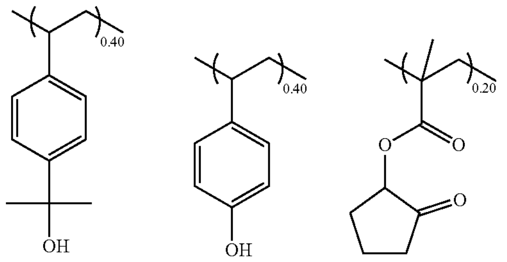

Mw = 6,900
Mw/Mn = 1.62

Examples 1 to 37 and Comparative Examples 1 to 3

Preparation and Evaluation of Resist Compositions (1) Preparation of Resist Compositions Resist compositions were prepared by dissolving components in a solvent in accordance with the recipe shown in Tables 1 to 3, and filtering the solution through a filter having a pore size of 0.2 μm. The resist compositions of Examples 1 to 36 and Comparative Examples 1 to 2 were of positive tone whereas the resist compositions of Example 37 and Comparative Example 3 were of negative tone The components in Tables 1 to 3 are identified below.

Organic Solvents:

PGMEA (propylene glycol monomethyl ether acetate)

DAA (diacetone alcohol)

Acid generators: PAG-1to PAG-3

PAG-1

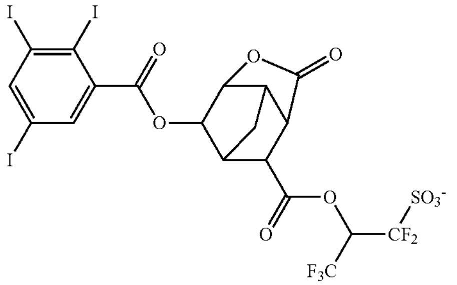

-continued

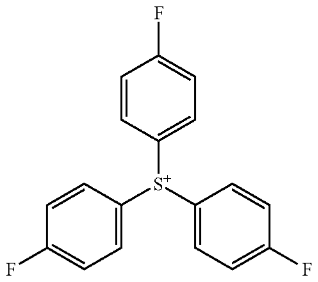

PAG-2

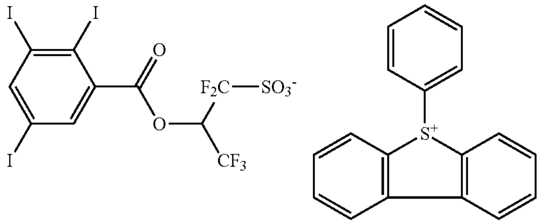

PAG-3

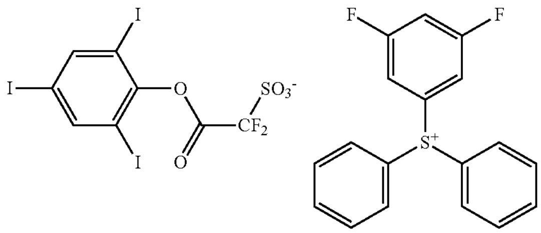

Blend quenchers: bQ-1 to bQ-5 bQ-1

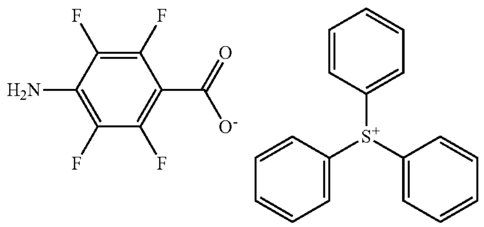

bQ-2

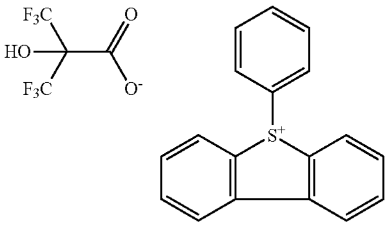

bQ-3

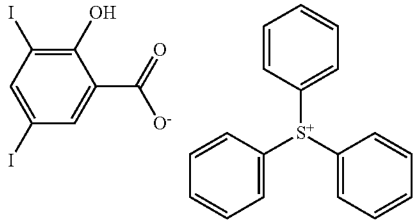

-continued bQ-4

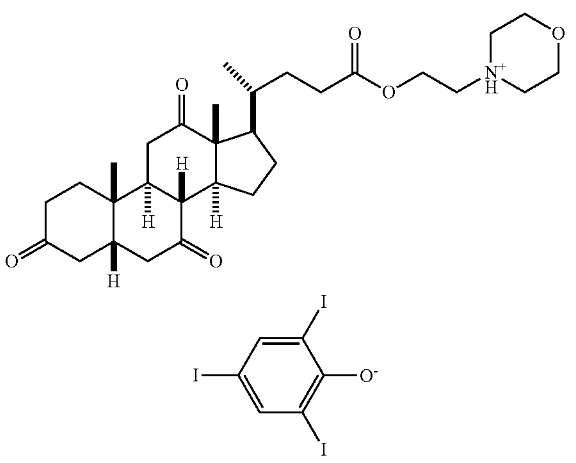

bQ-5

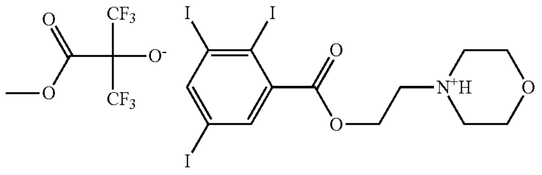

Comparative quenchers: cQ-1 and cQ-2 cQ-1

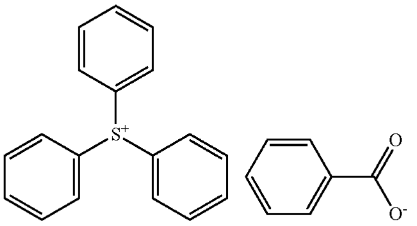

-continued cQ-2

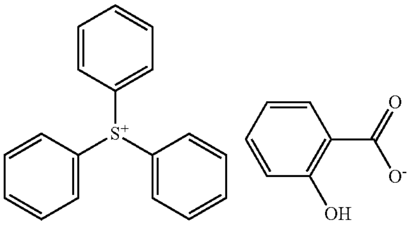

(2) EUV Lithography Test

Each of the resist compositions in Tables 1 to 3 was spin coated on a silicon substrate having a 20-nm coating of silicon-containing spin-on hard mask SHB-A940 (Shin-Etsu Chemical Co., Ltd., Si content 43 wt %) and prebaked on a hotplate at 100° C. for 60 seconds to form a resist film of 50 nm thick. Using an EUV scanner NXE3400 (ASML, NA 0.33, σ 0.9/0.6, quadrupole illumination), the resist film was exposed to EUV through a mask bearing a hole pattern at a pitch 44 nm (on-wafer size) and +20% bias. The resist film was baked (PEB) on a hotplate at the temperature shown in Tables 1 to 3 for 60 seconds and developed in a 2.38 wt % TMAH aqueous solution for 30 seconds to form a hole pattern having a size of 22 nm in Examples 1 to 36 and Comparative Examples 1 to 2 or a dot pattern having a size of 22 nm in Example 37 and Comparative Example 3.

The resist pattern was observed under CD-SEM (CG6300, Hitachi High-Technologies Corp.). The exposure dose that provides a hole or dot pattern having a size of 22 nm is reported as sensitivity. The size of 50 holes or dots was measured, from which a 3-fold value (3σ) of standard deviation (σ) was computed and reported as size variation, i.e., CDU.

The resist compositions are shown in Tables 1 to 3 together with the sensitivity and CDU of EUV lithography.

TABLE 1

| | | Polymer (pbw) | Acid generator (pbw) | Quencher (pbw) | Organic solvent (pbw) | PEB temp. (° C.) | Sensitivity ($mJ/cm^2$) | CDU (nm) |
|---|---|---|---|---|---|---|---|---|
| Example | 1 | P-1 (100) | PAG-1 (30) | Q-1 (4.29) | PGMEA (3,000) DAA (500) | 80 | 31 | 3.4 |
| | 2 | P-1 (100) | PAG-2 (30) | Q-2 (4.83) | PGMEA (3,000) DAA (500) | 80 | 31 | 3.3 |
| | 3 | P-1 (100) | PAG-2 (30) | Q-3 (5.13) | PGMEA (3,000) DAA (500) | 80 | 30 | 3.1 |
| | 4 | P-1 (100) | PAG-2 (30) | Q-4 (4.27) | PGMEA (3,000) DAA (500) | 80 | 29 | 3.3 |
| | 5 | P-1 (100) | PAG-2 (30) | Q-5 (4.45) | PGMEA (3,000) DAA (500) | 80 | 32 | 3.4 |
| | 6 | P-1 (100) | PAG-2 (30) | Q-6 (4.47) | PGMEA (3,000) DAA (500) | 80 | 32 | 3.2 |
| | 7 | P-1 (100) | PAG-2 (30) | Q-7 (4.65) | PGMEA (3,000) DAA (500) | 80 | 31 | 3.4 |
| | 8 | P-1 (100) | PAG-2 (30) | Q-8 (4.47) | PGMEA (3,000) DAA (500) | 80 | 31 | 3.5 |
| | 9 | P-1 (100) | PAG-3 (30) | Q-9 (5.25) | PGMEA (3,000) DAA (500) | 80 | 32 | 3.1 |
| | 10 | P-1 (100) | PAG-3 (30) | Q-10 (4.89) | PGMEA (3,000) DAA (500) | 80 | 37 | 3.4 |
| | 11 | P-1 (100) | PAG-3 (30) | Q-11 (4.43) | PGMEA (3,000) DAA (500) | 80 | 33 | 3.4 |
| | 12 | P-1 (100) | PAG-3 (30) | Q-12 (4.87) | PGMEA (3,000) DAA (500) | 80 | 34 | 3.2 |
| | 13 | P-1 (100) | PAG-3 (30) | Q-13 (6.41) | PGMEA (3,000) DAA (500) | 80 | 33 | 3.6 |

TABLE 1-continued

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| | 14 | P-1 (100) | PAG-3 (30) | Q-14 (5.40) | PGMEA (3,000) DAA (500) | 80 | 31 | 3.4 |
| | 15 | P-1 (100) | PAG-3 (30) | Q-15 (5.76) | PGMEA (3,000) DAA (500) | 80 | 33 | 3.5 |
| | 16 | P-1 (100) | PAG-3 (30) | Q-16 (6.06) | PGMEA (3,000) DAA (500) | 80 | 34 | 3.4 |
| | 17 | P-2 (100) | — | Q-7 (4.65) | PGMEA (3,000) DAA (500) | 90 | 31 | 3.2 |
| | 18 | P-3 (100) | — | Q-7 (4.65) | PGMEA (3,000) DAA (500) | 90 | 31 | 3.2 |
| | 19 | P-1 (100) | PAG-2 (30) | bQ-1 (2.36) Q-7 (2.32) | PGMEA (3,000) DAA (500) | 80 | 32 | 3.3 |
| | 20 | P-1 (100) | PAG-2 (30) | bQ-2 (2.36) Q-7 (2.32) | PGMEA (3,000) DAA (500) | 80 | 32 | 3.2 |

TABLE 2

| | | Polymer (pbw) | Acid generator (pbw) | Quencher (pbw) | Organic solvent (pbw) | PEB temp. (° C.) | Sensitivity (mJ/cm2) | CDU (nm) |
|---|---|---|---|---|---|---|---|---|
| Example | 21 | P-1 (100) | PAG-2 (30) | bQ-3 (3.81) Q-10 (2.45) | PGMEA (3,000) DAA (500) | 80 | 31 | 3.3 |
| | 22 | P-1 (100) | PAG-2 (30) | bQ-4 (493) Q-10 (2.45) | PGMEA (3,000) DAA (500) | 80 | 30 | 3.3 |
| | 23 | P-1 (100) | PAG-2 (30) | bQ-5 (4.19) Q-10 (2.45) | PGMEA (3,000) DAA (500) | 80 | 29 | 3.2 |
| | 24 | P-1 (100) | PAG-2 (30) | Q-17 (5.51) | PGMEA (3,000) DAA (500) | 80 | 29 | 3.2 |
| | 3 5 | P-1 (100) | PAG-2 (30) | Q-18 (6.78) | PGMEA (3,000) DAA (500) | 80 | 29 | 3.2 |
| | 26 | P-1 (100) | PAG-2 (30) | Q-19 (4.43) | PGMEA (3,000) DAA (500) | 80 | 34 | 3 5 |
| | 27 | P-1 (100) | PAG-2 (30) | Q-20 (4.79) | PGMEA (3,000) DAA (500) | 80 | 29 | 3.3 |
| | 28 | P-1 (100) | PAG-2 (30) | Q-21 (4.88) | PGMEA (3,000) DAA (500) | 80 | 36 | 3.4 |
| | 29 | P-1 (100) | PAG-2 (30) | Q-22 (4.45) | PGMEA (3,000) DAA (500) | 80 | 32 | 3.4 |
| | 30 | P-1 (100) | PAG-2 (30) | Q-23 (4.90) | PGMEA (3,000) DAA (500) | 80 | 36 | 3.3 |
| | 31 | P-1 (100) | PAG-2 (30) | Q-24 (5.00) | PGMEA (3,000) DAA (500) | 80 | 33 | 3.2 |
| | 32 | P-1 (100) | PAG-2 (30) | Q-25 (5.52) | PGMEA (3,000) DAA (500) | 80 | 31 | 3.4 |
| | 33 | P-1 (100) | PAG-2 (30) | Q-26 (4.61) | PGMEA (3,000) DAA (500) | 80 | 32 | 3.3 |
| | 34 | P-1 (100) | PAG-2 (30) | Q-27 (3.93) | PGMEA (3,000) DAA (500) | 80 | 29 | 3.3 |
| | 15 | P-1 (100) | PAG-2 (30) | Q-28 (3.93) | PGMEA (3,000) DAA (500) | 80 | 28 | 3.3 |
| | 36 | P-2 (100) | — | Q-28 (3.93) | PGMEA (3,000) DAA (500) | 80 | 29 | 3.2 |
| | 37 | P-4 (100) | PAG-1 (20) | Q-7 (4.65) | PGMEA (3,000) DAA (500) | 110 | 40 | 4.1 |

TABLE 3

| | | Polymer (pbw) | Acid generator (pbw) | Quencher (pbw) | Organic solvent (pbw) | PEB temp. (° C.) | Sensitivity (mJ/cm2) | CDU (nm) |
|---|---|---|---|---|---|---|---|---|
| Comparative Example | 1 | P-1 (100) | PAG-2 (30) | cQ-1 (3.84) | PGMEA (3,000) DAA (500) | 85 | 42 | 4.6 |
| | 2 | P-1 (100) | PAG-2 (30) | cQ-2 (400) | PGMEA (3,000) DAA (500) | 85 | 38 | 4.3 |
| | 3 | P-4 (100) | PAG-1 (20) | cQ-1 (3.84) | PGMEA (3,000) DAA (500) | 110 | 44 | 5.0 |

It is demonstrated in Tables 1 to 3 that resist compositions comprising a sulfonium salt of a carboxylic acid having a specific nitrobenzene ring offer a high sensitivity and improved CDU.

Japanese Patent Application No. 2021-068375 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a sulfonium salt of a carboxylic acid having a benzene ring substituted with at least one nitro group, wherein the carboxylic acid is free of iodine and bromine, wherein the sulfonium salt has the formula (A):

(A)

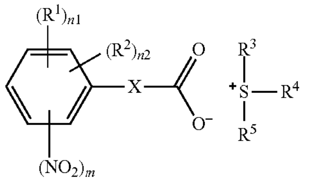

wherein $R^1$ is each independently chlorine, hydroxy group, amino group, or a $C_1$-$C_{20}$ hydrocarbyl group, $C_1$-$C_{20}$ hydrocarbyloxy group, $C_2$-$C_{20}$ hydrocarbylcarbonyloxy group, $C_2$-$C_{20}$ hydrocarbyloxycarbonyl group, $C_2$-$C_{20}$ hydrocarbyloxycarbonyloxy group, or $C_1$-$C_{20}$ hydrocarbylsulfonyl group, which may contain chlorine, hydroxy, amino, ether bond or ester bond, or —N($R^{1A}$)($R^{1B}$), —N($R^{1C}$)—C(═O)—$R^{1D}$, —N($R^{1C}$)—C(═O)—O—$R^{1D}$, or —N($R^{1E}$)—S(═O)$_2$—$R^{1F}$, $R^{1A}$ and $R^{1B}$ are each independently hydrogen or a $C_1$-$C_6$ saturated hydrocarbyl group, $R^{1C}$ and RIE are each independently hydrogen or a $C_1$-$C_6$ saturated hydrocarbyl group which may contain halogen, hydroxy moiety, $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety, $R^{1D}$ and $R^{1F}$ are each independently a $C_1$-$C_{16}$ aliphatic hydrocarbyl group, $C_6$-$C_{14}$ aryl group or $C_7$-$C_{15}$ aralkyl group, which may contain halogen, hydroxy moiety, $C_1$-$C_6$ saturated hydrocarbyloxy moiety, $C_2$-$C_6$ saturated hydrocarbylcarbonyl moiety or $C_2$-$C_6$ saturated hydrocarbylcarbonyloxy moiety, $R^2$ is fluorine, $R^3$ to $R^5$ are each independently halogen or a $C_1$-$C_{20}$ hydrocarbyl group which may contain a heteroatom, $R^3$ and $R^4$ may bond together to form a ring with the sulfur atom to which they are attached, X is a single bond or a $C_1$-$C_{20}$ divalent linking group which may contain an ether bond, carbonyl moiety, ester bond, amide bond, sultone ring, lactam ring, carbonate bond, halogen, hydroxy moiety or carboxy moiety, m is an integer of 1 to 3, n1 is an integer of 0 to 3, n2 is 0, and $1 \le m+n1+n2 \le 5$.

2. The resist composition of claim 1 wherein the sulfonium salt has the formula (A)-1:

(A)-1

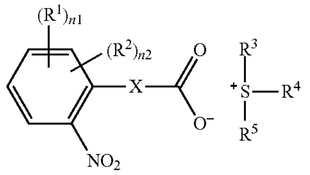

wherein $R^1$ to $R^5$, X, n1, and n2 are as defined above.

3. The resist composition of claim 1, further comprising an acid generator capable of generating a strong acid.

4. The resist composition of claim 3 wherein the acid generator generates a sulfonic acid, imide acid or methide acid.

5. The resist composition of claim 1, further comprising an organic solvent.

6. The resist composition of claim 1, further comprising a base polymer.

7. The resist composition of claim 6 wherein the base polymer comprises repeat units having the formula (a1) or repeat units having the formula (a2):

(a1)

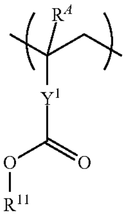

(a2)

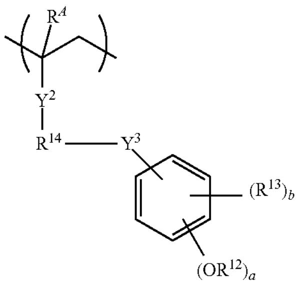

wherein $R^A$ is each independently hydrogen or methyl, $Y^1$ is a single bond, phenylene group, naphthylene group, or a $C_1$-$C_{12}$ linking group containing an ester bond and/or lactone ring, $Y^2$ is a single bond or ester bond, $Y^3$ is a single bond, ether bond or ester bond, $R^{11}$ and $R^{12}$ are each independently an acid labile group, $R^{13}$ is fluorine, trifluoromethyl, cyano or a $C_1$-$C_6$ saturated hydrocarbyl group, $R^{14}$ is a single bond or a $C_1$-$C_6$ alkanediyl group in which some carbon may be replaced by an ether bond or ester bond, a is 1 or 2, b is an integer of 0 to 4, and the sum of a+b is from 1 to 5.

8. The resist composition of claim 7 which is a chemically amplified positive resist composition.

9. The resist composition of claim 6 wherein the base polymer is free of an acid labile group.

10. The resist composition of claim 9 which is a chemically amplified negative resist composition.

11. The resist composition of claim 1, further comprising a surfactant.

12. The resist composition of claim 6 wherein the base polymer further comprises repeat units of at least one type selected from repeat units having the formulae (f1) to (f3):

(f1)

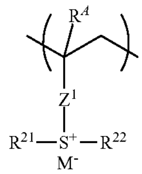

(f2)

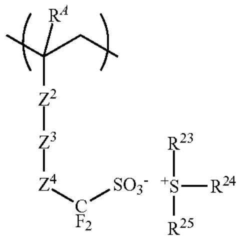

(f3)

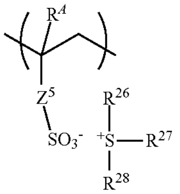

wherein $R^A$ is each independently hydrogen or methyl, $Z^1$ is a single bond, a $C_1$-$C_6$ aliphatic hydrocarbylene group, phenylene, naphthylene, or a $C_7$-$C_{18}$ group obtained by combining the foregoing, or —O—$Z^{11}$—, —C(═O)—O—$Z^{11}$— or —C(═O)—NH—$Z^{11}$, $Z^{11}$ is a $C_1$-$C_6$ aliphatic hydrocarbylene group, phenylene, naphthylene, or a $C_7$-$C_{18}$ group obtained by combining the foregoing, which may contain a carbonyl moiety, ester bond, ether bond or hydroxy moiety, $Z^2$ is a single bond or ester bond, $Z^3$ is a single bond, —$Z^{31}$—C(═O)—O—, —$Z^{31}$—O— or —$Z^{31}$—O—C(═O)—, $Z^{31}$ is a $C_1$-$C_{12}$ hydrocarbylene group, phenylene group, or a $C_7$-$C_{18}$ group obtained by combining the foregoing, which may contain a carbonyl moiety, ester bond, ether bond, iodine or bromine, $Z^4$ is a methylene, 2,2,2-trifluoro-1,1-ethanediyl or carbonyl group, $Z^5$ is a single bond, methylene, ethylene, phenylene, fluorinated phenylene, trifluoromethyl-substituted phenylene, —O—$Z^{51}$—, —C(═O)—O—$Z^{51}$— or —C(═O)—NH—$Z^{51}$, $Z^{51}$ is a $C_1$-$C_6$ aliphatic hydrocarbylene group, phenylene, fluorinated phenylene, or trifluoromethyl-substituted phenylene group, which may contain a carbonyl moiety, ester bond, ether bond or hydroxy moiety, $R^{21}$ to $R^{28}$ are each independently halogen or a $C_1$-$C_{20}$ hydrocarbyl group which may contain a heteroatom, $R^{23}$ and $R^{24}$, or $R^{26}$ and $R^{27}$ may bond together to form a ring with the sulfur atom to which they are attached, and $M^-$ is a non-nucleophilic counter ion.

13. A pattern forming process comprising the steps of applying the resist composition of claim 1 onto a substrate to form a resist film thereon, exposing the resist film to high-energy radiation, and developing the exposed resist film in a developer.

14. The pattern forming process of claim 13 wherein the high-energy radiation is i-line of wavelength 365 nm, ArF excimer laser of wavelength 193 nm, or KrF excimer laser of wavelength 248 nm.

15. The pattern forming process of claim 13 wherein the high-energy radiation is EB or EUV of wavelength 3 to 15 nm.

* * * * *